US010695349B2

(12) United States Patent
Sadhu et al.

(10) Patent No.: US 10,695,349 B2
(45) Date of Patent: Jun. 30, 2020

(54) INHIBITORS OF HUMAN PHOSPHATIDYLINOSITOL 3-KINASE DELTA

(71) Applicant: ICOS Corporation, Indianapolis, IN (US)

(72) Inventors: Chanchal Sadhu, North Potomac, MD (US); Ken Dick, Bothell, WA (US); Jennifer Treiberg, Redmond, WA (US); C. Gregory Sowell, San Francisco, CA (US); Edward A. Kesicki, Bothell, WA (US); Amy Oliver, Bothell, WA (US)

(73) Assignee: ICOS Corporation, Bothell, WA (US)

( * ) Notice: Subject to any disclaimer, the term of this patent is extended or adjusted under 35 U.S.C. 154(b) by 0 days.

(21) Appl. No.: 16/529,213

(22) Filed: Aug. 1, 2019

(65) Prior Publication Data
US 2020/0061062 A1 Feb. 27, 2020

Related U.S. Application Data

(60) Continuation of application No. 15/993,299, filed on May 30, 2018, now Pat. No. 10,398,695, which is a continuation of application No. 15/589,910, filed on May 8, 2017, now Pat. No. 10,010,550, which is a continuation of application No. 15/281,702, filed on Sep. 30, 2016, now abandoned, which is a division of application No. 14/092,287, filed on Nov. 27, 2013, now Pat. No. 9,487,772, which is a continuation of application No. 12/575,277, filed on Oct. 7, 2009, now Pat. No. 8,623,881, which is a continuation of application No. 11/110,204, filed on Apr. 20, 2005, now Pat. No. 8,138,195, which is a continuation of application No. 10/697,912, filed on Oct. 30, 2003, now Pat. No. 6,949,535, which is a division of application No. 10/027,591, filed on Oct. 19, 2001, now Pat. No. 6,667,300, which is a continuation-in-part of application No. 09/841,341, filed on Apr. 24, 2001, now Pat. No. 6,518,277.

(60) Provisional application No. 60/238,057, filed on Oct. 5, 2000, provisional application No. 60/199,655, filed on Apr. 25, 2000.

(51) Int. Cl.
C07C 233/66 (2006.01)
A61K 31/506 (2006.01)
C07D 403/12 (2006.01)
C07D 473/00 (2006.01)
C07D 473/16 (2006.01)
C07D 473/24 (2006.01)
C07D 473/30 (2006.01)
C12N 9/99 (2006.01)
C07D 473/38 (2006.01)
C07D 473/40 (2006.01)
C07D 487/04 (2006.01)
C12N 9/12 (2006.01)
C07D 473/32 (2006.01)
C07D 473/34 (2006.01)
C07D 233/66 (2006.01)

(52) U.S. Cl.
CPC .......... *A61K 31/506* (2013.01); *C07C 233/66* (2013.01); *C07D 233/66* (2013.01); *C07D 403/12* (2013.01); *C07D 473/00* (2013.01); *C07D 473/16* (2013.01); *C07D 473/24* (2013.01); *C07D 473/30* (2013.01); *C07D 473/32* (2013.01); *C07D 473/34* (2013.01); *C07D 473/38* (2013.01); *C07D 473/40* (2013.01); *C07D 487/04* (2013.01); *C12N 9/1205* (2013.01); *C12N 9/99* (2013.01); *C12Y 207/01137* (2013.01)

(58) Field of Classification Search
CPC .................................................... C07C 233/66
See application file for complete search history.

(56) References Cited

U.S. PATENT DOCUMENTS

| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hidebrand et al. |
| 4,225,489 A | 9/1980 | Rolf et al. |
| 4,229,537 A | 10/1980 | Hodgins et al. |

(Continued)

FOREIGN PATENT DOCUMENTS

| EP | 0525960 A1 | 2/1993 |
| EP | 0675124 A2 | 10/1995 |

(Continued)

OTHER PUBLICATIONS

Abu-Duhier et al., Br. J. Haematol. (2001) 113:983-988.

(Continued)

*Primary Examiner* — Alexander R Pagano
(74) *Attorney, Agent, or Firm* — Morrison & Foerster LLP

(57) ABSTRACT

Methods of inhibiting phosphatidylinositol 3-kinase delta isoform (PI3Kδ) activity, and methods of treating diseases, such as disorders of immunity and inflammation, in which PI3Kδ plays a role in leukocyte function are disclosed. Preferably, the methods employ active agents that selectively inhibit PI3Kδ, while not significantly inhibiting activity of other PI3K isoforms. Compounds are provided that inhibit PI3Kδ activity, including compounds that selectively inhibit PI3Kδ activity. Methods of using PI3Kδ inhibitory compounds to inhibit cancer cell growth or proliferation are also provided. Accordingly, the invention provides methods of using PI3Kδ inhibitory compounds to inhibit PI3Kδ-mediated processes in vitro and in vivo.

2 Claims, 9 Drawing Sheets

Specification includes a Sequence Listing.

(56) References Cited

U.S. PATENT DOCUMENTS

| | | | |
|---|---|---|---|
| 4,247,642 A | 1/1981 | Hirohara et al. | |
| 4,289,872 A | 9/1981 | Denkewalter et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,925,673 A | 5/1990 | Steiner et al. | |
| 5,013,556 A | 5/1991 | Woodle et al. | |
| 5,225,347 A | 7/1993 | Goldberg et al. | |
| 5,229,490 A | 7/1993 | Tam | |
| 5,378,725 A | 1/1995 | Bonjouklian et al. | |
| 5,480,906 A | 1/1996 | Creemer et al. | |
| RE35,862 E | 7/1998 | Steiner et al. | |
| 5,858,753 A | 1/1999 | Chantry et al. | |
| 5,882,910 A | 3/1999 | Chantry et al. | |
| 5,948,664 A | 9/1999 | Williams et al. | |
| 5,985,589 A | 11/1999 | Chantry et al. | |
| 6,046,049 A | 4/2000 | Monia et al. | |
| 6,048,970 A | 4/2000 | Lal et al. | |
| 6,277,981 B1 | 8/2001 | Tu et al. | |
| 6,291,220 B1 | 9/2001 | Williams et al. | |
| 6,369,038 B1 | 4/2002 | Blumenfeld et al. | |
| 6,410,224 B1 | 6/2002 | Stinchcomb et al. | |
| 6,426,337 B1 | 7/2002 | Cox et al. | |
| 6,482,623 B1 | 11/2002 | Vanhaesebroeck et al. | |
| 6,518,277 B1 * | 2/2003 | Sadhu | C07D 473/34 514/266.1 |
| 6,627,755 B1 | 9/2003 | Chenard et al. | |
| 6,667,300 B2 * | 12/2003 | Sadhu | C07D 403/12 514/183 |
| 6,696,250 B1 | 2/2004 | Cech et al. | |
| 6,800,620 B2 * | 10/2004 | Sadhu | C07D 473/16 514/183 |
| 6,921,764 B2 | 7/2005 | Chenard et al. | |
| 6,949,535 B2 * | 9/2005 | Sadhu | C07D 403/12 514/183 |
| 7,932,260 B2 | 4/2011 | Fowler et al. | |
| 8,138,195 B2 * | 3/2012 | Sadhu | C07D 403/12 514/263.1 |
| 8,183,253 B2 * | 5/2012 | Kompella | C07C 323/62 514/275 |
| 8,207,153 B2 | 6/2012 | Fowler et al. | |
| 8,492,389 B2 * | 7/2013 | Sadhu | C07D 403/12 514/263.1 |
| RE44,599 E | 11/2013 | Fowler et al. | |
| 8,586,597 B2 | 11/2013 | Fowler et al. | |
| RE44,638 E | 12/2013 | Fowler et al. | |
| 8,623,881 B2 * | 1/2014 | Sadhu | C07D 403/12 514/263.1 |
| 8,637,533 B2 * | 1/2014 | Sadhu | C07D 403/12 514/266.1 |
| 8,653,077 B2 * | 2/2014 | Sadhu | C07D 403/12 514/249 |
| 8,779,131 B2 | 7/2014 | Kesicki et al. | |
| 8,865,730 B2 | 10/2014 | Carra et al. | |
| 8,980,901 B2 | 3/2015 | Fowler et al. | |
| 8,993,583 B2 | 3/2015 | Fowler et al. | |
| 9,149,477 B2 | 10/2015 | Kesicki et al. | |
| 9,469,643 B2 | 10/2016 | Carra et al. | |
| 9,487,772 B2 * | 11/2016 | Sadhu | C07D 403/12 |
| 9,567,337 B2 | 2/2017 | Bremmer et al. | |
| 9,708,327 B2 | 7/2017 | Buttar et al. | |
| 10,010,550 B2 * | 7/2018 | Sadhu | A61K 31/506 |
| 10,047,060 B2 | 8/2018 | Bremner et al. | |
| 10,059,677 B2 | 8/2018 | Bremner et al. | |
| 10,336,756 B2 | 7/2019 | Kesicki et al. | |
| 10,398,695 B2 * | 9/2019 | Sadhu | C07D 403/12 |
| 10,414,737 B2 | 9/2019 | Bremner et al. | |
| 10,442,805 B2 | 10/2019 | Buttar et al. | |
| 2004/0023390 A1 | 2/2004 | Davidson et al. | |
| 2004/0049039 A1 | 3/2004 | Chenard et al. | |
| 2004/0092561 A1 | 5/2004 | Ruckle et al. | |
| 2004/0121996 A1 | 6/2004 | Barvian et al. | |
| 2004/0138199 A1 | 7/2004 | Goglietti et al. | |
| 2004/0242631 A1 | 12/2004 | Garlich et al. | |
| 2004/0248953 A1 | 12/2004 | Gogliotti et al. | |
| 2004/0248954 A1 | 12/2004 | Gogliotti et al. | |
| 2004/0259926 A1 | 12/2004 | Bruendle et al. | |
| 2005/0004195 A1 | 1/2005 | Para et al. | |
| 2005/0020630 A1 | 1/2005 | Connolly et al. | |
| 2005/0020631 A1 | 1/2005 | Gogliotti et al. | |
| 2005/0043239 A1 | 2/2005 | Douangpanya et al. | |
| 2005/0054614 A1 | 3/2005 | Diacovo et al. | |
| 2005/0239809 A1 | 10/2005 | Watts et al. | |
| 2006/0079538 A1 | 4/2006 | Hallahan et al. | |
| 2006/0106038 A1 | 5/2006 | Bouscary et al. | |
| 2008/0287469 A1 | 11/2008 | Diacovo et al. | |
| 2010/0029693 A1 | 2/2010 | Douangpanya et al. | |
| 2010/0202963 A1 | 8/2010 | Gallatin et al. | |
| 2010/0249155 A1 | 9/2010 | Evarts et al. | |
| 2010/0256167 A1 | 10/2010 | Fowler et al. | |
| 2011/0044942 A1 | 2/2011 | Puri et al. | |
| 2011/0230465 A1 | 9/2011 | Stammers et al. | |
| 2012/0015964 A1 | 1/2012 | Fowler et al. | |
| 2012/0040980 A1 | 2/2012 | Huggins et al. | |
| 2016/0376274 A1 | 12/2016 | Carra et al. | |
| 2017/0049772 A1 | 2/2017 | Chanchal et al. | |

FOREIGN PATENT DOCUMENTS

| | | | |
|---|---|---|---|
| EP | 0716857 A1 | 6/1996 | |
| EP | 0884310 A1 | 12/1998 | |
| EP | 0900568 A2 | 3/1999 | |
| GB | 1356763 A | 6/1974 | |
| GB | 1 554 057 A | 10/1979 | |
| GB | 2017097 A | 10/1979 | |
| JP | 55-118917 A2 | 9/1980 | |
| JP | 55-118918 A2 | 9/1980 | |
| JP | 56-002322 A2 | 1/1981 | |
| JP | S-6310777 A | 1/1988 | |
| WO | WO-93/21259 A1 | 10/1993 | |
| WO | WO-94/17090 A1 | 8/1994 | |
| WO | WO-95/24379 A1 | 9/1995 | |
| WO | WO-96/04923 A1 | 2/1996 | |
| WO | WO-96/25488 A1 | 8/1996 | |
| WO | WO-96/32478 A1 | 10/1996 | |
| WO | WO-97/34631 A1 | 9/1997 | |
| WO | WO-97/41097 A2 | 11/1997 | |
| WO | WO-97/43276 A1 | 11/1997 | |
| WO | WO-97/46688 A1 | 12/1997 | |
| WO | WO-98/33802 A1 | 8/1998 | |
| WO | WO-98/38173 A1 | 9/1998 | |
| WO | WO-99/08501 A2 | 2/1999 | |
| WO | WO-99/34804 A1 | 7/1999 | |
| WO | WO-01/00881 A1 | 1/2001 | |
| WO | WO-01/030768 A1 | 5/2001 | |
| WO | WO-01/030768 C1 | 5/2001 | |
| WO | WO-01/53266 A1 | 7/2001 | |
| WO | WO-01/57034 A1 | 8/2001 | |
| WO | WO-01/81346 A2 | 11/2001 | |
| WO | WO-01/81346 A3 | 11/2001 | |
| WO | WO-0181346 A2 * | 11/2001 | C07D 473/34 |
| WO | WO-03/035075 A1 | 5/2003 | |
| WO | WO-03/106622 A2 | 12/2003 | |
| WO | WO-04/007491 A1 | 1/2004 | |
| WO | WO-04/012768 A1 | 2/2004 | |
| WO | WO-04/026285 A2 | 4/2004 | |
| WO | WO-04/026285 A3 | 4/2004 | |
| WO | WO-04/029055 A1 | 4/2004 | |
| WO | WO-04/052373 A1 | 6/2004 | |
| WO | WO-04/056820 A1 | 7/2004 | |
| WO | WO-04/089925 A1 | 10/2004 | |
| WO | WO-04/108708 A1 | 12/2004 | |
| WO | WO-04/108709 A1 | 12/2004 | |
| WO | WO-04/108713 A1 | 12/2004 | |
| WO | WO-04/108715 A1 | 12/2004 | |
| WO | WO-05/016348 A1 | 2/2005 | |
| WO | WO-05/016349 A1 | 2/2005 | |
| WO | WO-05/067901 A2 | 7/2005 | |
| WO | WO-05/113556 A1 | 12/2005 | |

(56) References Cited

FOREIGN PATENT DOCUMENTS

| WO | WO-05/120511 A1 | 12/2005 |
| WO | WO-2009/058361 A1 | 5/2009 |
| WO | WO-2010/065923 A2 | 6/2010 |
| WO | WO-2010/065923 A3 | 6/2010 |
| WO | WO-2010/123931 A1 | 10/2010 |
| WO | WO-2011/146882 A1 | 11/2011 |
| WO | WO-2014/023083 A1 | 2/2014 |
| WO | WO-2015/051241 A1 | 4/2015 |
| WO | WO-2015/191726 A1 | 12/2015 |

OTHER PUBLICATIONS

Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html>, 2 pages.
Advisory Action from U.S. Appl. No. 11/596,092, dated Jul. 27, 2010.
Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, Url: http://www.weizmann.ac.il/Biology/open_day_2002/book/ronen_alon.pdf.
Amendment from U.S. Appl. No. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," Indian Journal of Chemistry 37B(11):1153-1156.
Angel, Activities of Phosphoinositide Kinase-3 (PI3K) (1999) retrieved from the internet on May 22, 2003, URL: http://www.chem.csustan.edu/chem4400/SJBR/angel99.htm Angio World, "How Angiogenesis Complicates Psoriasis" (2001) retrieved from the internet on Apr. 13, 2004, URL: http://www.angioworld.com/psoriasis.htm.
Annabi et al., J. Cell. Biochem. (2004) 91:1146-1158.
Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.
Anonymous (2006). "Heart Disease", WebMD, located at <http://www.webmd.com/content/pages/9/1675_57842.htm> as retrieved on Sep. 14, 2006, 1 page.
Anonymous (2010) "Systemic Lupus Erythematosus", located at <http://www.nlm.nih.gov/medlineplus/ency/article/000435.htm>, last visited Aug. 1, 2010, 4 pages.
Anonymous (2010). "Spinal Cord Injury", located at <http://www.medicinenet.com/spinal_cord_injury/page.htm>, last visited on Aug. 1, 2010, 3 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Australian Re-Examination Report dated Sep. 3, 2015, for Australian Patent No. 2001255667, filed Apr. 24, 2001, 7 pages. (4.41).
Azenabor, A.A. et al. (2006). "Macrophage Antioxidant Enyzmes Regulate Chlamydia Pneumoniaechronicity: Evidence of the Effect of Redox Balance on Host-Pathogen Relationship," Immunobiology 211(5):325-339.
Bader, A.G. et al. (2005). "Oncogenic P13K Deregulates Transcription and Translation," Nature Reviews Cancer 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," Az. J. Pharm. Sci. 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Barrientos, J.C. (2016, e-pub. May 18, 2016). "Idelalisib for the Treatment of Indolent Non-Hodgkin Lymphoma: A Review of its Clinical Potential," Onco Targets Ther. 9:2945-2953.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," Haematologica 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 111-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry et al., J. Biol. Chem. (1997) 272:19236-19241.

(56) References Cited

OTHER PUBLICATIONS

Chapman-Kirkland, E.S. et al. (1991). "Superoxide Anion Production From Human Neutrophils Measured with an Improved Kinetic and Endpoint Microassay," J Immunol Meth 142(1):95-104.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," Curr. Oncol. Rep. 12:87-94.
Coligan et al., Current Protocols in Protein Science (2002) 3:15-20.
Computer Search (8 pages), Cart Navigator, retrieved from the internet on Mar. 22, 2001, URL: http://www.chemnavigator.com/members/CartNavigator.asp#sample1.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Dey, S. et al. (Nov. 2000). "Synthesis of tert-Butoxycarbonyl (Boc)-Protected Purines", The Journal of Organic Chemistry 65(22):7697-7699.
Doggett et al., Biophys. J. (2002) 83:194-205.
Domanig, R. (1981). "Chinazolinone, 2. Mitt: Synthese Und Einige Reaktionen Von 2-Azidomethyl-3-Aryl-4-Chinazolinonen," Monatshefte fuer Chemie 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H)Quinazolinone," Bollettino Chimico Farmaceutico 137(7):286-289.
El-Feky, S.A. et al. (1985). "Synthesis of Certain New Sulfur-Containing Quinazolinone Derivatives Likely to Possess CNS Depressant Action," Egyptian Journal of Pharmaceutical Sciences 24(1-4):39-47.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm, 4 pages. Erbagci et al., Clin. Biochem. (2001) 34:645-650.
Estey, Cancer (2001) 92:1059-1073.
Etzioni, Pediatr. Res. (1996) 39:191-198.

European Minutes of the Oral Proceedings before the Opposition Division dated Nov. 15, 2018, for Patent Application No. 05752122.1, filed Dec. 5, 2006, 6 pages.
European Notice of Information about the Result of the Oral Proceedings dated Oct. 12, 2018, for Patent Application No. 05752122.1, filed Dec. 5, 2006, 1 page.
European Notice of Termination of Oppositions and Findings dated Feb. 26, 2019, for Patent Application No. 05752122.1, filed Dec. 5, 2006, 1 page.
European Office Action dated Feb. 24, 2017 for EP Application No. 15200992.4, filed on Apr. 24, 2010, 4 pages.
European Opposition Division Decision Rejecting the Opposition dated Nov. 15, 2018, for Patent Application No. 05752122.1, filed Dec. 5, 2006, 11 pages.
European Search Report dated Jun. 6, 2013 for EP Patent Application No. 13150110.8, filed May 12, 2005, 6 pages.
European Search Report dated Mar. 29, 2011, for EP Patent Application No. 10163434.3, filed on Apr. 24, 2001, 9 pages.
European Submission by Opponent STADA Arzneimittel AG in Opposition Proceedings, filed Oct. 4, 2018, for Patent Application No. 05752122.1, 10 pages. (German only).
European Submission in Opposition Proceedings filed Aug. 10, 2018, for Patent Application No. 05752122.1, to "Summons to attend Oral Proceedings Pursuant to Rule 115(1) EPC", on behalf of ICOS Corporation, 17 pages.
European Submission in Opposition Proceedings filed Aug. 10, 2018, for Patent Application No. 05752122.1, to "Summons to attend Oral Proceedings Pursuant to Rule 115(1) EPC", on behalf of STADA Arzneimittel AG, 13 pages. (German only).
European Summons to attend Oral Proceedings Pursuant to Rule 115(1) EPC dated Mar. 27, 2018, for Patent Application No. 05752122.1, filed Dec. 5, 2006, 12 pages.
Extended European Search Report dated Dec. 10, 2013, for EP Patent Application No. 13150110.8, filed May 12, 2005, 10 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, dated Jan. 8, 2009.
Final Office Action from U.S. Appl. No. 11/129,006, dated Oct. 5, 2010.
Final Office Action from U.S. Appl. No. 11/596,092, dated May 18, 2010.
Final Office Action dated Feb. 15, 2012, for U.S. Appl. No. 12/732,124, filed Mar. 25, 2010, 12 pages.
Final Office Action dated Feb. 26, 2016, for U.S. Appl. No. 14/092,287, filed Nov. 27, 2013, 6 pages.
Final Office Action dated Jul. 9, 2013, for U.S. Appl. No. 13/399,828, filed Feb. 17, 2012, 6 pages.
Final Office Action dated Jun. 7, 2012, for U.S. Appl. No. 11/129,006, filed May 12, 2005, 14 pages.
Final Office Action dated Oct. 24, 2011, for U.S. Appl. No. 12/732,128, filed Mar. 25, 2010, 8 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (P13K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," Blood 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Fraser et al., Science (1991) 251:313-316.

(56) References Cited

OTHER PUBLICATIONS

Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," Clinical Advances in Hematology & Oncology 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Green, S.J. et al. (1994). "Oxidative Metabolism of Murine Macrophages," Chapter 14, Unit 14.5 in Current Protocols in Immunology, vol. 3, John Wiley & Sons, Inc., pp. 14.5.1-14.5.11.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," Communicative and Integrative Biology 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," Blood 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Kγ in Endothelial Cells and its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hungarian Office Action dated Aug. 27, 2018, for Patent Application No. E030839, filed Feb. 22, 2017, 2 pages. (English translation only).
Hunter, Cell (1995) 83:1-4.
Hussong et al., Blood (2000) 95:309-313.
Ikeda, H. et al. (Feb. 2009). "CAL-101: A Selective Inhibitor of P13K p110δ for the Treatment of Multiple Myeloma," Clinical Lymphoma and Myeloma 9(Supp. 1):598-599.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," Blood 112(11):950, Abstract No. 2753.
Ikeda, H. et al. (Sep. 2, 2010). "PI3K/p110δ is a Novel Therapeutic Target in Multiple Myeloma," Blood 116(9):1460-1468.
International Preliminary Report on Patentability for PCT/US2006/005621, dated Aug. 21, 2007, 8 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report dated Aug. 29, 2005, for PCT Application No. PCT/US2005/016778, filed on May 12, 2005, 4 pages.
International Search Report dated Sep. 15, 2006 for PCT Application No. PCT/US2006/005621, filed on Feb. 16, 2006, 4 pages.
International Search Report dated Sep. 29, 2015 for PCT Application No. PCT/US2015/035126, Internationally filed on Jun. 10, 2015, 4 pages.
Interview Summary from U.S. Appl. No. 10/918,825, dated Jun. 14, 2006.

(56) References Cited

OTHER PUBLICATIONS

Ishida-Okawara, A. et al. (Dec. 12, 1996). "Modulation of Degranulation and Superoxide Generation in Human Neutrophils by Unsaturated Fatty Acids of Odd Carbon Numbers," BioChimica et Biophysica Acta 1314(3):239-246.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Israel Office Action dated Jun. 21, 2018, for Patent Application No. 241732, filed Sep. 20, 2015, 15 pages. (including English translation).
Israel Office Action dated Jun. 5, 2019, for Patent Application No. 245146, filed Apr. 14, 2016, 7 pages. (including English translation).
Israel Office Action dated May 17, 2018, for Patent Application No. 245146, filed Apr. 14, 2016, 7 pages. (including English translation).
Israeli Notification of defects dated Nov. 6, 2016 for IL Application No. 245146, filed on Apr. 14, 2016, 8 pages.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," Clinical Advances in Hematology & Oncology 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Keating, G. (Mar. 2015, e-pub. Feb. 1, 2015). "Idelalisib: A Review of its Use in Chronic Lymphoctic Leukaemia and Indolent non-Hodgkin's Lymphoma," Targ Oncol. 10:141-151.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," Proceedings of the American Association for Cancer Research 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," Blood 112(11):12, Abstract No. 16.
Lannutti, B.J. et al. (Nov. 20, 2009). "CAL-101, An Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," Blood 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," Haematologica 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," Haematologica 94(52):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Levin, T.N. et al. (1997). "Acute Congestive Heart Failure. The Need for Aggressive Therapy," Postgraduate Medicine 101(1):97-100, 103-104, and 108-111.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marchione, et al. (2006). "Drugs hold promise in kidney cancer fight", located at <http://www.ledger-enquirer.com/mld/ledgerenquirer/living/health/14744763.htm>, last visited on Sep. 2, 2006, 3 pages.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," Blood 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, dated Dec. 24, 2009.
Non-Final Office Action from U.S. Appl. No. 09/841,341, dated Apr. 25, 2002.
Non-Final Office Action from U.S. Appl. No. 10/027,591, dated Feb. 26, 2003.
Non-Final Office Action from U.S. Appl. No. 10/918,803, dated Apr. 1, 2008.
Non-Final Office Action from U.S. Appl. No. 10/918,803, dated Mar. 16, 2010.
Non-Final Office Action from U.S. Appl. No. 10/918,825, dated Nov. 7, 2005.
Non-Final Office Action from U.S. Appl. No. 11/110,204, dated Aug. 5, 2008.
Non-Final Office Action from U.S. Appl. No. 11/110,204, dated Feb. 4, 2010.
Non-Final Office Action from U.S. Appl. No. 11/110,204, dated Jun. 17, 2009.
Non-Final Office Action from U.S. Appl. No. 11/129,006, dated Dec. 15, 2009.
Non-Final Office Action from U.S. Appl. No. 11/596,092, dated Jun. 10, 2009.
Non-Final Office Action from U.S. Appl. No. 11/884,566, dated Aug. 3, 2010.
Non-Final Office Action dated Oct. 8, 2015, for U.S. Appl. No. 14/323,925, filed Jul. 3, 2014, 8 pages.
Non-Final Office Action dated Aug. 2, 2012 for U.S. Appl. No. 12/575,277, filed Oct. 7, 2009, 8 pages.

(56) References Cited

OTHER PUBLICATIONS

Non-Final Office Action dated Aug. 7, 2012 for U.S. Appl. No. 12/575,367, filed Oct. 7, 2009, 9 pages.
Non-Final Office Action dated Feb. 13, 2013 for U.S. Appl. No. 13/247,962, filed Sep. 28, 2011, 21 pages.
Non-Final Office Action dated Feb. 3, 2015, for U.S. Appl. No. 14/284,331, filed May 21, 2014, 16 pages.
Non-Final Office Action dated Feb. 7, 2017, for U.S. Appl. No. 15/281,702, filed Sep. 30, 2016, seven pages.
Non-Final Office Action dated Jan. 19, 2017, for U.S. Appl. No. 14/826,096, filed Aug. 13, 2015, ten pages.
Non-Final Office Action dated Jan. 20, 2012 for U.S. Appl. No. 13/163,597, filed Jun. 17, 2011, 14 pages.
Non-Final Office Action dated Jun. 25, 2014, for U.S. Appl. No. 14/049,154, filed Oct. 8, 2013, 15 pages.
Non-Final Office Action dated Jun. 25, 2014, for U.S. Appl. No. 14/049,163, filed Oct. 8, 2013, 15 pages.
Non-Final Office Action dated Jun. 26, 2013 for U.S. Appl. No. 13/765,610, filed Feb. 12, 2013, 9 pages.
Non-Final Office Action dated Jun. 28, 2011, for U.S. Appl. No. 12/732,124, filed Mar. 25, 2010, 11 pages.
Non-Final Office Action dated Mar. 1, 2013 for U.S. Appl. No. 13/399,828, filed Feb. 17, 2012, 6 pages.
Non-Final Office Action dated Mar. 25, 2013 for U.S. Appl. No. 13/728,807, filed Dec. 27, 2012, 13 pages.
Non-Final Office Action dated Nov. 16, 2015, for U.S. Appl. No. 14/092,287, filed Nov. 27, 2013, 11 pages.
Non-Final Office Action dated Oct. 17, 2011 for U.S. Appl. No. 12/732,124, filed Mar. 25, 2010, 8 pages.
Non-Final Office Action dated Sep. 11, 2017 for U.S. Appl. No. 15/589,910, 5 pages.
Notice of Allowance from U.S. Appl. No. 09/841,341, dated Oct. 7, 2002.
Notice of Allowance from U.S. Appl. No. 10/027,591, dated Jul. 29, 2003.
Notice of Allowance from U.S. Appl. No. 10/337,192, dated Mar. 11, 2004.
Notice of Allowance from U.S. Appl. No. 10/697,912, dated Dec. 30, 2004.
Notice of Allowance dated Aug. 15, 2017 for U.S. Appl. No. 14/826,096, filed Aug. 13, 2015, 9 pages.
Notice of Allowance dated Feb. 21, 2019 for U.S. Appl. No. 14/826,096, filed Aug. 13, 2015, 9 pages.
Notice of Allowance dated Feb. 27, 2018, for U.S. Appl. No. 15/589,910, filed May 8, 2017, 7 pages.
Notice of Allowance dated Jan. 29, 2018 for U.S. Appl. No. 14/826,096, filed Aug. 13, 2015, 9 pages.
Notice of Allowance dated Jan. 9, 2019, for U.S. Appl. No. 15/993,299, filed May 30, 2018, 5 pages.
Notice of Allowance dated Jul. 17, 2018 for U.S. Appl. No. 14/826,096, filed Aug. 13, 2015, 9 pages.
Notice of Allowance dated May 1, 2017, for U.S. Appl. No. 14/826,096, filed Aug. 13, 2015, 8 pages.
Notice of Allowance dated May 2, 2019, for U.S. Appl. No. 15/993,299, filed May 30, 2018, 5 pages.
Notice of Allowance dated Oct. 18, 2018 for U.S. Appl. No. 14/826,096, filed Aug. 13, 2015, 9 pages.
Notice of Allowance dated Aug. 28, 2013, for U.S. Appl. No. 12/575,277, filed Oct. 7, 2009, 6 pages.
Notice of Allowance dated Feb. 21, 2013, for U.S. Appl. No. 12/575,367, filed Oct. 7, 2009, 5 pages.
Notice of Allowance dated Feb. 21, 2014, for U.S. Appl. No. 13/765,610, filed Feb. 12, 2013, 9 pages.
Notice of Allowance dated Jul. 8, 2013 for U.S. Appl. No. 13/728,807, filed Dec. 27, 2012, 9 pages.
Notice of Allowance dated Jul. 8, 2013, for U.S. Appl. No. 13/730,256, filed Dec. 28, 2012, 9 pages.
Notice of Allowance dated Jun. 26, 2012 for U.S. Appl. No. 12/732,124, filed Mar. 25, 2010, 11 pages.
Notice of Allowance dated May 14, 2015, for U.S. Appl. No. 14/284,331, filed May 21, 2014, 9 pages.
Notice of Allowance dated May 20, 2013, for U.S. Appl. No. 13/730,276, filed Dec. 28, 2012, 7 pages.
Notice of Allowance dated Nov. 13, 2012 for U.S. Appl. No. 12/732,124, filed Mar. 25, 2010, 11 pages.
Notice of Allowance dated Nov. 8, 2010, for U.S. Appl. No. 11/110,204, filed Apr. 20, 2005, 6 pages.
Notice of Allowance dated Oct. 10, 2014, for U.S. Appl. No. 14/049,163, filed Oct. 8, 2013, 8 pages.
Notice of Allowance dated Oct. 18, 2013, for U.S. Appl. No. 13/765,610, filed Feb. 12, 2013, 10 pages.
Notice of Allowance dated Oct. 3 2013, for U.S. Appl. No. 13/247,962, filed Sep. 28, 2011, 9 pages.
Notice of Allowance dated Oct. 9, 2014, for U.S. Appl. No. 14/049,154, filed Oct. 8, 2013, 8 pages.
Notice of Allowance dated Sep. 19, 2013, for U.S. Appl. No. 13/399,828, filed Feb. 17, 2012, 6 pages.
Notice of Allowance dated Sep. 26, 2018, for U.S. Appl. No. 15/993,299, filed May 30, 2018, 7 pages.
Notice of Opposition dated Jul. 4, 2017, for European Patent Application No. 05752122.1, filed Dec. 5, 2006, 28 pages.
Notice of Reexamination for Chinese Patent Application No. 0811654.X, dated Nov. 5, 2009; 7 pages.
Notice Regarding Non-Compliant Amendment from U.S. Appl. No. 10/918,803, dated Nov. 19, 2009.
Notification of Reasons for Rejection for Japanese Patent Application No. 2003-537642, dated May 26, 2009, 4 pages.
Office Action for European Patent Application No. 04 816 855.3, dated Oct. 21, 2008, 4 pages.
Office Action for European Patent Application No. 05 752 122.1, dated Mar. 25, 2013, 4 pages.
Office Action for European Patent Application No. 05752122.1, dated Nov. 5, 2014, 3 pages.
Office Action dated Mar. 30, 2016, for Israel Patent Application No. 241732, filed Sep. 20, 2015, 9 pages.
Office Action dated May 25, 2017 for Israel Patent Application No. 241732, filed on Sep. 20, 2015, 9 pages. (W/ Eng Translation).
Office Action dated Sep. 29, 2017, for Hungary Patent Application No. P1500607 filed on Dec. 11, 2015, 3 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," Haematologica 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," Chem Rev. 96(8):3147-3176.
Pawelczyk, E. (Ed.) (1986). "Chemia Leków," PZWL, Warszawa, see part 1.2.2.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.

(56) References Cited

OTHER PUBLICATIONS

Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers Presented at the 12th International Congress of Immunology and 4th Annual Conference of FOCIS Medimond International Proceedings in Montreal, Canada on Jul. 18, 23, 2004, pp. 303-307.
Quirici et al., Br. J. Haematol. (2001) 115:186-194.
Rada, B.K. et al. (Nov. 1, 2004, e-published Jul. 13, 2004). "Dual Role of Phagocytic NADPH Oxidase in Bacterial Killing,"Blood 104(9):2947-2953.
Rameh et al., Cell (1995) 83:821-830.
Rameh et al., J. Biol. Chem. (1999) 274:8347-8350.
Rathman et al., J. Org. Chem. (1980) 45:2169-2176.
Remington's Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed May 7, 2009.
Response filed Dec. 13, 2017, for European Patent Application No. 05752122.1, to "Communication of Notices of Opposition (Rule 79(1) EPC) dated Aug. 4, 2017", on behalf of ICOS Corporation, 20 pages.
Response to Election of Species Requirement from U.S. Appl. No. 10/918,803, filed Jun. 27, 2007.
Response to Non-Final Office Action filed Sep. 16, 2010, for U.S. Appl. No. 10/918,803, filed Aug. 13, 2004, 25 pages.
Response to Non-Final Office Action from U.S. Appl. No. 10/918,803, filed Dec. 18, 2009.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Response to Rule 312 Communication dated Oct. 4, 2012, for U.S. Appl. No. 12/732,124, filed Mar. 25, 2010, 7 pages.
Restriction Requirement from U.S. Appl. No. 10/918,803, dated Jun. 12, 2009.
Restriction Requirement from U.S. Appl. No. 10/918,803, dated Mar. 13, 2007.
Restriction Requirement from U.S. Appl. No. 10/918,803, dated Sep. 7, 2007.
Restriction Requirement from U.S. Appl. No. 11/110,204, dated Mar. 10, 2008.
Restriction Requirement from U.S. Appl. No. 11/129,006, dated Nov. 12, 2008.
Restriction Requirement from U.S. Appl. No. 11/137,901, dated Aug. 6, 2007.
Restriction Requirement from U.S. Appl. No. 11/137,901, dated May 23, 2008.
Restriction Requirement from U.S. Appl. No. 11/596,092, dated Jan. 28, 2009.
Restriction Requirement from U.S. Appl. No. 11/884,566, dated Apr. 5, 2010.
Restriction Requirement dated Dec. 1, 2011, for U.S. Appl. No. 13/163,597, filed Jun. 17, 2011, 7 pages.
Restriction Requirement dated Jul. 17, 2012, for U.S. Appl. No. 13/247,962, filed Sep. 28, 2011, 27 pages.
Restriction Requirement dated Jun. 7, 2012, for U.S. Appl. No. 13/399,828, filed Feb. 17, 2012, 5 pages.
Restriction Requirement dated May 8, 2015, for U.S. Appl. No. 14/092,287, filed Nov. 27, 2013, 8 pages.
Restriction Requirement dated Oct. 14, 2010, for U.S. Appl. No. 12/732,124, filed Mar. 25, 2010, 9 pages.
Restriction Requirement dated Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1477.
Schuch et al., Blood (2002) 100:4622-4628.
Schueneman et al., Canc. Res. (2003) 63:4009-4016.
Second Preliminary Amendment and Response to Notice to File Missing Parts of U.S. Appl. No. 12/575,277, filed Jan. 20, 2010.
Second Preliminary Amendment and Response to Notice to File Missing Parts of U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stanovnik, B. et al. (2006). "The Tautomerism of Heterocycles: Substituent Tautomerism of Six-Membered Ring Heterocycles," Advances in Heterocyclic Chemistry 91:1-134.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, dated Jun. 29, 2004.
Sutton, A. (Jun. 9, 2006). "Baylor, St. Luke's study uses gene therapy as pancreatic cancer", located at <http://www.bcm.edu/news/item.cfm?newsID=640>, last visited on Sep. 2, 2006, 2 pages.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," International Journal of Radiation: Oncology Biology Physics 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.

(56) References Cited

OTHER PUBLICATIONS

U.S. Appl. No. 16/418,558, filed May 21, 2019, by Bremner et al. (U.S. Patent Application is not submitted herewith pursuant to the waiver of 37 C.F.R § 1.98(a)(2)(iii) issued by the Office dated Sep. 21, 2004.)
U.S. Appl. No. 16/533,506, filed Aug. 6, 2019, by Kesicki et al. (U.S. Patent Application is not submitted herewith pursuant to the waiver of 37 C.F.R § 1.98(a)(2)(iii) issued by the Office dated Sep. 21, 2004.)
Vacca et al., Blood (1999) 9:3064-3073.
Van Dijk et al., Blood (2000) 96:3406-3413.
Van Eeden, S.F. et al. (Dec. 17, 1999). "The Use of Flow Cytometry to Measure Neutrophil Function," Journal Immunol Meth 232:23-43.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," Advanced Drug Delivery 48:3-26.
Vivanco et al., Nat. Rev. Cancer (2002) 2:489-501.
Vlahos et al., J. Immunol. (1995) 154:2413-2422.
Vogel, A.I. (1984). "Preparatyka Organiczna," ed. by WNT, Warszawa, p. e.g. 83.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," Proceedings of the American Association for Cancer Research 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Whitten, J.P. et al. (May 1986). "[2-(Trimethylsilyl)ethoxy]methyl (SEM) as a Novel and Effective Imidazole and Fused Aromatic Imidazole Protecting Group", The Journal of Organic Chemistry 51(10):1891-1894.
Williams et al., Chem. Biol. (2010) 17:123-134.
Williams, D.A. et al.(2002). Foye's Principles of Medicinal Chemistry, Lippincott, Williams & Wilkins, Baltimore MD, Fifth Edition, pp. 50 and 59-61.
Williams, Methods Mol. Med. (2004) 98:207-216.
Wolff, ed., Burger's Medicinal Chemistry and Drug Discovery, 5th edition (1996) vol. 1, New York: John Wiley & Sons, pp. 975-977.
Written Opinion dated Sep. 29, 2015 for Application No. PCT/US2015/035126, Internationally filed on Jun. 10, 2015, 6 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Zu, Y-L et al. (1998). "p38 Mitogen-Activated Protein Kinase Activation is Required for Human Neutrophil Function Triggered by TNF-α or FMLP Stimulation", J Immunol 160:1982-1989.

\* cited by examiner

Effect of D-000 on S. aureus killing by neutrophils

SEQUENCE LISTING

<160> NUMBER OF SEQ ID NOS: 6

<210> SEQ ID NO 1
<211> LENGTH: 5220
<212> TYPE: DNA
<213> ORGANISM: Homo sapiens
<220> FEATURE:
<221> NAME/KEY: misc_feature
<222> LOCATION: (1)...(5220)
<223> OTHER INFORMATION: p110delta complete cDNA
<220> FEATURE:
<221> NAME/KEY: CDS
<222> LOCATION: (196)..(3327)

<400> SEQUENCE: 1

```
cagtcgctcc gagcggccgc gagcagagcc gcccagccct gtcagctgcg ccgggacgat      60
aaggagtcag gccagggcgg gatgacactc attgattcta aagcatcttt aatctgccag     120
gcggaggggg ctttgctggt ctttcttgga ctattccaga gaggacaact gtcatctggg     180
aagtaacaac gcagg atg ccc cct ggg gtg gac tgc ccc atg gaa ttc tgg      231
                 Met Pro Pro Gly Val Asp Cys Pro Met Glu Phe Trp
                  1               5                  10 acc aag gag gag aat cag agc gtt gtg gtt gac ttc ctg ctg ccc aca       279
Thr Lys Glu Glu Asn Gln Ser Val Val Val Asp Phe Leu Leu Pro Thr
         15                  20                  25 ggg gtc tac ctg aac ttc cct gtg tcc cgc aat gcc aac ctc agc acc       327
Gly Val Tyr Leu Asn Phe Pro Val Ser Arg Asn Ala Asn Leu Ser Thr
 30                  35                  40 atc aag cag ctg ctg tgg cac cgc gcc cag tat gag ccg ctc ttc cac       375
Ile Lys Gln Leu Leu Trp His Arg Ala Gln Tyr Glu Pro Leu Phe His
45                  50                  55                  60 atg ctc agt ggc ccc gag gcc tat gtg ttc acc tgc atc aac cag aca       423
Met Leu Ser Gly Pro Glu Ala Tyr Val Phe Thr Cys Ile Asn Gln Thr
                 65                  70                  75 gcg gag cag caa gag ctg gag gac gag caa cgg cgt ctg tgt gac gtg       471
Ala Glu Gln Gln Glu Leu Glu Asp Glu Gln Arg Arg Leu Cys Asp Val
         80                  85                  90 cag ccc ttc ctg ccc gtc ctg cgc ctg gtg gcc cgt gag ggc gac cgc       519
Gln Pro Phe Leu Pro Val Leu Arg Leu Val Ala Arg Glu Gly Asp Arg
 95                 100                 105 gtg aag aag ctc atc aac tca cag atc agc ctc ctc atc ggc aaa ggc       567
Val Lys Lys Leu Ile Asn Ser Gln Ile Ser Leu Leu Ile Gly Lys Gly
    110                 115                 120 ctc cac gag ttt gac tcc ttg tgc gac cca gaa gtg aac gac ttt cgc       615
Leu His Glu Phe Asp Ser Leu Cys Asp Pro Glu Val Asn Asp Phe Arg
125                 130                 135                 140 gcc aag atg tgc caa ttc tgc gag gag gcg gcc gcc cgc cgg cag cag       663
Ala Lys Met Cys Gln Phe Cys Glu Glu Ala Ala Ala Arg Arg Gln Gln
                145                 150                 155 ctg ggc tgg gag gcc tgg ctg cag tac agt ttc ccc ctg cag ctg gag       711
Leu Gly Trp Glu Ala Trp Leu Gln Tyr Ser Phe Pro Leu Gln Leu Glu
        160                 165                 170 ccc tcg gct caa acc tgg ggg cct ggt acc ctg cgg ctc ccg aac cgg       759
Pro Ser Ala Gln Thr Trp Gly Pro Gly Thr Leu Arg Leu Pro Asn Arg
    175                 180                 185 gcc ctt ctg gtc aac gtt aag ttt gag ggc agc gag gag agc ttc acc       807
Ala Leu Leu Val Asn Val Lys Phe Glu Gly Ser Glu Glu Ser Phe Thr
190                 195                 200 ttc cag gtg tcc acc aag gac gtg ccg ctg gcg ctg atg gcc tgt gcc       855
Phe Gln Val Ser Thr Lys Asp Val Pro Leu Ala Leu Met Ala Cys Ala
205                 210                 215                 220
```

```
ctg cgg aag aag gcc aca gtg ttc cgg cag ccg ctg gtg gag cag ccg    903
Leu Arg Lys Lys Ala Thr Val Phe Arg Gln Pro Leu Val Glu Gln Pro
            225                 230                 235 gaa gac tac acg ctg cag gtg aac ggc agg cat gag tac ctg tat ggc    951
Glu Asp Tyr Thr Leu Gln Val Asn Gly Arg His Glu Tyr Leu Tyr Gly
        240                 245                 250 aac tac ccg ctc tgc cag ttc cag tac atc tgc agc tgc ctg cac agt    999
Asn Tyr Pro Leu Cys Gln Phe Gln Tyr Ile Cys Ser Cys Leu His Ser
            255                 260                 265 ggg ttg acc cct cac ctg acc atg gtc cat tcc tcc tcc atc ctc gcc   1047
Gly Leu Thr Pro His Leu Thr Met Val His Ser Ser Ser Ile Leu Ala
        270                 275                 280 atg cgg gat gag cag agc aac cct gcc ccc cag gtc cag aaa ccg cgt   1095
Met Arg Asp Glu Gln Ser Asn Pro Ala Pro Gln Val Gln Lys Pro Arg
285                 290                 295                 300 gcc aaa cca cct ccc att cct gcg aag aag cct tcc tct gtg tcc ctg   1143
Ala Lys Pro Pro Pro Ile Pro Ala Lys Lys Pro Ser Ser Val Ser Leu
                305                 310                 315 tgg tcc ctg gag cag ccg ttc cgc atc gag ctc atc cag ggc agc aaa   1191
Trp Ser Leu Glu Gln Pro Phe Arg Ile Glu Leu Ile Gln Gly Ser Lys
            320                 325                 330 gtg aac gcc gac gag cgg atg aag ctg gtg gtg cag gcc ggg ctt ttc   1239
Val Asn Ala Asp Glu Arg Met Lys Leu Val Val Gln Ala Gly Leu Phe
            335                 340                 345 cac ggc aac gag atg ctg tgc aag acg gtg tcc agc tcg gag gtg agc   1287
His Gly Asn Glu Met Leu Cys Lys Thr Val Ser Ser Ser Glu Val Ser
        350                 355                 360 gtg tgc tcg gag ccc gtg tgg aag cag cgg ctg gag ttc gac atc aac   1335
Val Cys Ser Glu Pro Val Trp Lys Gln Arg Leu Glu Phe Asp Ile Asn
365                 370                 375                 380 atc tgc gac ctg ccc cgc atg gcc cgt ctc tgc ttt gcg ctg tac gcc   1383
Ile Cys Asp Leu Pro Arg Met Ala Arg Leu Cys Phe Ala Leu Tyr Ala
                385                 390                 395 gtg atc gag aaa gcc aag aag gct cgc tcc acc aag aag aag tcc aag   1431
Val Ile Glu Lys Ala Lys Lys Ala Arg Ser Thr Lys Lys Lys Ser Lys
            400                 405                 410 aag gcg gac tgc ccc att gcc tgg gcc aac ctc atg ctg ttt gac tac   1479
Lys Ala Asp Cys Pro Ile Ala Trp Ala Asn Leu Met Leu Phe Asp Tyr
            415                 420                 425 aag gac cag ctt aag acc ggg gaa cgc tgc ctc tac atg tgg ccc tcc   1527
Lys Asp Gln Leu Lys Thr Gly Glu Arg Cys Leu Tyr Met Trp Pro Ser
430                 435                 440 gtc cca gat gag aag ggc gag ctg ctg aac ccc acg ggc act gtg cgc   1575
Val Pro Asp Glu Lys Gly Glu Leu Leu Asn Pro Thr Gly Thr Val Arg
445                 450                 455                 460 agt aac ccc aac acg gat agc gcc gct gcc ctc ctc atc tgc ctg ccc   1623
Ser Asn Pro Asn Thr Asp Ser Ala Ala Ala Leu Leu Ile Cys Leu Pro
                465                 470                 475 gag gtg gcc ccg cac ccc gtg tac tac ccc gcc ctg gag aag atc ttg   1671
Glu Val Ala Pro His Pro Val Tyr Tyr Pro Ala Leu Glu Lys Ile Leu
            480                 485                 490 gag ctg ggg cga cac agc gag tgt gtg cat gtc acc gag gag gag cag   1719
Glu Leu Gly Arg His Ser Glu Cys Val His Val Thr Glu Glu Glu Gln
            495                 500                 505 ctg cag ctg cgg gaa atc ctg gag cgg cgg ggg tct ggg gag ctg tat   1767
Leu Gln Leu Arg Glu Ile Leu Glu Arg Arg Gly Ser Gly Glu Leu Tyr
        510                 515                 520 gag cac gag aag gac ctg gtg tgg aag ctg cgg cat gaa gtc cag gag   1815
Glu His Glu Lys Asp Leu Val Trp Lys Leu Arg His Glu Val Gln Glu
525                 530                 535                 540
```

```
cac ttc ccg gag gcg cta gcc cgg ctg ctg ctg gtc acc aag tgg aac    1863
His Phe Pro Glu Ala Leu Ala Arg Leu Leu Leu Val Thr Lys Trp Asn
            545                 550                 555 aag cat gag gat gtg gcc cag atg ctc tac ctg ctg tgc tcc tgg ccg    1911
Lys His Glu Asp Val Ala Gln Met Leu Tyr Leu Leu Cys Ser Trp Pro
            560                 565                 570 gag ctg ccc gtc ctg agc gcc ctg gag ctg cta gac ttc agc ttc ccc    1959
Glu Leu Pro Val Leu Ser Ala Leu Glu Leu Leu Asp Phe Ser Phe Pro
            575                 580                 585 gat tgc cac gta ggc tcc ttc gcc atc aag tcg ctg cgg aaa ctg acg    2007
Asp Cys His Val Gly Ser Phe Ala Ile Lys Ser Leu Arg Lys Leu Thr
            590                 595                 600 gac gat gag ctg ttc cag tac ctg ctg cag ctg gtg cag gtg ctc aag    2055
Asp Asp Glu Leu Phe Gln Tyr Leu Leu Gln Leu Val Gln Val Leu Lys
605                 610                 615                 620 tac gag tcc tac ctg gac tgc gag ctg acc aaa ttc ctg ctg gac cgg    2103
Tyr Glu Ser Tyr Leu Asp Cys Glu Leu Thr Lys Phe Leu Leu Asp Arg
                625                 630                 635 gcc ctg gcc aac cgc aag atc ggc cac ttc ctt ttc tgg cac ctc cgc    2151
Ala Leu Ala Asn Arg Lys Ile Gly His Phe Leu Phe Trp His Leu Arg
            640                 645                 650 tcc gag atg cac gtg ccg tcg gtg gcc ctg cgc ttc ggc ctc atc ctg    2199
Ser Glu Met His Val Pro Ser Val Ala Leu Arg Phe Gly Leu Ile Leu
            655                 660                 665 gag gcc tac tgc agg ggc agc acc cac cac atg aag gtg ctg atg aag    2247
Glu Ala Tyr Cys Arg Gly Ser Thr His His Met Lys Val Leu Met Lys
            670                 675                 680 cag ggg gaa gca ctg agc aaa ctg aag gcc ctg aat gac ttc gtc aag    2295
Gln Gly Glu Ala Leu Ser Lys Leu Lys Ala Leu Asn Asp Phe Val Lys
685                 690                 695                 700 ctg agc tct cag aag acc ccc aag ccc cag acc aag gag ctg atg cac    2343
Leu Ser Ser Gln Lys Thr Pro Lys Pro Gln Thr Lys Glu Leu Met His
                705                 710                 715 ttg tgc atg cgg cag gag gcc tac cta gag gcc ctc tcc cac ctg cag    2391
Leu Cys Met Arg Gln Glu Ala Tyr Leu Glu Ala Leu Ser His Leu Gln
            720                 725                 730 tcc cca ctc gac ccc agc acc ctg ctg gct gaa gtc tgc gtg gag cag    2439
Ser Pro Leu Asp Pro Ser Thr Leu Leu Ala Glu Val Cys Val Glu Gln
            735                 740                 745 tgc acc ttc atg gac tcc aag atg aag ccc ctg tgg atc atg tac agc    2487
Cys Thr Phe Met Asp Ser Lys Met Lys Pro Leu Trp Ile Met Tyr Ser
750                 755                 760 aac gag gag gca ggc agc ggc ggc agc gtg ggc atc atc ttt aag aac    2535
Asn Glu Glu Ala Gly Ser Gly Gly Ser Val Gly Ile Ile Phe Lys Asn
765                 770                 775                 780 ggg gat gac ctc cgg cag gac atg ctg acc ctg cag atg atc cag ctc    2583
Gly Asp Asp Leu Arg Gln Asp Met Leu Thr Leu Gln Met Ile Gln Leu
                785                 790                 795 atg gac gtc ctg tgg aag cag gag ggg ctg gac ctg agg atg acc ccc    2631
Met Asp Val Leu Trp Lys Gln Glu Gly Leu Asp Leu Arg Met Thr Pro
            800                 805                 810 tat ggc tgc ctc ccc acc ggg gac cgc aca ggc ctc att gag gtg gta    2679
Tyr Gly Cys Leu Pro Thr Gly Asp Arg Thr Gly Leu Ile Glu Val Val
            815                 820                 825 ctc cgt tca gac acc atc gcc aac atc caa ctc aac aag agc aac atg    2727
Leu Arg Ser Asp Thr Ile Ala Asn Ile Gln Leu Asn Lys Ser Asn Met
            830                 835                 840 gca gcc aca gcc gcc ttc aac aag gat gcc ctg ctc aac tgg ctg aag    2775
Ala Ala Thr Ala Ala Phe Asn Lys Asp Ala Leu Leu Asn Trp Leu Lys
845                 850                 855                 860
```

| | |
|---|---|
| tcc aag aac ccg ggg gag gcc ctg gat cga gcc att gag gag ttc acc<br>Ser Lys Asn Pro Gly Glu Ala Leu Asp Arg Ala Ile Glu Glu Phe Thr<br>             865                    870                   875 | 2823 |
| ctc tcc tgt gct ggc tat tgt gtg gcc aca tat gtg ctg ggc att ggc<br>Leu Ser Cys Ala Gly Tyr Cys Val Ala Thr Tyr Val Leu Gly Ile Gly<br>             880                    885                   890 | 2871 |
| gat cgg cac agc gac aac atc atg atc cga gag agt ggg cag ctg ttc<br>Asp Arg His Ser Asp Asn Ile Met Ile Arg Glu Ser Gly Gln Leu Phe<br>             895                    900                   905 | 2919 |
| cac att gat ttt ggc cac ttt ctg ggg aat ttc aag acc aag ttt gga<br>His Ile Asp Phe Gly His Phe Leu Gly Asn Phe Lys Thr Lys Phe Gly<br>             910                    915                   920 | 2967 |
| atc aac cgc gag cgt gtc cca ttc atc ctc acc tat gac ttt gtc cat<br>Ile Asn Arg Glu Arg Val Pro Phe Ile Leu Thr Tyr Asp Phe Val His<br>925                   930                    935                   940 | 3015 |
| gtg att cag cag ggg aag act aat aat agt gag aaa ttt gaa cgg ttc<br>Val Ile Gln Gln Gly Lys Thr Asn Asn Ser Glu Lys Phe Glu Arg Phe<br>             945                    950                   955 | 3063 |
| cgg ggc tac tgt gaa agg gcc tac acc atc ctg cgg cgc cac ggg ctt<br>Arg Gly Tyr Cys Glu Arg Ala Tyr Thr Ile Leu Arg Arg His Gly Leu<br>             960                    965                   970 | 3111 |
| ctc ttc ctc cac ctc ttt gcc ctg atg cgg gcg gca ggc ctg cct gag<br>Leu Phe Leu His Leu Phe Ala Leu Met Arg Ala Ala Gly Leu Pro Glu<br>             975                    980                   985 | 3159 |
| ctc agc tgc tcc aaa gac atc cag tat ctc aag gac tcc ctg gca ctg<br>Leu Ser Cys Ser Lys Asp Ile Gln Tyr Leu Lys Asp Ser Leu Ala Leu<br>             990                    995                 1000 | 3207 |
| ggg aaa aca gag gag gag gca ctg aag cac ttc cga gtg aag ttt<br>Gly Lys Thr Glu Glu Glu Ala Leu Lys His Phe Arg Val Lys Phe<br>1005                   1010                  1015 | 3252 |
| aac gaa gcc ctc cgt gag agc tgg aaa acc aaa gtg aac tgg ctg<br>Asn Glu Ala Leu Arg Glu Ser Trp Lys Thr Lys Val Asn Trp Leu<br>1020                   1025                  1030 | 3297 |
| gcc cac aac gtg tcc aaa gac aac agg cag tagtggctcc tcccagccct<br>Ala His Asn Val Ser Lys Asp Asn Arg Gln<br>1035                   1040 | 3347 |
| gggcccaaga ggaggcggct gcgggtcgtg gggaccaagc acattggtcc taaaggggct | 3407 |
| gaagagcctg aactgcacct aacgggaaag aaccgacatg gctgcctttt gtttacactg | 3467 |
| gttatttatt tatgacttga aatagtttaa ggagctaaac agccataaac ggaaacgcct | 3527 |
| ccttcattca gcggcggtgc tgggcccccc gaggctgcac ctggctctcg gctgaggatt | 3587 |
| gtcaccccaa gtcttccagc tggtggatct gggcccagca aagactgttc tcctcccgag | 3647 |
| ggaaccttct tcccaggcct cccgccagac tgcctgggtc ctggcgcctg cggtcacct | 3707 |
| ggtgcctact gtccgacagg atgcctcgat cctcgtgcga cccaccctgt gtatcctccc | 3767 |
| tagactgagt tctggcagct ccccgaggca gccggggtac cctctagatt cagggatgct | 3827 |
| tgctctccac ttttcaagtg ggtcttgggt acgagaattc cctcatcttt ctctactgta | 3887 |
| aagtgatttt gtttgcaggt aagaaaataa tagatgactc accacacctc tacggctggg | 3947 |
| gagatcaggc ccagccccat aaaggagaat ctacgctggt cctcaggacg tgttaaagag | 4007 |
| atctgggcct catgtagctc accccggtca cgcatgaagg caaaagcagg tcagaagcga | 4067 |
| atactctgcc attatctcaa aaatcttttt tttttttttt ttgagatggg tcttcctct | 4127 |
| gttgcccagg ctggagtgca gtggtgcaat cttggctcac tgtaacctcc gcctcccagg | 4187 |
| ttcaagtgat tcttccttgcc tcagcctcct gagtagctgg gattacaggt gtgcaccacc | 4247 |
| cgtacccagc taatttttgt attttagtag agacgggggt ttcaccatgt tggctgggct | 4307 |

-continued

```
ggtctcgaac tcctgacctc aggtgatcca cccgcctgag cctcccaaag tgctgggatt    4367
acaggcatga gccaccacgc ccggcccact ctgccattgt ctaagccacc tctgaaagca    4427
ggttttaaca aaaggatgag gccagaactc ttccagaacc atcacctttg ggaacctgct    4487
gtgagagtgc tgaggtacca gaagtgtgag aacgagggg cgtgctggga tctttctctc     4547
tgactatact tagtttgaaa tggtgcaggc ttagtcttaa gcctccaaag gcctggattt    4607
gagcagcttt agaaatgcag gttctagggc ttctcccagc cttcagaagc caactaactc    4667
tgcagatggg gctaggactg tgggcttta gcagcccaca ggtgatccta acatatcagg     4727
ccatggactc aggacctgcc cggtgatgct gttgatttct caaaggtctt ccaaaactca    4787
acagagccag aagtagccgc ccgctcagcg gctcaggtgc cagctctgtt ctgattcacc    4847
aggggtccgt cagtagtcat tgccacccgc ggggcacctc cctggccaca cgcctgttcc    4907
cagcaagtgc tgaaactcac tagaccgtct gcctgtttcg aaatggggaa agccgtgcgt    4967
gcgcgttatt tatttaagtg cgcctgtgtg cgcgggtgtg ggagcacact ttgcaaagcc    5027
acagcgtttc tggttttggg tgtacagtct tgtgtgcctg gcgagaagaa tattttctat    5087 tttttaagt catttcatgt ttctgtctgg ggaaggcaag ttagttaagt atcactgatg     5147
tgggttgaga ccagcactct gtgaaacctt gaaatgagaa gtaaaggcag atgaaaagaa    5207
aaaaaaaaaa aaa                                                      5220
```

<210> SEQ ID NO 2
<211> LENGTH: 1044
<212> TYPE: PRT
<213> ORGANISM: Homo sapiens
<220> FEATURE:
<221> NAME/KEY: misc_feature
<222> LOCATION: (1)...(1044)
<223> OTHER INFORMATION: p110delta protein

<400> SEQUENCE: 2

```
Met Pro Pro Gly Val Asp Cys Pro Met Glu Phe Trp Thr Lys Glu Glu
1               5                  10                  15

Asn Gln Ser Val Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190
```

```
Asn Val Lys Phe Glu Gly Ser Glu Ser Phe Thr Phe Gln Val Ser
        195                 200                 205
Thr Lys Asp Val Pro Leu Ala Leu Met Ala Cys Ala Leu Arg Lys Lys
210                 215                 220
Ala Thr Val Phe Arg Gln Pro Leu Val Glu Gln Pro Glu Asp Tyr Thr
225                 230                 235                 240
Leu Gln Val Asn Gly Arg His Glu Tyr Leu Tyr Gly Asn Tyr Pro Leu
                245                 250                 255
Cys Gln Phe Gln Tyr Ile Cys Ser Cys Leu His Ser Gly Leu Thr Pro
            260                 265                 270
His Leu Thr Met Val His Ser Ser Ile Leu Ala Met Arg Asp Glu
        275                 280                 285
Gln Ser Asn Pro Ala Pro Gln Val Gln Lys Pro Arg Ala Lys Pro Pro
    290                 295                 300
Pro Ile Pro Ala Lys Lys Pro Ser Ser Val Ser Leu Trp Ser Leu Glu
305                 310                 315                 320
Gln Pro Phe Arg Ile Glu Leu Ile Gln Gly Ser Lys Val Asn Ala Asp
                325                 330                 335
Glu Arg Met Lys Leu Val Val Gln Ala Gly Leu Phe His Gly Asn Glu
            340                 345                 350
Met Leu Cys Lys Thr Val Ser Ser Glu Val Ser Val Cys Ser Glu
        355                 360                 365
Pro Val Trp Lys Gln Arg Leu Glu Phe Asp Ile Asn Ile Cys Asp Leu
    370                 375                 380
Pro Arg Met Ala Arg Leu Cys Phe Ala Leu Tyr Ala Val Ile Glu Lys
385                 390                 395                 400
Ala Lys Lys Ala Arg Ser Thr Lys Lys Lys Ser Lys Lys Ala Asp Cys
                405                 410                 415
Pro Ile Ala Trp Ala Asn Leu Met Leu Phe Asp Tyr Lys Asp Gln Leu
            420                 425                 430
Lys Thr Gly Glu Arg Cys Leu Tyr Met Trp Pro Ser Val Pro Asp Glu
        435                 440                 445
Lys Gly Glu Leu Leu Asn Pro Thr Gly Thr Val Arg Ser Asn Pro Asn
    450                 455                 460
Thr Asp Ser Ala Ala Leu Leu Ile Cys Leu Pro Glu Val Ala Pro
465                 470                 475                 480
His Pro Val Tyr Tyr Pro Ala Leu Glu Lys Ile Leu Glu Leu Gly Arg
                485                 490                 495
His Ser Glu Cys Val His Val Thr Glu Glu Gln Leu Gln Leu Arg
            500                 505                 510
Glu Ile Leu Glu Arg Arg Gly Ser Gly Glu Leu Tyr Glu His Glu Lys
        515                 520                 525
Asp Leu Val Trp Lys Leu Arg His Glu Val Gln Glu His Phe Pro Glu
    530                 535                 540
Ala Leu Ala Arg Leu Leu Leu Val Thr Lys Trp Asn Lys His Glu Asp
545                 550                 555                 560
Val Ala Gln Met Leu Tyr Leu Leu Cys Ser Trp Pro Glu Leu Pro Val
                565                 570                 575
Leu Ser Ala Leu Glu Leu Leu Asp Phe Ser Phe Pro Asp Cys His Val
            580                 585                 590
Gly Ser Phe Ala Ile Lys Ser Leu Arg Lys Leu Thr Asp Asp Glu Leu
        595                 600                 605
```

```
Phe Gln Tyr Leu Leu Gln Leu Val Gln Val Leu Lys Tyr Glu Ser Tyr
610             615                 620
Leu Asp Cys Glu Leu Thr Lys Phe Leu Asp Arg Ala Leu Ala Asn
625             630                 635                 640
Arg Lys Ile Gly His Phe Leu Phe Trp His Leu Arg Ser Glu Met His
            645                 650                 655
Val Pro Ser Val Ala Leu Arg Phe Gly Leu Ile Leu Glu Ala Tyr Cys
            660                 665                 670
Arg Gly Ser Thr His His Met Lys Val Leu Met Lys Gln Gly Glu Ala
            675                 680                 685
Leu Ser Lys Leu Lys Ala Leu Asn Asp Phe Val Lys Leu Ser Ser Gln
690                 695                 700
Lys Thr Pro Lys Pro Gln Thr Lys Glu Leu Met His Leu Cys Met Arg
705             710                 715                 720
Gln Glu Ala Tyr Leu Glu Ala Leu Ser His Leu Gln Ser Pro Leu Asp
                725                 730                 735
Pro Ser Thr Leu Leu Ala Glu Val Cys Val Glu Gln Cys Thr Phe Met
            740                 745                 750
Asp Ser Lys Met Lys Pro Leu Trp Ile Met Tyr Ser Asn Glu Glu Ala
            755                 760                 765
Gly Ser Gly Gly Ser Val Gly Ile Ile Phe Lys Asn Gly Asp Asp Leu
            770                 775             780
Arg Gln Asp Met Leu Thr Leu Gln Met Ile Gln Leu Met Asp Val Leu
785                 790                 795                 800
Trp Lys Gln Glu Gly Leu Asp Leu Arg Met Thr Pro Tyr Gly Cys Leu
                805                 810                 815
Pro Thr Gly Asp Arg Thr Gly Leu Ile Glu Val Val Leu Arg Ser Asp
            820                 825                 830
Thr Ile Ala Asn Ile Gln Leu Asn Lys Ser Asn Met Ala Ala Thr Ala
            835                 840                 845
Ala Phe Asn Lys Asp Ala Leu Leu Asn Trp Leu Lys Ser Lys Asn Pro
850                 855                 860
Gly Glu Ala Leu Asp Arg Ala Ile Glu Glu Phe Thr Leu Ser Cys Ala
865                 870                 875                 880
Gly Tyr Cys Val Ala Thr Tyr Val Leu Gly Ile Gly Asp Arg His Ser
                885                 890                 895
Asp Asn Ile Met Ile Arg Glu Ser Gly Gln Leu Phe His Ile Asp Phe
            900                 905                 910
Gly His Phe Leu Gly Asn Phe Lys Thr Lys Phe Gly Ile Asn Arg Glu
            915                 920                 925
Arg Val Pro Phe Ile Leu Thr Tyr Asp Phe Val His Val Ile Gln Gln
            930                 935                 940
Gly Lys Thr Asn Asn Ser Glu Lys Phe Glu Arg Phe Arg Gly Tyr Cys
945                 950                 955                 960
Glu Arg Ala Tyr Thr Ile Leu Arg Arg His Gly Leu Leu Phe Leu His
                965                 970                 975
Leu Phe Ala Leu Met Arg Ala Ala Gly Leu Pro Glu Leu Ser Cys Ser
            980                 985                 990
Lys Asp Ile Gln Tyr Leu Lys Asp Ser Leu Ala Leu Gly Lys Thr Glu
            995                 1000                1005
Glu Glu Ala Leu Lys His Phe Arg Val Lys Phe Asn Glu Ala Leu
    1010                1015                1020
```

```
Arg Glu Ser Trp Lys Thr Lys Val Asn Trp Leu Ala His Asn Val
   1025                1030                1035

Ser Lys Asp Asn Arg Gln
   1040
```

<210> SEQ ID NO 3
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(69)
<223> OTHER INFORMATION: 5' primer for p110beta

<400> SEQUENCE: 3

```
gatcgaattc ggcgccacca tggactacaa ggacgacgat gacaagtgct tcagtttcat      60
aatgcctcc                                                              69
```

<210> SEQ ID NO 4
<211> LENGTH: 42
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(42)
<223> OTHER INFORMATION: 3' primer for p110beta

<400> SEQUENCE: 4

```
gatcgcggcc gcttaagatc tgtagtcttt ccgaactgtg tg                         42
```

<210> SEQ ID NO 5
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(40)
<223> OTHER INFORMATION: 5' primer for p110gamma

<400> SEQUENCE: 5

```
agaatgcggc cgcatggagc tggagaacta taaacagccc                            40
```

<210> SEQ ID NO 6
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)...(37)
<223> OTHER INFORMATION: 3' primer for p110gamma

<400> SEQUENCE: 6

```
cgcggatcct taggctgaat gtttctctcc ttgtttg                               37
```

INHIBITORS OF HUMAN PHOSPHATIDYLINOSITOL 3-KINASE DELTA

CROSS-REFERENCE TO RELATED APPLICATIONS

This application is a continuation of U.S. application Ser. No. 15/993,299, filed on May 30, 2018, which is a continuation of U.S. application Ser. No. 15/589,910, filed May 8, 2017, now U.S. Pat. No. 10,010,550, which is a continuation of U.S. application Ser. No. 15/281,702, filed Sep. 30, 2016, now abandoned, which is a divisional of U.S. application Ser. No. 14/092,287, filed Nov. 27, 2013, now U.S. Pat. No. 9,487,772, which is a continuation of U.S. application Ser. No. 12/575,277, filed Oct. 7, 2009, now U.S. Pat. No. 8,623,881, which is a continuation of U.S. application Ser. No. 11/110,204, filed Apr. 20, 2005, now U.S. Pat. No. 8,138,195, which is a continuation of U.S. application Ser. No. 10/697,912, filed Oct. 30, 2003, now U.S. Pat. No. 6,949,535, which is a divisional of U.S. application Ser. No. 10/027,591, filed Oct. 19, 2001, now U.S. Pat. No. 6,667,300, which is a continuation-in-part of U.S. Ser. No. 09/841,341, filed Apr. 24, 2001, now U.S. Pat. No. 6,518,277, which claims the benefit of U.S. provisional application Ser. No. 60/199,655, filed Apr. 25, 2000 and U.S. provisional application Ser. No. 60/238,057, filed Oct. 5, 2000, each of which is incorporated herein by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 616082000408SEQLIST.TXT, date recorded: Jul. 29, 2019, size: 28 KB).

FIELD OF THE INVENTION

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., *J. Biol Chem*, 274:8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., *Trends Cell Biol* 2:358-60 (1992)).

The levels of phosphatidylinositol-3,4,5-triphosphate (PIP3), the primary product of PI 3-kinase activation, increase upon treatment of cells with a variety of agonists. PI 3-kinase activation, therefore, is believed to be involved in a range of cellular responses including cell growth, differentiation, and apoptosis (Parker et al., *Current Biology*, 5:577-99 (1995); Yao et al., *Science*, 267:2003-05 (1995)). Though the downstream targets of phosphorylated lipids generated following PI 3-kinase activation have not been well characterized, emerging evidence suggests that pleckstrin-homology domain- and FYVE-finger domain-containing proteins are activated when binding to various phosphatidylinositol lipids (Sternmark et al., *J Cell Sci*, 112:4175-83 (1999); Lemmon et al., *Trends Cell Biol*, 7:237-42 (1997)). In vitro, some isoforms of protein kinase C (PKC) are directly activated by PIP3, and the PKC-related protein kinase, PKB, has been shown to be activated by PI 3-kinase (Burgering et al., *Nature*, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate, whereas Class III PI3Ks can only phosphorylate PI.

The initial purification and molecular cloning of PI 3-kinase revealed that it was a heterodimer consisting of p85 and p110 subunits (Otsu et al., *Cell*, 65:91-104 (1991); Hiles et al., *Cell*, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are largely unknown.

Cloning of bovine p110a has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., *Cell*, 70, 419-29 (1992).

The cloning of a second human p110 isoform, designated p110β, is described in Hu et al., *Mol Cell Biol*, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., *J Biol Chem*, 272:19236-41 (1997). It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. Details concerning the P110δ isoform also can be found in U.S. Pat. Nos. 5,858,753; 5,822,910; and 5,985,589. See also, Vanhaesebroeck et al., *Proc Natl Acad Sci USA*, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., *Cell*, 83:821-30 (1995)). Two isoforms of p85 have been identified, p85a, which is ubiquitously expressed, and p850, which is primarily found in the brain and lymphoid tissues (Volinia et al., *Oncogene*, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., *Science*, 269:690-93 (1995)). The p110γ isoform is closely related to p110α and p110β (45-48% identity in the catalytic domain), but as noted does not make use of p85 as a targeting subunit. Instead, p110γ contains an additional domain termed a "pleckstrin homology domain" near its amino terminus. This domain allows interaction of p110γ with the βγ subunits of heterotrimeric G proteins and this interaction appears to regulate its activity.

The p101 regulatory subunit for PI3Kgamma was originally cloned in swine, and the human ortholog identified subsequently (Krugmann et al., *J Biol Chem*, 274:17152-8 (1999)). Interaction between the N-terminal region of p101 with the N-terminal region of p110γ appears to be critical for the PI3Kγ activation through Gβγ mentioned above.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., *Mol Cell Biol*, 14:2675-85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, *Cell*, 83:1-4 (1995).

PI 3-kinase also appears to be involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., *Nature*, 369:327-29. (1994); Rudd, *Immunity*, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., *Science*, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the $IC_{50}$ values of wortmannin against each of the various Class I PI 3-kinases are in the range of 1-10 nM. Similarly, the $IC_{50}$ values for LY294002 against each of these PI 3-kinases is about 1 μM (Fruman et al., *Ann Rev Bio-chem*, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., *Proc Natl Acad Sci USA*, 91:4960-64 (1994)). Moreover, it has been shown that wortmannin and LY294002 block neutrophil migration and superoxide release. However, inasmuch as these compounds do not distinguish among the various isoforms of PI3K, it remains unclear which particular PI3K isoform or isoforms are involved in these phenomena.

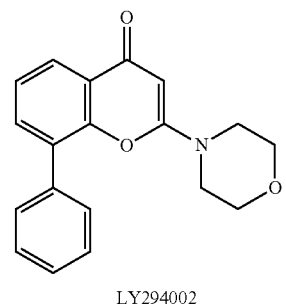 [SMILES: O=c1cc(N2CCOCC2)oc2c(-c3ccccc3)cccc12]

LY294002

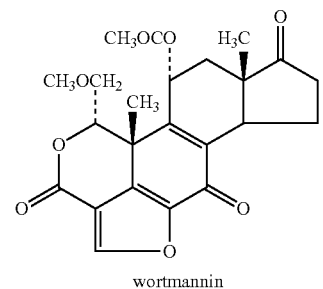

wortmannin

In view of the above considerations, it is clear that existing knowledge is lacking with respect to structural and functional features of the PI 3-kinase enzymes, including subcellular localization, activation states, substrate affinities, and the like. Moreover, the functions that these enzymes perform in both normal and diseased tissues remains to be elucidated. In particular, the function of PI3Kδ in leukocytes has not previously been characterized, and knowledge concerning its function in human physiology remains limited. The coexpression in these tissues of other PI3K isoforms has heretofore confounded efforts to segregate the activities of each enzyme. Furthermore, separation of the activities of the various PI3K isozymes may not be possible without identification of inhibitors that demonstrate selective inhibition characteristics. Indeed, Applicants are not presently aware that such selective, or better, specific, inhibitors of PI3K isozymes have been demonstrated.

Thus, there exists a need in the art for further structural characterization of the PI3Kδ polypeptide. There also exists a need for functional characterization of PI3Kδ. Furthermore, our understanding of PI3Kδ requires further elaboration of the structural interactions of p110δ, both with its regulatory subunit and with other proteins in the cell. There also remains a need for selective or specific inhibitors of PI3K isozymes, in order that the functions of each isozyme can be better characterized. In particular, selective or specific inhibitors of PI3Kδ are desirable for exploring the role of this isozyme and for development of pharmaceuticals to modulate the activity of the isozyme.

One aspect of the present invention is to provide compounds that can inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

SUMMARY OF THE INVENTION

It has now been discovered that these and other aspects can be achieved by the present invention, which, in one aspect, is a method for disrupting leukocyte function, comprising contacting leukocytes with a compound that selectively inhibits phosphatidylinositol 3-kinase delta (PI3Kδ) activity in the leukocytes. According to the method, the leukocytes can comprise cells selected from the group consisting of neutrophils, B lymphocytes, T lymphocytes, and basophils.

For example, in cases in which the leukocytes comprise neutrophils, the method can comprise disrupting at least one neutrophil function selected from the group consisting of stimulated superoxide release, stimulated exocytosis, and chemotactic migration. Preferably, the method does not substantially disrupt bacterial phagocytosis or bacterial killing by the neutrophils. In cases wherein the leukocytes comprise B lymphocytes, the method can comprise disrupting proliferation of the B lymphocytes or antibody production by the B lymphocytes. In cases wherein the leukocytes comprise T lymphocytes, the method can comprise disrupting proliferation of the T lymphocytes. In cases wherein the leukocytes comprise basophils, the method can comprise disrupting histamine release by the basophils.

In the methods of the invention wherein a selective PI3Kδ inhibitor is employed, it is preferred that the compound be at least about 10-fold selective for inhibition of PI3Kδ relative to other Type I PI3K isoforms in a cell-based assay. More preferably, the compound is at least about 20-fold selective for inhibition of PI3Kδ relative to other Type I PI3K isoforms in a cell-based assay. Still more preferably, the compound is at least about 50-fold selective for inhibition of PI3Kδ relative to other Type I PI3K isoforms in a biochemical assay.

Preferred selective compounds useful according to the methods include compounds having the structure (I):

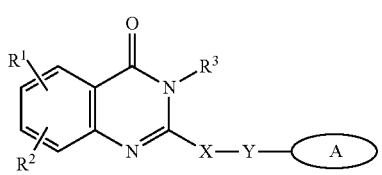

(I)

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, O, C(=O), OC(=O), C(=O)O, and NHC(=O) $CH_2S$;

$R^1$ and $R^2$, independently, are selected from the group consisting of hydrogen, $C_{1-6}$alkyl, aryl, heteroaryl, halo, NHC(=O) $C_{1-3}$alkyleneN($R^a$), $NO_2$, $OR^a$, $CF_3$, $OCF_3$, $N(R^a)_2$, CN, OC(=O)$R^a$, C(=O)$R^a$, C(=O)$OR^a$, aryl$OR^b$, Het, $NR^aC$(=O) $C_{1-3}$alkyleneC(=O)$OR^a$, aryl$OC_{1-3}$ alkyleneN($R^a$)$_2$, aryl$OC$(=O)$R^a$, $C_{1-4}$alkyleneC(=O)$OR^a$, $OC_{1-4}$alkyleneC(=O)$OR^a$, $C_{1-4}$alkyleneOC$_{1-4}$alkyleneC(=O)$OR^a$, C(=O)$NR^aSO_2R^a$, $C_{1-4}$alkyleneN($R^a$)$_2$, $C_{2-6}$alkenyleneN($R^a$)$_2$, C(=O) $NR^aC_{1-4}$alkyleneOR$^a$, C(=O) $NR^aC_{1-4}$alkyleneHet, $OC_{2-4}$-alkyleneN($R^a$)$_2$, $OC_{1-4}$alkyleneCH($OR^b$) $CH_2N(R^a)_2$, $OC_{1-4}$alkyleneHet, $OC_{2-4}$alkyleneOR$^a$, $OC_{2-4}$alkyleneNR$^a$C(=O)$OR^a$, $NR^aC_{1-4}$alkyleneN($R^a$)$_2$, $NR^aC$(=O)$R^a$, $NR^aC$(=O) N($R^a$)$_2$, $N(SO_2C_{1-4}$alkyl)$_2$, $NR^a$ ($SO_2C_{3-4}$alkyl), $SO_2N(R^a)_2$, $OSO_2CF_3$, $C_{1-3}$alkylenearyl, $C_{3-4}$alkyleneHet, $C_{3-6}$alkyleneOR$^b$, $C_{1-3}$alkyleneN($R^a$)$_2$, C(=O)N($R^a$)$_2$, NHC(=O) $C_3$-$C_3$alkylenearyl, $C_{3-8}$cycloalkyl, $C_{3-8}$heterocycloalkyl, aryl$OC_{1-3}$-alkyleneN($R^a$)$_2$, aryl$OC$(=O)$R^b$, NHC(=O) $C_{1-3}$alkyleneC$_{3-8}$-heterocycloalkyl, NHC(=O) $C_{1-3}$alkyleneHet, $OC_{3-4}$alkyleneOC$_{3-4}$alkyleneC(=O)$OR^b$, C(=O) $C_{1-4}$alkyleneHet, and NHC(=O)halo$C_{1-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, C(=O)$R^a$, aryl, heteroaryl, C(=O) $OR^a$, C(=O)N($R^a$)$_2$, C(=S)N($R^a$)$_2$, $SO_2R^a$, $SO_2N(R^a)_2$, S(=O)$R^a$, S(=O)N($R^a$)$_2$, C(=O)$NR^aC_{1-4}$-alkyleneOR$^a$, C(=O) $NR^aC_{1-4}$alkyleneHet, C(=O) $C_{1-4}$alkylenearyl, C(=O) $C_{1-4}$alkyleneheteroaryl, $C_{1-4}$alkylenearyl optionally substituted with one or more of halo, $SO_2N(R^a)_2$, $N(R^a)_2$, C(=O)$OR^a$, $NR^aSO_2CF_3$, CN, $NO_2$, C(=O)$R^a$, $OR^a$, $C_{3-4}$alkyleneN($R^a$)$_2$, and $OC_{1-4}$alkyleneN($R^a$)$_2$, $C_{1-4}$-alkyleneheteroaryl, $C_{1-4}$alkyleneHet, $C_{1-4}$alkyleneC(=O)—$C_{1-4}$alkylenearyl, $C_{1-4}$alkyleneC(=O) $C_{3-4}$alkyleneheteroaryl, $C_{3-4}$alkyleneC(=O)Het, $C_{3-4}$alkyleneC(=O)N($R^a$)$_2$, $C_{1-4}$alkyleneOR$^a$, $C_{1-4}$alkyleneNR$^a$C(=O)$R^a$, $C_{1-4}$alkyleneO-$C_{1-4}$alkyleneOR$^a$, $C_{1-4}$alkyleneN($R^a$)$_2$, $C_{1-4}$alkyleneC(=O)—$OR^a$, and $C_{1-4}$alkyleneOC$_{1-4}$alkyleneC(=O)$OR^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN($R^c$)$_2$, aryl, aryl$C_{1-3}$alkyl, $C_{1-3}$-alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, hetero$C_{1-3}$alkyl, $C_{1-3}$alkylene-hetero$C_{1-3}$alkyl, arylhetero$C_{1-3}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)$OR^a$;

and pharmaceutically acceptable salts and solvates (e.g., hydrates) thereof, wherein the compound has at least about a 10-fold selective inhibition for PI3Kδ relative other Type-I PI3K isoforms in a cell-based assay.

In another embodiment, the invention is a method for treating a medical condition mediated by neutrophils, comprising administering to an animal in need thereof an effective amount of a compound that selectively inhibits phosphatidylinositol 3-kinase delta (PI3Kδ) activity in the neutrophils. Exemplary medical conditions that can be treated according to the method include those conditions characterized by an undesirable neutrophil function selected from the group consisting of stimulated superoxide release, stimulated exocytosis, and chemotactic migration. Preferably, according to the method, phagocytic activity or bacterial killing by the neutrophils is substantially uninhibited.

In another embodiment, the invention is a method for disrupting a function of osteoclasts comprising contacting osteoclasts with a compound that selectively inhibits phosphatidylinositol 3-kinase delta (PI3Kδ) activity in the osteoclasts. According to the method, the compound can comprise a moiety that preferentially binds to bone.

In another embodiment, the invention is a method of ameliorating a bone-resorption disorder in an animal in need thereof comprising administering to the animal an effective amount of a compound that inhibits phosphatidylinositol 3-kinase delta (PI3Kδ) activity in osteoclasts of the animal. A preferred bone-resorption disorder amenable to treatment according to the method is osteoporosis.

In another embodiment, the invention is a method for inhibiting the growth or proliferation of cancer cells of hematopoietic origin, comprising contacting the cancer cells with a compound that selectively inhibits phosphatidylinositol 3-kinase delta (PI3Kδ) activity in the cancer cells. The method can be advantageous in inhibiting the growth or proliferation of cancers selected from the group consisting of lymphomas, multiple myelomas, and leukemias.

In another embodiment, the invention is a method of inhibiting kinase activity of a phosphatidylinositol 3-kinase delta (PI3Kδ) polypeptide, comprising contacting the PI3Kδ polypeptide with a compound having the generic structure (I).

Preferred compounds useful according to the method include compounds selected from the group consisting of:

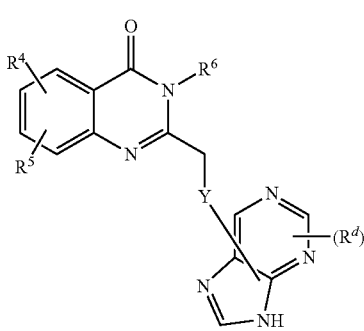

(II)

wherein Y is selected from the group consisting of null, S, and NH;
$R^4$ is selected from the group consisting of H, halo, $NO_2$, OH, $OCH_3$, $CH_3$, and $CF_3$;
$R^5$ is selected from the group consisting of H, $OCH_3$, and halo;
or $R^4$ and $R^5$ together with C-6 and C-7 of the quinazoline ring system define a 5- or 6-membered aromatic ring optionally containing one or more O, N, or S atoms;
$R^6$ is selected from the group consisting of $C_1$-$C_6$alkyl, phenyl, halophenyl, alkoxyphenyl, alkylphenyl, biphenyl, benzyl, pyridinyl, 4-methylpiperazinyl, $C(=O)OC_2H_5$, and morpholinyl;
$R^d$, independently, is selected from the group consisting of $NH_2$, halo, $C_{1-3}$alkyl, $S(C_{1-3}$alkyl), OH, $NH(C_{1-3}$alkyl), $N(C_{1-3}$alkyl)$_2$, $NH(C_{1-3}$alkylenephenyl), and

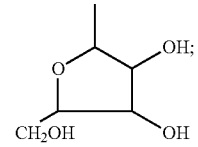

and
q is 1 or 2,
provided that at least one of $R^4$ and $R^5$ is other than H when $R^6$ is phenyl or 2-chlorophenyl.

More preferably, the compound is selected from the group consisting of:

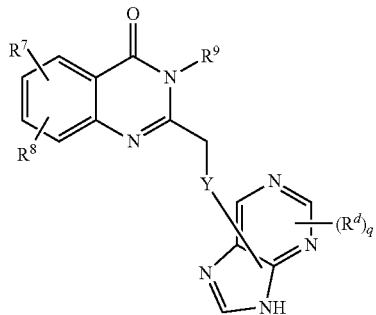

(III)

wherein Y is selected from the group consisting of null, S, and NH;
$R^7$ is selected from the group consisting of H, halo, OH, $OCH_3$, $CH_3$, and $CF_3$;
$R^8$ is selected from the group consisting of is H, $OCH_3$, and halo;
or $R^7$ and $R^8$ together with C-6 and C-7 of the quinazoline ring system define a 5- or 6-membered aromatic ring optionally containing one or more O, N, or S atoms;
$R^9$ is selected from the group consisting of $C_1$-$C_6$alkyl, phenyl, halophenyl, alkylphenyl, biphenyl, benzyl, pyridinyl, 4-methylpiperazinyl, $C(=O)$—$OC_2H_5$, and morpholinyl;
$R^d$, independently, is selected from the group consisting of $NH_2$, halo, $C_{1-3}$alkyl, $S(C_{1-3}$alkyl), OH, $NH(C_{1-3}$alkyl), $N(C_{1-3}$alkyl)$_2$, $NH(C_{1-3}$alkylenephenyl); and
q is 1 or 2,
provided that at least one of $R^7$ and $R^8$ is different from 6-halo or 6,7-dimethoxy groups, and that $R^9$ is different from 4-chlorophenyl.

In another embodiment, the invention is a method for disrupting leukocyte function, comprising contacting leukocytes with a compound having a general structure (I).

In another embodiment, the invention is a class of compounds that have been observed to inhibit PI3Kδ activity in biochemical and cell-based assays, and are expected to exhibit therapeutic benefit in medical conditions in which PI3Kδ activity is excessive or undesirable. Thus, the invention provides a class, of compounds having the structure (II).

Preferably, the compounds have a general structure (IV)

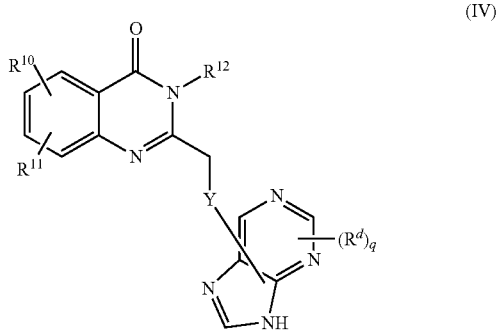

(IV)

wherein Y is selected from the group consisting of null, S, and NH;

$R^{10}$ is selected from the group consisting of H, halo, OH, $OCH_3$, $CH_3$, and $CF_3$;

$R^{11}$ is selected from the group consisting of H, $OCH_3$, and halo;

or $R^{10}$ and $R^{11}$ together with C-6 and C-7 of the quinazoline ring system define a 5- or 6-membered aromatic ring optionally containing one or more O, N, or S atoms;

$R^{12}$ is selected from the group consisting of $C_1$-$C_6$alkyl, phenyl, halophenyl, alkylphenyl, biphenyl, benzyl, pyridinyl, 4-methylpiperazinyl, C(=O)$C_2H_5$, and morpholinyl;

$R^d$, independently, is selected from the group consisting of $NH_2$, halo, $C_{1-3}$alkyl, S($C_{1-3}$alkyl), OH, NH($C_{1-3}$alkyl), N($C_{1-3}$alkyl)$_2$, NH($C_{1-3}$alkylenephenyl), and q is 1 or 2, provided that:

(a) at least one of $R^{10}$ and $R^{11}$ is different from 6-halo or 6,7-dimethoxy groups;

(b) $R^{12}$ is different from 4-chlorophenyl; and (c) at least one of $R^{10}$ and $R^{11}$ is different from H when $R^{12}$ is phenyl or 2-chlorophenyl and X is S.

These and other features and advantages of the present invention will be appreciated from the detailed description and examples that are set forth herein. The detailed description and examples are provided to enhance the understanding of the invention, but are not intended to limit the scope of the invention.

DETAILED DESCRIPTION OP THE PREFERRED EMBODIMENTS

Figure 1:
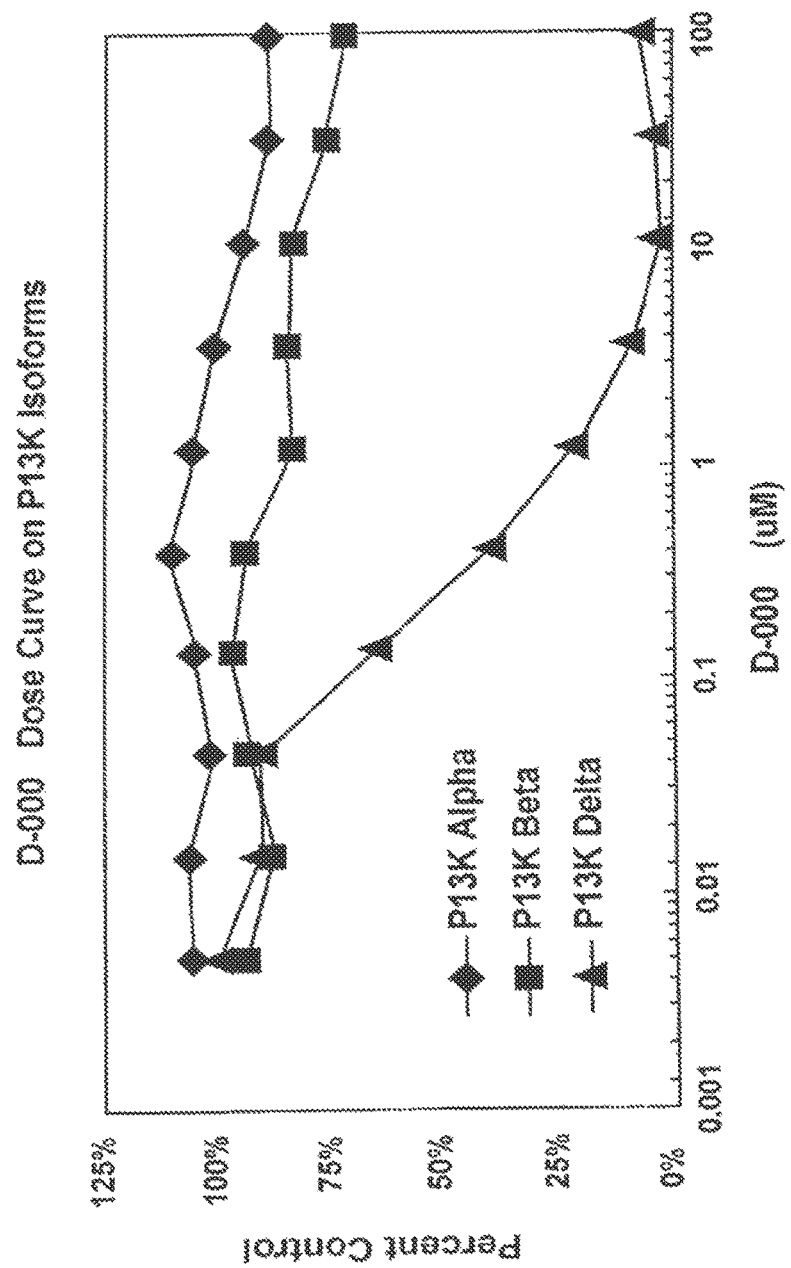
FIG. 1 shows the effect of a selective PI3Kδ inhibitor of the invention on the activity of three PI3K isoforms.

The invention provides compounds that selectively inhibit the activity of PI3Kδ. The invention further provides methods of inhibiting PI3Kδ activity, including methods of selectively modulating the activity of the PI3Kδ isozyme in cells, especially leukocytes, osteoclasts, and cancer cells. The methods include in vitro, in vivo, and ex vivo applications.

Of particular benefit are methods of selectively modulating PI3Kδ activity in the clinical setting in order to ameliorate disease or disorders mediated by PI3Kδ activity. Thus, treatment of diseases or disorders characterized by excessive or inappropriate PI3Kδ activity can be treated through use of selective modulators of PI3Kδ according to the invention.

Other methods of the invention include enabling the further characterization of the physiological role of the isozyme. Moreover, the invention provides pharmaceutical compositions comprising selective PI3Kδ inhibitors. Also provided are articles of manufacture comprising a selective PI3Kδ inhibitor compound (or a pharmaceutical composition comprising the compound) and instructions for using the compound. Details of these and other useful embodiments of the invention are now described.

The methods described herein benefit from the use of compounds that selectively inhibit, and preferably specifically inhibit, the activity of PI3Kδ in cells, including cells in vitro, in vivo, or ex vivo. Cells useful in the methods include those that express endogenous PI3Kδ, wherein endogenous indicates that the cells express PI3Kδ absent recombinant introduction into the cells of one or more polynucleotides encoding a PI3Kδ polypeptide or a biologically active fragment thereof. Methods also encompass use of cells that express exogenous PI3Kδ, wherein one or more polynucleotides encoding PI3Kδ or a biologically active fragment thereof have been introduced into the cell using recombinant procedures.

Of particular advantage, the cells can be in vivo, i.e., in a living subject, e.g., an animal or human, wherein a PI3Kδ inhibitor can be used as a therapeutic to inhibit PI3Kδ activity in the subject. Alternatively, the cells can be isolated as discrete cells or in a tissue, for ex vivo or in vitro methods. In vitro methods also encompassed by the invention can comprise the step of contacting a PI3Kδ enzyme or a biologically active fragment thereof with an inhibitor compound of the invention. The PI3Kδ enzyme can include a purified and isolated enzyme, wherein the enzyme is isolated from a natural source (e.g., cells or tissues that normally express a PI3Kδ polypeptide absent modification by recombinant technology) or isolated from cells modified by recombinant techniques to express exogenous enzyme.

The term "selective PI3Kδ inhibitor" as used herein refers to a compound that inhibits the PI3Kδ isozyme more effectively than other isozymes of the PI3K family. A "selective PI3Kδ inhibitor" compound is understood to be more selective for PI3Kδ than compounds conventionally and generically designated PI3K inhibitors, e.g., wortmannin or LY294002. Concomitantly, wortmannin and LY294002 are deemed "nonselective PI3K inhibitors." Compounds of any type that selectively negatively regulate PI3Kδ expression or activity can be used as selective PI3Kδ inhibitors in the methods of the invention. Moreover, compounds of any type that selectively negatively regulate PI3Kδ expression or activity and that possess acceptable pharmacological properties can be used as selective PI3Kδ inhibitors in the therapeutic methods of the invention.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective PI3Kδ inhibitor" alternatively can be understood to refer to a compound that exhibits a 50% inhibitory concentration ($IC_{90}$) with respect to PI3Kδ that is at least at least 10-fold, preferably at least 20-fold, and more preferably at least 30-fold, lower than the $IC_{50}$ value with respect to any or all of the other Class PI3K family members. The term "specific PI3Kδ inhibitor" can be understood to refer to a selective PI3Kδ inhibitor compound that exhibits an $IC_{50}$ with respect to PI3Kδ that is at least 50-fold, preferably at least 100-fold, more preferably at least 200-fold, and still more preferably at least 500-fold, lower than the $IC_{50}$ with respect to any or all of the other PI3K Class I family members.

Among other things, the invention provides methods of inhibiting leukocyte function. More particularly, the invention provides methods of inhibiting or suppressing functions of neutrophils and T and B lymphocytes. With respect to neutrophils, it has unexpectedly been found that inhibition of PI3Kδ activity inhibits functions of neutrophils. For example, it has been observed that the compounds of the invention elicit inhibition of classical neutrophil functions such as stimulated superoxide release, stimulated exocytosis, and chemotactic migration. However, it has been further observed that the method of the invention permits suppression of certain functions of neutrophils, while not substantially affecting other functions of these cells. For example, it has been observed that phagocytosis of bacteria by neutrophils is not substantially inhibited by the selective PI3Kδ inhibitor compounds of the invention.

Thus, the invention includes methods for inhibiting neutrophil functions, without substantially inhibiting phagocytosis of bacteria. Neutrophil functions suitable for inhibition according to the method include any function that is mediated by PI3Kδ activity or expression. Such functions include, without limitation, stimulated superoxide release, stimulated exocytosis or degranulation, chemotactic migration, adhesion to vascular endothelium (e.g., tethering/rolling of neutrophils, triggering of neutrophil activity, and/or latching of neutrophils to endothelium), transmural diapedesis or emigration through the endothelium to peripheral tissues. In general, these functions can be collectively termed "inflammatory functions," as they are typically related to neutrophil response to inflammation. The inflammatory functions of neutrophils can be distinguished from the bacterial killing functions exhibited by these cells, e.g., phagocytosis and killing of bacteria. Accordingly, the invention further includes methods of treating disease states in which one or more of the inflammatory functions of neutrophils are abnormal or undesirable.

It has further been established through the invention that PI3Kδ plays a role in the stimulated proliferation of lymphocytes, including B cells and T cells. Moreover, PI3Kδ appears to play a role in stimulated secretion of antibodies by B cells. Selective PI3Kδ inhibitor compounds of the invention have been employed to establish that these phenomena can be abrogated by inhibition of PI3Kδ. Thus, the invention includes methods of inhibiting lymphocyte proliferation, and methods of inhibiting antibody production by B lymphocytes. Other methods enabled by the invention include methods of treating disease states in which one or more of these lymphocyte functions are abnormal or undesirable.

It has now been determined that PI3Kδ activity can be inhibited selectively or specifically to facilitate treatment of a PI3Kδ-mediated disease while reducing or eliminating complications that are typically associated with concomitant inhibition of the activity of other Class I PI 3-kinases. To illustrate this embodiment, methods of the invention can be practiced using members of a class of compounds that have been found to exhibit selective inhibition of PI3Kδ relative to other PI3K isoforms.

The methods of this embodiment can be practiced using compounds having the general structure (III). Preferred methods employ compounds that have been empirically determined to exhibit at least 10-fold selective inhibition of PI3Kδ relative to other PI3K isoforms. For example, the methods can be practiced using the following compounds: 3-(2-isopropylphenyl)-5-methyl-2-(9H-purin-6-yl-sulfanylmethyl)-3H-quinazolin-4-one; 5-chloro-2-(9H-purin-6-yl-sulfanylmethyl)-3-o-tolyl-3H-quinazolin-4-one; 5-chloro-3-(2-fluorophenyl)-2-(9H-purin-6-ylsulfanylmethyl)-3H-quinazolin-4-one; 3-(2-fluorophenyl)-5-methyl-2-(9H-purin-6-ylsulfanylmethyl)-3H-quinazolin-4-one; 3-(2-methoxyphenyl)-5-methyl-2-(9H-purin-y-ylsulfanylmethyl-3H-quinazolin-4-one; 3-(2,6-dichlorophenyl)-5-methyl-2-(9H-purin-6-ylsulfanylmethyl)-3H-quinazolin-4-one; 3-(2-chiorophenyl)-6-fluoro-2-(9h-purin-6-ylsulfanylmethyl-3H-quinazolin-4-one; 5-chloro-3-(2-chlorophenyl)-2-(9H-purin-6-ylsulfanylmethyl-3H-quinazolin-4-one; 3-(2-chlorophenyl)-5-methyl-2-(9H-purin-6-ylsulfanylmethyl)-3H-quinazolin-4-one; 3-(3-methoxyphenyl-2-(9H-purin-6-ylsulfanylmethyl-3H-quinazolin-4-one; 3-(2-chlorophenyl)-5-fluoro-2-(9H-purin-6-ylsulfanylmethyl)-3H-quinazolin-4-one; 3-benzyl-2-(9H-purin-6-ylsulfanylmethyl)-3H-quinazolin-4-one; 3-butyl-2-(9H-purin-6-ylsulfanylmethyl)-3H-quinazolin-4-one; 3-(2-chlorophenyl)-7-fluoro-2-(9H-purin-6-ylsulfanylmethyl)-3H-quinazolin-4-one; 3-morpholin-4-yl-2-(9H-purin-6-ylsulfanylmethyl)-3H-quinazolin-4-one, acetate salt; 8-chloro-3-(2-chlorophenyl)-2-(9H-purin-6-ylsulfanylmethyl)-3H-quinazolin-4-one; 3-(2-chlorophenyl)-6,7-difluoro-2-(9H-purin-6-ylsulfanylmethyl)-3H-quinazolin-4-one; 3-(2-methoxyphenyl-2-(9H-purin-6-ylsulfanylmethyl)-3H-quinazolin-4-one; 6-chloro-3-(2-chlorophenyl)-2-(9H- purin-6-ylsulfanylmethyl)-3H-quinazolin-4-one; 3-(3-chlorophenyl)-2-(9H-purin-6-ylsulfanylmethyl)-3H-quinazolin-4-one; 2-(9H-purin-6-ylsulfanylmethyl)-3-pyridin-4-yl-3H-quinazolin-4-one; 3-(2-chlorophenyl)-2-(9H-purin-6-ylsulfanylmethyl)-trifluoromethyl-3H-quinazolin-4-one; 3-benzyl-5-fluoro-2-(9H-purin-6-ylsulfanylmethyl)-3H-quinazolin-4-one; 3-(4-methylpiperazin-1-yl)-2-(9H-purin-6-ylsulfanylmethyl)-3H-quinazolin-4-one, acetate salt; 3-(2-chlorophenyl)-6-hydroxy-2-(9H-purin-6-ylsulfanylmethyl)-3H-quinazolin-4-one; [5-fluoro-4-oxo-2-(9H-purin-6-ylsulfanylmethyl)-4H-quinazolin-3-yl]acetic acid ethyl ester; 3-(2,4-dimethoxyphenyl)-2-(9H-purin-6-ylsulfanyl-methyl)-3H-quinazolin-4-one; 3-biphenyl-2-yl-5-chloro-2-(9H-purin-6-ylsulfanyl-methyl)-3H-quinazolin-4-one; 2-(6-aminopurin-9-ylmethyl)-3-(2-isopropylphenyl)-5-methyl-3H-quinazolin-4-one; 2-(6-aminopurin-9-ylmethyl)-5-methyl-3-o-tolyl-3H-quinazolin-4-one; 2-(6-aminopurin-9-ylmethyl)-3-biphenyl-2-yl-5-chloro-3H-quinazolin-4-one; 5-chloro-3-(2-methoxyphenyl)-2-(9H-purin-6-ylsulfanylmethyl)-3H-quinazolin-4-one; 2-(6-aminopurin-9-ylmethyl)-3-(2-fluorophenyl)-5-methyl-3H-quinazolin-4-one; 2-(6-aminopurin-9-ylmethyl)-5-chloro-3-(2-fluoro-phenyl)-3H-quinazolin-4-one; 2-(6-aminopurin-9-ylmethyl)-8-chloro-3-(2-chloro-phenyl)-3H-quinazolin-4-one; 2-(6-aminopurin-9-ylmethyl)-5-chloro-3-(2-chloro-phenyl)-3H-quinazolin-4-one; 2-(6-aminopurin-9-ylmethyl)-3-(2-chlorophenyl)-5-methyl-3H-quinazolin-4-one; 2-(6-aminopurin-9-ylmethyl)-3-(2-chlorophenyl)-5-fluoro-3H-quinazolin-4-one; 2-(6-aminopurin-9-ylmethyl)-3-benzyl-5-fluoro-3H-quinazolin-4-one; 2-(6-aminopurin-9-ylmethyl)-3-butyl-3H-quinazolin-4-one; 2-(6-aminopurin-9-ylmethyl)-3-morpholin-4-yl-3H-quinazolin-4-one; 2-(6-aminopurin-9-ylmethyl)-3-(2-chlorophenyl)-7-fluoro-3H-quinazolin-4-one; 3-(2-chlorophenyl)-2-(9H-purin-6-ylsulfanylmethyl)-3H-quinazolin-4-one; 3-phenyl-2-(9H-purin-6-ylsulfanylmethyl)-3H-quinazolin-4-one; 2-(6-aminopurin-9-ylmethyl)-5-chloro-3-(2-isopropyl-phenyl)-3H-quinazolin-4-one; and 2-(6-aminopurin-9-ylmethyl)-5-chloro-3-o-tolyl-3H-quinazolin-4-one.

It has further been determined that the methods of the invention can be advantageously practiced using members of a class of compounds that exhibit PI3Kδ inhibitory activity, thereby facilitating inhibitions of PI3Kδ activity in diseases mediated thereby. For example, in this embodiment, the methods of the invention can be practiced using compounds having the general structure (I).

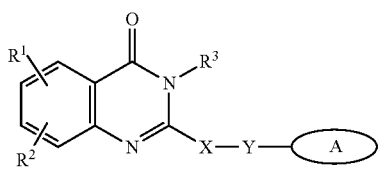

(I)

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, O, C(=O), OC(=O), C(=O)O, and NHC(=O) $CH_2S$;

$R^1$ and $R^2$, independently, are selected from the group consisting of hydrogen, $C_{3-6}$alkyl, aryl, heteroaryl, halo, NHC(=O)$C_{1-3}$alkyleneN$(R^a)_2$, $NO_2$, $OR^a$, $CF_3$, $OCF_3$, N$(R^a)_2$, CN, OC(=O)$R^a$, C(=O)$R^a$, C(=O)$OR^a$, arylO$R^6$, Het, NR$^a$C(=O) $C_{1-3}$alkyleneC(=O)$OR^a$, arylO$C_{1-3}$-alkyleneN$(R^a)_2$, arylOC(=O)$R^a$, $C_{1-4}$alkyleneC(=O)$OR^a$, OC$_{1-4}$alkyleneC(=O)$OR^a$, $C_{1-4}$alkyleneOC$_{1-4}$alkyleneC(=O)$OR^a$, C(=O)NR$^a$SO$_2$R$^a$, $C_{1-4}$alkyleneN$(R^a)_2$, $C_{2-6}$alkenyleneN$(R^a)_2$, C(=O)NR$^a$$C_{1-4}$alkyleneOR$^a$, C(=O)NR$^a$$C_{1-4}$alkyleneHet, OC$_{2-4}$-alkyleneN$(R^a)_2$, OC$_{1-4}$alkyleneCH (OR$^b$) CH$_2$N$(R^a)_2$, OC$_{2-4}$-alkyleneHet, OC$_{2-4}$alkyleneOR$^a$, OC$_{2-4}$alkyleneNR$^a$C(=O)OR$^a$, NR$^a$$C_{1-4}$alkyleneN$(R^a)_2$, NR$^a$C(=O)R$^a$, NR$^a$C(=O)N$(R^a)_2$, N(SO$_2$$C_{1-4}$alkyl)$_2$, NR$^a$(SO$_2$$C_{1-4}$alkyl), SO$_2$N$(R^a)_2$, OSO$_2$CF$_3$, $C_{1-3}$alkylenearyl, $C_{1-4}$alkyleneHet, $C_{1-6}$alkylene-OR$^b$, $C_{1-3}$alkyleneN$(R^a)_2$, C(=O)N$(R^a)_2$, NHC(=O) $C_1$-$C_3$alkylenearyl, $C_{3-8}$cycloalkyl, $C_{3-8}$heterocycloalkyl, arylOC$_{1-3}$-alkyleneN$(R^a)_2$, arylOC(=O)R$^b$, NHC(=O) $C_{1-3}$alkyleneC$_{3-8}$-heterocycloalkyl, NHC(=O) $C_{1-3}$alkyleneHet, OC$_{1-4}$alkyleneOC$_{1-4}$alkyleneC(=O)OR$^b$, C(=O) $C_{1-4}$alkyleneHet, and NHC(=O)haloC$_{1-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-6}$cycloalkyl, $C_{3-8}$heterocycloalkyl, $C_{1-4}$alkylenecycloalkyl, $C_{2-6}$alkenyl, $C_{1-3}$alkylenearyl, arylC$_{1-3}$alkyl, C(=O)R$^a$, aryl, heteroaryl, C(=O) OR$^a$, C(=O)N$(R^a)_2$, C(=S)N$(R^a)_2$, SO$_2$R$^a$, SO$_2$N$(R^a)_2$, S(=O)R$^a$, S(=O)N$(R^a)_2$, C(=O)NR$^a$$C_{1-4}$-alkyleneOR$^a$, C(=O) NR$^a$$C_{1-4}$alkyleneHet, C(=O) $C_{1-4}$alkylenearyl, C(=O) $C_{1-4}$alkyleneheteroaryl, $C_{1-4}$alkylenearyl optionally substituted with one or more of halo SO$_2$N$(R^a)_2$, N$(R^a)_2$, C(=O)OR$^a$, NR$^a$SO$_2$CF$_3$, CN, NO$_2$, C(=O)R$^a$, OR$^a$, $C_{1-4}$alkyleneN$(R^a)_2$, and OC$_{1-4}$alkyleneN$(R^a)_2$, $C_{1-4}$alkyleneheteroaryl, $C_{1-4}$alkyleneHet, $C_{1-4}$alkyleneC(=O) $C_{1-4}$alkylenearyl, $C_{1-4}$alkyleneC(=O)$C_{1-4}$alkyleneheteroaryl, $C_{1-4}$alkyleneC(=O)Het, $C_{1-4}$alkyleneC(=O)—N $(R^a)_2$, $C_{1-4}$alkyleneOR$^a$, $C_{1-4}$alkyleneNR$^a$C(=O)R$^a$, $C_{1-4}$alkyleneOC$_{1-4}$alkyleneOR$^a$, $C_{1-4}$alkyleneN$(R^a)_2$, $C_{1-4}$alkyleneC(=O)OR$^a$, and $C_{1-4}$alkyleneOC$_{1-4}$alkyleneC(=O)OR$^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN$(R^c)_2$, aryl, arylC$_{1-3}$alkyl, $C_{1-3}$alkylenearyl, heteroaryl, heteroarylC$_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, heteroC$_{1-3}$alkyl, $C_{1-3}$alkyleneheteroC$_{1-3}$alkyl, arylheteroC$_{1-3}$alkyl, aryl, heteroaryl, arylC$_{1-3}$alkyl, heteroarylC$_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^a$;

and pharmaceutically acceptable salts and solvates (e.g., hydrates) thereof.

For example, methods of the invention can employ compounds that possess PI3Kδ inhibitory activity, as follows: 3-(2-isopropylphenyl)-5-methyl-2-(9H-purin-6-yl-sulfanylmethyl)-3H-quinazolin-4-one; 5-chloro-2-(9H-purin-6-ylsulfanylmethyl)-3-o-tolyl-3H-quinazolin-4-one; 5-chloro-3-(2-fluorophenyl)-2-(9H-purin-6-ylsulfanylmethyl)-3H-quinazolin-4-one; 3-(2-fluorophenyl)-5-methyl-2-(9H-purin-6-ylsulfanylmethyl)-3H-quinazolin-4-one; 3-(2-methoxyphenyl)-5-methyl-2-(9H-purin-6-ylsulfanylmethyl)-3H-quinazolin-4-one; 3-(2,6-dichlorophenyl)-5-methyl-2-(9H-purin-6-ylsulfanylmethyl)-3H-quinazolin-4-one; 3-(2-chlorophenyl)-6-fluoro-2-(9H-purin-6-ylsulfanylmethyl)-3h-quinazolin-4-one; 5-chloro-3-(2-chlorophenyl)-2-(9H-purin-6-ylsulfanylmethyl)-3H-quinazolin-4-one; 3-(2-chlorophenyl)-5-methyl-2-(9H-purin-6-ylsulfanylmethyl)-3H-quinazolin-4-one; 3-(2-methoxyphenyl)-2-(9H-purin-6-ylsulfanylmethyl)-3H-quinazolin-4-one; 3-(2-chlorophenyl)-5-fluoro-2-(9H-purin-6-ylsulfanylmethyl)-3H-quinazolin-4-one; 3-benzyl-2-(9H-purin-6-ylsulfanylmethyl)-3H-quinazolin-4-one; 3-butyl-2-(9H-purin-6-ylsulfanylmethyl)-3H-quinazolin-4-one; 3-(2-chlorophenyl)-7-fluoro-2-(9H-purin-6-ylsulfanylmethyl)-3H-quinazolin-4-one; 3-morpholin-4-yl-2-(9H-purin-6-ylsulfanylmethyl)-3H-quinazolin-4-one, acetate salt; 8-chloro-3-(2-chlorophenyl)-2-(9H-purin-6-ylsulfanylmethyl)-3H-quinazolin-4-one; 3-(2-chlorophenyl)-6,7-difluoro-2-(9H-purin-6-ylsulfanylmethyl)-3H-quinazolin-4-one; 3-(3-methoxyphenyl)-2-(9H-purin-6-ylsulfanylmethyl)-3H-quinazolin-4-one; 6-chloro-3-(2-chlorophenyl)-2-(9H-purin-6-ylsulfanylmethyl)-3H-quinazolin-4-one; 3-(3-chlorophenyl)-2-(9H-purin-6-ylsulfanylmethyl)-3H-quinazolin-4-one; 2-(9H-purin-6-ylsulfanylmethyl)-3-pyridin-4-yl-3H-quinazolin-4-one; 3-(2-chlorophenyl)-2-(9H-purin-6-ylsulfanylmethyl)-trifluoromethyl-3H-quinazolin-4-one; 3-benzyl-5-fluoro-2-(9H-purin-6-ylsulfanylmethyl)-3H-quinazolin-4-one; 3-(4-methylpiperazin-1-yl)-2-(9H-purin-6-ylsulfanylmethyl)-3H-quinazolin-4-one, acetate salt; 3-(2-chlorophenyl)-6-hydroxy-2-(9H-purin-6-ylsulfanylmethyl)-3H-quinazolin-4-one; [5-fluoro-4-oxo-2-(9H-purin-6-ylsulfanylmethyl)-4H-quinazolin-3-yl]acetic acid ethyl ester; 3-biphenyl-2-yl-5-chloro-2-(9H-purin-6-ylsulfanyl-methyl)-3H-quinazolin-4-one; 5-chloro-3-(2-methoxyphenyl)-2-(9H-purin-6-ylsulfanylmethyl)-3H-quinazolin-4-one; 2-(6-aminopurin-9-ylmethyl)-3-(2-isopropylphenyl)-5-methyl-3H-quinazolin-4-one; 2-(6-aminopurin-9-ylmethyl)-5-methyl-3-o-tolyl-3H-quinazolin-4-one; 2-(6-aminopurin-9-ylmethyl)-3-biphenyl-2-yl-t-chloro-3H-quinazolin-4-one; 2-(6-aminopurin-9-ylmethyl)-3-(2-fluorophenyl)-5-methyl-3H-quinazolin-4-one; 2-(6-aminopurin-9-ylmethyl)-5-chloro-3-(2-fluoro-phenyl)-3H-quinazolin-4-one; 2-(6-aminopurin-9-ylmethyl)-8-chloro-3-(2-chloro-phenyl)-3H-quinazolin-4-one; 2-(6-aminopurin-9-ylmethyl)-5-chloro-3-(2-chloro-phenyl)-3H-quinazolin-4-one; 2-(6-aminopurin-9-ylmethyl)-3-(2-chiorophenyl)-5-methyl-3H-quinazolin-4-one; 2-(6-aminopurin-9-ylmethyl)-3-(2-chiorophenyl)-5-fluoro-3H-quinazolin-4-one; 2-(6-aminopurin-9-ylmethyl)-3-benzyl-5-fluoro-3H-quinazolin-4-one; 2-(6-aminopurin-9-ylmethyl)-3-butyl-3H-quinazolin-4-one; 2-(6-aminopurin-9-ylmethyl)-3-morpholin-4-yl-3H-quinazolin-4-one; 2-(6-aminopurin-9-ylmethyl)-3-(2-chlorophenyl)-7-fluoro-3H-quinazolin-4-one; 3-(2-chiorophenyl)-2-(9H-purin-6-ylsulfanylmethyl)-3H-quinazolin-4-one; 3-phenyl-2-(9H-purin-6-ylsulfanylmethyl)-3H-quinazolin-4-one; 2-(6-aminopurin-9-ylmethyl)-5-chloro-3-(2-chloro-phenyl)-3H-quinazolin-4-one; 3-(4-chiorophenyl)-2-(9H-purin-6-ylsulfanylmethyl)-3H-quinazolin-4-one; 3-(2-chiorophenyl)-6,7-dimethoxy-2-(9H-purin-6-ylsulfanylmethyl)-3H-quinazolin-4-one; 3-(2-chiorophenyl)-7-nitro-2-(9H-purin-6-ylsulfanyl-methyl)-3H-quinazolin-4-one; 2-(6-aminopurin-9-ylmethyl)-6-bromo-3-(2-chloro-phenyl)-3H-quinazolin-4-one; 2-(6-aminopurin-9-ylmethyl)-3-(2-chiorophenyl)-6,7-dimethoxy-3H-quinazolin-4-one; 6-bromo-3-(2-chlorophenyl)-2-(9H-purin-6-ylsulfanyl-methyl)-3H-quinazolin-4-one; 3-(2-chlorophenyl)-2-(9H-purin-6-ylsulfanylmethyl)-3H-benzo[g]quinazolin-4-one; 2-(6-aminopurin-9-ylmethyl)-5-chloro-3-o-tolyl-3H-quinazolin-4-one; and 2-(6-aminopurin-9-ylmethyl)-5-chloro-3-(2-methoxy-phenyl)-3H-quinazolin-4-one.

The invention further provides compounds that are selective inhibitors of PI3Kδ activity. The compounds exhibit inhibition of PI3Kδ in biochemical assays, and selectively disrupt function of PI3Kδ-expressing cells in cell-based assays. As described elsewhere herein, the compounds of the invention have been demonstrated to inhibit certain functions in neutrophils and other leukocytes, as well as functions of osteoclasts.

In general, compounds provided by the invention have the general structure (I), a pharmaceutically acceptable salt thereof, or a prodrug thereof:

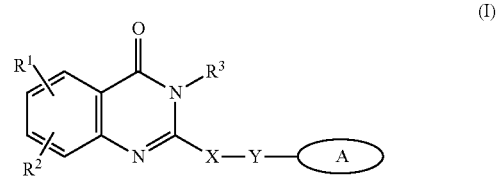

(I)

wherein A is an optionally substituted monocyclic or bicyclic ring system containing at least two nitrogen atoms, and at least one ring of the system is aromatic;

X is selected from the group consisting of $C(R^b)_2$, $CH_2CHR^b$, and $CH=C(R^b)$;

Y is selected from the group consisting of null, S, SO, $SO_2$, NH, O, $C(=O)$, $OC(=O)$, $C(=O)O$, and $NHC(=O)$ $CH_2S$;

$R^1$ and $R^2$, independently, are selected from the group consisting of hydrogen, $C_{1-6}$alkyl, aryl, heteroaryl, halo, $NHC(=O)$ $C_{1-3}$alkyleneN$(R^a)_2$, $NO_2$, $OR^a$, $CF_3$, $OCF_3$, $N(R^a)_2$, CN, $OC(=O)R^a$, $C(=O)R^a$, $C(=O)OR^a$, aryl$OR^b$, Het, $NR^aC(=O)$ $C_{1-3}$alkyleneC$(=O)OR^a$, aryl$OC_{1-3}$-alkyleneN$(R^a)_2$, aryl$OC(=O)R^a$, $C_{1-4}$alkyleneC$(=O)OR^a$, $OC_{1-4}$alkyleneC$(=O)OR^a$, $C_{1-4}$alkyleneOC$_{1-4}$alkyleneC$(=O)OR^a$, $C(=O)NR^aSO_2R^a$, $C_{1-4}$alkyleneN$(R^a)_2$, $C_{2-6}$alkenyleneN$(R^a)_2$, $C(=O)$ $NR^aC_{1-4}$alkyleneOR$^a$, $C(=O)$ $NR^aC_{1-4}$alkyleneHet, $OC_{2-4}$-alkyleneN$(R^a)_2$, $OC_{1-4}$alkyleneCH $(OR^b)$ $CH_2N(R^a)_2$, $OC_{1-4}$alkyleneHet, $OC_{2-4}$alkyleneOR$^a$, $OC_{2-4}$alkyleneNR$^a$C$(=O)OR^a$, $NR^aC_{1-4}$alkyleneN$(R^a)_2$, $NR^aC(=O)R^a$, $NR^aC(=O)$ $N(R^a)_2$, $N(SO_2C_{1-4}alkyl)_2$, $NR^a(SO_2C_{1-4}alkyl)$, $SO_2N(R^a)_2$, $OSO_2CF_3$, $C_{1-3}$alkylenearyl, $C_{3-4}$alkyleneHet, $C_{3-6}$alkylene-$OR^b$, $C_{1-3}$alkyleneN$(R^a)_2$, $C(=O)N(R^a)_2$, $NHC(=O)$ $C_1$-$C_3$alkylenearyl, $C_{3-8}$cycloalkyl, $C_{3-8}$heterocycloalkyl, aryl$OC_{1-3}$-alkyleneN$(R^a)_2$, aryl$OC(=O)R^b$, $NHC(=O)$ $C_{1-3}$alkyleneC$_{3-8}$-heterocycloalkyl, $NHC(=O)C_{1-3}$alkyleneHet, $OC_{1-4}$alkyleneOC$_{1-4}$alkyleneC$(=O)OR^b$, $C(=O)$ $C_{1-4}$alkyleneHet, and $NHC(=O)$haloC$_{3-6}$alkyl;

or $R^1$ and $R^2$ are taken together to form a 3- or 4-membered alkylene or alkenylene chain component of a 5- or 6-membered ring, optionally containing at least one heteroatom;

$R^3$ is selected from the group consisting of optionally substituted hydrogen, $C_{1-6}$alkyl, $C_{3-8}$cycloalkyl, $C_{3-8}$heterocycloalkyl, $C_{1-4}$alkylenecycloalkyl, $C_{2-6}$alkenyl, $C_{1-3}$alkylenearyl, aryl$C_{1-3}$alkyl, C(=O)$R^a$, aryl, heteroaryl, C(=O) O$R^a$, C(=O)N($R^a$)$_2$, C(=S)N($R^a$)$_2$, SO$_2R^a$, SO$_2$N($R^a$)$_2$, S(=O)$R^a$, S(=O)N($R^a$)$_2$, C(=O) N$R^aC_{1-4}$-alkyleneO$R^a$, C(=O) N$R^aC_{1-4}$alkyleneHet, C(=O) $C_{1-4}$alkylenearyl, C(=O) $C_{1-4}$alkyleneheteroaryl, $C_{1-4}$alkylenearyl optionally substituted with one or more of halo SO$_2$N($R^a$)$_2$, N($R^a$)$_2$, C(=O)O$R^a$, N$R^a$SO$_2$CF$_3$, CN, NO$_2$, C(=O)$R^a$, O$R^a$, $C_{1-4}$alkyleneN($R^a$)$_2$, and OC$_{3-4}$alkyleneN($R^a$)$_2$, $C_{1-4}$-alkyleneheteroaryl, $C_{1-4}$alkyleneHet, $C_{1-4}$alkyleneC(=O)—$C_{1-4}$ alkylenearyl, $C_{1-4}$alkyleneC(=O)$C_{1-4}$alkyleneheteroaryl, $C_{1-4}$alkyleneC(=O)Het, $C_{1-4}$alkyleneC(=O) N($R^a$)$_2$, $C_{1-4}$alkyleneO$R^a$, $C_{1-4}$alkyleneN$R^a$C(=O)$R^a$, $C_{3-4}$alkyleneO-$C_{1-4}$alkyleneO$R^a$, $C_{1-4}$alkyleneN($R^a$)$_2$, $C_{1-4}$alkyleneC(=O)—O$R^a$, and $C_{1-4}$alkyleneOC$_{1-4}$alkyleneC(=O)O$R^a$;

$R^a$ is selected from the group consisting of hydrogen, $C_{1-6}$alkyl, $C_{3-8}$cycloalkyl, $C_{3-8}$heterocycloalkyl, $C_{1-3}$alkyleneN($R^c$)$_2$, aryl, aryl$C_{1-3}$alkyl, $C_{1-3}$alkylenearyl, heteroaryl, heteroaryl$C_{1-3}$alkyl, and $C_{1-3}$alkyleneheteroaryl;

or two $R^a$ groups are taken together to form a 5- or 6-membered ring, optionally containing at least one heteroatom;

$R^b$ is selected from the group consisting of hydrogen, $C_{1-6}$alkyl, hetero$C_{1-3}$alkyl, $C_{1-3}$alkyleneheteroC$_{1-3}$alkyl, arylheteroC$_{1-3}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

$R^c$ is selected from the group consisting of hydrogen, $C_{1-6}$alkyl, $C_{3-8}$cycloalkyl, aryl, and heteroaryl;

Het is a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)O$R^a$;

and pharmaceutically acceptable salts and solvates (e.g., hydrates) thereof.

As used herein, the term "alkyl" is defined as straight chained and branched hydrocarbon groups containing the indicated number of carbon atoms, typically methyl, ethyl, and straight chain and branched propyl and butyl groups. The hydrocarbon group can contain up to 16 carbon atoms, preferably one to eight carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2]octyl, bicyclo-[2.2.1]heptyl, bicyclo[3.2.1]octyl, or decahydro-naphthyl. The term "cycloalkyl" is defined as a cyclic $C_3$-$C_6$ hydrocarbon group, e.g., cyclopropyl, cyclobutyl, cyclohexyl, and cyclopentyl.

The term "alkenyl" is defined identically as "alkyl," except for containing a carbon-carbon double bond. "Cycloalkenyl" is defined similarly to cycloalkyl, except a carbon-carbon double bond is present in the ring.

The term "alkylene" is defined as an alkyl group having a substituent. For example, the term "$C_{1-3}$alkylenearyl" refers to an alkyl group containing one to three carbon atoms, and substituted with an aryl group.

The term "hetero$C_{1-3}$alkyl" is defined as a $C_{1-3}$alkyl group further containing a heteroatom selected from O, S, and N$R^a$. For example, —CH$_2$OCH$_3$ or —CH$_3$CH$_2$SCH$_3$. The term "arylheteroC$_{1-3}$alkyl" refers to an aryl group having a heteroC$_{1-3}$alkyl substituent.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, phenyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, biphenyl, tetrahydronaphthyl, chlorophenyl, fluorophenyl, aminophenyl, methylphenyl, methoxyphenyl, trifluoromethylphenyl, nitrophenyl, carboxyphenyl, and the like. The terms "aryl$C_{1-3}$alkyl" and "heteroaryl-$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl isoxazolyl, imidazolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolane, 2-pyrazoline, pyrazolidine, pyrrolidine, piperazine, a pyrroline, 2H-pyran, 4H-pyran, morpholine, thioproline, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O) N, wherein R is alkyl or aryl.

The term "alkylthio" is defined as —SR, wherein R is alkyl.

The term "alkylsulfinyl" is defined as R—SO$_2$, wherein R is alkyl.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

In preferred embodiments, X is selected from the group consisting of CH$_2$, CH$_2$CH$_2$, CH=CH, CH(CH$_3$), CH(CH$_2$CH$_3$), CH$_2$CH(CH$_3$), and C(CH$_3$)$_2$. In further preferred embodiments, Y is selected from the group consisting of null, S, and NH.

The A ring can be monocyclic or bicyclic. Monocyclic A ring systems are aromatic. Bicyclic A ring systems contain at least one aromatic ring, but both rings can be aromatic. Examples of A ring systems include, but are not limited to, imidazolyl, pyrazolyl, 1,2,3-triazolyl, pyridizinyl, pyrimidinyl, pyrazinyl, 1,3,5-triazinyl, purinyl, cinnolinyl, phthalazinyl, quinazolinyl, quinoxalinyl, 1,8-naphthyridinyl, pteridinyl, 1H-indazolyl, and benz-imidazolyl.

In a preferred group of compounds of formula (I), A is represented by an optionally substituted ring system selected from the group consisting of

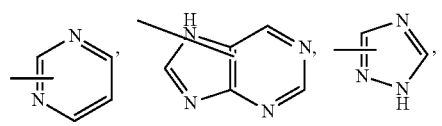

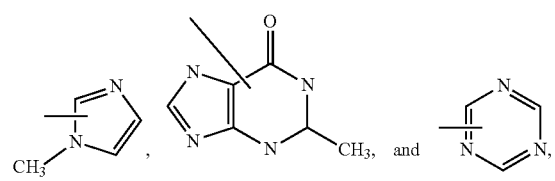

The A ring system optionally can be substituted with one to three, and preferably one to two, substituents selected from the group consisting of N(R$^a$)$_2$, halo, C$_{1-3}$alkyl, S(C$_{1-3}$alkyl), OR$^a$, and

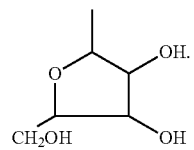

Specific substituents include, but are not limited to, NH$_2$, NH(CH$_3$), N(CH$_3$)$_2$, NHCH$_2$C$_6$H$_5$, NH(C$_2$H$_5$), Cl, F, CH$_3$, SCH$_3$, OH, and

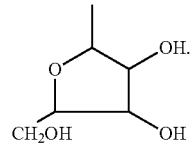

In another preferred group of compounds of formula (I), R$^1$ and R$^3$, independently, are represented by hydrogen, OR$^a$, halo, C$_{1-6}$alkyl, CF$_3$, NO$_2$, N(R$^a$)$_2$, NR$^a$C$_{1-3}$alkyleneN(R$^a$)$_2$, and OC$_{1-3}$alkyleneOR$^a$. Specific substituents include, but are not limited to, H, OCH$_3$, Cl, Br, F, CH$_3$, CF$_3$, NO$_2$, OH, N(CH$_3$)$_2$,

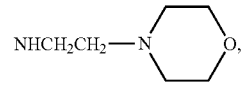

and O(CH$_2$)$_2$OCH$_2$C$_6$H$_5$. R$^1$ and R$^3$ also can be taken together to form a ring, for example, a phenyl ring.

In a preferred embodiment, R$^3$ is selected from the group consisting of optionally substituted C$_{1-6}$alkyl, aryl, heteroaryl, C$_{3-8}$cycloalkyl, C$_{3-8}$heterocycloalkyl, C(=O)OR$^a$, C$_{3-4}$alkyleneHet, C$_{1-4}$alkylenecycloalkyl, C$_{1-4}$alkylenearyl, C$_{1-4}$alkyleneC(=O) C$_{1-4}$-alkylenearyl, C$_{1-4}$alkyleneC(=O) OR$^a$, C$_{1-4}$alkyleneC(=O)N(R$^a$)$_2$, C$_{1-4}$alkyleneC(=O)Het, C$_{1-4}$alkyleneN(R$^a$)$_2$, and C$_{1-4}$alkyleneNR$^a$C(=O)R$^a$. Specific R$^3$ groups include, but are not limited to

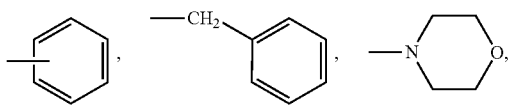

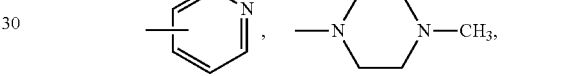

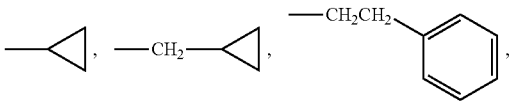

The R$^3$ group can be substituted with one to three substituents, for example, halo, OR$^a$, C$_{1-6}$alkyl, aryl, heteroaryl, NO$_2$, N(R$^a$)$_2$, NR$^a$SO$_2$CF$_3$, NR$^a$C(=O)R$^a$, C(=O)OR$^a$, N(R$^a$)C$_{1-4}$alkylene (R$^a$)$_2$, SO$_2$N(R$^a$)$_2$, CN, C(=O)R$^a$, C$_{1-4}$alkyleneN(R$^a$)$_2$, OC$_{1-4}$alkyleneC≡CR$^a$, OC$_{1-4}$alkyleneC(=O)N(R$^a$)$_2$, OC$_{1-4}$alkylenearyl, OC$_{1-4}$alkyleneheteroaryl, OC$_{1-4}$alkyleneHet, OC$_{3-4}$alkyleneN(R$^a$)$_2$, and N(R$^a$)—C$_{1-4}$alkyleneN(R$^a$)$_2$. Specific substituents for the R$^3$ group include, but are not limited to, Cl, F, CH$_3$, CH(CH$_3$)$_2$, OH, OCH$_3$, O(CH$_2$)$_3$N(CH$_3$)$_2$, OCH$_2$C=CH, OCH$_2$C(=O)—NH$_2$, C$_6$H$_5$, NO$_2$, NH$_2$, NHC(=O)CH$_3$, CO$_2$H, N(CH$_3$)CH$_2$CH$_2$N—(CH$_3$)$_2$, and

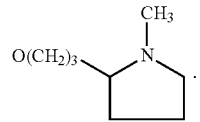

As used herein, the quinazoline ring structure, and numbering of the ring structure, is

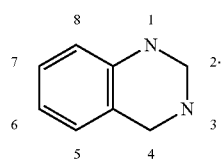

The purine ring structure, and numbering of the ring structure, is

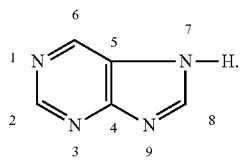

The compounds provided by the invention are exemplified as follows:
3-(2-isopropylphenyl)-5-methyl-2-(9H-purin-6-ylsulfanylmethyl)-3H-quinazolin-4-one;
5-chloro-2-(9H-purin-6-ylsulfanylmethyl)-3-o-tolyl-3H-quinazolin-4-one;
5-chloro-3-(2-fluorophenyl)-2-(9H-purin-6-ylsulfanylmethyl)-3H-quinazolin-4-one;
3-(2-fluorophenyl)-5-methyl-2-(9H-purin-6-ylsulfanylmethyl)-3H-quinazolin-4-one;
3-(2-methoxyphenyl)-5-methyl-2-(9H-purin-6-ylsulfanylmethyl)-3H-quinazolin-4-one;
3-(2,6-dichlorophenyl)-5-methyl-2-(9H-purin-6-ylsulfanylmethyl)-3H-quinazolin-4-one;
3-(2-chlorophenyl)-6-fluoro-2-(9H-purin-6-ylsulfanylmethyl)-3h-quinazolin-4-one;
5-chloro-3-(2-chlorophenyl)-2-(9H-purin-6-ylsulfanylmethyl)-3H-quinazolin-4-one;
3-(2-chlorophenyl)-5-methyl-2-(9H-purin-6-ylsulfanylmethyl)-3H-quinazolin-4-one;
3-(2-methoxyphenyl)-2-(9H-purin-6-ylsulfanylmethyl)-3H-quinazolin-4-one;
3-(2-chlorophenyl)-5-fluoro-2-(9H-purin-6-ylsulfanylmethyl)-3H-quinazolin-4-one;
3-benzyl-2-(9H-purin-6-ylsulfanylmethyl)-3H-quinazolin-4-one;
3-butyl-2-(9H-purin-6-ylsulfanylmethyl)-3H-quinazolin-4-one;
3-(2-chlorophenyl)-7-fluoro-2-(9H-purin-6-ylsulfanylmethyl)-3H-quinazolin-4-one;
3-morpholin-4-yl-2-(9H-purin-6-ylsulfanylmethyl)-3H-quinazolin-4-one, acetate salt;
8-chloro-3-(2-chlorophenyl)-2-(9H-purin-6-ylsulfanylmethyl)-3H-quinazolin-4-one;
3-(2-chlorophenyl)-6,7-difluoro-2-(9H-purin-6-ylsulfanylmethyl)-3H-quinazolin-4-one;
3-(3-methoxyphenyl)-2-(9H-purin-6-ylsulfanylmethyl)-3H-quinazolin-4-one;
6-chloro-3-(2-chlorophenyl)-2-(9H-purin-6-ylsulfanylmethyl)-3H-quinazolin-4-one;
3-(3-chlorophenyl)-2-(9H-purin-6-ylsulfanylmethyl)-3H-quinazolin-4-one;
2-(9H-purin-6-ylsulfanylmethyl)-3-pyridin-4-yl-3H-quinazolin-4-one;
3-(2-chlorophenyl)-8-trifluoromethyl-2-(9H-purin-6-ylsulfanylmethyl)-3H-quinazolin-4-one;
3-benzyl-5-fluoro-2-(9H-purin-6-ylsulfanylmethyl)-3H-quinazolin-4-one;
3-(4-methylpiperazin-1-yl)-2-(9H-purin-6-ylsulfanylmethyl)-3H-quinazolin-4-one, acetate salt;
3-(2-chlorophenyl)-6-hydroxy-2-(9H-purin-6-ylsulfanylmethyl)-3H-quinazolin-4-one;
[5-fluoro-4-oxo-2-(9H-purin-6-ylsulfanylmethyl)-4H-quinazolin-3-yl]acetic acid ethyl ester;
3-(2-methoxyphenyl)-2-(9H-purin-6-ylsulfanylmethyl)-3H-quinazolin-4-one;
3-biphenyl-2-yl-5-chloro-2-(9H-purin-6-ylsulfanylmethyl)-3H-quinazolin-4-one;
5-chloro-3-(2-methoxyphenyl)-2-(9H-purin-6-ylsulfanylmethyl)-3H-quinazolin-4-one;
2-(6-aminopurin-9-ylmethyl)-3-(2-isopropylphenyl)-5-methyl-3H-quinazolin-4-one;
2-(6-aminopurin-9-ylmethyl)-5-methyl-3-o-tolyl-3H-quinazolin-4-one;
2-(6-aminopurin-9-ylmethyl)-3-biphenyl-2-yl-5-chloro-3H-quinazolin-4-one;
2-(6-aminopurin-9-ylmethyl)-3-(2-fluorophenyl)-5-methyl-3H-quinazolin-4-one;
2-(6-aminopurin-9-ylmethyl)-5-chloro-3-(2-fluoro-phenyl)-3H-quinazolin-4-one;
2-(6-aminopurin-9-ylmethyl)-8-chloro-3-(2-chloro-phenyl)-3H-quinazolin-4-one;
2-(6-aminopurin-9-ylmethyl)-5-chloro-3-(2-chloro-phenyl)-3H-quinazolin-4-one;
2-(6-aminopurin-9-ylmethyl)-3-(2-chlorophenyl)-5-methyl-3H-quinazolin-4-one;
2-(6-aminopurin-9-ylmethyl)-3-(2-chlorophenyl)-5-fluoro-3H-quinazolin-4-one;
2-(6-aminopurin-9-ylmethyl)-3-benzyl-5-fluoro-3H-quinazolin-4-one;
2-(6-aminopurin-9-ylmethyl)-3-butyl-3H-quinazolin-4-one;
2-(6-aminopurin-9-ylmethyl)-3-morpholin-4-yl-3H-quinazolin-4-one;
2-(6-aminopurin-9-ylmethyl)-3-(2-chlorophenyl)-7-fluoro-3H-quinazolin-4-one;
2-(6-aminopurin-9-ylmethyl)-6-chloro-3-(2-chloro-phenyl)-3H-quinazolin-4-one;
3-(4-chlorophenyl)-2-(9H-purin-6-ylsulfanylmethyl)-3H-quinazolin-4-one;
3-(2-chlorophenyl)-6,7-dimethoxy-2-(9H-purin-6-ylsulfanylmethyl)-3H-quinazoline-4-one;
3-(2-chlorophenyl)-7-nitro-2-(9H-purin-6-ylsulfanylmethyl)-3H-quinazolin-4-one;
2-(6-aminopurin-9-ylmethyl)-6-bromo-3-(2-chlorophenyl)-3H-quinazolin-4-one;
2-(6-aminopurin-9-ylmethyl)-3-(2-chlorophenyl)-6,7-dimethoxy-3H-quinazolin-4-one;
6-bromo-3-(2-chlorophenyl)-2-(9H-purin-6-ylsulfanylmethyl)-3H-quinazolin-4-one;
3-(2-chlorophenyl)-2-(9H-purin-6-ylsulfanylmethyl)-3H-benzo[g]quinazolin-4-one;
2-(6-aminopurin-9-ylmethyl)-5-chloro-3-o-tolyl-3H-quinazolin-4-one; and
2-(6-aminopurin-9-ylmethyl)-5-chloro-3-(2-methoxy-phenyl)-3H-quinazolin-4-one.

The preferred compounds provided by the invention have the structure (IV), exemplified as follows:
3-(2-isopropylphenyl)-5-methyl-2-(9H-purin-6-ylsulfanylmethyl)-3H-quinazolin-4-one;
5-chloro-2-(9H-purin-6-ylsulfanylmethyl)-3-o-tolyl-3H-quinazolin-4-one;
5-chloro-3-(2-fluorophenyl)-2-(9H-purin-6-ylsulfanylmethyl)-3H-quinazolin-4-one;

3-(2-fluorophenyl)-5-methyl-2-(9H-purin-6-ylsulfanylmethyl)-3H-quinazolin-4-one;
3-(2,6-dichlorophenyl)-5-methyl-2-(9H-purin-6-ylsulfanylmethyl)-3H-quinazolin-4-one;
3-(2-chiorophenyl)-6-fluoro-2-(9H-purin-6-ylsulfanylmethyl)-3h-quinazolin-4-one;
5-chloro-3-(2-chiorophenyl)-2-(9H-purin-6-ylsulfanylmethyl)-3H-quinazolin-4-one;
3-(2-chlorophenyl)-5-methyl-2-(9H-purin-6-ylsulfanylmethyl)-3H-quinazolin-4-one;
3-(2-chlorophenyl)-5-fluoro-2-(9H-purin-6-ylsulfanylmethyl)-3H-quinazolin-4-one;
3-benzyl-2-(9H-purin-6-ylsulfanylmethyl)-3H-quinazolin-4-one;
3-butyl-2-(9H-purin-6-ylsulfanylmethyl)-3H-quinazolin-4-one;
3-(2-chlorophenyl)-7-fluoro-2-(9H-purin-6-ylsulfanylmethyl)-3H-quinazolin-4-one;
3-morpholin-4-yl-2-(9H-purin-6-ylsulfanylmethyl)-3H-quinazolin-4-one, acetate salt;
8-chloro-3-(2-chlorophenyl)-2-(9H-purin-6-ylsulfanylmethyl)-3H-quinazolin-4-one;
3-(2-chlorophenyl)-6,7-difluoro-2-(9H-purin-6-ylsulfanylmethyl)-3H-quinazolin-4-one;
6-chloro-3-(2-chlorophenyl)-2-(9H-purin-6-ylsulfanylmethyl)-3H-quinazolin-4-one;
3-(3-chlorophenyl)-2-(9H-purin-6-ylsulfanylmethyl)-3H-quinazolin-4-one;
2-(9H-purin-6-ylsulfanylmethyl)-3-pyridin-4-yl-3H-quinazolin-4-one;
3-(2-chlorophenyl)-2-(9H-purin-6-ylsulfanylmethyl)-trifluoromethyl-3H-quinazolin-4-one;
3-benzyl-5-fluoro-2-(9H-purin-6-ylsulfanylmethyl)-3H-quinazolin-4-one;
3-(4-methylpiperazin-1-yl)-2-(9H-purin-6-ylsulfanylmethyl)-3H-quinazolin-4-one, acetate salt;
3-(2-chlorophenyl)-6-hydroxy-2-(9H-purin-6-ylsulfanylmethyl)-3H-quinazolin-4-one;
[5-fluoro-4-oxo-2-(9H-purin-6-ylsulfanylmethyl)-4H-quinazolin-3-yl]acetic acid ethyl ester;
3-biphenyl-2-yl-5-chloro-2-(9H-purin-6-ylsulfanylmethyl)-3H-quinazolin-4-one;
2-(6-aminopurin-9-ylmethyl)-3-(2-isopropylphenyl)-5-methyl-3H-quinazolin-4-one;
2-(6-aminopurin-9-ylmethyl)-5-methyl-3-o-tolyl-3H-quinazolin-4-one;
2-(6-aminopurin-9-ylmethyl)-3-biphenyl-2-yl-5-chloro-3H-quinazolin-4-one;
2-(6-aminopurin-9-ylmethyl)-3-(2-fluorophenyl)-5-methyl-3H-quinazolin-4-one;
2-(6-aminopurin-9-ylmethyl)-5-chloro-3-(2-fluoro-phenyl)-3H-quinazolin-4-one;
2-(6-aminopurin-9-ylmethyl)-8-chloro-3-(2-chloro-phenyl)-3H-quinazolin-4-one;
2-(6-aminopurin-9-ylmethyl)-5-chloro-3-(2-chloro-phenyl)-3H-quinazolin-4-one;
2-(6-aminopurin-9-ylmethyl)-3-(2-chlorophenyl)-5-methyl-3H-quinazolin-4-one;
2-(6-aminopurin-9-ylmethyl)-3-(2-chlorophenyl)-5-fluoro-3H-quinazolin-4-one;
2-(6-aminopurin-9-ylmethyl)-3-benzyl-5-fluoro-3H-quinazolin-4-one;
2-(6-aminopurin-9-ylmethyl)-3-butyl-3H-quinazolin-4-one;
2-(6-aminopurin-9-ylmethyl)-3-morpholin-4-yl-3H-quinazolin-4-one;
2-(6-aminopurin-9-ylmethyl)-3-(2-chlorophenyl)-7-fluoro-3H-quinazolin-4-one; and
2-(6-aminopurin-9-ylmethyl)-5-chloro-3-o-tolyl-3H-quinazoline-4-one.

It is generally accepted that biological systems can exhibit very sensitive activities with respect to the absolute stereochemical nature of compounds. (See, E. J. Ariens, *Medicinal Research Reviews*, 6:451-466 (1986); E. J. Ariens, *Medicinal Research Reviews*, 7:367-387 (1987); K. W. Fowler, Handbook of Stereoisomers: Therapeutic Drugs, CRC Press, edited by Donald P. Smith, pp. 35-63 (1989); and S. C. Stinson, *Chemical and Engineering News*, 75:38-70 (1997.)

Therefore, the present invention includes all possible stereoisomers and geometric isomers of compounds of structural formulae (I)-(IV), and includes not only racemic compounds, but also the optically active isomers as well. When a compound of structural formulae (I)-(IV) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formulae (I)-(IV) are possible, the present invention is intended to include all tautomeric forms of the compounds. Specific stereoisomers exhibit an excellent ability to inhibit kinase activity of PI3Kδ.

The term "prodrug" as used herein refers to compounds that are rapidly transformed in vivo to a compound having structural formula (I) herein-above, for example, by hydrolysis. Prodrug design is discussed generally in Hardma et al. (Eds.), *Goodman and Gilman's The Pharmacological Basis of Therapeutics*, 9th ed., pp. 11-16 (1996). A thorough discussion is provided in Higuchi et al., *Prodrugs as Novel Delivery Systems*, Vol. 14, *AS CD Symposium Series*, and in Roche (ed.), *Bioreversible Carriers in Drug Design*, American Pharmaceutical Association and Pergamon Press (1987). Briefly, administration of a drug is followed by elimination from the body or some biotransformation whereby biological activity of the drug is reduced or eliminated. Alternatively, a biotransformation process can lead to a metabolic by-product, which is itself more active or equally active as compared to the drug initially administered. Increased understanding of these biotransformation processes permits the design of so-called "prodrugs," which, following a biotransformation, become more physiologically active in their altered state. Prodrugs, therefore, encompass pharmacologically inactive compounds that are converted to biologically active metabolites.

To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

Methods for Identifying Negative Regulators of PI3Kδ Activity

The PI3Kδ protein, as well as fragments thereof possessing biological activity, can be used for screening putative negative regulator compounds in any of a variety of drug screening techniques. A negative regulator of PI3Kδ is a compound that diminishes or abolishes the ability of PI3Kδ to carry out any of its biological functions. An example of such compounds is an agent that decreases the ability of a PI3Kδ polypeptide to phosphorylate phosphatidylinositol or to target appropriate structures within a cell. The selectivity of a compound that negatively regulates PI3Kδ activity can be evaluated by comparing its activity on the PI3Kδ to its activity on other proteins. Selective negative regulators include, for example, antibodies and other proteins or peptides that specifically bind to a PI3Kδ polypeptide, oligonucleotides that specifically bind to PI3Kδ polypeptides, and other nonpeptide compounds (e.g., isolated or synthetic organic molecules) that specifically interact with PI3Kδ polypeptides. Negative regulators also include compounds as described above, but which interact with a specific binding partner of PI3Kδ polypeptides.

Presently preferred targets for the development of selective negative regulators of PI3Kδ include, for example:

(1) cytoplasmic regions of PI3Kδ polypeptides that contact other proteins and/or localize PI3Kδ within a cell;

(2) regions of PI3Kδ polypeptides that bind specific binding partners;

(3) regions of the PI3Kδ polypeptides that bind substrate;

(4) allosteric regulatory sites of the PI3Kδ polypeptides that can or cannot interact directly with the active site upon regulatory signal;

(5) regions of the PI3Kδ polypeptides that mediate multimerization.

For example, one target for development of modulators is the identified regulatory interaction of p85 with p110δ, which can be involved in activation and/or subcellular localization of the p110δ moiety. Still other selective modulators include those that recognize specific regulatory or PI3Kδ-encoding nucleotide sequences. Modulators of PI3Kδ activity can be therapeutically useful in treatment of a wide range of diseases and physiological conditions in which aberrant PI3Kδ activity is involved.

Accordingly, the invention provides methods of characterizing the potency of a test compound as an inhibitor of PI3Kδ polypeptide, said method comprising the steps of (a) measuring activity of a PI3Kδ polypeptide in the presence of a test compound; (b) comparing the activity of the PI3Kδ polypeptide in the presence of the test compound to the activity of the PI3Kδ polypeptide in the presence of an equivalent amount of a reference compound (e.g., a PI3Kδ inhibitor compound of the invention as described herein), wherein a lower activity of the PI3Kδ polypeptide in the presence of the test compound than in the presence of the reference indicates that the test compound is a more potent inhibitor than the reference compound, and a higher activity of the PI3Kδ polypeptide in the presence of the test compound than in the presence of the reference indicates that the test compound is a less potent inhibitor than the reference compound.

The invention further provides methods of characterizing the potency of a test compound as an inhibitor of PI3Kδ polypeptide, comprising the steps of (a) determining an amount of a control compound (e.g., a PI3Kδ inhibitor compound of the invention as described herein) that inhibits an activity of a PI3Kδ polypeptide by a reference percentage of inhibition, thereby defining a reference inhibitory amount for the control compound, (b) determining an amount of a test compound that inhibits an activity of a PI3Kδ polypeptide by a reference percentage of inhibition, thereby defining a reference inhibitory amount for the test compound; (c) comparing the reference inhibitory amount for the test compound to the reference inhibitory amount for the control compound, wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. In one aspect, the method uses a reference inhibitory amount which is the amount of the compound than inhibits the activity of the PI3Kδ polypeptide by 50%, 60%, 70%, or 80%. In another aspect the method employs a reference inhibitory amount that is the amount of the compound that inhibits the activity of the PI3Kδ polypeptide by 90%, 95%, or 99%. These methods comprise determining the reference inhibitory amount of the compounds in an in vitro biochemical assay, in an in vitro cell-based assay, or in an in vivo assay.

The invention further provides methods of identifying a negative regulator of PI3Kδ activity, comprising the steps of (i) measuring activity of a PI3Kδ polypeptide in the presence and absence of a test compound, and (ii) identifying as a negative regulator a test compound that decreases PI3Kδ activity and that competes with a compound of the invention for binding to PI3Kδ. Furthermore, the invention provides methods for identifying compounds that inhibit PI3Kδ activity, comprising the steps of (i) contacting a PI3Kδ polypeptide with a compound of the invention in the presence and absence of a test compound, and (ii) identifying a test compound as a negative regulator of PI3Kδ activity wherein the compound competes with a compound of the invention for binding to PI3Kδ. The invention therefore provides a method for screening for candidate negative regulators of PI3Kδ activity and/or to confirm the mode of action of candidate such negative regulators. Such methods can be employed against other PI3K isoforms in parallel to establish comparative activity of the test compound across the isoforms and/or relative to a compound of the invention.

In these methods, the PI3Kδ polypeptide can be a fragment of p110δ that exhibits kinase activity, i.e., a fragment comprising the catalytic site of p110δ. Alternatively, the PI3Kδ polypeptide can be a fragment from the p110δ-binding domain of p85 and provides a method to identify allosteric modulators of PI3Kδ. The methods can be employed in cells expressing cells expressing PI3Kδ or its subunits, either endogenously or exogenously. Accordingly, the polypeptide employed in such methods can be free in solution, affixed to a solid support, modified to be displayed on a cell surface, or located intracellularly. The modulation of activity or the formation of binding complexes between the PI3Kδ polypeptide and the agent being tested then can be measured.

Human PI3K polypeptides are amenable to biochemical or cell-based high throughput screening (HTS) assays according to methods known and practiced in the art, including melanophore assay systems to investigate receptor-ligand interactions, yeast-based assay systems, and mammalian cell expression systems. For a review, see Jayawickreme and Kost, *Curr Opin Biotechnol*, 8:629-34 (1997). Automated and miniaturized HTS assays also are comprehended as described, for example, in Houston and Banks, *Curr Opin Biotechnol*, 8:734-40 (1997).

Such HTS assays are used to screen libraries of compounds to identify particular compounds that exhibit a desired property. Any library of compounds can be used, including chemical libraries, natural product libraries, and combinatorial libraries comprising random or designed oligopeptides, oligonucleotides, or other organic compounds.

Chemical libraries can contain known compounds, proprietary structural analogs of known compounds, or compounds that are identified from natural product screening.

Natural product libraries are collections of materials isolated from naturals sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, nonribosomal peptides, and variants (including nonnaturally occurring variants) thereof. For a review, see Cane et al., *Science,* 282:63-68 (1998).

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning, or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, *Curr Opin Biotechnol,* 8:701-07 (1997).

Once compounds have been identified that show activity as negative regulators of PI3Kδ function, a program of optimization can be under-taken in an effort to improve the potency and or selectivity of the activity. This analysis of structure-activity relationships (SAR) typically involves of iterative series of selective modifications of compound structures and their correlation to biochemical or biological activity. Families of related compounds can be designed that all exhibit the desired activity, with certain members of the family, namely those possessing suitable pharmacological profiles, potentially qualifying as therapeutic candidates.

Therapeutic Uses of Inhibitors of PI3Kδ Activity

The invention provides a method for selectively or specifically inhibiting PI3Kδ activity therapeutically or prophylactically. The method comprises administering a selective or specific inhibitor of PI3Kδ activity in an amount effective therefor. This method can be employed in treating humans or animals who are or can be subject to any condition whose symptoms or pathology is mediated by PI3Kδ expression or activity.

"Treating" as used herein refers to preventing a disorder from occurring in an animal that can be predisposed to the disorder, but has not yet been diagnosed as having it; inhibiting the disorder, i.e., arresting its development; relieving the disorder, i.e., causing its regression; or ameliorating the disorder, i.e., reducing the severity of symptoms associated with the disorder. "Disorder" is intended to encompass medical disorders, diseases, conditions, syndromes, and the like, without limitation.

The methods of the invention embrace various modes of treating an animal subject, preferably a mammal, more preferably a primate, and still more preferably a human. Among the mammalian animals that can be treated are, for example, companion animals (pets), including dogs and cats; farm animals, including cattle, horses, sheep, pigs, and goats; laboratory animals, including rats, mice, rabbits, guinea pigs, and nonhuman primates, and zoo specimens. Nonmammalian animals include, for example, birds, fish, reptiles, and amphibians.

In one aspect, the method of the invention can be employed to treat subjects therapeutically or prophylactically who have or can be subject to an inflammatory disorder. One aspect of the present invention derives from the involvement of PI3Kδ in mediating aspects of the inflammatory process. Without intending to be bound by any theory, it is theorized that, because inflammation involves processes are typically mediated by leukocyte (e.g., neutrophil, lymphocyte, etc.) activation and chemotactic transmigration, and because PI3Kδ can mediate such phenomena, antagonists of PI3Kδ can be used to suppress injury associated with inflammation.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes, reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia.

The therapeutic methods of the present invention include methods for the treatment of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The compounds of the invention have been found to inhibit superoxide release by neutrophils. Superoxide is released by neutrophils in response to any of a variety of stimuli, including signals of infection, as a mechanism of cell killing. For example, superoxide release is known to be induced by tumor necrosis factor alpha (TNFα), which is released by macrophages, mast cells, and lymphocytes upon contact with bacterial cell wall components such as lipopolysaccharide (LPS). TNFα is an extraordinarily potent and promiscuous activator of inflammatory processes, being involved in activation of neutrophils and various other cell types, induction of leukocyte/endothelial cell adhesion, pyrexia, enhanced MHC class I production, and stimulation of angiogenesis. Alternatively, superoxide release can be stimulated by formyl-Met-Leu-Phe (fMLP) or other peptides blocked at the N-terminus by formylated methionine. Such peptides are not normally found in eukaryotes, but are fundamentally characteristic of bacteria, and signal the presence of bacteria to the immune system. Leukocytes expressing the fMLP receptor, e.g., neutrophils and macrophages, are stimulated to migrate up gradients of these peptides (i.e., chemotaxis) toward loci of infection. As demonstrated herein, the compounds of the invention inhibit stimulated superoxide release by neutrophils in response to either TNFα or fMLP. Other functions of neutrophils, including stimulated exocytosis and directed chemotactic migration, also have been shown to be inhibited by the PI3Kδ inhibitors of the invention. Accordingly, the compounds of the invention can be expected to be useful in treating disorders, such as inflammatory disorders, that are mediated by any or all of these neutrophil functions.

The present invention enables methods of treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The method can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3Kδ activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolytic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage can develop in the initial minutes following the cessation of blood flow to the brain.

Ischemia also can occur in the heart in myocardial infarction and other cardiovascular disorders in which the coronary arteries have been obstructed as a result of atherosclerosis, thrombus, or spasm. Accordingly, the invention is believed to be useful for treating cardiac tissue damage, particularly damage resulting from cardiac ischemia or caused by reperfusion injury in mammals.

In another aspect, selective inhibitors of PI3Kδ activity, such as the compounds of the invention, can be employed in methods of treating diseases of bone, especially diseases in which osteoclast function is abnormal or undesirable. As shown in Example 6, below, compounds of the invention inhibit osteoclast function in vitro. Accordingly, the use of such compounds and other PI3Kδ selective inhibitors can be of value in treating osteoporosis, Paget's disease, and related bone resorption disorders.

In a further aspect, the invention includes methods of using PI3Kδ inhibitory compounds to inhibit the growth or proliferation of cancer cells of hematopoietic origin, preferably cancer cells of lymphoid origin, and more preferably cancer cells related to or derived from B lymphocytes or B lymphocyte progenitors. Cancers amenable to treatment using the method of the invention include, without limitation, lymphomas, e.g., malignant neoplasms of lymphoid and reticuloendothelial tissues, such as Burkitt's lymphoma, Hodgkins' lymphoma, non-Hodgkins lymphomas, lymphocytic lymphomas and the like; multiple myelomas; as well as leukemias such as lymphocytic leukemias, chronic myeloid (myelogenous) leukemias, and the like. In a preferred embodiment, PI3Kδ inhibitory compounds can be used to inhibit or control the growth or proliferation of chronic myeloid (myelogenous) leukemia cells.

In another aspect, the invention includes a method for suppressing a function of basophils and/or mast cells, and thereby enabling treatment of diseases or disorders characterized by excessive or undesirable basophil and/or mast cell activity. According to the method, a compound of the invention can be used that selectively inhibits the expression or activity of phosphatidylinositol 3-kinase delta (PI3Kδ) in the basophils and/or mast cells. Preferably, the method employs a PI3Kδ inhibitor in an amount sufficient to inhibit stimulated histamine release by the basophils and/or mast cells. Accordingly, the use of such compounds and other PI3Kδ selective inhibitors can be of value in treating diseases characterized by histamine release, i.e., allergic disorders, including disorders such as chronic obstructive pulmonary disease (COPD), asthma, ARDS, emphysema, and related disorders.

Pharmaceutical Compositions of Inhibitors of PI3Kδ Activity

A compound of the present invention can be administered as the neat chemical, but it is typically preferable to administer the compound in the form of a pharmaceutical composition or formulation. Accordingly, the present invention also provides pharmaceutical compositions that comprise a chemical or biological compound ("agent") that is active as a modulator of PI3Kδ activity and a biocompatible pharmaceutical carrier, adjuvant, or vehicle. The composition can include the agent as the only active moiety or in combination with other agents, such as oligo- or polynucleotides, oligo- or polypeptides, drugs, or hormones mixed with excipient(s) or other pharmaceutically acceptable carriers. Carriers and other ingredients can be deemed pharmaceutically acceptable insofar as they are compatible with other ingredients of the formulation and not deleterious to the recipient thereof.

Techniques for formulation and administration of pharmaceutical compositions can be found in *Remington's Pharmaceutical Sciences*, 18th Ed., Mack Publishing Co, Easton, Pa., 1990. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. However, the optimal pharmaceutical formulation will be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions are formulated to contain suitable pharmaceutically acceptable carriers, and can optionally comprise excipients and auxiliaries that facilitate processing of the active compounds into preparations that can be used pharmaceutically. The administration modality will generally determine the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, or dextran. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT® series available from Röhm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the active agent also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), *Methods in Cell Biology, Vol. XIV*, p. 33, Academic Press, New York (1976).

The pharmaceutical compositions comprising the agent in dosages suitable for oral administration can be formulated using pharmaceutically acceptable carriers well known in the art. The preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or excipients, which include, without limitation:

a) diluents, such as sugars, including lactose, dextrose, sucrose, mannitol, or sorbitol;

b) binders, such as magnesium aluminum silicate, starch from corn, wheat, rice, potato, etc.;

c) cellulose materials, such as methyl-cellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a salt of the active agent. Salts tend to be more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of structural formula (I) that contain basic moieties can form pharmaceutically acceptable acid addition salts with suitable acids. For example, Berge et al. describe pharmaceutically acceptable salts in detail in *J Pharm Sci*, 66:1 (1977). The salts can be prepared in situ during the final isolation and purification of the compounds of the invention or separately by reacting a free base function with a suitable acid.

Representative acid addition salts include, but are not limited to, acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoate, fumarate, hydrochloride, hydrobromide, hydroiodide, 2-hydroxyethanesulfonate (isothionate), lactate, maleate, methanesulfonate or sulfate, nicotinate, 2-naphthalenesulfonate, oxalate, pamoate, pectinate, persulfate, 3-phenylpropionate, picrate, pivalate, propionate, succinate, tartrate, thiocyanate, phosphate or hydrogen phosphate, glutamate, bicarbonate, p-toluenesulfonate, and undecanoate. Examples of acids that can be employed to form pharmaceutically acceptable acid addition salts include, without limitation, such inorganic acids as hydrochloric acid, hydrobromic acid, sulfuric acid, and phosphoric acid, and such organic acids as oxalic acid, maleic acid, succinic acid, and citric acid.

In light of the foregoing, any reference to compounds of the present invention appearing herein is intended to include compounds of structural formula (I)-(IV), as well as pharmaceutically acceptable salts and solvates, and prodrugs, thereof.

Basic addition salts can be prepared in situ during the final isolation and purification of the compounds of the invention or separately by reacting a carboxylic acid-containing moiety with a suitable base such as the hydroxide, carbonate, or bicarbonate of a pharmaceutically acceptable metal cation, or with ammonia or organic primary, secondary, or tertiary amine. Pharmaceutically acceptable basic addition salts include, but are not limited to, cations based on alkali metals or alkaline earth metals such as lithium, sodium, potassium, calcium, magnesium, and aluminum salts and the like, and nontoxic quaternary ammonium and amine cations including ammonium, tetramethylammonium, tetraethylammonium, methylammonium, dimethylammonium, trimethylammonium, ethylammonium, diethylammonium, triethylammonium, and the like. Other representative organic amines useful for the formation of base addition salts include ethylenediamine, ethanolamine, diethanolamine, piperidine, piperazine, and the like.

Basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain alkyl halides such as decyl, lauryl, myristyl, and stearyl chlorides, bromides, and iodides; aryl-alkyl halides such as benzyl and phenethyl bromides; and others. Products having modified solubility or dispersibility are thereby obtained.

Compositions comprising a compound of the invention formulated in a pharmaceutical acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits are also contemplated under the invention. For example, the kit can comprise a dosage form of a pharmaceutical composition and a package insert containing instructions for use of the composition in treatment of a medical condition. In either case, conditions indicated on the label can include treatment of inflammatory disorders, cancer, etc.

Methods of Administration of Inhibitors of PI3Kδ Activity

Pharmaceutical compositions comprising an inhibitor of PI3Kδ activity can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT®.

Surgical techniques include implantation of depot (reservoir) compositions, osmotic pumps, and the like. A preferred route of administration for treatment of inflammation can be local or topical delivery for localized disorders such as arthritis, or systemic delivery for distributed disorders, e.g., intravenous delivery for reperfusion injury or for systemic conditions such as septicemia. For other diseases, including those involving the respiratory tract, e.g., chronic obstructive pulmonary disease, asthma, and emphysema, administration can be accomplished by inhalation or deep lung administration of sprays, aerosols, powders, and the like.

For the treatment of neoplastic diseases, especially leukemias and other distributed cancers, parenteral administration is typically preferred. Formulations of the compounds to optimize them for biodistribution following parenteral administration would be desirable. The PI3Kδ inhibitor compounds can be administered before, during, or after administration of chemotherapy, radiotherapy, and/or surgery.

Moreover, the therapeutic index of the PI3Kδ inhibitor compounds can be enhanced by modifying or derivatizing the compounds for targeted delivery to cancer cells expressing a marker that identifies the cells as such. For example, the compounds can be linked to an antibody that recognizes a marker that is selective or specific for cancer cells, so that the compounds are brought into the vicinity of the cells to exert their effects locally, as previously described (see for example, Pietersz et al., *Immunol Rev,* 229:57 (1992); Trail et al., *Science,* 261:212 (1993); and Rowlinson-Busza et al., *Curr Opin Oncol,* 4:1142 (1992)). Tumor-directed delivery of these compounds enhances the therapeutic benefit by, inter alia, minimizing potential nonspecific toxicities that can result from radiation treatment or chemotherapy. In another aspect, PI3Kδ inhibitor compounds and radio-isotopes or chemotherapeutic agents can be conjugated to the same anti-tumor antibody.

For the treatment of bone resorption disorders or osteoclast-mediated disorders, the PI3Kδ inhibitors can be delivered by any suitable method. Focal administration can be desirable, such as by intraarticular injection. In some cases, it can be desirable to couple the compounds to a moiety that can target the compounds to bone. For example, a PI3Kδ inhibitor can be coupled to compounds with high affinity for hydroxyapatite, which is a major constituent of bone. This can be accomplished, for example, by adapting a tetracycline-coupling method developed for targeted delivery of estrogen to bone (Orme et al., *Bioorg Med Chem Lett,* 4 (11):1375-80 (1994)).

To be effective therapeutically in modulating central nervous system targets, the agents used in the methods of the invention should readily penetrate the blood brain barrier when peripherally administered. Compounds that cannot penetrate the blood brain barrier, however, can still be effectively administered by an intravenous route.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays. Then, dosage can be formulated in animal models to achieve a desirable circulating concentration range that modulates PI3Kδ expression or activity. As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which typically is expressed as the ratio LD50/ED50. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the $ED_{50}$ with little or no toxicity.

For the methods of the invention, any effective administration regimen regulating the timing and sequence of doses can be used. Doses of the agent preferably include pharmaceutical dosage units comprising an effective amount of the agent. As used herein, "effective amount" refers to an amount sufficient to modulate PI3Kδ expression or activity and/or derive a measurable change in a physiological parameter of the subject through administration of one or more of the pharmaceutical dosage units.

Exemplary dosage levels for a human subject are of the order of from about 0.001 milligram of active agent per kilogram body weight (mg/kg) to about 100 mg/kg. Typically, dosage units of the active agent comprise from about 0.01 mg to about 10,000 mg, preferably from about 0.1 mg to about 1,000 mg, depending upon the indication, route of administration, etc. Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

The following Examples are provided to further aid in understanding the invention, and pre-suppose an understanding of conventional methods well-known to those persons having ordinary skill in the art to which the examples pertain, e.g., the construction of vectors and plasmids, the insertion of genes encoding polypeptides into such vectors and plasmids, or the introduction of vectors and plasmids into host cells. Such methods are described in detail in numerous publications including, for example, Sambrook et al., *Molecular Cloning: A Laboratory Manual*, Cold Spring Harbor Laboratory Press (1989), Ausubel et al. (Eds.), *Current Protocols in Molecular Biology*, John Wiley & Sons, Inc. (1994); and Ausubel et al. (Eds.), *Short Protocols in Molecular Biology*, 4th ed., John Wiley & Sons, Inc. (1999). The particular materials and conditions described hereunder are intended to exemplify particular aspects of the invention and should not be construed to limit the reasonable scope thereof.

Example 1

Preparation and Purification of Recombinant PI3Kα, β, and δ

Recombinant PI3K heterodimeric complexes consisting of a p110 catalytic subunit and a p85 regulatory subunit were overexpressed using the BAC-TO-BAC® HT baculovirus expression system (GIBCO/-BRL), and then purified for use in biochemical assays. The four Class I PI 3-kinases were cloned into baculovirus vectors as follows:

p110δ: A FLAG®-tagged version of human p110δ (SEQ ID NO:1) (see Chantry et al., *J Biol Chem*, 272:19236-41 (1997)) was subcloned using standard recombinant DNA techniques into the BamH1-Xba1 site of the insect cell expression vector pFastbac HTb (Life Technologies, Gaithersburg, Md.), such that the clone was in frame with the His tag of the vector. The FLAG® system is described in U.S. Pat. Nos. 4,703,004; 4,782,137; 4,851,341; and 5,011,912, and reagents are available from Eastman Kodak Co.

p110α: Similar to the method used for p110δ, described above, a FLAG®-tagged version of p110α (see Volinia et al., *Genomics*, 24(3):427-477 (1994)) was subcloned in BamH1-HindIII sites of pFastbac HTb (Life Technologies) such that the clone was in frame with the His tag of the vector.

p110β: A p110β (see Hu et al., *Mol Cell Biol*, 13:7677-88 (1993)) clone was amplified from the human MARATHON® Ready spleen cDNA library (Clontech, Palo Alto Calif.) according to the manufacturer's protocol using the following primers:

```
5' Primer
                                     (SEQ ID NO: 3)
5'-GATCGAATTCGGCGCCACCATGGACTACAAGGAC

GACGATGACAAGTGCTTCAGTTTCATAATGCCTCC-3'

3' Primer
                                     (SEQ ID NO: 4)
5'-GATCGCGGCCGCTTAAGATCTGTAGTCTTTCCGA

ACTGTGTG-3'
```

The 5' primer was built to contain a FLAG® tag in frame with the p110β sequence. After amplification, the FLAG®-p110β sequence was subcloned using standard recombinant techniques into the EcoR1-Not1 sites of pFastbac HTa (Life Technologies), such that the clone was in frame with the His tag of the vector.

p110γ: The p110γ cDNA (see Stoyanov et al., *Science*, 269:690-93 (1995)) was amplified from a human Marathon Ready spleen cDNA library (Clontech) according to the manufacturer's protocol using the following primers:

```
5' Primer
                                     (SEQ ID NO: 5)
5'-AGAATGCGGCCGCATGGAGCTGGAGAACTATAAA

CAGCCC-3'

3' Prime
                                     (SEQ ID NO: 6)
5'-CGCGGATCCTTAGGCTGAATGTTTCTCTCCTTG

TTTG-3'
```

A FLAG® tag was subsequently attached to the 5' end of the p110γ sequence and was cloned in the BamH1-Spe1 sites of pFastbac HTb (Life Technologies) using standard recombinant DMA techniques, with the FLAG®-110γ sequence in-frame with the His tag of the vector.

p85α: A BamH1-EcoR1 fragment of FLAG®-tagged p85 cDNA (see Skolnik et al., *Cell*, 65:83-89 (1991)) was subcloned into the BamH1-EcoR1 sites of the vector pFastbac dual (Life Technologies).

Recombinant baculoviruses containing the above clones were generated using manufacturer's recommended protocol (Life Technologies). Baculoviruses expressing His-tagged p110α, p110β, or p110δ catalytic subunit and p85 subunit were coinfected into Sf21 insect cells. To enrich the heterodimeric enzyme complex, an excess amount of baculovirus expressing p85 subunit was infected, and the His-tagged p110 catalytic subunit complexed with p85 was purified on nickel affinity column. Since p110γ does not associate with p85, Sf21 cells were infected with recombinant baculoviruses expressing His-tagged p110γ only. In an alternate approach, p101 can be cloned into baculovirus, to permit coexpression with its preferred binding partner p110γ.

The 72-hour post-infected Sf21 cells (3 liters) were harvested and homogenized in a hypotonic buffer (20 mM HEPES-KOH, pH 7.8, 5 mM KCl, complete protease inhibitor cocktail (Roche Biochemicals, Indianapolis, Ind.), using a Bounce homogenizer. The homogenates were centrifuged at 1,000×g for 15 min. The supernatants were further centrifuged at 10,000×g for 20 min, followed by ultracentrifugation at 100,000×g for 60 min. The soluble fraction was immediately loaded onto 10 mL of HITRAP® nickel affinity column (Pharmacia, Piscataway, N.J.) equilibrated with 50 mL of Buffer A (50 mM HEPES-KOH, pH 7.8, 0.5 M NaCl, 10 mM imidazole). The column was washed extensively with Buffer A, and eluted with a linear gradient of 10-500 mM imidazole. Free p85 subunit was removed from the column during the washing step and only the heterodimeric enzyme complex eluted at 250 mM imidazole. Aliquots of nickel fractions were analyzed by 10% SDS-polyacrylamide gel electrophoresis (SDS-PAGE), stained with SYPRO® Red (Molecular Probes, Inc., Eugene, Oreg.), and quantitated with STORM® PhosphoImager (Molecular Dynamics, Sunnyvale, Calif.). The active fractions were pooled and directly loaded onto a 5 mL Hi-trap heparin column pre-equilibrated with Buffer B containing 50 mM HEPES-KOH, pH 7.5, 50 mM NaCl, 2 mM dithiothreitol (DTT). The column was washed with 50 mL of Buffer B and eluted with a linear gradient of 0.05-2 M NaCl. A single peak containing PI3K enzyme complex eluted at 0.8 M NaCl. SDS-polyacrylamide gel analysis showed that the purified PI3K enzyme fractions contained a 1:1 stoichiometric complex of p110 and p85 subunits. The protein profile of the enzyme complex during heparin chromatography corresponded to that of lipid kinase activity. The active fractions were pooled and frozen under liquid nitrogen.

Example 2

PI3Kδ High Throughput Screen (HTS) and Selectivity Assay

A high throughput screen of a proprietary chemical library was performed to identify candidate inhibitors of PI3Kδ activity. PI3Kδ catalyzes a phosphotransfer from γ-[$^{32}$P]ATP to PIP$_2$/PS liposomes at the D3' position of the PIP$_2$ lipid inositol ring. This reaction is MgCl$_2$ dependent and is quenched in high molarity potassium phosphate buffer pH 8.0 containing 30 mM EDTA. In the screen, this reaction is performed in the presence or absence of library compounds. The reaction products (and all unlabelled products) are transferred to a 96-well, prewetted PVDF filter plate, filtered, and washed in high molarity potassium phosphate. Scintillant is added to the dried wells and the incorporated radioactivity is quantitated.

The majority of assay operations were performed using a BIOMEK® 1000 robotics workstations (Beckman) and all plates were read using Wallac liquid scintillation plate counter protocols.

The 3× assay stocks of substrate and enzyme were made and stored in a trough (for robotics assays) or a 96-well, V-bottom, polypropylene plate (for manual assays). Reagents were stable for at least 3 hours at room temperature.

The 3× substrate for the HTS contained 0.6 mM Na$_2$ATP, 0.10 mCi/mL γ-[$^{32}$P]ATP (NEN, Pittsburgh, Pa.), 6 µM PIP$_2$/PS liposomes (Avanti Polar Lipids, Inc., Atlanta, Ga.), in 20 mM HEPES, pH 7.4.

The 3× enzyme stock for the HTS contained 1.8 nM PI3Kδ, 150 µg/mL horse IgG (used only as a stabilizer), 15 mM MgCl$_2$, 3 mM DTT in 20 mM HEPES, pH 7.4.

The chemical high throughput screen (HTS) library samples (each containing a pool of 22 compounds) in dimethyl sulfoxide (DMSO) were diluted to 18.75 µM or 37.8 µM in double distilled water, and 20 µL of the dilutions were placed in the wells of a 96-well polypropylene plate for assaying. The negative inhibitor control (or positive enzyme control) was DMSO diluted in water, and the positive inhibitor controls employed concentrations of LY294002 sufficient to provide 50% and 100% inhibition.

To the 20 µL pooled chemical library dilutions, 20 µL of 3× substrate was added. The reaction was initiated with 20 µL of 3× enzyme, incubated at room temperature for 10 minutes. This dilution established a final concentration of 200 µM ATP in the reaction volume. The reaction was stopped with 150 µL quench buffer (1.0 M potassium phosphate pH 8.0, 30 mM EDTA). A portion of the quenched solution (180 µL) was then transferred to a PVDF filter plate (Millipore #MAIP NOB prewetted with sequential 200 µL washes of 100% methanol, water, and finally 1.0 M potassium phosphate pH 8.0 wash buffer).

The PVDF filter plate was aspirated under moderate vacuum (2-5 mm Hg), washed with 5×200 µL of wash buffer, and then dried by aspiration. The filter was subsequently blotted, allowed to air dry completely, and inserted into a Wallac counting cassette with 50 µL of Ecoscint scintillation cocktail added per well. The incorporated radioactivity was quantitated, and data were analyzed, after normalizing to the enzyme positive control (set at 100%), to identify the curve intersection at the 50% inhibition value to estimate IC$_{50}$ values for the inhibitors.

A total of 57 pooled master wells were selected for deconvolution, based on combined criteria of <42% residual activity at the tested concentration, and a total accepted hit rate of no more than 0.2%. At 22 compounds per well, a total of 1254 compounds were identified through this deconvolution and individually assayed at the 1× concentration of 27.7 µM to identify which compounds exhibited the desired activity. From these assays, 73 compounds were selected and assayed further to develop IC$_{50}$ curves. From the IC$_{50}$ curve results, 34 compounds were selected for selectivity assays against PI3Kα and PI3Kβ (see assay protocol in Example 11).

From the selectivity assays, one compound, 3-(2-chiorophenyl)-2-(9H-purin-6-ylsulfanylmethyl)-3H-quinazolin-4-one (Compound D-000), was selected as being a relatively potent and selective compound. Catalog searches and selectivity assays of many analogous compounds of the potent and/or selective hits yielded only one compound that was both an active and selective analogue of D-000. This compound was purchased from Contract Services Corporation (Catalog #7232154) and differed from D-000 in substituting a phenyl group for the 2-chlorophenyl group of D-000.

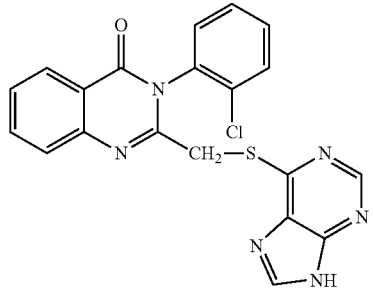

D-000

As described above, the PI 3-kinase inhibitor LY294002 (Calbiochem, La Jolla, Calif.) does not have significant selectivity among the different PI 3-kinase isoforms tested. Under our assay conditions, LY294002 inhibited all three isoforms of PI 3-kinases with an IC$_{50}$ of 0.3 to 1 µM. However, when the compound D-000 was tested against the same PI 3-kinase isoforms distinct selectivity was observed. Specifically, as shown in FIG. 1, D-000 inhibited the activity of the δ isoform of PI3K with an IC$_{50}$ of approximately 0.3 µM, whereas under similar conditions it did not inhibit activities of the α and β isoforms at a limit of 100 µM compound. These results show that D-000 selectively inhibits PI3Kδ activity.

Examples 3-7

Since PI3Kδ is expressed at significant levels only in leukocytes, it is important to study the effects of the PI3Kδ-selective inhibitor on leukocyte functions. Accordingly, the effects of PI3Kδ inhibition in several types of leukocytes were examined. Neutrophils were examined to determine the effects that selective inhibition of PI3Kδ might elicit (Example 3, below). It surprisingly was found that selective inhibition of PI3Kδ activity appears to be significantly associated with inhibition of some but not all functions characteristic of activated neutrophils. In addition, the effects of PI3Kδ inhibition on B cell and T cell function also were tested (Examples 4-5, below). Moreover, as PI3Kδ also is expressed in osteoclasts, the effect of PI3Kδ inhibition on the function of these specialized cells was studied (Example 6, below).

Example 3

Characterization of Role of PI3Kδ in Neutrophil Function

The effects of a PI3Kδ inhibitor of the invention, i.e., D-000, on neutrophil functions such as superoxide generation, elastase exocytosis, chemotaxis, and bacterial killing were tested.

A. Preparation of Neutrophils from Human Blood

Aliquots (8 mL) of heparinized blood from healthy volunteers were layered on 3 mL cushions of 7.3% FICOLL® (Sigma, St. Louis, Mo.) and 15.4% HYPAQUE® (Sigma) and centrifuged at 900 rpm for 30 min at room temperature in a table top centrifuge (Beckman). The neutrophil-rich band just above the FICOLL®-HYPAQUE® cushion was collected and washed with Hanks' balanced salt solution (HBSS) containing 0.1% gelatin. Residual erythrocytes were removed by hypotonic lysis with 0.2% NaCl. The neutrophil preparation was washed twice with HBSS containing 0.1% gelatin and used immediately.

B. Measurement of Super Oxide Production from Neutrophils

Superoxide generation is one of the hall-marks of neutrophil activation. A variety of activators potentiate superoxide generation by neutrophils. The effect of the PI3Kδ inhibitor D-000 on superoxide generation by three different agonists: TNF1α, IgG, and fMLP, each representing separate classes of activator, was measured. Superoxide generated by the neutrophils was measured by monitoring the change in absorbance upon reduction of cytochrome C by modification of the method described by Green et al., (pp. 14.5.1-14.5.11 in Supp. 12, *Curr Protocols Immunol* (Eds., Colligan et al.) (1994)), as follows. Individual wells of a 96-well plate were coated overnight at 4° C. with 50 µL of 2 mg/mL solution of human fibrinogen or IgG. The wells were washed with PBS and the following reagents were added to each well: 50 µL of HBSS or superoxide dismutase (1 mg/mL), 50 µL of HBSS or TNF1α (50 ng/mL), 50 µL cytochrome C (2.7 mg/mL), and 100 µL of purified human neutrophil suspension ($2\times10^6$ cells/mL). The plate was centrifuged for 2 min at 200 rpm and absorbance at 550 nm was monitored for 2 hr. To measure the relative amounts of superoxide generated, values obtained from the superoxide dismutase-containing wells were subtracted from all, and normalized to the values obtained from the wells without any inhibitor.

Figure 2:
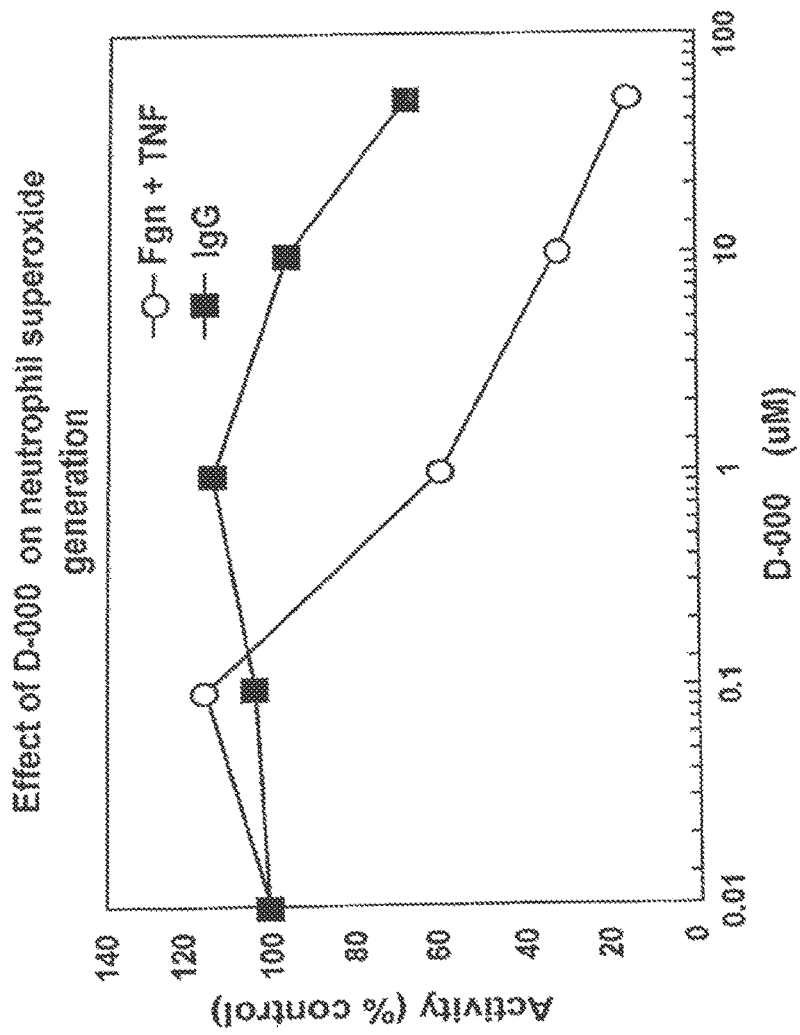
FIG. 2 shows the effect of a selective PI3Kδ inhibitor on superoxide generation by human neutrophils in the presence of TNF or IgG.

As shown in FIG. 2, the PI3Kδ inhibitor D-000 inhibits TNF-induced superoxide generation by neutrophils in a concentration dependent manner. Superoxide generation induced by TNF was reduced to its half-maximal value at about 3 µM D-000. FIG. 2 also reveals that superoxide generation induced by IgG was not significantly inhibited by D-000. In fact, even at 10 µM this PI3Kδ inhibitor did not have any effect on superoxide generation induced by IgG.

Figure 3:
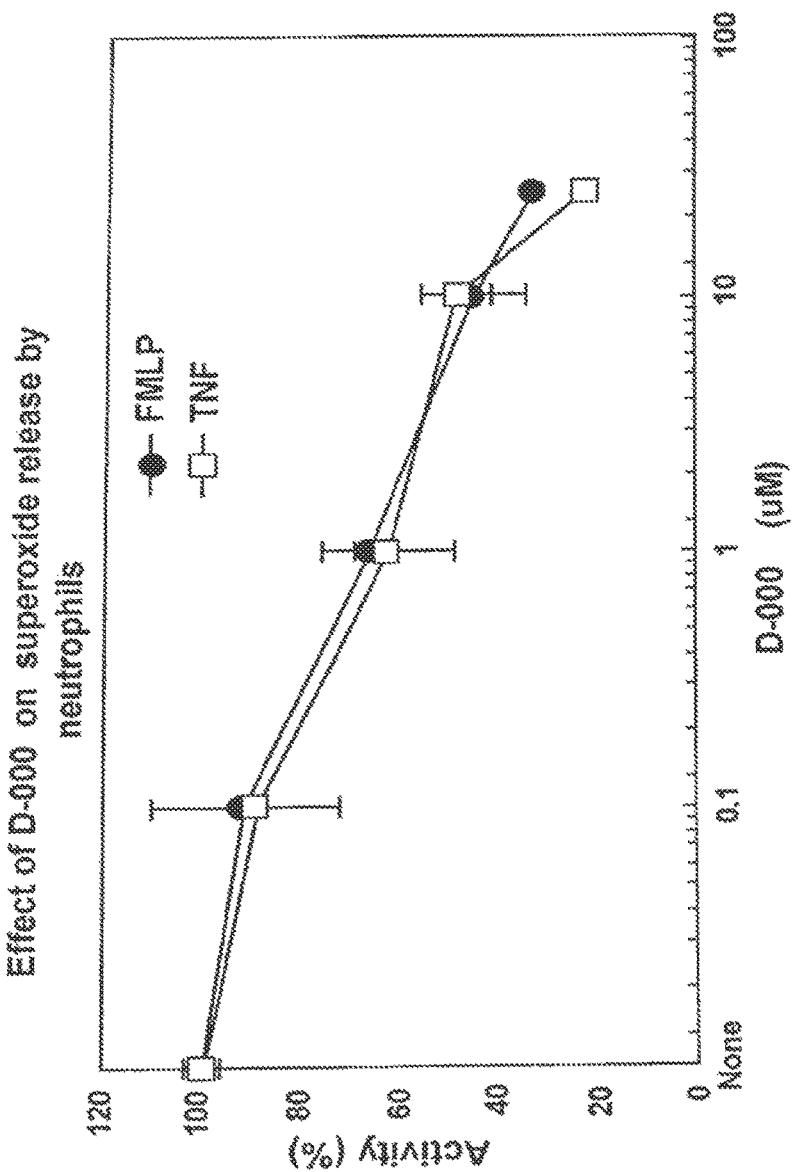
FIG. 3 shows the effect of a selective PI3Kδ inhibitor on superoxide generation by human neutrophils in the presence of TNF or fMLP.

Next, the effect of D-000 on superoxide generation induced by another potent inducer, the bacterial peptide, formylated-Met-Leu-Phe (fMLP) was studied. Like the TNF-induced superoxide generation, fMLP-induced superoxide generation also was inhibited by D-000 (FIG. 3). These results show that the PI3Kδ inhibitor D-000 can prevent stimulus specific induction of superoxide generation by neutrophils, indicating that PI3Kδ is involved in this process.

C. Measurement of Elastase Exocytosis from Neutrophils

Figure 4:
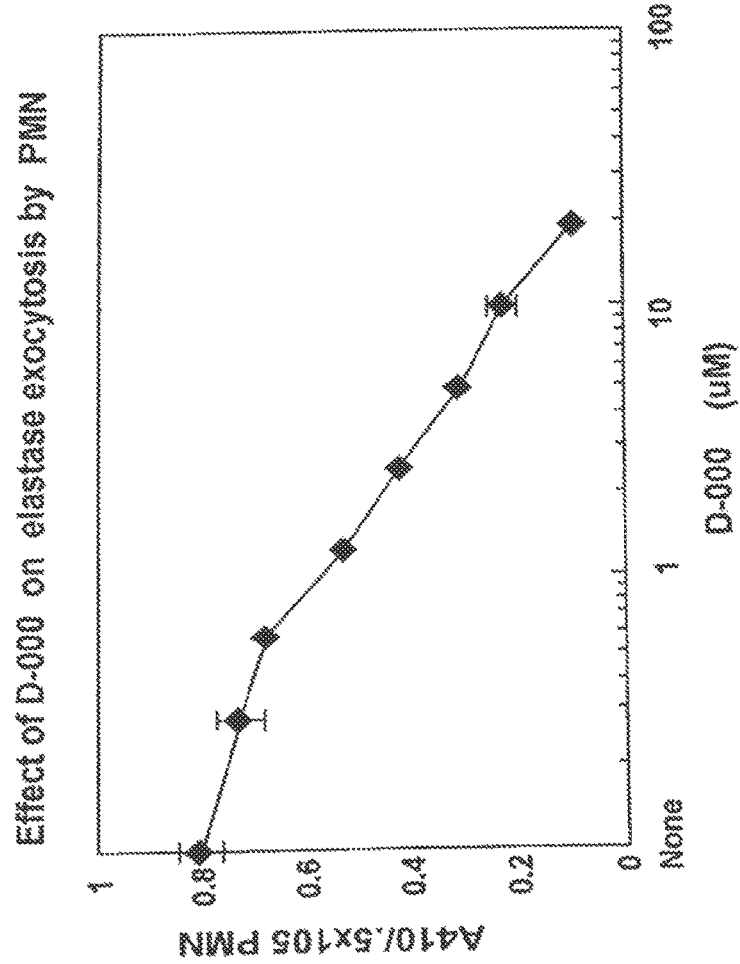
FIG. 4 shows the effect of a selective PI3Kδ inhibitor on elastase exocytosis in the presence of fMLP by human neutrophils.

In addition to superoxide generation, activated neutrophils also respond by releasing several proteases that are responsible for the destruction of tissues and cartilage during inflammation. As an indication of protease release, the effect of D-000 on elastase exocytosis was measured. Elastase exocytosis was quantitated by modification of the procedure described by Ossanna et al. (J Clin Invest, 77:1939-1951 (1986)), as follows. Purified human neutrophils ($0.2\times10^6$) (treated with either DMSO or a serial dilution of D-000 in DMSO) were stimulated with fMLP in PBS containing 0.01 mg/mL cytochalasin B, 1.0 µM sodium azide ($NaN_3$), 5 µg/mL L-methionine and 1 µM fMLP for 90 min at 37° C. in a 96-well plate. At the end of the incubation period, the plate was centrifuged for 5 min at 1000 rpm, and 90 µL of the supernatant was transferred to 10 µL of 10 mM solution of an elastase substrate peptide, MeO-sue-Ala-Ala-Pro-Val-pNA, wherein MeO-suc=methoxy-succinyl; pNA=p-nitroanilide (Calbiochem, San Diego, Calif.). Absorbance at 410 nm was monitored for 2 hr in a 96-well plate reader. To measure the relative amounts of elastase exeytosed, all absorbance values were normalized to the values without any inhibitor. As shown in FIG. 4, the PI3Kδ inhibitor D-000 inhibits fMLP-induced elastase exocytosis significantly, and does so in a dose-dependent fashion. Inhibition was half-maximal at a concentration of about 2-3 µM D-000.

D. Measurement of fMLP-Induced Human Neutrophil Migration

Neutrophils have the intrinsic capacity to migrate through tissues, and are one of the first cell types to arrive at the sites of inflammation or tissue injury. The effect of D-000 on neutrophil migration towards a concentration gradient of fMLP was measured. The day before the migration assays were performed, 6-well plates were coated with recombinant ICAM-1/Fc fusion protein (Van der Vieren et al., *Immunity*, 3:683-690 (1995)) (25 µg/mL in bicarbonate buffer, pH 9.3) and left overnight at 4° C. After washing, 1% agarose solution, in RPMI-1640 with 0.5% bovine serum albumin (BSA), was added to wells with or without an inhibitor, and plates were placed into a refrigerator before punching holes in the gelled agarose to create plaques (1 central hole surrounded by 6 peripheral ones per well).

Human neutrophils were obtained as described above, and resuspended in RPMI medium supplemented with 0.5% BSA at $5\times10^6$ cells/mL. After combining equal volumes of neutrophil suspension and medium (either with DMSO or a serial dilution of the test compound in DMSO), neutrophils were aliquoted into the peripheral holes, while the central hole received fMLP (5 µM). Plates were incubated at 37° C. in the presence of 5% $CO_2$ for 4 hr, followed by termination of migration by the addition of 1% glutaraldehyde solution in D-PBS. After re-moving the agarose layer, wells were washed with distilled water and dried.

Analysis of neutrophil migration was conducted on a Nikon DIAPHOT® inverted microscope (lx objective) video workstation using the NIH 1.61 program. Using Microsoft Excel and Table Curve 4 (SSPS Inc., Chicago Ill.) programs, a migration index was obtained for each of the studied conditions. Migration index was defined as the area under a curve representing number of migrated neutrophils versus the net distance of migration per cell.

Figure 5:
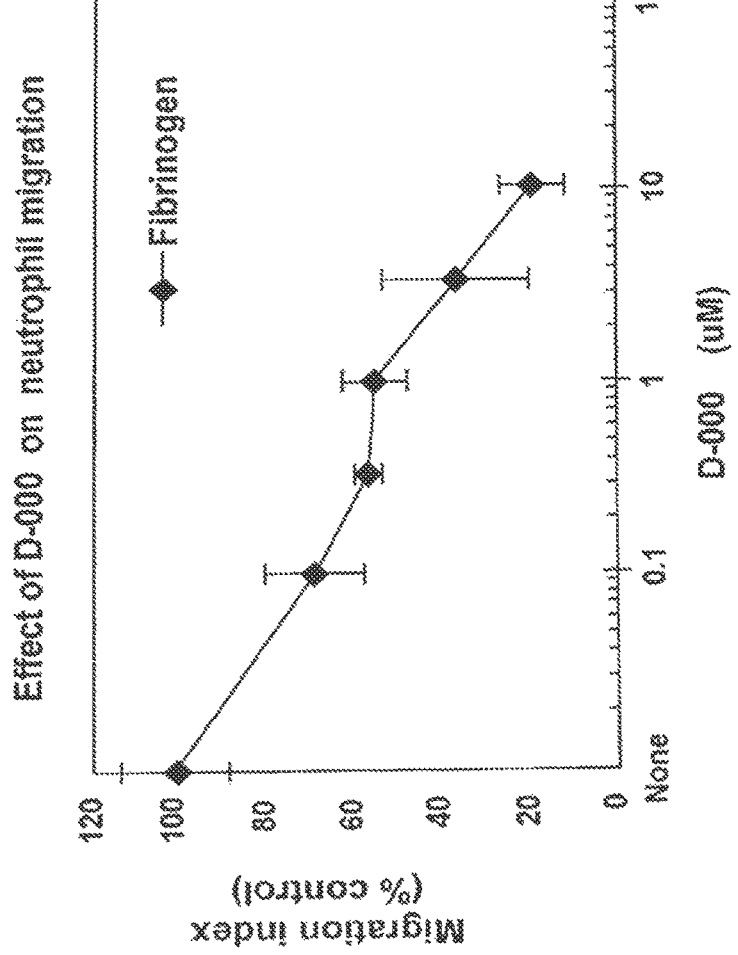
FIG. 5 shows the effect of a selective PI3Kδ inhibitor on fMLP-induced chemotaxis by human neutrophils.

As shown in FIG. 5, the PI3Kδ inhibitor D-000 had a profound effect on neutrophil migration, inhibiting this activity in a dose-dependent manner. The $EC_{50}$ of this compound for inhibition of neutrophil migration in this assay is about 1 µM. Based on a visual inspection of the recorded paths of the cells in this assay, it appears that the total path length for the neutrophils was not significantly affected by the test compound. Rather, the compound affected neutrophil orientation or sense of direction, such that instead of migrating along the axis of the chemoattractant gradient, the cells migrated in an undirected or less directed manner.

E. Measurement of Bactericidal Capacity of Neutrophils

Given that the PI3Kδ inhibitor D-000 affects certain neutrophil functions detailed above, it was of interest to see whether the compound affects neutrophil-mediated bacterial killing. The effect of D-000 on neutrophil-mediated *Staphylococcus aureus* killing was studied according to the method described by Clark and Nauseef (pp. 7.23.4-7.23.6 in Vol. 2, Supp. 6, *Curr Protocols Immunol* (Eds., Colligan et al.) (1994)). Purified human neutrophils ($5 \times 10^6$ cells/mL) (treated with either DMSO or a serial dilution of D-000 in DMSO) were mixed with autologous serum. Overnight-grown *S. aureus* cells were washed, resuspended in HBSS, and added to the serum-opsonized neutrophils at a 10:1 ratio. Neutrophils were allowed to internalize the bacteria by phagocytosis by incubation at 37° C. for 20 min. The noninternalized bacteria were killed by 10 units/mL lysostaphin at 37° C. for 5 min and the total mixture was rotated at 37° C. Samples were withdrawn at various times for up to 90 min and the neutrophils were lysed by dilution in water. Viable bacteria were counted by plating appropriate dilutions on trypticase-soy-agar plate and counting the *S. aureus* colonies after overnight growth.

Figure 6:
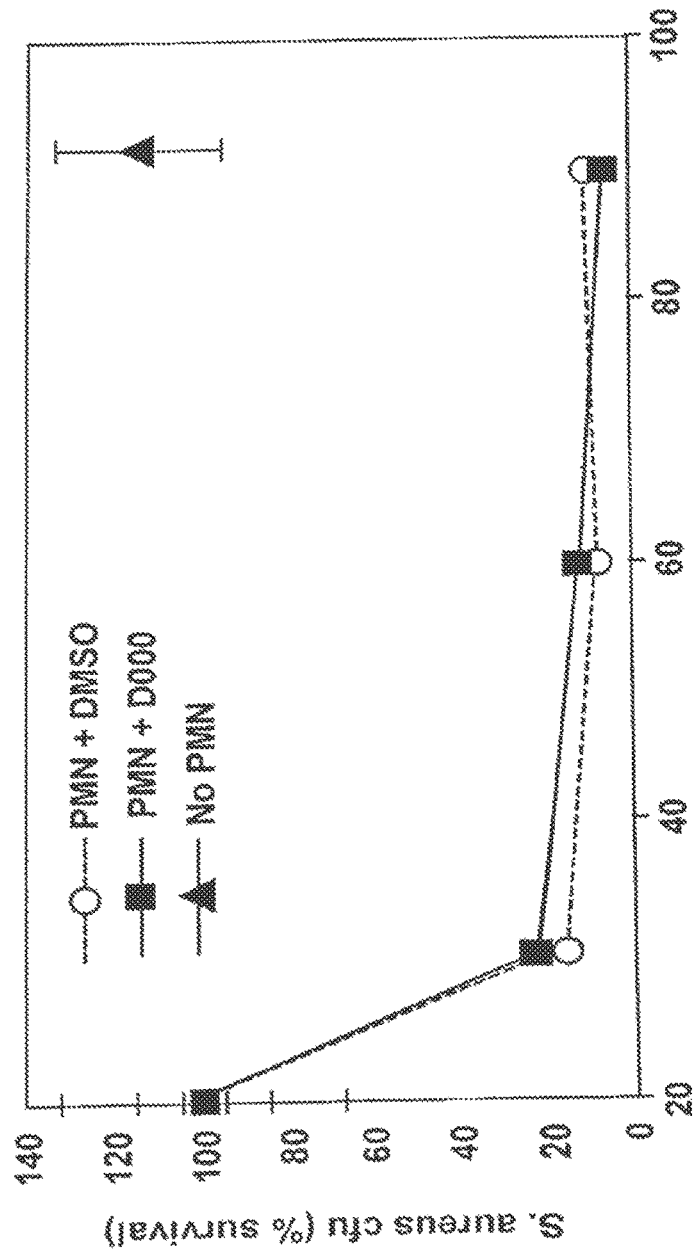
FIG. 6 shows that a selective PI3Kδ inhibitor does not affect phagocytosis and killing of S. aureus by neutrophils.

As shown in FIG. 6, neutrophil-mediated killing of *S. aureus* was similar in samples treated with DMSO (control) and with D-000. These results indicate that the PI3Kδ inhibitor does not significantly affect the ability of neutrophils to kill *S. aureus*, suggesting that PI3Kδ is not involved in this pathway of neutrophil function.

Example 4

Characterization of Role of PI3Kδ in B Lymphocyte Function

The effects of the PI 3-kinase inhibitor on B cell functions including classical indices such as antibody production and specific stimulus-induced proliferation also were studied.

A. Preparation and Stimulation of B Cells from Peripheral Human Blood

Heparinized blood (200 mL) from healthy volunteers was mixed with an equal volume of D-PBS, layered on 10×10 mL FICOLL-PAQUE® (Pharmacia), and centrifuged at 1600 rpm for 30 min at room temperature. Peripheral blood mononuclear cells (PBMC) were collected from the FICOLL®/serum interface, overlayed on 10 mL fetal bovine serum (FBS) and centrifuged at 800 rpm for 10 min to remove platelets. After washing, cells were incubated with DYNAL® Antibody Mix (B cell kit) (Dynal Corp., Lake Success, N.Y.) for 20 min at 4-8° C. Following the removal of unbound antibody, PBL were mixed with anti-mouse IgG coated magnetic beads (Dynal) for 20 min at 4-8° C. with gentle shaking followed by elimination of labeled non-B cells on the magnetic bead separator. This procedure was repeated once more. The B cells were resuspended in RPMI-1640 with 10% FBS, and kept on ice until further use.

B. Measurement of Antibody Production by Human B Cells

To study antibody production, B cells were aliquoted at $50-75 \times 10^3$ cells/well into 96-well plate with or without inhibitor, to which IL-2 (100 U/mL) and PANSORBIN® (Calbiochem) *Staphylococcus aureus* cells (1:90,000) were added. Part of the media was removed after 24-36 hr, and fresh media (with or without inhibitor) and IL-2 were added. Cultures were incubated at 37° C., in the presence of a $CO_2$ incubator for additional 7 days. Samples from each condition (in triplicate) were removed, and analyzed for IgG and IgM, as measured by ELISA. Briefly, IMMULON® 4 96-well plates were coated (50 µL/well) with either 150 ng/mL donkey antihuman IgG (H+L) (Jackson ImmunoResearch, West Grove Pa.), or 2 µg/mL donkey antihuman IgG+IgM (H+L) (Jackson ImmunoResearch) in bicarbonate buffer, and left overnight at 4° C. After 3× washing with phosphate buffered saline containing 0.1% TWEEN®-80 (PBST) (350 µL/well), and blocking with 3% goat serum in PBST (100 µL/well) for 1 hr at room temperature, samples (100 µL/well) of B cell spent media diluted in PBST were added. For IgG plates the dilution range was 1:500 to 1:10000, and for IgM 1:50 to 1:1000. After 1 hr, plates were exposed to biotin-conjugated antihuman IgG (100 ng/mL) or antihuman IgM (200 ng/mL) (Jackson ImmunoResearch) for 30 min, following by streptavidin-HRP (1:20000) for 30 min, and finally, to TMB solution (1:100) with $H_2O_2$ (1:10000) for 5 min, with 3×PBST washing between steps. Color development was stopped by $H_2SO_4$ solution, and plates were read on an ELISA plate reader.

Figure 7:
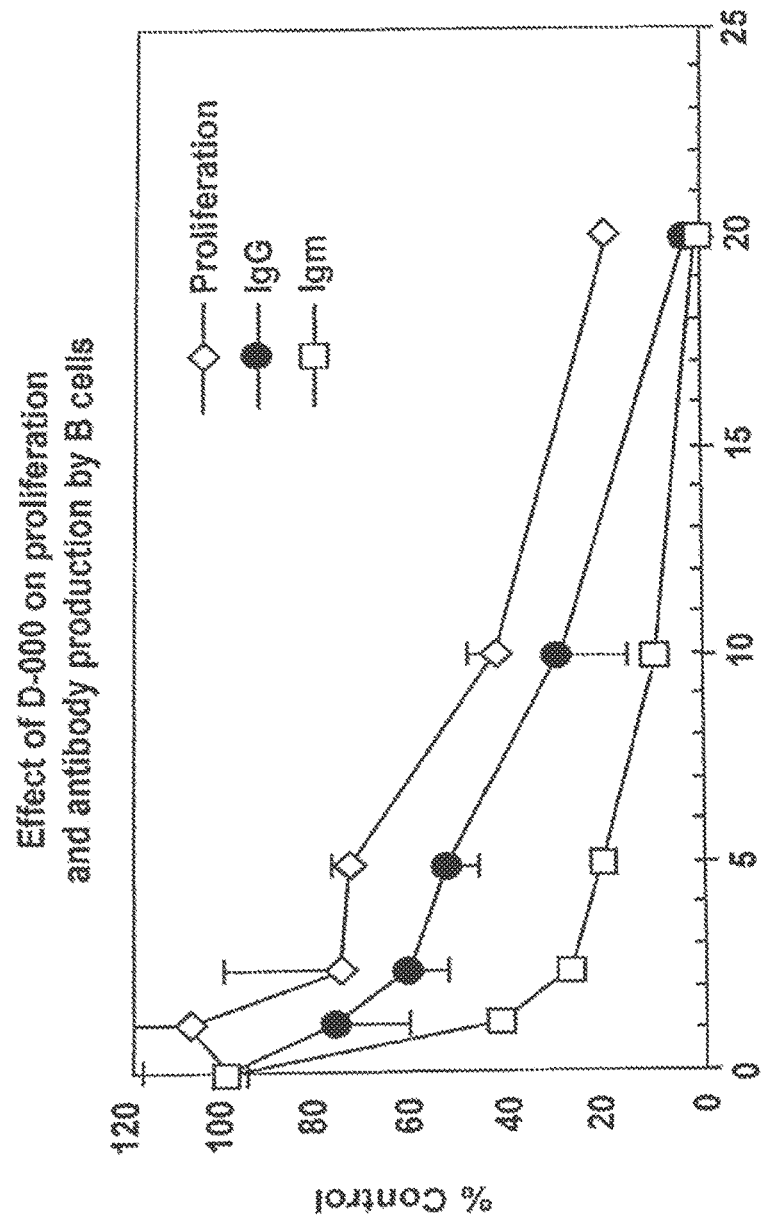
FIG. 7 shows the effect of a selective PI3Kδ inhibitor on proliferation and antibody production by human B lymphocytes.

As shown in FIG. 7, D-000 significantly inhibited antibody production. IgM production was affected more than IgG production: half-maximal inhibition of IgM production was observed at about 1 µM, versus about 7 µM for comparable inhibition of IgG production.

C. Measurement of B Cell Proliferation in Response to Cell Surface IgM Stimulation In the above experiment, the B cells were stimulated using PANSORBIN®. The effect of D-000 on B cell proliferation response when they were stimulated through their cell surface IgM using anti-IgM antibody also was measured. Murine splenocytes (Balb/c) were plated into 96-well microtiter plates at $2 \times 10^5$ cells per well in 10% FBS/RPMI. Appropriate dilutions of test inhibitor in complete medium were added to the cells and the plates were incubated for 30-60 minutes prior to the addition of stimulus. Following the preincubation with test inhibitor an $F(ab')_2$ preparation of goat antibody specific for the µ-chain of mouse IgM was added to the wells at a final concentration of 25 µg/mL. The plates were incubated at 37° C. for 3 days and 1 µCi of [$^3$H]-thymidine was added to each well for the final four hours of culture. The plates were harvested onto fiber filters washed and the incorporation of radiolabel was determined using a beta counter (Matrix 96, Packard Instrument Co., Downers Grove, Ill.) and expressed as counts per minute (CPM).

Figure 8:
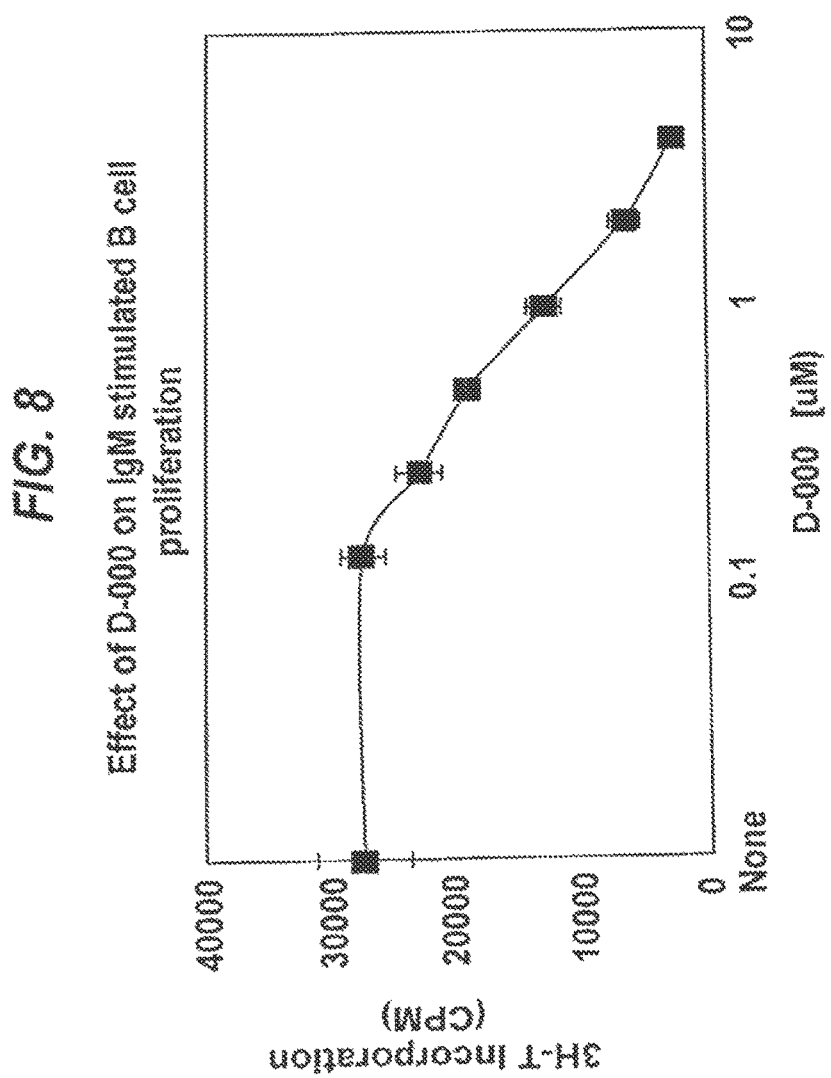
FIG. 8 shows the effect of a selective PI3Kδ inhibitor on anti-IgM stimulated mouse splenic B lymphocyte proliferation.

FIG. 8 shows the effect of D-000 on anti-IgM stimulated proliferation of B cells. The compound inhibited anti-IgM-stimulated B cell proliferation in a dose-dependent manner. At about 1 μM, proliferation was reduced to its half-maximal value.

Because the compound D-000 inhibits B cell proliferation, it is envisioned that this compound and other PI3Kδ inhibitors could be used to suppress undesirable proliferation of B cells in clinical settings. For example, in B cell malignancy, B cells of various stages of differentiation show unregulated proliferation. Based on the results shown above, one can infer that PI3Kδ selective inhibitors could be used to control, limit, or inhibit growth of such cells.

Example 5

Characterization of Role of PI3Kδ in T Lymphocyte Function

T cell proliferation in response to costimulation of CD3+ CD28 was measured. T cells were purified from healthy human blood by negative selection using antibody coated magnetic beads according to the manufacturer's protocol (Dynal) and resuspended in RPMI. The cells were treated with either DMSO or a serial dilution of D-000 in DMSO and plated at 1×10$^5$ cells/well on a 96-well plate precoated with goat antimouse IgG. Mouse monoclonal anti-CD3 and anti-CD28 antibodies were then added to each well at 0.2 ng/mL and 0.2 μg/mL, respectively. The plate was incubated at 37° C. for 24 hr and [$^3$H]-thymidine (1 μCi/well) was added. After another 18 hr incubation the cells were harvested with an automatic cell harvester, washed and the incorporated radioactivity was quantified.

Although the PI3Kδ inhibitor D-000 inhibited anti-CD3- and anti-CD28-induced proliferation of T cells, its effect is not as strong as its effect on B cells or on some of the functions of neutrophils. Half-maximal inhibition of thymidine incorporation was not achieved at the highest tested concentration, i.e., 10 μM D-000.

Example 6

Characterization of Role of PI3Kδ in Osteoclast Function

To analyze the effect of the PI3Kδ inhibitor D-000 on osteoclasts, mouse bone marrow cells were isolated and differentiated them to osteoclasts by treating the cells with Macrophage Colony Stimulating Factor$^{-1}$ (mCSF$^{-1}$) and Osteoprotegerin Ligand (OPGL) in serum-containing medium (αMEM with 10% heat-inactivated FBS; Sigma) for 3 days. On day four, when the osteoclasts had developed, the medium was removed and cells were harvested. The osteoclasts were plated on dentine slices at 10$^5$ cells/-well in growth medium, i.e., αMEM containing 1% serum and 2% BSA with 55 μg/mL OPGL and 10 ng/mL mCSF-1. After 3 hr, the medium was changed to 1% serum and 1% BSA, with or without osteopontin (25 μg/mL) and the PI3K inhibitors (100 nM). The medium was changed every 24 hours with fresh osteopontin and the inhibitors. At 72 hr, the medium was removed, and the dentine surfaces were washed with water to remove cell debris and stained with acid hematoxylin. Excess stain was washed and the pit depths were quantitated using confocal microscopy.

As shown in Table 1, in two experiments, the PI 3-kinase inhibitors had an inhibitory effect on osteoclast function. Both the nonspecific inhibitors LY294002 and wortmannin inhibited osteoclast activity. However, the PI3Kδ inhibitor D-000 had the most profound effect, as at 100 nM this compound almost completely inhibited the osteoclast activity.

TABLE 1

| Osteopontin (OPN) | D-000 + OPN | LY294002 + OPN | Wortmannin + OPN |
|---|---|---|---|
| 10 ± 0.5 | 1 | 4.6 ± 0.22 | 5.7 ± 0.6 |
| 9 ± 0.4 | 1 | 5.8 ± 0.5 | 5 ± 0.5 |

Example 7

Characterization of Role of PI3Kδ in Basophil Function

Assessment of the effect of a compound of the invention on basophil function was tested using a conventional histamine release assay, generally in accordance with the method described in Miura et al., *J Immunol,* 162:4198-206 (1999). Briefly, enriched basophils were preincubated with test compounds at several concentrations from 0.1 nM to 1,000 nM, for 10 min at 37° C. Then, polyclonal goat antihuman IgE (0.1 μg/mL) or fMLP was added, and allowed to incubate for an additional 30 min. Histamine released into the supernatant was measured using an automated fluorometric technique. Two compounds were tested, shown below.

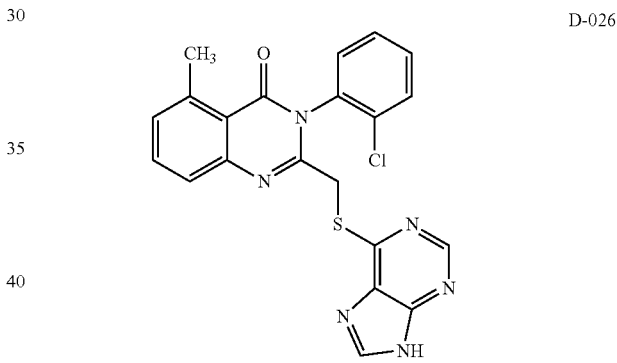

D-026

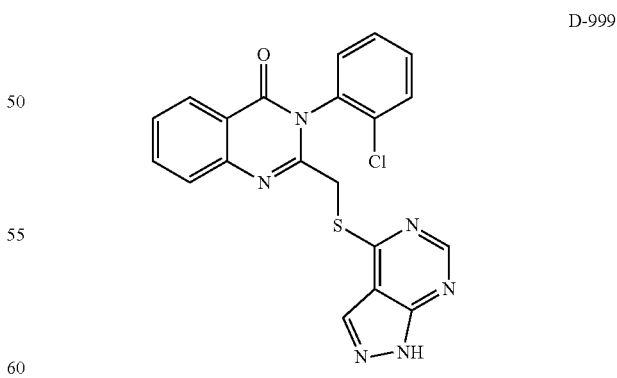

D-999

A dose-dependent decrease in histamine release was observed for 3-(2-chlorophenyl)-5-methyl-2-(9H-purin-6-ylsulfanylmethyl)-3H-quinazolin-4-one (D-026) when the basophils were stimulated with anti-IgE. This suppression of histamine release was essentially 100% at 1,000 nM, with an EC$_{50}$ of about 25 nM. Another compound, 3-(2-chlorophenyl)-2-(1H-pyrazolo[3,4-d]pyrimidin-4-ylsulfanylmethyl)-3H-quinazolin-4-one (D-999), in which the purine ring structure is rearranged, was less efficacious in the inhibition of histamine release. Neither compound elicited any effect when the basophils were stimulated with fMLP. For comparison, the nonselective PI3K inhibitor LY294002 was tested at 0.1 nM and 10,000 nM, showing close to 100% inhibition of histamine release at the highest concentration.

These data indicate that inhibitors of PI 3-kinase delta activity can be used to suppress release of histamine, which is one of the mediators of allergy. Since the activity of various PI 3-kinases are required for protein trafficking, secretion, and exocytosis in many cell types, the above data suggest that histamine release by other cells, such as mast cells, also can be disrupted by PI 3-kinase delta-selective inhibitors.

CHEMICAL SYNTHESIS EXAMPLES

Specific nonlimiting examples of compounds of the invention are provided below. It is understood in the art that protecting groups can be employed where necessary in accordance with general principles of synthetic chemistry. These protecting groups are removed in the final steps of the synthesis under basic, acidic, or hydrogenolytic conditions readily apparent to those persons skilled in the art. By employing appropriate manipulation and protection of any chemical functionalities, synthesis of compounds of structural formula (I) not specifically set forth herein can be accomplished by methods analogous to the schemes set forth below.

Unless otherwise noted, all starting materials were obtained from commercial suppliers and used without further purification. All reactions and chromatography fractions were analyzed by thin-layer chromatography (TLC) on 250 mm silica gel plates, visualized with ultraviolet (UV) light or iodine ($I_2$) stain. Products and intermediates were purified by flash chromatography or reverse-phase high performance liquid chromatography.

The following abbreviations are used in the synthetic examples: aq (aqueous), $H_2O$ (water), $CHCl_3$ (chloroform), HCl (hydrochloric acid), MeOH (methanol), NaOH (sodium hydroxide), NaOMe (sodium methoxide), TFA (trifluoroacetic acid), $K_2CO_3$ (potassium carbonate), $SOCl_2$ (thionyl chloride), $CH_2Cl_2$ (methylene chloride), EtOAC (ethyl acetate), DMF (dimethylformamide), EtOH (ethanol), DMSO (dimethyl sulfoxide), $NaHCO_3$ (sodium bicarbonate), TLC (thin layer chromatography), HPLC (high performance liquid chromatography), HOBT (hydroxybenzotriazole), EDC (ethyldiethylaminopropylcarbodiimide), DIEA (diisopropylethylamine), and HOAc (acetic acid).

I. General Procedures

Procedure A

Thionyl chloride was added to a rapidly stirring solution of anthranilic acid or benzoic acid in benzene, and the mixture was stirred at reflux for 5 to 18 hours. The reaction was concentrated in vacuo, and stripped down twice with benzene. The resulting oil was dissolved in $CHCl_3$ and to that solution was added the appropriate aniline. The reaction mixture was heated to reflux and stirred until complete, as determined by TLC, at which point the reaction mixture was cooled to ambient temperature. The precipitate was removed by filtration, and the filtrate concentrated in vacuo. The crude product was purified by chromatography and/or recrystallization from MeOH to provide amides 1a-1r.

Procedure B

To a rapidly stirring suspension of an amide in glacial acetic acid was added chloroacetyl chloride. The reaction mixture was heated to 120° C., and allowed to stir at that temperature until complete, as determined by TLC. After brief cooling, the reaction mixture was concentrated in vacuo. The crude residue was purified by extraction, chromatography, and/or recrystallization to provide chlorides 2a-2r.

Procedure C

A mixture of a chloride, either a nitrogen or a sulfur nucleophile, for example, mercaptopurine monohydrate or adenine, and $K_2CO_3$ in DMF was stirred at room temperature for 15-72 hours. The resulting suspension was poured into water, and kept at 4° C. for several hours. The crude solid was filtered, washed with water, and purified by chromatography or recrystallization to provide the final product.

Example 8

Preparation of Intermediate Compounds: Amides

2-Amino-N-(2-chlorophenyl)-4,5-dimethoxybenzamide
(1a)

Prepared according to Procedure A using 4,5-dimethoxyanthranilic acid (5.0 g, 25.4 mmol) and $SOCl_2$ (5.5 mL, 76.1 mmol) in benzene (100 mL), followed by 2-chloroaniline (6.7 mL, 63.5 mmol) and $CHCl_3$ (75 mL). The product was washed with aqueous $NaHCO_3$ (2×25 mL) and HCl (0.5 M, 75 mL) and purified by chromatography in $CH_2Cl_2$ to provide 4.3 g of a brown foam (55%). $^1$H NMR ($CDCl_3$) δ: 8.42 (dd, J=1.5, 8.3 Hz, 1H); 8.32 (br s, 1H); 7.40 (dd, J=1.4, 8.0 Hz, 1H); 7.31 (dt, J=1.4, 7.9 Hz, 1H); 7.05 (dt, J=1.5, 7.7 Hz, 1H); 7.03 (s, 1H); 6.24 (s, 1H); 3.88 (s, 3H); 3.87 (s, 3H). MS (ES): m/z 307.0 (M+).

2-Amino-5-bromo-N-(2-chlorophenyl)benzamide
(1b)

Prepared according to Procedure A using 2-amino-5-bromobenzoic acid (5.0 g, 23.1 mmol) and $SOCl_2$ (7.0 mL, 95.9 mmol) in benzene (50 mL), followed by 2-chloroaniline (7.3 mL, 69.3 mmol) and $CHCl_3$ (50 mL). The product was purified by two chromatographies in $CH_2Cl_2$ to provide 1.48 g of a yellow orange solid (20%). $^1$H NMR ($CDCl_3$) δ: 8.36 (dd, J=1.2, 8.2 Hz, 1H); 8.20 (br s, 1H); 7.62 (d, J=2.1 Hz, 1H); 7.42 (dd, J=1.3, 8.0 Hz, 1H); 7.34 (dd, J=2.2, 8.8 Hz, 1H); 7.28-7.33 (m, 1H); 7.09 (dt, J=1.4, 7.7 Hz, 1H); 6.62 (d, J=8.7 Hz, 1H); 5.57 (br s, 2H).

2-Amino-N-(2-chlorophenyl)-4-fluorobenzamide
(1c)

Prepared according to Procedure A using 2-amino-4-fluorobenzoic acid (1.15 g, 7.41 mmol) and $SOCl_2$ (1.4 mL, 18.5 mmol) in benzene (25 mL), followed by 2-chloroaniline (1.6 mL, 14.8 mmol) and $CHCl_3$ (25 mL). The product was chromatographed in $CH_2Cl_2$, then triturated from hexanes to provide 1.02 g of an off-white solid (52%). $^1$H NMR ($CDCl_3$) δ: 12.91 (br s, 1H); 8.72 (dd, J=2.7, 12 Hz, 1H); 8.34 (dd, J=6.4, 9.2 Hz, 1H); 8.29 (dd, J=5.9, 8.8 Hz, 1H); 7.81 (dd, J=6.2, 8.8 Hz, 1H); 7.28 (dt, J=2.4, 8.4 Hz, 1H); 7.21 (dd, J=2.4, 9.0 Hz, 1H); 6.92 (ddd, J=2.4, 7.3, 9.1

Hz, 1H); 6.54 (ddd, J=2.4, 7.8, 8.8 Hz, 1H); 6.45 (dd, J=2.4, 11 Hz, 1H); 5.93 (br s, 2H). MS (ES): m/z 265.0 (M+).

2-Amino-5-chloro-N-(2-chlorophenyl)benzamide (1d)

Prepared according to Procedure A using 2-amino-5-chlorobenzoic acid (2.0 g, 11.7 mmol) and $SOCl_2$ (2.2 mL, 29.2 mmol) in benzene (50 mL), followed by 2-chloroaniline (2.5 mL, 23.3 mmol) and $CHCl_3$ (50 mL). The product was purified by recrystallization from MeOH to provide 1.72 g of a dark yellow solid (52%). $^1$H NMR ($CDCl_3$) δ: 8.37 (dd, J=1.5, 8.3 Hz, 1H); 8.22 (br s, 1H); 7.48 (d, J=2.3 Hz, 1H); 7.42 (dd, J=1.5, 8.1 Hz, 1H); 7.31 (dt, J=1.4, 7.8 Hz, 1H); 7.22 (dd, J=2.4, 8.8 Hz, 1H); 7.09 (dt, J=1.5, 7.7 Hz, 1H); 6.67 (d, J=8.8 Hz, 1H); 5.56 (br s, 2H).

2-Amino-N-(2-chlorophenyl)-6-fluorobenzamide (1e)

Prepared according to Procedure A using 2-amino-6-fluorobenzoic acid (2.0 g, 12.9 mmol) and $SOCl_2$ (2.3 mL, 32.2 mmol) in benzene (50 mL), followed by 2-chloroaniline (2.7 mL, 25.8 mmol) and $CHCl_3$ (50 mL). The product was purified by chromatography in EtOAc/hexanes to provide 2.06 g of a pale orange solid (60%). $^1$H NMR ($CDCl_3$) δ: 9.00 (d, J=17 Hz, 1H); 8.47 (d, J=8.3 Hz, 1H); 7.41 (d, J=8.0 Hz, 1H); 7.30 (t, J=7.9 Hz, 1H); 7.10-7.20 (m, 1H); 7.07 (t, J=7.7 Hz, 1H); 6.49 (d, J=8.3 Hz, 1H); 6.03 (br s, 2H). MS (ES): m/z 265.0 (M+).

2-Amino-6-chloro-N-(2-chlorophenyl)benzamide (1f)

Prepared according to Procedure A using 2-amino-6-chlorobenzoic acid (2.5 g, 14.6 mmol) and $SOCl_2$ (2.7 mL, 36.4 mmol) in benzene (75 mL), followed by 2-chloroaniline (3.1 mL, 29.1 mmol) and $CHCl_3$ (75 mL). The product chromatographed in $CH_2Cl_2$ to provide 1.05 g of a yellow orange solid (26%). 1H NMR ($CDCl_3$) δ: 8.54 (d, J=8.1 Hz, 1); 8.30 (br s, 1H); 7.41 (dd, J=1.5, 8.0 Hz, 1H); 7.33 (t, J=7.8 Hz, 1H); 7.10 (t, J=8.1 Hz, 1H); 7.09 (dt, J=1.6, 7.8 Hz, 1H); 6.78 (dd, J=0.4, 7.9 Hz, 1H); 6.63 (dd, J=0.9, 8.2 Hz, 1H); 4.69 (br s, 2H). MS (ES): m/z 303.0 (M+22), 281.0 (M+).

2-Amino-N-(2-chlorophenyl)-6-methylbenzamide (1g)

Prepared according to Procedure A using 2-amino-6-methylbenzoic acid (2.5 g, 16.5 mmol) and $SOCl_2$ (3.0 mL, 41.3 mmol) in benzene (75 mL), followed by 2-chloroaniline (3.5 mL, 33.0 mmol) and $CHCl_3$ (75 mL). The product was chromatographed in $CH_2Cl_2$ to provide 2.19 g of a brown oil (51%). $^1$H NMR ($CDCl_3$) δ: 8.58 (d, J=8.1 Hz, 1H); 7.99 (br s, 1H); 7.40 (dd, J=1.4, 8.0 Hz, 1H); 7.34 (t, J=7.7 Hz, 1H); 7.11 (t, J=7.8 Hz, 1H); 7.09 (dt, J=1.5, 7.7 Hz, 1H); 6.64 (d, J=7.5 Hz, 1H); 6.59 (d, J=8.1 Hz, 1H); 4.29 (br s, 2H); 2.45 (s, 3H). MS (ES): m/z 283.0 (M+22).

2-Amino-3-chloro-N-(2-chlorophenyl)benzamide (1h)

Prepared according to Procedure A using 2-amino-3-chlorobenzoic acid (1.0 g, 5.82 mmol) and $SOCl_2$ (1.1 mL, 14.6 mmol) in benzene (25 mL), followed by 2-chloroaniline (1.2 mL, 11.7 mmol) and $CHCl_3$ (25 mL). The product was recrystallized from MeOH to provide 1.29 g of a yellow solid (78%). $^1$H NMR ($CDCl_3$) δ: 8.43 (dd, J=1.4, 8.3 Hz, 1H); 8.30 (br s, 1H); 7.47 (dd, J=1.1, 8.0 Hz, 1H); 7.42 (d, J=8.0 Hz, 2H); 7.33 (dt, J=1.4, 7.9 Hz, 1H); 7.09 (dt, J=1.5, 7.7 Hz, 1H); 6.68 (t, J=7.9 Hz, 1H); 6.13 (br s, 2H). MS (ES): m/z 281.0 (M+).

2-Amino-N-biphenyl-2-yl-6-chlorobenzamide (1i)

Prepared according to Procedure A using 2-amino-6-chlorobenzoic acid (2.0 g, 11.7 mmol) and $SOCl_2$ (2.1 mL, 29.3 mmol) in benzene (60 mL), followed by 2-aminodiphenylamine (4.15 g, 24.5 mmol) and $CHCl_3$ (60 mL). The product was chromatographed in $CH_2Cl_2$ to provide 2.16 g of a foamy dark-amber residue (57%). $^1$H NMR ($CDCl_3$) δ: 8.48 (d, J=8.2 Hz, 1H); 7.79 (br s, 1H); 7.34-7.46 (m, 6H); 7.20-7.30 (m, 2H); 7.00 (t, J=8.1 Hz, 1H); 6.63 (dd, J=0.6, 7.9 Hz, 1H); 6.54 (d, J=8.3 Hz, 1H); 4.58 (br s, 2H). MS (ES): m/z 323.1 (M+).

2-Amino-6-chloro-N-o-tolylbenzamide (1j)

Prepared according to Procedure A using 2-amino-6-chlorobenzoic acid (1.0 g, 5.83 mmol) and $SOCl_2$ (1.1 mL, 14.6 mmol) in benzene (30 mL), followed by o-toluidine (1.4 mL, 12.8 mmol) and $CHCl_3$ (30 mL). The product was chromatographed in $CH_2Cl_2$ to provide 840 mg of an oily yellow solid (55%). $^1$H NMR ($CDCl_3$) δ: 7.96 (d, J=7.9 Hz, 1H); 7.60 (br s, 1H); 7.23-7.30 (m, 2H); 7.14 (t, J=7.5 Hz, 1H); 7.11 (t, J=8.3 Hz, 1H); 6.78 (d, J=7.9 Hz, 1H); 6.64 (d, J=8.2 Hz, 1H); 4.73 (br s, 2H); 2.35 (s, 3H). MS (ES): m/z 261.0 (M+).

2-Amino-6-chloro-N-(2-fluorophenyl)benzamide (1k)

Prepared according to Procedure A using 2-amino-6-chlorobenzoic acid (2.0 g, 11.7 mmol) and $SOCl_2$ (2.1 mL, 29.1 mmol) in benzene (60 mL), followed by 2-fluoroaniline (2.3 mL, 23.4 mmol) and $CHCl_3$ (60 mL). The product was chromatographed in $CH_2Cl_2$ to provide 1.05 g of a yellow solid (34%). $^1$H NMR ($CDCl_3$) δ: 8.45 (t, J=8.0 Hz, 1H); 8.01 (br s, 1H); 7.02-7.22 (m, 4H); 6.78 (dd, J=0.5, 7.9 Hz, 1H); 6.64 (dd, J=0.8, 8.2 Hz, 1H); 4.73 (br s, 2H). MS (ES): m/z 265.0 (M+).

2-Amino-6-chloro-N-(2-methoxyphenyl)benzamide (1l)

Prepared according to Procedure A using 2-amino-6-chlorobenzoic acid (2.0 g, 11.7 mmol) and $SOCl_2$ (2.1 mL, 29.1 mmol) in benzene (60 mL), followed by o-anisidine (2.6 mL, 23.4 mmol) and $CHCl_3$ (60 mL). The product was chromatographed in $CH_2Cl_2$ to provide 2.61 g of a dark yellow oil (81%). $^1$H NMR ($CDCl_3$) δ: 8.53 (dd, J=1.7, 7.9 Hz, 1H); 8.39 (br s, 1H); 7.11 (dt, J=1.6, 7.8 Hz, 1H); 7.09 (t, J=8.1 Hz, 1H); 7.02 (dt, J=1.4, 7.8 Hz, 1H); 6.92 (dd, J=1.4, 8.0 Hz, 1H); 6.62 (dd, J=0.9, 8.2 Hz, 1H); 4.66 (br s, 2H); 3.87 (s, 3H). MS (ES): m/z 277.0 (M+).

2-Amino-N-(2-chlorophenyl)-3-trifluoromethyl-benzo-amide (1m)

Prepared according to Procedure A using 3-trifluoromethylanthranilic acid (2.0 g, 9.75 mmol) and $SOCl_2$ (1.8 mL, 24.4 mmol) in benzene (50 mL), followed by 2-chloroaniline (2.1 mL, 19.5 mmol) and $CHCl_3$ (50 mL). The product was purified by recrystallization from MeOH to provide 2.38 g yellow crystals (78%). $^1$H NMR (CDCl$_3$) δ: 8.40 (dd, J=1.4, 8.3 Hz, 1H); 8.25 (br s, 1H); 7.71 (d, J=7.8 Hz, 1H); 7.60 (d, J=7.8 Hz, 1H); 7.43 (dd, J=1.4, 8.0 Hz, 1H); 7.34 (dt, J=1.3, 7.9 Hz, 1H); 7.11 (dt, J=1.5, 7.7 Hz, 1H); 6.77 (t, J=7.8 Hz, 1H); 6.24 (br s, 2H). MS (ES): m/z 315.0 (M+).

3-Aminonaphthalene-2-carboxylic acid (2-chlorophen-yl)amide (1n)

Prepared according to Procedure A using 3-amino-2-napthoic acid (2.0 g, 10.7 mmol) and SOCl$_2$ (1.9 mL, 26.7 mmol) in benzene (50 mL), followed by 2-chloroaniline (2.3 mL, 21.4 mmol) and CHCl$_3$ (50 mL). The product was recrystallized from MeOH to provide 1.71 g of a brown solid (54%). $^1$H NMR (CDCl$_3$) δ: 10.88 (br s, 1H); 9.21 (s, 1H); 8.91 (s, 1H); 8.70 (dd, J=1.0, 8.3 Hz, 1H); 7.95-8.01 (m, 1H); 7.87-7.94 (m, 1H); 7.60-7.68 (m, 2H); 7.41 (dd, J=1.3, 8.0 Hz, 1H); 7.34 (dt, J=1.2, 7.8 Hz, 1H); 7.07 (dt, J=1.4, 7.7 Hz, 1H). MS (ES): m/z 297.1 (M+).

2-Amino-N-(2-chlorophenyl)-4-nitrobenzamide (1o)

Prepared according to Procedure A using 4-nitroanthranilic acid (5.0 g, 27.5 mmol) and SOCl$_2$ (5.0 mL, 68.6 mmol) in benzene (150 mL), followed by 2-chloroaniline (5.8 mL, 55.0 mmol) and CHCl$_3$(150 mL). The product was purified by chromatography in CH$_2$Cl$_2$ followed by recrystallization from MeOH to provide 2.20 g of an orange-brown solid (31%). $^1$H NMR (CDCl$_3$) δ: 8.41 (dd, J=1.3, 8.3 Hz, 1H); 8.31 (br s, 1H); 7.67 (d, J=8.6 Hz, 1H); 7.57 (d, J=2.1 Hz, 1H); 7.52 (dd, J=2.2, 8.5 Hz, 1H); 7.44 (dd, J=1.3, 8.1 Hz, 1H); 7.35 (dt, J=1.3, 7.9 Hz, 1H); 7.13 (dt, J=1.4, 7.8 Hz, 1H); 5.88 (br s, 2H). MS (ES): m/z 292.0 (M+).

2-Amino-N-(2-chlorophenyl)-5-hydroxybenzamide (1p)

Prepared according to Procedure A using 2-amino-5-hydroxybenzoic acid (5.0 g, 32.7 mmol) and SOCl$_2$ (6.0 mL, 81.6 mmol) in benzene (150 mL), followed by 2-chloroaniline (6.9 mL, 65.4 mmol) and CHCl$_3$ (150 mL). The product was purified by two chromatographies in MeOH/CH$_2$Cl$_2$ to provide 990 mg of a brown solid (12%). $^1$H NMR (MeOH-d) δ: 7.92 (dd, J=1.6, 8.1 Hz, 1H); 7.48 (dd, J=1.5, 7.7 Hz, 1H); 7.34 (dt, J=1.5, 7.7 Hz, 1H); 7.20 (dt, J=1.7, 7.7 Hz, 1H); 7.16 (d, J=2.7 Hz, 1H); 6.83 (dd, J=2.7, 8.7 Hz, 1H); 6.76 (d, J=8.7 Hz, 1H); [6.24 (br s, 2H)). MS (ES): m/z 263.0 (M+).

2-Amino-N-(2-chlorophenyl)-4,5-difluorobenzamide (1q)

Prepared according to Procedure A using 4,5-difluoroanthranilic acid (2.0 g, 11.6 mmol) and SOCl$_2$ (2.1 mL, 28.9 mmol) in benzene (60 mL), followed by 2-chloroaniline (2.4 mL, 23.2 mmol) and CHCl$_3$ (60 mL). The product was purified by two chromatographies in CH$_2$Cl$_2$ and EtOAc/hexanes to provide 769 mg of a yellow solid (23%). $^1$H NMR (CDCl$_3$) δ: 8.69-8.82 (m, 1H); 8.00 (dd, J=8.4, 9.0 Hz, 1H); 7.90 (dd, J=8.9, 12 Hz, 1H); 7.39 (dd, J=6.8, 10 Hz, 1H); 6.53 (dd, J=6.6, 12 Hz, 1H); 6.41 (br s, 2H); 5.79 (br s, 1H). MS (ES): m/z 283.1 (M+).

2-Amino-N-(2-chlorophenyl)-5-fluorobenzamide (1r)

Prepared according to Procedure A using 2-amino-5-fluorobenzoic acid (1.0 g, 6.45 mmol) and SOCl$_2$ (1.2 mL, 16.1 mmol) in benzene (30 mL), followed by 2-chloroaniline (1.4 mL, 12.9 mmol) and CHCl$_3$ (30 mL). The product was triturated from CH$_2$Cl$_2$ to provide 985 mg of a mustard-yellow solid (58%). $^1$H NMR (CDCl$_3$) δ: 7.66 (dd, J=2.9, 8.7 Hz, 1H); 7.52-7.55 (m, 1H); 7.32-7.37 (m, 3H); 7.09 (dt, J=3.0, 8.5 Hz, 1H); 6.71 (dd, J=4.3, 8.7 Hz, 1H). MS (ES): m/z 305.0 (M+40).

Example 9

Preparation of Intermediate Compounds Chlorides

2-Chloromethyl-3-(2-chlorophenyl)-6,7-dimethoxy-3H-quinazolin-4-one (2a)

Prepared according to Procedure B with 1a (2.95 g, 9.63 mmol) and chloroacetyl chloride (2.3 mL, 28.9 mmol) in acetic acid (30 mL). Purified by extraction from aq. K$_2$CO$_3$ and recrystallization from isopropanol to afford 1.61 g of a brown crystalline solid (46%). $^1$H NMR (CDCl$_3$) δ: 7.59-7.66 (m, 2H); 7.45-7.56 (m, 3H); 7.20 (s, 1H); 4.37 (d, J=12 Hz, 1H), 4.08 (d, J=12 Hz, 1H); 4.04 (s, 3H); 4.00 (s, 3H). MS (ES): m/z 365.0 (M+).

6-Bromo-2-chloromethyl-3-(2-chlorophenyl)-3H-quinazolin-4-one (2b)

Prepared according to Procedure B with 1b (500 mg, 1.54 mmol) and chloroacetyl chloride (0.37 mL, 4.61 mmol) in acetic acid (10 mL). Purified by recrystallization from isopropanol to afford 490 mg of an off-white solid (83%). $^1$H NMR (CDCl$_3$) δ: 8.43 (d, J=2.3 Hz, 1H); 7.91 (dd, J=2.3, 8.7 Hz, 1H); 7.67 (d, J=8.7 Hz, 1H); 7.60-7.65 (m, 1H); 7.47-7.56 (m, 2H); 7.52 (t, J=5.3 Hz, 1H); 7.47-7.56 (m, 1H); 4.37 (d, J=12 Hz, 1H), 4.06 (d, J=12 Hz, 1H). MS (ES): m/z 385.0 (M+).

2-Chloromethyl-3-(2-chlorophenyl)-7-fluoro-3H-quinazolin-4-one (2c)

Prepared according to Procedure B with 1c (500 mg, 1.89 mmol) and chloroacetyl chloride (0.45 mL, 5.67 mmol) in acetic acid (10 mL). Purified by extraction from aqueous K$_2$CO$_3$, followed by recrystallization from isopropanol to afford 501 mg of a yellow crystalline solid (82%). $^1$H NMR (CDCl$_3$) δ: 8.32 (dd, J=6.0, 8.9 Hz, 1H); 7.59-7.66 (m, 1H); 7.50-7.55 (m, 3H); 7.44 (dd, J=2.4, 9.4 Hz, 1H); 7.27 (dt, J=2.5, 8.5 Hz, 1H); 4.37 (d, J=12 Hz, 1H), 4.07 (d, J=12 Hz, 1H). MS (ES): m/z 323.0 (M+).

6-Chloro-2-chloromethyl-3-(2-chlorophenyl)-3H-quinazolin-4-one (2d)

Prepared according to Procedure B with 1d (500 mg, 1.78 mmol) and chloroacetyl chloride (0.42 mL, 5.33 mmol) in acetic acid (10 mL). Purified by recrystallization from isopropanol to afford 555 mg of a yellow solid (92%). $^1$H NMR (CDCl$_3$) δ: 8.27 (d, J=1.9 Hz, 1H); 7.74-7.78 (m, 2H); 7.60-7.66 (m, 1H); 7.48-7.57 (m, 3H); 4.37 (d, J=12 Hz, 1H), 4.07 (d, J=12 Hz, 1H). MS (ES): m/z 339.0 (M+).

2-Chloromethyl-3-(2-chlorophenyl)-5-fluoro-3H-quinazolin-4-one (2e)

Prepared according to Procedure B with 1e (500 mg, 1.89 mmol) and chloroacetyl chloride (0.45 mL, 5.67 mmol) in acetic acid (10 mL). Purified by extraction from aq. K$_2$CO, and recrystallization from isopropanol to afford 430 mg of an off-white crystalline solid (70%). $^1$H NMR (CDCl$_3$) δ: 7.76 (dt, J=5.3, 8.2 Hz, 1H); 7.56-7.65 (m, 2H); 7.47-7.56 (m, 3H); 7.16-7.25 (m, 1H); 4.35 (d, J=12 Hz, 1H), 4.07 (d, J=12 Hz, 1H). MS (ES): m/z 323.0 (M+).

5-Chloro-2-chloromethyl-3-(2-chlorophenyl)-3H-quinazolin-4-one (2f)

Prepared according to Procedure B with 1f (1.00 g, 3.56 mmol) and chloroacetyl chloride (0.85 mL, 10.7 mmol) in acetic acid (15 mL). Purified by recrystallization from isopropanol to afford 791 mg of an off-white crystalline solid (65%). $^1$H NMR (CDCl$_3$) δ: 7.70 (s, 1H); 7.68 (d, J=3.8 Hz, 1H); 7.61-7.65 (m, 1H); 7.55 (dd, J=2.7, 6.4 Hz, 1H); 7.51 (d, J=3.1 Hz, 1H); 7.50 (s, 2H); 4.35 (d, J=12 Hz, 1H), 4.05 (d, J=12 Hz, 1H). MS (ES): m/z 339.0 (M+).

2-Chlormethyl-3-(2-chlorophenyl)-5-methyl-3H-quinazolin-4-one (2g)

Prepared according to Procedure B with 1g (2.18 g, 8.36 mmol) and chloroacetyl chloride (2.0 mL, 25.1 mmol) in acetic acid (40 mL). Purified by two chromatographies in CH$_2$Cl$_2$ and EtOAc/hexanes, followed by recrystallization from isopropanol to afford 638 mg of an off-white crystalline solid (24%). $^1$H NMR (DMSO-d$_6$) δ: 7.73-7.80 (m, 3H); 7.58-7.64 (m, 3H); 7.41 (d, J=7.4 Hz, 1H); 4.40 (d, J=12 Hz, 1H), 4.26 (d, J=12 Hz, 1H); 2.74 (s, 3H). MS (ES): m/z 319.0 (M+).

8-Chloro-2-chloromethyl-3-(2-chlorophenyl)-3H-quinazolin-4-one (2h)

Prepared according to Procedure B with 1h (500 mg, 1.78 mmol) and chloroacetyl chloride (0.49 mL, 6.13 mmol) in acetic acid (10 mL). Purified by extraction from aqueous K$_2$CO, followed by recrystallization from isopropanol to afford 448 mg of a yellow solid (74%). $^1$H NMR (CDCl$_3$) δ: 8.23 (dd, J=1.4, 8.0 Hz, 1H); 7.90 (dd, J=1.4, 7.8 Hz, 1H); 7.61-7.66 (m, 1H); 7.51-7.55 (m, 3H); 7.47 (t, J=8.0 Hz, 1H); 4.48 (d, J=12 Hz, 1H), 4.12 (d, J=12 Hz, 1H). MS (ES): m/z 339.0 (M+).

3-Biphenyl-2-yl-5-chloro-2-chloromethyl-3H-quinazolin-4-one (2i)

Prepared according to Procedure B with 1i (2.0 g, 6.20 mmol) and chloroacetyl chloride (1.5 mL, 18.6 mmol) in acetic acid (30 mL). Purified by chromatography in CH$_2$Cl$_2$, followed by recrystallization from isopropanol to afford 1.44 g of an off-white solid (61%). $^1$H NMR (CDCl$_3$) δ: 7.61-7.64 (m, 1H); 7.58-7.59 (m, 1H); 7.54-7.57 (m, 2H); 7.52-7.53 (m, 1H); 7.45-7.52 (m, 2H); 7.24 (s, 5H); 3.92-4.03 (m, 2H). MS (ES): m/z 381.0 (M+).

5-Chloro-2-chloromethyl-3-o-tolyl-3H-quinazolin-4-one (2j)

Prepared according to Procedure B with 1j (750 mg, 2.88 mmol) and chloroacetyl chloride (0.69 mL, 8.63 mmol) in acetic acid (15 mL). Purified by chromatography in CH$_2$Cl$_2$, followed by recrystallization from isopropanol to afford 340 mg of a white solid (37%). $^1$H NMR (CDCl$_3$) δ: 7.69 (d, J=2.1 Hz, 1H); 7.68 (q, J=7.4 Hz, 1H); 7.54 (dd, J=2.2, 7.0 Hz, 1H); 7.35-7.47 (m, 3H); 7.21-7.25 (m, 1H); 4.27 (d, J=12 Hz, 1H); 4.11 (d, J=12 Hz, 1H); 2.18 (s, 3H). MS (ES): m/z 319.0 (M+).

5-Chloro-2-chloromethyl-3-(2-fluorophenyl)-3H-quinazolin-4-one (2k)

Prepared according to Procedure B with 1k (1.0 g, 3.78 mmol) and chloroacetyl chloride (0.90 mL, 11.3 mmol) in acetic acid (20 mL). Purified by chromatography in CH$_2$Cl$_2$ to afford 484 mg of a pale pink solid (40%). $^1$H NMR (CDCl$_3$) δ: 7.69 (s, 1H); 7.68 (d, J=3.2 Hz, 1H); 7.56 (d, J=3.0 Hz, 1H); 7.54 (d, J=3.0 Hz, 1H); 7.40-7.47 (m, 1H); 7.35-7.38 (m, 1H); 7.27-7.32 (m, 1H); 4.35 (d, J=12 Hz, 1H); 4.18 (d, J=12 Hz, 1H). MS (ES): m/z 323.0 (M+).

5-Chloro-2-chloromethyl-3-(2-methoxyphenyl)-3H-quinazolin-4-one (2l)

Prepared according to Procedure B with 1l (2.6 g, 9.41 mmol) and chloroacetyl chloride (2.2 mL, 28.2 mmol) in acetic acid (40 mL). Purified by chromatography in CH$_2$Cl$_3$, followed by recrystallization from isopropanol to afford 874 mg of a pale yellow solid (28%). $^1$H NMR (CDCl$_3$) δ: 7.55-7.74 (m, 2H); 7.47-7.54 (m, 2H); 7.34 (dd, J=1.7, 7.8 Hz, 1H); 7.13 (dt, J=1.2, 7.7 Hz, 1H); 7.08 (dd, J=1.0, 8.4 Hz, 1H); 4.29 (d, J=12 Hz, 1H); 4.11 (d, J=12 Hz, 1H); 3.80 (s, 3H). MS (ES): m/z 335.0 (M+).

2-Chloromethyl-3-(2-chlorophenyl)-8-trifluoromethyl-3H-quinazolin-4-one (2m)

Prepared according to Procedure B with 1m (500 mg, 1.59 mmol) and chloroacetyl chloride (0.38 mL, 4.77 mmol) in acetic acid (10 mL). Purified by recrystallization from isopropanol to afford 359 mg of a white crystalline solid (61%). $^1$H NMR (CDCl$_3$) δ: 8.51 (dd, J=1.0, 8.0 Hz, 1H); 8.14 (d, J=7.3 Hz, 1H); 7.65 (dd, J=2.5, 5.6 Hz, 1H); 7.62 (d, J=3.9 Hz, 1H); 7.48-7.60 (m, 3H); 4.44 (d, J=12 Hz, 1H), 4.12 (d, J=12 Hz, 1H). MS (ES): m/z 373.0 (M+).

2-Chloromethyl-3-(2-chlorophenyl)-3H-benzo[g]quinazolin-4-one (2n)

Prepared according to Procedure B with 1n (500 mg, 1.68 mmol) and chloroacetyl chloride (0.40 mL, 5.05 mmol) in acetic acid (10 mL). Purified by chromatography in CH$_2$Cl$_2$ followed by recrystallization from isopropanol to afford 232 mg of a light-brown solid (39%). $^1$H NMR (CDCl$_3$) δ: 8.92 (s, 1H); 8.29 (s, 1H); 8.81 (d, J=8.3, 1H); 8.32 (d, J=8.3 Hz, 1H); 7.51-7.69 (m, 4H); 7.55 (d, J=5.2 Hz, 1H); 7.53 (d, J=3.8 Hz, 1H); 4.43 (d, J=12 Hz, 1H), 4.12 (d, J=12 Hz, 1H). MS (ES): m/z 355.0 (M+).

2-Chloromethyl-3-(2-chlorophenyl)-7-nitro-3H-quinazolin-4-one (2o)

Prepared according to Procedure B with 1o (500 mg, 1.71 mmol) and chloroacetyl chloride (0.41 mL, 5.14 mmol) in acetic acid (10 mL). Purified by extraction from aqueous K$_2$CO$_3$, followed by two chromatographies in CH$_2$Cl$_2$ to afford 338 mg of a yellow oil (56%). $^1$H NMR (CDCl$_3$) δ: 8.64 (d, J=2.2 Hz, 1H); 8.48 (d, J=8.8 Hz, 1H); 8.32 (dd, J=2.2, 8.7 Hz, 1H); 7.66 (dd, J=2.5, 6.0 Hz, 1H); 7.52-7.59 (m, 3H); 4.41 (d, J=12 Hz, 1H), 4.10 (d, J=12 Hz, 1H). MS (ES): m/z 350.0 (M+).

Acetic acid 2-chlormethyl-3-(2-chlorophenyl)-4-oxo-3,4-dihydro-quinazolin-6-yl eater (2p)

Prepared according to Procedure B with 1p (670 mg, 2.55 mmol) and chloroacetyl chloride (0.61 mL, 7.65 mmol) in acetic acid (10 mL). Purified by chromatography in 0-3% MeOH/CH$_2$Cl$_2$, followed by recrystallization from isopropanol to afford 523 mg of the acetate as pale-peach crystals (57%). $^1$H NMR (CDCl$_3$) δ: 8.00 (d, J=2.7 Hz, 1H); 7.82 (d, J=8.8 Hz, 1H); 7.60-7.66 (m, 1H); 7.56 (dd, J=2.7, 8.8 Hz, 1H); 7.51 (t, J=4.7 Hz, 2H); 7.50 (s, 1H); 4.38 (d, J=12 Hz, 1H), 4.08 (d, J=12 Hz, 1H); 2.36 (s, 3H). MS (ES): m/z 363.0 (M+).

2-Chloromethyl-3-(2-chlorophenyl)-6,7-difluoro-3H-quinazolin-4-one (2q)

Prepared according to Procedure B with 1q (700 mg, 2.48 mmol) and chloroacetyl chloride (0.60 mL, 7.43 mmol) in acetic acid (12 mL). Purified by chromatography in CH$_2$Cl$_2$, followed by recrystallization from isopropanol to afford 219 mg of a yellow crystalline solid (26%). $^1$H NMR (CDCl$_3$) δ: 8.07 (dd, J=8.5, 9.7 Hz, 1H); 7.64 (dd, J=2.5, 5.6 Hz, 1H); 7.60 (dd, J=3.5, 11 Hz, 1H); 7.55 (q, J=2.9 Hz, 3H); 7.52 (d, J=1.9 Hz, 1H); 7.49-7.51 (m, 1H); 4.36 (d, J=12 Hz, 1H), 4.06 (d, J=12 Hz, 1H). MS (ES): m/z 341.0 (M+).

2-Chloromethyl-3-(2-chlorophenyl)-6-fluoro-3H-quinazolin-4-one (2r)

Prepared according to Procedure B with 1r (850 mg, 3.21 mmol) and chloroacetyl chloride (0.77 mL, 9.63 mmol) in acetic acid (15 mL). Purified by extraction from aqueous K$_2$CO$_3$, followed by chromatography in EtOAc/hexanes. A second chromatography in acetone/hexanes afforded 125 mg of a white solid (12%). $^1$H NMR (CDCl$_3$) δ: 7.95 (dd, J=2.9, 8.2 Hz, 1H); 7.81 (dd, J=4.8, 9.0 Hz, 1H); 7.61-7.66 (m, 1H); 7.57 (dd, J=2.7, 8.6 Hz, 1H); 7.57 (dd, J=2.7, 8.6 Hz, 1H); 7.52 (dd, J=3.2, 6.9 Hz, 1H); 7.52 (br s, 2H); 4.38 (d, J=12 Hz, 1H), 4.08 (d, J=12 Hz, 1H). MS (ES): m/z 323.0 (M+).

Example 10

Preparation of PI3Kδ Inhibitor Compounds

Compound D-001

2-(6-Aminopurin-9-ylmethyl)-3-(2-chlorophenyl)-6,7-dimethoxy-3H-quinazolin-4-one Prepared according to Procedure C using Intermediate 2a (200 mg, 0.546 mmol), adenine (81 mg, 0.601 mmol), K$_2$CO$_3$ (83 mg, 0.601 mmol), and DMF (4 mL). The crude product was recrystallized from ethanol (EtOH) to provide 164 mg of a beige solid (65%), mp 281.5-282.7° C. (decomposes). $^1$H NMR (DMSO-d) δ: 8.06 (s, 1H); 8.04 (s, 1H); 7.76-7.81 (m, 1H); 7.70-7.76 (m, 1H); 7.60-7.67 (m, 2H); 7.45 (s, 1H); 7.22 (s, 2H); 6.90 (s, 1H); 5.08 (d, J=17 Hz, 1H); 4.91 (d, J=17 Hz, 1H); 3.87 (s, 3H); 3.87 (s, 3H). $^{13}$C NMR (DMSO-d$_6$) ppm: 159.9, 156.2, 155.4, 152.9, 150.0, 149.7, 149.4, 143.0, 141.9, 133.7, 132.1, 131.9, 131.2, 130.8, 129.3, 118.4, 113.6, 108.4, 105.8, 56.5, 56.1, 44.7. MS (ES): m/z 464.1 (M+). Anal. calcd. for C$_{22}$H$_{18}$ClN$_7$O$_3$.0.1C$_2$H$_6$O.0.05KCl: C, 56.47; H, 3.97; Cl, 7.88; N, 20.76. Found: C, 56.54; H, 4.05; Cl, 7.77; N, 20.55.

Compound D-002

2-(6-Aminopurin-o-ylmethyl)-6-bromo-3-(2-chlorophenyl)-3H-quinazolin-4-one

Prepared according to Procedure C using Intermediate 2b (100 mg, 0.260 mmol), adenine (39 mg, 0.286 mmol), K$_2$CO$_3$ (40 mg, 0.286 mmol), and DMF (2 mL). The crude product was recrystallized from EtOH to provide 52 mg of an off-white solid (41%), mp 284.2-284.7° C. (decomposes). $^1$H NMR (DMSO-d$_6$) δ: 8.24 (d, J=2.0 Hz, 1H); 8.05 (s, 1H); 8.03 (s, 1H); 7.98 (dd, J=1.9, 8.6 Hz, 1H); 7.74-7.83 (m, 2H); 7.59-7.68 (m, 2H); 7.46 (d, J=8.7 Hz, 1H); 7.22 (s, 2H); 5.12 (d, J=17 Hz, 1H); 4.94 (d, J=17 Hz, 1H). $^{13}$C NMR (DMSO-d$_6$) ppm: 159.5, 156.2, 152.9, 152.0, 150.1, 145.8, 141.8, 138.4, 133.1, 132.2, 131.9, 131.1, 130.9, 130.1, 129.4, 128.9, 122.4, 120.4, 118.4, 45.0. MS (ES): m/z 482.0 (M+). Anal. calcd. for C$_{20}$H$_{13}$ClBrN$_7$O.0.1KCl: C, 49.01; H, 2.67; Cl, 7.96; N, 20.00. Found: C, 48.82; H, 2.82; Cl, 8.00; N, 19.79.

Compound D-003

2-(6-Aminopurin-o-ylmethyl)-3-(2-chlorophenyl)-7-fluoro-3N-quinazolin-4-one

Prepared according to Procedure C using Intermediate 2c (100 mg, 0.310 mmol), adenine (46 mg, 0.340 mmol), K$_3$CO$_3$ (47 mg, 0.340 mmol), and DMF (1 mL). The crude product was recrystallized from EtOH to provide 57 mg of a beige solid (44%), mp 216.8-217.2° C. $^1$H NMR (DMSO-d$_6$) δ: 8.22 (dd, J=6.3, 8.7 Hz, 1H); 8.05 (s, 1H); 8.03 (s, 1H); 7.78-7.80 (m, 2H); 7.61-7.64 (m, 2H); 7.46 (dt, J=2.1, 8.6 Hz, 1H); 7.32 (d, J=9.8 Hz, 1H); 7.22 (s, 2H); 5.13 (d, J=17 Hz, 1H); 4.95 (d, J=17 Hz, 1H). $^{13}$C NMR (DMSO-d$_6$) ppm: 166.1 (d, J=253 Hz), 159.6, 155.8, 152.5, 149.7, 148.6 (d, J=14 Hz), 141.4, 132.8, 131.8, 131.6, 130.8, 130.5, 129.8 (d, J=11 Hz), 129.0, 118.1, 117.4, 116.2 (d, J=24 Hz), 112.7 (d, J=22 Hz), 44.6. MS (ES): m/z 422.0 (M+). Anal. calcd. for C$_{20}$H$_{13}$ClFN$_7$O.1H$_2$O (0.15KCl: C, 55.25; H, 3.06; Cl, 9.38; N, 22.55. Found: C, 55.13; H, 2.92; Cl, 9.12; N, 22.30.

Compound D-004

2-(6-Aminopurin-9-ylmethyl)-6-chloro-3-(2-chlorophenyl)-3H-quinazolin-4-one

Prepared according to Procedure C using Intermediate 2d (100 mg, 0.294 mmol), adenine (44 mg, 0.323 mmol), K$_2$CO$_3$ (45 mg, 0.323 mmol), and DMF (1 mL). The crude product was recrystallized from EtOH to provide 50 mg of a yellow solid (39%), mp 294.5-294.8° C. (decomposes). $^1$H NMR (DMSO-d$_6$) b: 8.10 (d, J=2.2 Hz, 1H); 8.05 (s, 1H); 8.03 (s, 1H); 7.86 (dd, J=2.4, 8.8 Hz, 1H); 7.75-7.82 (m, 2H); 7.59-7.67 (m, 2H); 7.53 (d, J=8.7 Hz, 1H); 7.22 (br s, 2H); 5.13 (d, J=17 Hz, 1H); 4.95 (d, J=17 Hz, 1H). $^{13}$C NMR (DMSO-d$_6$) ppm: 159.7, 156.2, 152.9, 151.9, 150.1, 145.5, 141.8, 135.7, 133.1, 132.3, 132.2, 131.9, 131.1, 130.9, 130.0, 129.4, 125.9, 122.0, 118.4, 44.9. MS (ES): m/z 438.0 (M+). Anal. calcd. for C$_{20}$H$_{13}$Cl$_2$NO: C, 54.81; H, 2.99; N, 22.37. Found: C, 54.72; H, 2.87; N, 22.18.

Compound D-005

2-(6-Aminopurin-9-ylmethyl)-3-(2-chlorophenyl)-5-fluoro-3H-quinazolin-4-one

Prepared according to Procedure C using Intermediate 2e (200 mg, 0.619 mmol), adenine (92 mg, 0.681 mmol), K₂CO₀(94 mg, 0.680 mmol), and DMF (4 mL). The crude product was chromatographed in MeOH/CH₂Cl₂ to provide 168 mg of an off-white solid (64%), mp 159-172° C. (gradually decomposes). ¹H NMR (DMSO-d₆) δ: 8.10 (s, 1H); 8.08 (s, 1H); 7.73-7.89 (m, 3H); 7.57-7.71 (m, 2H); 7.37-7.48 (m, 2H); 7.34 (d, J=11 Hz, 1H); 7.30 (d, J=8.3 Hz, 1H); 5.14 (d, J=17 Hz, 1H); 4.94 (d, J=17 Hz, 1H). ¹³C NMR (DMSO-d₆) ppm: 160.8 (d, J=264 Hz), 157.5 (d, J=4.2 Hz), 155.8, 152.4, 152.4, 150.0, 148.7, 142.1, 136.4 (d, J=11 Hz), 133.0, 132.2, 132.1, 131.2, 130.9, 129.4, 123.8 (d, J=3.6 Hz), 118.4, 114.5 (d, J=20 Hz), 110.2 (d, J=6.0 Hz), 44.9. MS (ES): m/z 422.0 (M+). Anal. calcd. for C₂₀H₁₃ClFN₇O: C, 56.95; H, 3.11; Cl, 8.40; N, 23.24. Found: C, 54.62; H, 3.32; Cl, 9.40; N, 21.29.

Compound D-006

2-(6-Aminopurin-o-ylmethyl)-5-chloro-3-(2-chlorophenyl)-3H-quinazolin-4-one

Prepared according to Procedure C using Intermediate 2f (300 mg, 0.883 mmol), adenine (131 mg, 0.972 mmol), K₂CO₃ (134 mg, 0.972 mmol), and DMF (4 mL). The crude product was chromatographed in MeOH/CH₂Cl₂ and recrystallized from EtOH to provide 188 mg of a pale orange crystalline solid (49%), mp 245.7-246.0© (starts to sweat at 220° C.). ¹H NMR (DMSO-d₆) δ: 8.06 (s, 1H); 8.04 (s, 1H); 7.76-7.81 (m, 2H); 7.72 (d, J=8.0 Hz, 1H); 7.59-7.66 (m, 3H); 7.41 (d, J=8.1 Hz, 1H); 7.26 (br s, 2H); 5.11 (d, J=17 Hz, 1H); 4.93 (d, J=17 Hz, 1H). ¹³C NMR (DMSO-d₆) ppm: 158.5, 156.2, 152.9, 152.2, 150.1, 149.2, 141.8, 135.4, 133.3, 133.2, 132.1, 132.0, 131.2, 130.9, 130.4, 129.4, 127.3, 118.4, 117.7, 44.9. MS (ES): m/z 438.0 (M+). Anal. calcd. for C₂₀H₁₃Cl₂N₇O.0.1C₂H₆O.0.05H₂O: C, 54.67; H, 3.11; Cl, 15.98; N, 22.09. Found: C, 54.35; H, 3.00; Cl, 15.82; N, 22.31.

Compound D-007

2-(6-Aminopurin-9-ylmethyl)-3-(2-chlorophenyl)-5-methyl-3H-quinazolin-4-one

Prepared according to Procedure C using Intermediate 2g (250 mg, 0.783 mmol), adenine (116 mg, 0.862 mmol), K₂CO₃ (119 mg, 0.862 mmol), and DMF (4 mL). The crude product was recrystallized from EtOH to provide 93 mg of a pale yellow solid (28%), mp 190.7-190.9° C. ¹H NMR (DMSO-d₆) δ: 8.05 (s, 1H); 8.03 (s, 1H); 7.76-7.79 (m, 1H); 7.71-7.74 (m, 1H); 7.59-7.67 (m, 1H); 7.34 (d, J=7.4 Hz, 1H); 7.28 (d, J=8.2 Hz, 1H); 7.24 (br s, 2H); 5.07 (d, J=17 Hz, 1H); 4.92 (d, J=17 Hz, 1H); 2.73 (s, 3H). ¹³C NMR (DMSO-d₆) ppm: 161.1, 156.2, 152.8, 150.9, 150.1, 148.3, 141.9, 141.0, 134.6, 133.6, 132.2, 131.9, 131.3, 130.8, 130.3, 129.3, 125.9, 119.1, 118.4, 44.8, 22.8. MS (ES): m/z 418.1 (M+). Anal. calcd. for C₂₁H₁₆ClN₇O.H₂O: C, 57.87; H, 4.16; Cl, 8.13; N, 22.49. Found: C, 57.78; H, 3.99; Cl, 8.38; N, 22.32.

Compound D-008

2-(6-Aminopurin-9-ylmethyl)-8-chloro-3-(2-chlorophenyl)-3H-quinazolin-4-one

Prepared according to Procedure C using Intermediate 2h (100 mg, 0.294 mmol), adenine (44 mg, 0.324 mmol), K₂CO₃ (45 mg, 0.324 mmol), and DMF (1 mL). The crude product was chromatographed in MeOH/CH₂Cl₂ to provide 50 mg of a pale yellow solid (39%), mp 273.3-273.5° C. (discolors). ¹H NMR (DMSO-d₆) δ: 8.11 (dd, J=1.3, 8.0 Hz, 1H); 8.08 (s, 1H); 8.05 (8, 1H); 8.00 (dd, J=1.3, 7.8 Hz, 1H); 7.79-7.83 (m, 2H); 7.63-7.66 (m, 2H); 7.56 (t, J=7.9 Hz, 1H); 7.21 (br s, 2H); 5.17 (d, J=17 Hz, 1H); 4.97 (d, J=17 Hz, 1H). ¹³C NMR (DMSO-d₆) ppm: 160.2, 156.1, 152.8, 152.2, 150.2, 143.3, 142.0, 135.6, 133.1, 132.3, 131.9, 131.1, 131.0, 130.9, 129.4, 128.4, 126.0, 122.5, 118.4, 45.0. MS (ES): m/z 438.0 (M+). Anal. calcd. for C₂₀H₁₃Cl₂N₇O.0.1CH₄O.0.6H₂O (0.15KCl: C, 52.09; H, 3.18; N, 21.15. Found: C, 51.85; H, 2.93; N, 21.01.

Compound D-009

2-(6-Aminopurin-9-ylmethyl)-3-biphenyl-2-yl-5-chloro-3H-quinazolin-4-one

Prepared according to Procedure C using Intermediate 2i (400 mg, 1.05 mmol), adenine (155 mg, 1.15 mmol), K₂CO₃ (159 mg, 1.15 mmol), and DMF (5 mL). The crude product was recrystallized from EtOH to provide 344 mg of a white solid (68%), mp 299.9-300.1° C. (discolors). ¹H NMR (DMSO-d) δ: 8.08 (s, 1H); 7.89 (s, 1H); 7.58-7.73 (m, 5H); 7.51 (d, J=7.9 Hz, 1H); 7.46 (d, J=7.5 Hz, 2H); 7.27-7.41 (m, 3H); 7.14-7.27 (m, 3H); 5.14 (d, J=17 Hz, 1H); 4.82 (d, J=17 Hz, 1H). ¹³C NMR (DMSO-d₆) ppm: 159.6, 156.2, 152.8, 152.5, 150.0, 149.0, 141.7, 140.2, 137.7, 135.0, 133.3, 133.2, 131.8, 130.7, 130.1, 129.8, 129.5, 128.8, 128.6, 128.4, 127.1, 118.4, 117.6, 45.3. MS (ES): m/z 480.1 (M+). Anal. calcd. for C₂₆H₁₈ClN₇O: C, 65.07; H, 3.78; Cl, 7.39; N, 20.43. Found: C, 64.77; H, 3.75; Cl, 7.43; N, 20.35.

Compound D-010

5-Chloro-2-(9H-purin-6-ylsulfanylmethyl)-3-o-tolyl-3H-quinazolin-4-one

Prepared according to Procedure C using Intermediate 2j (200 mg, 0.626 mmol), 6-mercaptopurine monohydrate (93 mg, 0.546 mmol), K₂CO₃ (95 mg, 0.689 mmol), and DMF (4 mL). The crude product was recrystallized from EtOH to provide 125 mg of an off-white solid (46%), mp 213.9° C. ¹H NMR (DMSO-d₆) δ: 13.53 (br s, 1H); 8.49 (s, 1H); 8.44 (s, 1H); 7.78 (t, J=7.9 Hz, 1H); 7.63 (d, J=8.2 Hz, 1H); 7.59 (d, J=7.7 Hz, 1H); 7.49 (d, J=6.9 Hz, 1H); 7.24-7.41 (m, 3H); 4.32-4.45 (m, 2H); 2.14 (s, 3H). ¹³C NMR (DMSO-4d) ppm: 158.9, 157.2, 154.2, 151.5, 149.7, 149.6, 143.5, 136.1, 135.9, 135.1, 133.2, 131.3, 130.3, 130.0, 129.9, 129.1, 127.6, 127.1, 117.8, 32.4, 17.5. MS (ES): m/z 438.0 (M+). Anal. calcd. for C₂₁H₁₅ClN₆OS: C, 58.00; H, 3.48; Cl, 8.15; N, 19.32; S, 7.37. Found: C, 58.05; H, 3.38; Cl, 8.89; N, 18.38; S, 7.00.

Compound D-011

5-Chloro-3-(2-fluorophenyl)-2-(9H-purin-6-yl-sulfanylmethyl)-3H-quinazolin-4-one Prepared according to Procedure C using Intermediate 2k (210 mg, 0.650 mmol), 6-mercaptopurine monohydrate (122 mg, 0.715 mmol), K₂CO₃ (99 mg, 0.715 mmol), and DMF (4 mL). The crude product was recrystallized from EtOH to provide 240 mg of an off-white solid (84%), mp 244.0° C. ¹H NMR (DMSO-d₆) δ: 13.56 (br s, 1H); 8.50 (s, 1H); 8.45 (s, 1H); 7.81 (t, J=8.0 Hz, 1H); 7.74 (t, J=7.7 Hz, 1H); 7.67 (d, J=8.1 Hz, 1H); 7.62 (d, J=7.7 Hz, 1H); 7.46-7.55 (m, 1H); 7.29-7.42 (m, 2H); 4.47-4.59 (m, 2H). ¹³C NMR (DMSO-d$_6$) ppm: 158.4, 157.3 (d, J=249 Hz), 156.4, 153.8, 151.0, 149.1, 143.2, 135.0, 132.9, 131.8 (d, J=8.0 Hz), 130.8, 129.9, 126.7, 125.3 (d, J=3.5 Hz), 123.6 (d, J=13 Hz), 117.0, 116.2 (d, J=19 Hz), 31.7. MS (ES): m/z 439.0 (M+). Anal. calcd. for C$_{20}$H$_{12}$ClFN$_6$OS: C, 54.74; H, 2.76; Cl, 8.08; N, 19.15; S, 7.31. Found: C, 54.42; H, 2.88; Cl, 8.08; N, 18.87; S, 7.08.

Compound D-012

2-(6-Aminopurin-9-ylmethyl)-5-chloro-3-(2-fluorophenyl)-3H-quinazolin-4-one

Prepared according to Procedure C using Intermediate 2k (210 mg, 0.650 mmol), adenine (97 mg, 0.715 mmol), K$_2$CO$_3$ (99 mg, 0.715 mmol), and DMF (4 mL). The crude product was recrystallized from EtOH to provide 137 mg of a tan solid (50%), mp 295.6-295.8° C. (decomposes). $^1$H NMR (DMSO-d$_6$) b: 8.05 (s, 1H); 8.04 (s, 1H); 7.75 (t, J=7.6 Hz, 1H); 7.74 (t, J=7.9 Hz, 1H); 7.62-7.69 (m, 1H); 7.61 (d, J=7.6 Hz, 1H); 7.47-7.55 (m, 1H); 7.48 (d, J=7.8 Hz, 1H); 7.41 (d, J=8.0 Hz, 1H); 7.24 (br s, 2H); 5.19 (d, J=17 Hz, 1H); 5.03 (d, J=17 Hz, 1H). $^{13}$C NMR (DMSO-d$_6$) ppm: 158.7, 157.6 (d, J=250 Hz), 156.2, 152.8, 152.4, 150.0, 149.2, 141.8, 135.4, 133.3, 132.5 (d, J=8.0 Hz), 131.0, 130.4, 127.3, 126.2 (d, J=3.5 Hz), 123.1 (d, J=14 Hz), 118.4, 117.6, 117.2 (d, J=19 Hz), 45.1. MS (ES): m/z 422.0 (M+). Anal. calcd. for C$_{20}$H$_{13}$ClFN$_7$O*0.05C$_2$H$_6$O: C, 56.92; H, 3.16; Cl, 8.36; N, 23.12. Found: C, 56.79; H, 3.20; Cl, 8.46; N, 22.79.

Compound D-013

3-Biphenyl-2-yl-5-chloro-2-(9H-purin-6-ylsulfanylmethyl)-3H-quinazolin-4-one

Prepared according to Procedure C using Intermediate 2i (400 mg, 1.05 mmol), 6-mercaptopurine monohydrate (196 mg, 1.15 mmol), K$_2$CO$_3$ (159 mg, 1.15 mmol), and DMF (5 mL). The crude product was chromatographed in MeOH/CH$_2$Cl$_2$ and subsequently recrystallized from EtOH to provide 439 mg of a pale yellow crystalline solid (84%), mp 222.0-222.5° C. (dec). $^1$H NMR (DMSO-d$_6$) δ: 13.56 (br s, 1H); 8.55 (s, 1H); 8.45 (s, 1H); 7.73 (t, J=8.0 Hz, 1H); 7.64 (d, J=7.7 Hz, 1H); 7.50-7.59 (m, 4H); 7.41-7.48 (m, 1H); 7.25-7.38 (m, 5H); 4.41 (d, J=16 Hz, 1H); 4.16 (d, J=16 Hz, 1H). $^{13}$C NMR (DMSO-d$_6$) ppm: 160.2, 157.0, 153.7, 151.5, 149.7, 149.3, 143.5, 139.9, 137.8, 135.1, 134.1, 133.3, 131.5, 130.5, 130.3, 130.1, 129.1, 128.9, 128.4, 128.4, 126.9, 117.5, 32.3. MS (ES): m/z 497.0 (M+). Anal. calcd. for C$_{26}$H$_{17}$ClN$_6$OS: C, 62.84; H, 3.45; Cl, 7.13; N, 16.91; S, 6.45. Found: C, 62.60; H, 3.47; Cl, 7.15; N, 16.65; S, 6.41.

Compound D-014

5-Chloro-3-(2-methoxyphenyl)-2-(9H-purin-6-ylsulfanylmethyl)-3H-quinazolin-4-one Prepared according to Procedure C using Intermediate 2l (250 mg, 0.746 mmol), 6-mercaptopurine monohydrate (140 mg, 0.821 mmol), K$_2$CO$_3$ (113 mg, 0.821 mmol), and DMF (4 mL). The crude product was recrystallized from EtOH to provide 254 mg of an off-white solid (76%), mp 237.0° C. (dec; discolors at 154.6° C.). $^1$H NMR (DMSO-d$_6$) δ: 13.53 (br s, 1H); 8.52 (s, 1H); 8.45 (s, 1H); 7.78 (t, J=7.9 Hz, 1H); 7.64 (d, J=8.0 Hz, 1H); 7.59 (d, J=7.7 Hz, 1H); 7.48 (d, J=7.3 Hz, 1H); 7.42 (t, J=7.7 Hz, 1H); 7.15 (d, J=8.2 Hz, 1H); 7.03 (t, J=7.5 Hz, 1H); 4.45 (s, 2H); 3.76 (s, 3H). $^{13}$C NMR (DMSO-d$_6$) ppm: 158.9, 157.1, 154.8, 154.7, 151.5, 149.6, 143.6, 135.1, 133.2, 131.3, 130.4, 130.0, 127.0, 124.8, 121.2, 117.8, 112.7, 56.1, 32.0. MS (ES): m/z 451.0 (M+). Anal. calcd. for C$_{41}$H$_{15}$ClN$_6$O$_2$S.0.15C$_2$H$_6$O*0.05KCl: C, 55.43; H, 3.47; Cl, 8.07; N, 18.21; S, 6.95. Found: C, 55.49; H, 3.68; Cl, 7.95; N, 17.82; S, 6.82.

Compound D-015

3-(2-Chlorophenyl)-5-fluoro-2-(9H-purin-6-yl-sulfanylmethyl)-3H-quinazolin-4-one Prepared according to Procedure C using Intermediate 2e (200 mg, 0.619 mmol), 6-mercaptopurine monohydrate (116 mg, 0.681 mmol), K$_2$CO$_3$ (94 mg, 0.681 mmol), and DMF (5 mL). The crude product was recrystallized from EtOH to provide 152 mg of a white solid (56%), mp 222.7-223.8° C. (discolors). $^1$H NMR (DMSO-d$_6$) δ: 13.56 (br s, 1H); 8.48 (s, 1H); 8.44 (s, 1H); 7.89 (dt, J=5.6, 8.1 Hz, 1H); 7.76 (dd, J=1.6, 7.3 Hz, 1H); 7.67 (d, J=7.4 Hz, 1H); 7.56 (d, J=8.1 Hz, 1H); 7.47 (t, J=7.1 Hz, 1H), 7.41-7.53 (m, 2H); 7.37 (dd, J=8.7, 11 Hz, 1H); 4.38-4.52 (m, 2H). $^{13}$C NMR (DMSO-d$_6$) ppm: 160.9 (d, J=264 Hz), 157.6, 156.8, 154.1, 151.5, 149.6, 149.0, 143.6, 136.4 (d, J=11 Hz), 133.9, 132.2, 131.7, 131.6, 130.5, 130.2, 128.8, 123.6, 114.4 (d, J=20 Hz), 110.2, 32.0. MS (ES): m/z 439.0 (M+). Anal. calcd. for C$_{20}$H$_{12}$ClFN$_6$OS.0.5C$_2$H$_6$O: C, 54.61; H, 3.27; Cl, 7.68; N, 18.19; S, 6.94. Found: C, 54.37; H, 3.26; Cl, 7.89; N, 18.26; S, 6.55.

Compound D-016

3-(2-Chlorophenyl)-6,7-dimethoxy-2-(9H-purin-6-ylsulfanylmethyl)-3H-quinazolin-4-one Prepared according to Procedure C using Intermediate 2a (200 mg, 0.546 mmol), 6-mercaptopurine monohydrate (102 mg, 0.601 mmol), K$_2$CO$_3$ (83 mg, 0.601 mmol), and DMF (5 mL). The crude product was recrystallized from EtOH to provide 172 mg of an off-white solid (65%), mp 160-180° C. (gradually decomposes). $^1$H NMR (DMSO-d$_6$) δ: 13.55 (br s, 1H); 8.49 (s, 1H); 8.44 (s, 1H); 7.72 (d, J=6.9 Hz, 1H); 7.66 (d, J=6.9 Hz, 1H) 7.38-7.54 (m, 3H); 7.22 (s, 1H); 4.36-4.52 (m, 2H); 3.94 (s, 3H); 3.89 (s, 3H). $^{13}$C NMR (DMSO-d$_6$) ppm: 160.1, 155.4, 151.5, 151.1, 149.4, 143.2, 134.6, 132.3, 131.6, 131.5, 130.4, 128.7, 113.6, 108.4, 105.8, 56.5, 56.1, 32.0. MS (ES): m/z 481.1 (M+). Anal. calcd. for C$_{22}$H$_{17}$ClN$_6$O$_3$S.0.5C$_2$H$_6$O*0.05KCl: C, 54.41; H, 3.97; Cl, 7.33; N, 16.55; S, 6.32. Found: C, 54.43; H, 3.94; Cl, 7.69; N, 16.69; S, 6.52.

Compound D-017

6-Bromo-3-(2-chlorophenyl)-2-(9H-purin-6-yl-sulfanylmethyl)-3H-quinazolin-4-one

Prepared according to Procedure C using Intermediate 2b (200 mg, 0.519 mmol), 6-mercaptopurine monohydrate (97 mg, 0.570 mmol), K$_2$CO$_3$(79 mg, 0.572 mmol), and DMF (5 mL). The crude product was recrystallized from EtOH to provide 123 mg of an off-white solid (47%), mp 212-242° C. (gradually decomposes). $^1$H NMR (DMSO-d$_6$) δ: 13.07 (br s, 1H); 8.48 (s, 1H); 8.44 (s, 1H); 8.24 (d, J=2.3 Hz, 1H); 8.06 (dd, J=2.3, 8.7 Hz, 1H); 7.76 (dd, J=1.9, 7.4 Hz, 1H); 7.70 (d, J=8.7 Hz, 1H); 7.66 (d, J=8.1 Hz, 1H); 7.51 (dd, J=2.1, 7.9 Hz, 1H); 7.46 (dd, J=1.9, 7.9 Hz, 1H); 4.47 (s, 2H). ¹³C NMR (DMSO-d₆) ppm: 159.7, 156.8, 153.6, 151.5, 146.1, 143.6, 138.5, 134.0, 132.1, 131.8, 131.5, 130.5, 130.2, 129.9, 128.9, 128.8, 122.2, 120.3, 32.0. MS (ES): m/z 499.0 (M+). Anal. calcd. for C₂₀H₁₂ClBrN₆OS.0.2C₂H₆O.0.05KCl: C, 47.79; H, 2.59; N, 16.39; S, 6.25. Found: C, 47.56; H, 2.54; N, 16.25; S, 6.58.

Compound D-018

3-(2-Chlorophenyl)-(9H-purin-6-ylsulfanylmethyl)-trifluoromethyl-3H-quinazolin-4-one Prepared according to Procedure C using Intermediate 2m (200 mg, 0.536 mmol), 6-mercaptopurine monohydrate (100 mg, 0.588 mmol), K₂CO₃ (82 mg, 0.593 mmol), and DMF (4 mL). The crude product was recrystallized from EtOH to provide 148 mg of a white solid (56%), mp 218.5-219.4° C. ¹H NMR (DMSO-d₆) δ: 13.52 (br s, 1H); 8.48 (s, 1H); 8.44 (s, 1H); 8.43 (d, J=6.0 Hz, 1H); 8.26 (d, J=7.5 Hz, 1H); 7.84 (dd, J=2.5, 6.7 Hz, 1H); 7.70-7.75 (m, 2H); 7.51-7.59 (m, 2H); 4.40-4.55 (m, 2H). ¹³C NMR (DMSO-d₆) ppm: 160.0, 157.2, 154.2, 151.4, 149.6, 144.4, 143.4, 133.8, 133.0 (q, J=5.1 Hz), 132.0, 131.9, 131.6, 131.4, 130.6, 129.0, 127.3, 125.2 (q, J=30 Hz), 123.6 (q, J=273 Hz), 121.8, 32.6. MS (ES): m/z 489.0 (M+). Anal. calcd. for C₂₁H₁₂ClF₃N₆OS: C, 51.59; H, 2.47; Cl, 7.25; N, 17.19; S, 6.56. Found: C, 51.51; H, 2.55; Cl, 7.37; N, 17.05; S, 6.38.

Compound D-019

3-(2-Chlorophenyl)-2-(9H-purin-6-ylsulfanylmethyl)-3H-benzo[g]quinazolin-4-one

Prepared according to Procedure C using Intermediate 2n (200 mg, 0.563 mmol), 6-mercaptopurine monohydrate (105 mg, 0.619 mmol), K₂CO₃ (86 mg, 0.619 mmol), and DMF (4 mL). The crude product was recrystallized from EtOH to provide 128 mg of a dark yellow solid (48%), mp 247.8-254.4° C. (decomposes). ¹H NMR (DMSO-d) δ: 13.56 (br s, 1H); 8.90 (s, 1H); 8.50 (s, 1H); 8.46 (s, 1H); 8.34 (s, 1H); 8.27 (d, J=8.2 Hz, 1H); 8.16 (d, J=8.2 Hz, 1H); 7.81 (dd, J=1.6, 7.3 Hz, 1H); 7.70 (t, J=7.5 Hz, 1H); 7.61-7.74 (m, 2H); 7.49 (t, J=7.5 Hz, 1H); 7.44-7.53 (m, 1H); 4.44-4.56 (m, 2H). ¹³C NMR (DMSO-d₆) ppm: 161.3, 151.6, 151.5, 143.9, 142.2, 136.7, 134.4, 132.5, 131.8, 131.6, 130.5, 129.7, 129.3, 128.8, 128.6, 128.3, 128.3, 127.1, 125.2, 119.5, 32.4. MS (ES): m/z 471.0 (M+). Anal. calcd. for C₂₄H₁₅ClN₆OS.0.2C₂H₆O*0.05KCl: C, 60.57; H, 3.37; Cl, 7.69; N, 17.37; S, 6.63. Found: C, 60.24; H, 3.46; Cl, 7.50; N, 17.34; S, 6.69.

Compound D-020

6-Chloro-3-(2-chlorophenyl)-2-(9H-purin-6-yl-sulfanylmethyl)-3H-quinazolin-4-one Prepared according to Procedure C using Intermediate 2d (200 mg, 0.587 mmol), 6-mercaptopurine monohydrate (110 mg, 0.646 mmol), K₂CO₃ (90 mg, 0.651 mmol), and DMF (5 mL). The crude product was recrystallized from EtOH to provide 113 mg of a yellow crystalline solid (42%), mp 237.1-238.2° C. (decomposes). ¹H NMR (DMSO-d₆) δ: 13.55 (br s, 1H); 8.48 (s, 1H); 8.44 (s, 1H); 8.11 (s, 1H); 7.94 (d, J=8.3 Hz, 1H); 7.78 (d, J=8.1 Hz, 2H); 7.66 (d, J=6.7 Hz, 1H); 7.48-7.56 (m, 2H); 4.48 (s, 2H). ¹³C NMR (DMSO-d₆) ppm: 159.8, 156.8, 153.5, 151.5, 149.6, 145.8, 143.6, 135.7, 134.0, 132.2, 132.1, 131.7, 131.5, 130.5, 130.2, 129.8, 128.8, 125.8, 121.9, 32.0. MS (ES): m/z 455.0 (M+). Anal. calcd. for C₂₀H₁₂Cl₂N₆OS*0.1C₂HO*0.6H₂O (0.15KCl: C, 50.34; H, 2.89; Cl, 15.82; N, 17.44; S, 6.65. Found: C, 50.02; H, 2.63; Cl, 15.51; N, 17.39; S, 6.81.

Compound D-021

8-Chloro-3-(2-chlorophenyl)-2-(9H-purin-6-yl-sulfanylmethyl)-3H-quinazolin-4-one Prepared according to Procedure C using Intermediate 2h (200 mg, 0.589 mmol), 6-mercaptopurine monohydrate (124 mg, 0.726 mmol), K₂CO₃ (100 mg, 0.726 mmol), and DMF (4 mL). The crude product was recrystallized from EtOH to provide 202 mg of a white solid (75%), mp 211.9-212.7© (decomposes). ¹H NMR (DMSO-d₆) δ: 13.54 (br s, 1H); 8.47 (s, 1H); 8.44 (s, 1H); 8.12 (d, J=7.9 Hz, 1H); 8.07 (d, J=7.6 Hz, 1H); 7.78 (d, J=7.5 Hz, 1H); 7.67 (d, J=7.1 Hz, 1H); 7.58 (t, J=7.9 Hz, 1H); 7.42-7.54 (m, 2H); 4.52 (s, 2H). ¹¹C NMR (DMSO-d₆) ppm: 160.3, 156.9, 153.9, 151.5, 149.7, 143.5, 135.7, 134.0, 132.1, 131.8, 131.4, 131.1, 130.5, 130.3, 128.9, 128.3, 126.1, 122.4, 32.5. MS (ES): m/z 455.0 (M+). Anal. calcd. for C₂H₁₂Cl₂N₆OS: C, 52.76; H, 2.66; Cl, 15.57; N, 18.46; S, 7.04. Found: C, 52.65; H, 2.79; Cl, 15.32; N, 18.47; S, 7.18.

Compound D-022

3-(2-Chlorophenyl)-7-fluoro-2-(9H-purin-6-yl-sulfanylmethyl)-3H-quinazolin-4-one Prepared according to Procedure C using Intermediate 2c (200 mg, 0.619 mmol), 6-mercaptopurine monohydrate (116 mg, 0.681 mmol), K₂CO, (95 mg, 0.687 mmol), and DMF (4 mL). The crude product was recrystallized from EtOH to provide 143 mg of a white crystalline solid (53%), mp 151.4-154.2° C. (discolors). ¹H NMR (DMSO-d₆) δ: 13.55 (br s, 1H); 8.48 (s, 1H); 8.44 (s, 1H); 8.23 (dd, J=6.3, 8.7 Hz, 1H); 7.77 (dd, J=1.7, 7.4 Hz, 1H); 7.64 (d, J=7.4 Hz, 1H); 7.57 (d, J=9.8 Hz, 1H); 7.45-7.52 (m, 3H); 4.48 (s, 2H). ¹³C NMR (DMSO-d₆) ppm: 169.0 (d, J=253 Hz), 162.6, 159.3, 157.0, 154.0, 152.2, 151.7 (d, J=13 Hz), 146.1, 136.5, 134.7, 134.2, 134.0, 133.0, 132.6 (d, J=11 Hz), 131.3, 120.2, 118.9 (d, J=24 Hz), 115.3 (d, J=22 Hz), 34.6. MS (ES): m/z 439.0 (M+). Anal. calcd. for C₂₀H₁₂ClFN₆OS.0.4-C₂H₆O.0.4H₂O (0.15KCl: C, 52.52; H, 3.22; Cl, 8.57; N, 17.67. Found: C, 52.25; H, 3.11; Cl, 8.20; N, 17.69.

Compound D-023

3-(2-Chlorophenyl)-7-nitro-2-(9H-purin-6-yl-sulfanylmethyl)-3H-quinazolin-4-one

Prepared according to Procedure C using Intermediate 2o (216 mg, 0.617 mmol), 6-mercaptopurine monohydrate (116 mg, 0.681 mmol), K₂CO₃ (94 mg, 0.680 mmol), and DMF (4 mL). The crude product was recrystallized from EtOH to provide 212 mg of a yellow crystalline solid (74%), mp 218.0-218.3° C. (decomposes). ¹H NMR (DMSO-d₆) δ: 13.56 (br s, 1H); 8.49 (s, 1H); 8.42 (s, 1H); 8.38-8.45 (m, 2H); 8.31 (d, J=8.4 Hz, 1H); 7.81 (d, J=6.5 Hz, 1H); 7.68 (d, J=6.7 Hz, 1H); 7.43-7.58 (m, 2H); 4.53 (s, 2H). ¹³C NMR (DMSO-d₆) ppm: 157.7, 154.4, 153.3, 149.8, 149.3, 147.6, 145.2, 141.4, 131.5, 129.8, 129.7, 129.2, 128.4, 127.1, 126.7, 122.7, 120.3, 119.4, 29.9. MS (ES): m/z 466.0 (M+). Anal. calcd. for C₂₀H₁₂ClN₇O₃S.0.4C₂H₆O*0.05KCl: C, 51.19; H, 2.97; Cl, 7.63; N, 20.09; S, 6.57. Found: C, 51.27; H, 2.88; Cl, 7.40; N, 20.04; S, 6.52.

Compound D-024

3-(2-Chlorophenyl)-6-hydroxy-2-(9H-purin-6-yl-sulfanylmethyl)-3H-quinazolin-4-one Prepared according to Procedure C using Intermediate 2p (200 mg, 0.552 mmol), 6-mercaptopurine monohydrate (117 mg, 0.685 mmol), $K_2CO_3$ (95 mg, 0.687 mmol), and DMF (4 mL). The crude product was recrystallized from EtOH to provide 182 mg of a white solid, a mixture of the desired product and the acetyl derivative. A portion of this material (120 mg) was suspended in a mixture of MeOH (2 mL) and aqueous $NaHCO_3$ (satd., 1 mL) and stirred rapidly for 4 hours. The mixture was concentrated in vacuo, suspended in $H_2O$ (10 mL), and stored at 4° C. overnight. The white solid was collected and dried to 103 mg (66%), mp 186-214° C. (gradually decomposes). $^1H$ NMR (DMSO-$d_6$) δ: 8.48 (s, 1H); 8.45 (s, 1H); 7.71 (d, J=6.8 Hz, 1H); 7.62-7.64 (m, 2H); 7.43-7.51 (m, 2H); 7.40-7.43 (m, 1H); 7.35 (d, J=8.8 Hz, 1H); 4.39-4.52 (m, 2H). $^{13}C$ NMR (DMSO-$d_6$) ppm: 160.6, 157.1, 156.2, 151.4, 150.8, 149.3, 144.1, 140.2, 134.5, 132.2, 131.6, 131.4, 130.4, 129.3, 128.7, 124.8, 121.7, 109.8, 32.0. MS (ES): m/z 437.0 (M+). Anal. calcd. for (2 $C_{20}H_{13}ClN_6O_2S.0.1C_2H_6O.6H_2O$: C, 49.68; H, 3.88; Cl, 7.26; N, 17.21; S, 6.57. Found: C, 49.43; H, 3.62; Cl, 7.32; N, 17.07; S, 6.58.

Compound D-025

5-Chloro-3-(2-chlorophenyl)-2-(9H-purin-6-yl-sulfanylmethyl)-3H-quinazolin-4-one Prepared according to Procedure C using Intermediate 2f (300 mg, 0.883 mol), 6-mercaptopurine monohydrate (165 mg, 0.972 mmol), $K_2CO_3$ (134 mg, 0.972 mmol), and DMF (4 mL). The crude product was recrystallized from EtOH to provide 341 mg of a pale orange crystalline solid (85%), mp 233.7-234.4° C. (decomposes). $^1H$ NMR (DMSO-$d_6$) δ: 13.58 (br s, 1H); 8.50 (s, 1H); 8.47 (s, 1H); 7.77-7.85 (m, 2H); 7.68 (d, J=8.1 Hz, 2H); 7.65 (d, J=7.7 Hz, 1H); 7.41-7.56 (m, 2H); 4.45 (d, J=1.2 Hz, 2H). $^{13}C$ NMR (DMSO-$d_6$) ppm: 158.7, 156.8, 153.8, 151.5, 149.6, 149.5, 143.5, 135.4, 134.1, 133.3, 132.2, 131.6, 131.5, 130.2, 128.8, 127.1, 117.6, 32.0. MS (ES): m/z 455.0 (M+). Anal. calcd. for $C_{20}H_{12}Cl_2N_6$—$OS.C_2H_6O.0.3H$: C, 52.14; H, 3.70; Cl, 13.99; N, 16.58; S, 6.33. Found: C, 52.07; H, 3.37; Cl, 13.40; N, 16.65; S, 6.42.

Compound D-026

3-(2-Chlorophenyl)-5-methyl-2-(9H-purin-6-yl-sulfanylmethyl)-3H-quinazolin-4-one Prepared according to Procedure C using Intermediate 2g (300 mg, 0.940 mmol), 6-mercaptopurine monohydrate (176 mg, 1.03 mmol), $K_2CO_3$ (142 mg, 1.03 mmol), and DMF (5 mL). The crude product was recrystallized from EtOH to provide 324 mg of a white crystalline solid (79%), mp 227.8-230.1° C. (decomposes). $^1H$ NMR (DMSO-$d_6$) δ: 13.57 (br s, 1H); 8.49 (s, 1H); 8.47 (s, 1H); 7.69-7.78 (m, 2H); 7.66 (d, J=7.3 Hz, 1H); 7.55 (d, J=7.9 Hz, 1H); 7.39-7.52 (m, 2H); 7.36 (d, J=6.9 Hz, 1H); 4.38-4.50 (m, 2H); 2.74 (s, 3H). $^{13}C$ NMR (DMSO-$d_6$) ppm: 161.2, 156.3, 152.4, 151.5, 148.6, 143.9, 141.0, 134.6, 134.5, 132.3, 131.7, 131.4, 130.4, 130.2, 128.7, 125.7, 119.0, 32.0, 22.8. MS (ES): m/z 435.0 (M+). Anal. calcd. for $C_{21}H_{15}ClN_6OS*0.65C_2H_6O.0.1H_2O$: C, 57.40; H, 4.13; Cl, 7.60; N, 18.01; S, 6.87. Found: C, 57.11; H, 3.96; Cl, 7.45; N, 17.79; S, 6.90.

Compound D-027

3-(2-Chlorophenyl)-6,7-difluoro-2-(9H-purin-6-yl-sulfanylmethyl)-3H-quinazolin-4-one Prepared according to Procedure C using Intermediate 2q (200 mg, 0.586 mmol), 6-mercaptopurine monohydrate (110 mg, 0.645 mmol), $K_2CO_3$ (89 mg, 0.645 mmol), and DMF (4 mL). The crude product was recrystallized from EtOH to provide 143 mg of a pale yellow crystalline solid (53%), mp 207.8° C. (discolors; sweats at 136(C). $^1H$ NMR (DMSO-$d_6$) δ: 13.57 (br s, 1H); 8.49 (s, 1H); 8.46 (s, 1H); 8.11 (t, J=9.4 Hz, 1H); 7.88 (dd, J=7.3, 11 Hz, 1H); 7.77 (dd, J=1.7, 7.3 Hz, 1H); 7.67 (d, J=7.4 Hz, 1H); 7.42-7.55 (m, 2H); 4.48 (s, 2H). $^{13}C$ NMR (DMSO-$d_6$) ppm: 159.5 (d, J=2.5 Hz), 154.6 (dd, J=14, 255 Hz), 154.0 (d, J=1.5 Hz), 151.5, 149.3 (dd, J=14, 250 Hz), 145.1 (d, J=12 Hz), 143.9, 133.9, 132.1, 131.8, 131.4, 130.5, 128.9, 118.0 (d, J=4.9 Hz), 115.8 (d, J=18 Hz), 114.6 (d, J=20 Hz), 32.0. MS (ES): m/z 457.0 (M+). Anal. calcd. for $C_{20}H_{11}ClF_2N_6OS$: C, 52.58; H, 2.43; Cl, 7.76; N, 18.40; S, 7.02. Found: C, 51.81; H, 2.37; Cl, 7.49; N, 18.04; S, 7.55.

Compound D-028

3-(2-Chlorophenyl)-6-fluoro-2-(9H-purin-6-yl-sulfanylmethyl)-3H-quinazolin-4-one Prepared according to Procedure C using Intermediate 2r (118 mg, 0.365 mmol), 6-mercaptopurine monohydrate (68 mg, 0.402 mmol), $K_2CO_3$ (56 mg, 0.402 mmol), and DMF (2 mL). The crude product was recrystallized from EtOH to provide 103 mg of an off-white crystalline solid (64%), mp 232.8-233.0° C. (discolors). $^1H$ NMR (DMSO-$d_6$) δ: 13.56 (br s, 1H); 8.48 (s, 1H); 8.44 (s, 1H); 7.81-7.86 (m, 3H); 7.76 (d, J=7.5 Hz, 1H); 7.67 (d, J=7.5 Hz, 1H); 7.40-7.54 (m, 2H); 4.48 (br s, 2H). $^{13}C$ NMR (DMSO-$d_6$) ppm: 160.8 (d, J=247 Hz), 160.2 (d, J=3.3 Hz), 156.9, 152.3 (d, J=1.9 Hz), 151.5, 149.7, 144.0, 143.6, 134.1, 132.1, 131.7, 131.5, 130.5, 130.4, 130.2, 128.8, 124.0 (d, J=24 Hz), 122.0 (d, J=8.7 Hz), 111.7 (d, J=24 Hz), 32.0. MS (ES): m/z 439.0 (M+). Anal. calcd. for $C_{20}H_{12}ClFN_6OS*0.2C_2H_6O.0.1H_2O$: C, 54.46; H, 3.00; Cl, 7.88; N, 18.68. Found: C, 54.09; H, 2.73; Cl, 7.80; N, 18.77.

Compound D-029

2-(6-Aminopurin-9-ylmethyl)-3-(2-isopropylphenyl)-5-methyl-3H-quinazolin-4-one

Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with 2-isopropylaniline (2.83 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAc (50 mL) and treated with chloro-actyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS (MS (ES): m/z 327 (M+)), and concentrated in vacuo to afford 975 mg (30%) as a white foam. The white foam chloride (450 mg, 1.36 mmol) was dissolved in DMF (10 mL) and treated with adenine (275 mg, 2.04 mmol) and $K_2CO$, (281 mg, 2.04 mmol) and the mixture was stirred overnight at room temperature. The suspension was then poured into 200 mL of water, stirred at room temperature for 30 min then chilled in the refrigerator for 30 min. The resultant solid was collected by vacuum filtration and recrystallized from EtOH to afford 285 mg (49%) of an off white solid. mp 258.0-258.2° C. $^1$H NMR (DMSO-$d_6$) δ: 8.19 (s, 1H), 8.09 (s, 1H), 7.60 (m, 3H), 7.45 (m, 2H), 7.23 (m, 3H), 5.11 (d, J=17.5 Hz, 1H), 4.71 (d, J=17.5 Hz, 1H), 2.68 (s, 3H), 2.73 (q, J=6.9 Hz, 1H), 1.34 (d, J=6.8 Hz, 3H), 1.13 (d, J=6.8 Hz, 3H). $^{13}$C NMR (DMSO-$d_6$) ppm: 161.9, 156.2, 152.8, 151.6, 150.1, 148.4, 146.1, 142.2, 140.8, 134.3, 133.7, 130.6, 130.0, 129.0, 127.7, 127.6, 125.8, 119.2, 118.4, 44.8, 28.3, 24.4, 23.3, 22.9. MS (ES): m/z 426.4 (M+). Anal. calcd. for $C_{24}H_{21}N_7O$: C, 67.75; H, 5.45; N, 23.04. Found: C, 67.60; H, 5.45; N, 22.82.

Compound D-030

2-(6-Aminopurin-9-ylmethyl)-5-methyl-3-o-tolyl-3H-quinazolin-4-one

Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with o-toluidine (2.13 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAc (50 mL) and treated with chloroacetyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS [MS (ES): m/z 299 (M+)), and concentrated in vacuo to afford 476 mg (16%) as a white foam. The white foam chloride (470 mg, 1.57 mmol) was dissolved in DMF (10 mL) and treated with adenine (423 mg, 3.14 mmol) and $K_2CO_3$ (433 mg, 3.14 mmol) and the mixture was stirred overnight at room temperature. The suspension was then poured into 200 mL of $H_2O$, stirred at room temperature for 30 min then chilled in the refrigerator for 30 min. The resultant solid was collected by vacuum filtration and recrystallized from EtOH to afford 123 mg (20%) of an off white solid. mp 281.5-282.7° C. (decomposes). $^1$H NMR (DMSO-$d_6$) δ: 8.07 (s, 1H); 8.05 (s, 1H); 7.61 (t, J=7.8 Hz, 1H), 7.48 (m, 4H), 7.25 (m, 3H), 5.09 (d, J=17.4 Hz, 1H), 4.76 (d, J=17.4 Hz, 1H), 2.73 (s, 3H), 2.18 (s, 3H). $^{13}$C NMR (DMSO-$d_6$) ppm: 161.3, 156.2, 152.8, 151.4, 150.0, 148.5, 142.2, 140.9, 136.1, 135.4, 134.3, 131.7, 130.1, 130.0, 129.0, 128.0, 125.8, 119.2, 118.5, 44.8, 22.9, 17.4. MS (ES): m/z 398.2 (M+). Anal. calcd. for $C_{22}H_{19}N_7O$: C, 66.49; H, 4.82; N, 24.67. Found: C, 66.29; H, 4.78; N, 24.72.

Compound D-031

3-(2-Fluorophenyl)-5-methyl-2-(9H-purin-6-yl-sulfanylmethyl)-3H-quinazolin-4-one Thionyl chloride (2.2 mL, 30 mmol) was added to a stirred solution of 2-amino-6-methylbenzoic acid (1.51 g, 10 mmol) in benzene (50 mL) and the mixture was heated at reflux for 18 h. Once cooled, the solvent was removed in vacuo and stripped down twice with benzene (25 mL). The residue was dissolved in $CHCl_3$ (50 mL) and treated with 2-fluoroaniline (1.93 mL, 20 mmol). The slurry was then heated at reflux for 3 h. At that time TLC (50% EtOAc/hexane) indicated that the reaction was complete. After cooling to room temperature, the reaction mixture was poured atop a 4 cm plug of silica gel and flushed through with 20% EtOAc/hexane. The product containing fractions were combined and concentrated in vacuo. The residue was dissolved in HOAc (50 mL) and treated with chloroacetyl chloride (1.6 mL, 20 mmol) and the mixture was heated at reflux for 18 h. The reaction was cooled and concentrated in vacuo. The remaining HOAc was removed by azeotroping with toluene (25 mL) three times. The residue was dissolved in toluene (10 mL) and poured through a 4 cm plug of silica gel, flushing through with 20% EtOAc/hexane. The product containing fractions were identified by LCMS [MS (ES): m/z 303 (M+)), and concentrated in vacuo to afford 1.12 g (37%) as a white foam. The white foam chloride (455 mg, 1.50 mmol) was dissolved in DMF (10 mL) and treated with 6-mercaptopurine monohydrate (510 mg, 3.0 mmol) and $K_2CO_3$ (414 mg, 3.0 mmol) and the mixture was stirred overnight at room temperature. The suspension was then poured into 200 mL of water, stirred at room temperature for 30 min then chilled in the refrigerator for 30 min. The resultant solid was collected by vacuum filtration and recrystallized from EtOH to afford 487 mg (77%) of an off white solid. mp 151.9-152.2° C. $^1$H NMR (DMSO-$d_6$) δ: 8.48 (s, 1H0, 8.44 (s, 1H), 7.70 (m, 2H), 7.48 (m, 2H), 7.33 (m, 3H), 4.55 (d, J=15.1 Hz, 1H), 4.48 (d, J=15.1 Hz, 1H), 2.73 (s, 3H). $^{13}$C NMR (DMSO-$d_6$) ppm: 161.3, 157.8 (d, J=249.1 Hz), 156.9, 152.8, 151.5, 149.6, 148.6, 143.6, 140.9, 134.7, 131.9 (d, J=8.0 Hz), 131.4, 130.2, 125.6 (d, J=3.6 Hz), 125.5, 124.4 (d, J=13.5 Hz), 118.8, 116.6 (d, J=19.6 Hz), 56.4, 22.9. MS (ES): m/z 419.5 (M+). Anal. calcd. for $C_{21}H_{15}FN_6OS \cdot 0.15\ C_2H_6O$: C, 60.14; H, 3.77; F, 4.47; N, 19.76; S, 7.54. Found: C, 59.89; H, 3.88; F, 4.42; N, 19.42; S, 7.23.

Compound D-032

2-(6-Aminopurin-9-ylmethyl)-5-chloro-3-o-tolyl-3H-quinazolin-4-one

Prepared according to Procedure C using 2j (200 mg, 0.626 mmol), adenine (93 mg, 0.689 mmol), $K_2CO_3$ (95 mg, 0.689 mmol), and DMF (3 mL). The crude product was chromatographed in MeOH/$CH_2Cl_2$ to provide 101 mg of an off-white solid (39%), mp 262.0-266.5° C. $^1$H NMR (DMSO-d$_6$) δ: 8.08 (s, 1H); 8.07 (s, 1H); 7.70 (t, J=8.0 Hz, 1H); 7.58 (dd, J=0.6, 7.9 Hz, 1H); 7.43-7.57 (m, 4H); 7.36 (dd, J=0.7, 8.0 Hz, 1H); 7.26 (br s, 2H); 5.12 (d, J=18 Hz, 1H); 4.78 (d, J=18 Hz, 1H); 2.20 (s, 3H). $^{13}$C NMR (DMSO-d$_6$) ppm: 158.7, 156.2, 152.9, 152.7, 150.0, 149.4, 142.1, 136.1, 135.1, 135.0, 133.2, 131.8, 130.3, 130.1, 128.9, 128.1, 127.2, 118.5, 117.9, 44.9, 17.4. MS (ES): m/z 418.1 (M+). Anal. calcd. for C$_{21}$H$_{16}$ClN$_7$O.0.1H$_2$O.0.05KCl: C, 59.57; H, 3.86; Cl, 8.79; N, 23.16. Found: C, 59.65; H, 3.80; Cl, 8.70; N, 22.80.

Compound D-033

2-(6-Aminopurin-9-ylmethyl)-5-chloro-3-(2-methoxy-phenyl)-3H-quinazolin-4-one

Prepared according to Procedure C using 21 (250 mg, 0.746 mmol), adenine (111 mg, 0.821 mmol), K$_2$CO$_3$ (113 mg, 0.821 mmol), and DMF (4 mL). The crude product was chromatographed in MeOH/CH$_2$Cl$_2$ and recrystallized from EtOH to provide 124 mg of a brown solid (38%), mp 257.0-257.1° C. $^1$H NMR (DMSO-d$_6$) δ: 8.06 (s, 1H); 8.01 (s, 1H); 7.71 (t, J=8.0 Hz, 1H); 7.57 (dd, J=0.9, 7.9 Hz, 1H); 7.52-7.59 (m, 1H); 7.50 (dd, J=1.6, 7.8 Hz, 1H); 7.38 (dd, J=1.1, 8.2 Hz, 1H); 7.27 (dd, J=0.6, 8.3 Hz, 1H); 7.24 (br s, 2H); 7.17 (dt, J=0.9, 7.6 Hz, 1H); 5.07 (d, J=17 Hz, 1H); 4.97 (d, J=17 Hz, 1H); 3.79 (s, 3H). $^{13}$C NMR (DMSO-d$_6$) ppm: 158.8, 156.2, 154.7, 153.2, 152.8, 150.1, 149.3, 142.0, 135.1, 133.2, 131.8, 130.1, 130.1, 127.2, 123.8, 121.6, 118.4, 117.9, 113.1, 56.2, 44.8. MS (ES): m/z 434.0 (M+). Anal. calcd. for C$_{21}$H$_{16}$ClN$_7$O$_2$.0.5H$_2$O.0.04KCl: C, 56.57; H, 3.84; Cl, 8.27; N, 21.99. Found: C, 56.29; H, 3.75; Cl, 8.21; N, 21.61.

The following compounds were made generally in accordance with the above-described methods and serve to further illustrate specific embodiments of the compounds of the invention:

3-(2,6-dichlorophenyl)-5-methyl-2-(9H-purin-6-ylsulfanylmethyl)-3H-quinazolin-4-one (D-034)
3-(2-isopropylphenyl)-5-methyl-2-(9H-purin-6-ylsulfanylmethyl)-3H-quinazolin-4-one (D-035)
3-(2-methoxyphenyl)-2-(9H-purin-6-ylsulfanylmethyl)-3H-quinazolin-4-one (D-036)
3-benzyl-2-(9H-purin-6-ylsulfanylmethyl)-3H-quinazolin-4-one (D-037)
3-butyl-2-(9H-purin-6-ylsulfanylmethyl)-3H-quinazolin-4-one (D-038)
3-morpholin-4-yl-2-(9H-purin-6-ylsulfanylmethyl)-3H-quinazolin-4-one, acetate salt (D-039)
3-(3-methoxyphenyl)-2-(9H-purin-6-ylsulfanylmethyl)-3H-quinazolin-4-one (D-040)
3-(3-chlorophenyl)-2-(9H-purin-6-ylsulfanylmethyl)-3H-quinazolin-4-one (D-041)
2-(9H-purin-6-ylsulfanylmethyl)-3-pyridin-4-yl-3H-quinazolin-4-one (D-042)
3-benzyl-5-fluoro-2-(9H-purin-6-ylsulfanylmethyl)-3H-quinazolin-4-one (D-043)
3-(4-methylpiperazin-1-yl)-2-(9H-purin-6-ylsulfanylmethyl)-3H-quinazolin-4-one, acetate salt (D-044)
[5-fluoro-4-oxo-2-(9H-purin-6-ylsulfanylmethyl)-4H-quinazolin-3-yl]acetic acid ethyl ester (D-045)
3-(2-methoxyphenyl)-2-(9H-purin-6-ylsulfanylmethyl)-3H-quinazolin-4-one (D-046)
3-(2-methoxyphenyl)-5-methyl-2-(9H-purin-6-ylsulfanylmethyl)-3H-quinazolin-4-one (D-047)
2-(6-aminopurin-9-ylmethyl)-3-(2-fluorophenyl)-5-methyl-3H-quinazolin-4-one (D-048)
2-(6-aminopurin-9-ylmethyl)-3-benzyl-5-fluoro-3H-quinazolin-4-one (D-049)
2-(6-aminopurin-9-ylmethyl)-3-butyl-3H-quinazolin-4-one (D-050)
2-(6-aminopurin-9-ylmethyl)-3-morpholin-4-yl-3H-quinazolin-4-one, acetate salt (D-051)
3-(4-chlorophenyl)-2-(9H-purin-6-ylsulfanylmethyl)-3H-quinazolin-4-one (D-052).

Additional compounds of the present invention were prepared by the following synthetic procedures.

The following intermediates were prepared by the above-described Procedure A.

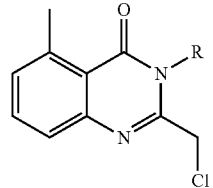

3a R=cyclopropyl
3b R=cyclopropylmethyl
3c R=phenethyl
3d R=cyclopentyl
3e R=3-(2-chloro)pyridyl
3f R=4-(2-methyl)benzoic acid
3g R=4-nitrobenzyl
3h R=cyclohexyl
3i R=E-(2-phenyl)cyclopropyl Additional compounds of the present invention (D-053 through D-070) having the following core structure are discussed in the following Experimental Section. All were prepared following Procedure C.

Core Structure:

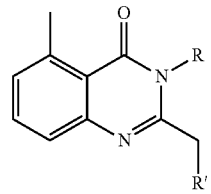

| Compound No. | R | R' |
|---|---|---|
| D-053 | cyclopropyl | C |
| D-054 | cyclopropylmethyl | B |
| D-055 | cyclopropylmethyl | A |
| D-056 | cyclopropylmethyl | C |
| D-057 | phenethyl | B |
| D-058 | phenethyl | C |
| D-059 | cyclopentyl | B |
| D-060 | cyclopentyl | A |
| D-061 | 3-(2-chloro)pyridyl | B |
| D-062 | 3-(2-chloro)pyridyl | A |
| D-063 | 4-(2-methyl)benzoic acid | B |
| D-064 | cyclopropyl | B |
| D-065 | cyclopropyl | A |
| D-066 | 4-nitrobenzyl | B |
| D-067 | cyclohexyl | B |
| D-068 | cyclohexyl | A |

| Compound No. | R | R' |
|---|---|---|
| D-069 | cyclohexyl | C |
| D-070 | E-(2-phenyl)cyclopropyl | B |

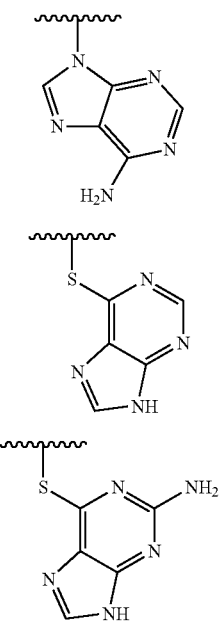

A

B

C

2-(2-Amino-9H-purin-6-ylsulfanylmethyl)-3-cyclopropyl-5-methyl-3H-quinazolin-4-one (D-053)

Prepared according to procedure C using 3a (100 mg, 0.4 mmol), 2-amino-6-mercaptopurine (80 mg, 0.48 mmol), and K$_2$CO$_3$ (77 mg, 0.56 mmol). The product was purified by trituration from H$_2$O. $^3$H NMR (DMSO-d$_6$) δ: 7.89 (d, J=0.9 Hz, 1H); 7.54 (t, J=7.4 Hz, 1H); 7.34 (d, J=8.1 Hz, 1H); 7.19 (d, J=7.2 Hz, 1H); 6.28 (e, 2H); 4.94 (s, 2H); 2.70 (s, 3H); 1.24 (d, J=6.5 Hz, 2H); 0.91 (s, 2H). MS (ES): m/z 380 (M+H), 190.

3-Cyclopropylmethyl-5-methyl-2-(9H-purin-6-ylsulfanylmethyl)-3H-quinazolin-4-one (D-054)

Prepared according to procedure C using 3b (300 mg, 1.14 mmol), 6-mercaptopurine monohydrate (214 mg, 1.26 mmol), and K$_2$CO$_3$ (189 mg, 1.37 mmol). The product was purified by trituration from H$_2$O, followed by recrystallization from MeOH. $^1$H NMR (DMSO-d$_6$) δ: 13.60 (br s, 1H); 8.72 (s, 1H); 8.48 (s, 1H); 7.63 (t, J=7.8 Hz, 1H); 7.42 (d, J=8.0 Hz, 1H); 7.28 (d, J=7.3 Hz, 1H); 5.01 (s, 2H); 4.11 (d, J=6.8 Hz, 2H); 2.78 (s, 3H); 1.35 (quint, J=6.2 Hz, 1H); 0.44-0.59 (m, 4H). MS (ES): m/z 379 (M+H), 325.

2-(6-Aminopurin-9-ylmethyl)-3-cyclopropylmethyl-5-methyl-3H-quinazolin-4-one (D-055)

Prepared according to procedure C using 3b (300 mg, 1.14 mmol), adenine (170 mg, 1.26 mmol), and K$_2$CO$_3$ (189 mg, 1.37 mmol). The product was purified by trituration from H$_2$O, followed by recrystallization from MeOH. $^1$H NMR (DMSO-d) δ: 8.21 (s, 1H); 8.10 (s, 1H); 7.52 (t, J=7.7 Hz, 1H); 7.18-7.31 (m, 3H); 7.06 (d, J=8.1 Hz, 1H); 5.68 (s, 2H); 4.14 (d, J=6.8 Hz, 2H); 2.77 (s, 3H); 1.34 (quint, J=6.4 Hz, 1H); 0.45-0.60 (m, 4H). MS (ES): m/z 362 (M+H), 308.

2-(2-Amino-9H-purin-6-ylsulfanylmethyl)-3-cyclopropylmethyl-5-methyl-3H-quinazolin-4-one (D-056)

Prepared according to procedure C using 3b (280 mg, 1.1 mmol), 2-amino-6-mercaptopurine (200 mg, 1.2 mmol), and K$_2$CO$_3$ (180 mg, 1.3 mmol). The product was purified by trituration from MeOH. $^1$H NMR (DMSO-d$_6$) δ: 12.70 (br s, 1H); 7.95 (s, 1H); 7.64 (t, J=7.8 Hz, 1H); 7.44 (d, J=7.9 Hz, 1H); 7.28 (d, J=7.4 Hz, 1H); 6.41 (s, 2H); 4.91 (s, 2H); 4.05 (d, J=6.8 Hz, 2H); 2.78 (s, 3H); 1.26-1.43 (m, 1H); 0.36-0.56 (m, 4H). MS (ES): m/z 394 (M+H), 340.

5-Methyl-3-phenethyl-2-(9H-purin-6-ylsulfanylmethyl)-3H-quinazolin-4-one (D-057)

Prepared according to procedure C using 3c (750 mg, 2.4 mmol), 6-mercaptopurine monohydrate (442 mg, 2.6 mmol), and K$_2$CO$_3$ (398 mg, 2.9 mmol). The product was purified by trituration from H$_2$O. $^1$H NMR (DMSO-d$_6$) δ: 13.61 (s, 1H); 8.71 (s, 1H); 8.48 (s, 1H); 7.65 (t, J=7.7 Hz, 1H); 7.44 (d, J=7.9 Hz, 1H); 7.16-7.35 (m, 6H); 4.89 (8, 2H); 4.29 (br t, J=7.9 Hz, 2H); 3.08 (br t, J=7.8 Hz, 2H); 2.81 (s, 3H). MS (ES): m/z 429 (M+H), 105.

2-(2-Amino-9H-purin-6-ylsulfanylmethyl)-5-methyl-3-phenethyl-3H-quinazolin-4-one (D-058)

Prepared according to procedure C using 3c (750 mg, 2.4 mmol), 2-amino-6-mercaptopurine (435 mg, 2.6 mmol), and K$_2$CO$_3$ (398 mg, 2.9 mmol). The product was purified by trituration from H$_2$O. $^1$H NMR (DMSO-d$_6$) δ: 12.61 (s, 1H); 7.95 (s, 1H); 7.65 (t, J=7.7 Hz, 1H); 7.45 (d, J=7.9 Hz, 1H); 7.14-7.32 (m, 6H); 6.44 (s, 2H); 4.81 (s, 2H); 4.24 (br t, J=7.9 Hz, 2H); 3.04 (br t, J=7.8 Hz, 2H); 2.81 (s, 3H). MS (ES): m/z 444 (M+H), 340.

3-Cyclopentyl-5-methyl-2-(9H-purin-6-ylsulfanylmethyl)-3H-quinazolin-4-one (D-059)

Prepared according to procedure C using 3d (100 mg, 0.36 mmol), 6-mercaptopurine monohydrate (73 mg, 0.43 mmol), and K$_2$CO$_3$ (100 mg, 0.72 mmol). The product was purified by recrystallization from MeOH. $^1$H NMR (DMSO-d) δ: 13.62 (br s, 1H); 8.77 (s, 1H); 8.48 (s, 1H); 7.62 (t, J=7.7 Hz, 1H); 7.42 (d, J=7.8 Hz, 2H); 7.26 (d, J=7.4 Hz, 1H); 5.03 (s, 2H); 4.80 (quint, J=8.0 Hz, 1H); 2.76 (s, 3H); 2.12-2.31 (m, 2H); 1.79-2.04 (m, 4H); 1.44-1.58 (m, 2H). MS (ES): m/z 393 (M+H), 325.

2-(6-Aminopurin-9-ylmethyl)-3-cyclopentyl-5-methyl-3H-quinazolin-4-one (D-060)

Prepared according to procedure C using 3d (100 mg, 0.36 mmol), adenine (58 mg, 0.43 mmol), and K$_2$CO$_3$ (100 mg, 0.72 mmol). The product was purified by recrystallization from MeOH. $^1$H NMR (DMSO-d$_6$) δ: 8.15 (s, 1H); 8.11 (s, 1H); 7.52 (t, J=7.7 Hz, 1H); 7.16-7.31 (m, 3H); 7.10 (d, J=8.0 Hz, 2H); 5.68 (s, 2H); 4.78 (quint, J=8.3 Hz, 1H); 2.74 (s, 3H); 2.09-2.32 (m, 2H); 1.86-2.04 (m, 2H); 1.68-1.86 (m, 2H); 1.43-1.67 (m, 2H). MS (ES): m/z 376 (M+H), 308, 154.

3-(2-Chloro-pyridin-3-yl)-5-methyl-2-(9H-purin-6-ylsulfanylmethyl)-3H-quinazolin-4-one (D-061)

Prepared according to procedure C using 3e (500 mg, 1.6 mmol), 6-mercaptopurine monohydrate (289 mg, 1.7 mmol), and $K_2CO_3$ (262 mg, 1.9 mmol). The product was purified by trituration from $H_2O$. MS (ES): m/z 436 (M+H), 200.

2-(6-Aminopurin-9-ylmethyl)-3-(2-chloro-pyridin-3-yl)-5-methyl-3N-quinazolin-4-one (D-062)

Prepared according to procedure C using 3e (500 mg, 1.6 mmol), adenine (230 mg, 1.7 mmol), and $K_2CO_3$ (262 mg, 1.9 mmol). The product was purified by trituration from $H_2O$. $^1$H NMR (DMSO-d) δ: 8.59 (dd, J=1.7, 4.8 Hz, 1H); 8.22 (dd, J=1.7, 7.8 Hz, 1H): 8.025 (s, 1H); 8.017 (s, 1H); 7.60-7.72 (m, 2H); 7.35 (t, J=8.2 Hz, 2H); 7.22 (s, 2H); 5.12 (d, J=17.0 Hz, 1H); 5.02 (d, J=17.0 Hz, 1H); 2.72 (s, 3H). MS (ES): m/z 419 (M+H).

3-Methyl-4-[5-methyl-4-oxo-2-(9H-purin-6-ylsulfanyl-methyl)-4H-quinazolin-3-yl]-benzoic acid (D-063)

Prepared according to procedure C using 3f (400 mg, 1.17 mmol), 6-mercaptopurine monohydrate (219 mg, 1.29 mmol), and $K_2CO_3$ (226 mg, 1.64 mmol).
The product was purified by recrystallization from MeOH. $^1$H NMR (DMSO-$d_6$) δ: 13.54 (br s, 1H); 8.44 (s, 1H); 8.42 (s, 1H); 7.80 (s, 2H); 7.71 (t, J=7.7 Hz, 1H); 7.59 (d, J=8.6 Hz, 1H); 7.52 (d, J=7.9 Hz, 1H); 7.34 (d, J=7.4 Hz, 1H); 4.46 (d, J=15.4 Hz, 1H); 4.34 (d, J=15.7 Hz, 1H); 3.17 (d, J=4.4 Hz, 1H); 2.73 (s, 3H); 2.17 (s, 3H). MS (ES): m/z 459 (M+H).

3-Cyclopropyl-5-methyl-2-(9H-purin-6-ylsulfanyl-methyl)-3H-quinazolin-4-one (D-064)

Prepared according to procedure C using 3a (100 mg, 0.40 mmol), 6-mercaptopurine monohydrate (90 mg, 0.53 mmol), and $K_2CO_3$ (97 mg, 0.7 mmol). The product was purified by trituration from $H_2O$. $^1$H NMR (DMSO-$d_6$) δ: 8.69 (d, J=0.8 Hz, 1H); 8.47 (s, 1H); 7.57 (d, J=7.9 Hz, 1H); 7.37 (d, J=8.1 Hz, 1H); 7.23 (d, J=7.3 Hz, 1H); 5.08 (s, 2H); 3.06-3.18 (m, 1H); 2.74 (s, 3H); 1.14-1.36 (m, 2H); 0.92-1.06 (m, 2H).

2-(6-Aminopurin-9-ylmethyl)-3-cyclopropyl-5-methyl-3H-quinazolin-4-one (D-065)

Prepared according to procedure C using 3a (100 mg, 0.40 mmol), adenine (94 mg, 0.7 mmol), and $K_2CO_3$ (121 mg, 0.88 mmol). The product was purified by trituration from $H_2O$. $^1$H NMR (DMSO-$d_6$) δ: 8.19 (d, J=0.9 Hz, 1H); 8.09 (d, J=1.0 Hz, 1H); 7.48 (t, J=7.8 Hz, 1H); 7.13-7.29 (m, 3H); 7.04 (d, J=8.1 Hz, 1H); 5.74 (s, 2H); 3.00-3.13 (m, 1H); 2.73 (s, 3H); 1.18-1.38 (m, 2H); 0.94-1.09 (m, 2H).

5-Methyl-3-(4-nitro-benzyl)-2-(9H-purin-6-ylsulfa-nylmethyl)-3H-quinazolin-4-one (D-066)

Prepared according to procedure C using 3g (200 mg, 0.58 mmol), 6-mercaptopurine monohydrate (148 mg, 0.87 mmol), and $K_2CO_3$ (160 mg, 1.16 mmol). The product was purified by trituration from MeOH. $^1$H NMR (DMSO-d) δ: 13.44 (br s, 1H); 8.50 (s, 1H); 8.31 (s, 1H); 8.03 (d, J=8.6 Hz, 2H); 7.58 (t, J=7.9 Hz, 1H); 7.37 (d, J=8.3 Hz, 3H); 7.22 (d, J=7.5 Hz, 1H); 5.44 (s, 2H); 4.70 (s, 2H); 2.66 (s, 3H). MS (ES): m/z 460 (M+H).

3-Cyclohexyl-5-methyl-2-(9H-purin-6-ylsulfanyl-methyl)-3H-quinazolin-4-one (D-067)

Prepared according to procedure C using 3h (150 mg, 0.52 mmol), 6-mercaptopurine monohydrate (97 mg, 0.57 mmol), and $K_2CO_3$ (86 mg, 0.62 mmol). The product was purified by trituration from MeOH. $^1$H NMR (DMSO-$d_6$) δ: 13.66 (br s, 1H); 8.82 (s, 1H); 8.50 (s, 1H); 7.62 (t, J=7.7 Hz, 1H); 7.42 (d, J=8.0 Hz, 1H); 7.26 (d, J=7.3 Hz, 1H); 5.01 (s, 2H); 4.11 (br s, 1H); 2.75 (s, 3H); 2.38-2.65 (m, 2H); 1.58-1.90 (m, 4H); 1.37-1.57 (m, 1H); 0.71-1.26 (m, 3H). MS (ES): m/z 407 (M+H), 325.

2-(6-Aminopurin-9-ylmethyl)-3-cyclohexyl-5-methyl-3H-quinazolin-4-one (D-068)

Prepared according to procedure C using 3h (150 mg, 0.52 mmol), adenine (77 mg, 0.57 mmol), and $K_2CO_3$ (86 mg, 0.62 mmol). The product was purified by trituration from MeOH. $^1$H NMR (DMSO-$d_6$) δ: 8.15 (s, 2H); 7.54 (t, J=7.9 Hz, 1H); 7.06-7.35 (m, 4H); 5.65 (s, 2H); 4.09 (br s, 1H); 2.73 (s, 3H); 1.41-1.90 (m, 6H); 0.99-1.34 (m, 4H). MS (ES): m/z 390 (M+H), 308.

2-(2-Amino-9H-purin-6-ylsulfanylmethyl)-3-cyclo-hexyl-5-methyl-3H-quinazolin-4-one (D-069)

Prepared according to procedure C using 3h (150 mg, 0.52 mmol), 2-amino-6-mercaptopurine (95 mg, 0.57 mmol), and K?$CO_3$ (86 mg, 0.62 mmol). The product was purified by reversed-phase HPLC (C18 Luna column, 4.6× 250 mm, 4.7 mL/min, 10-75% acetonitrile/water over 15 min, 100% acetonitrile at 18 min, detector at 220). MS (ES): m/z 422 (M+H), 340, 170.

5-Methyl-3-(E-2-phenyl-cyclopropyl)-2-(9H-purin-6-ylsulfanylmethyl)-3H-quinazolin-4-one (D-070)

Prepared according to procedure C using 3i and 6-mer-captopurine monohydrate). The product was purified by reversed-phase HPLC (C18 Luna column, 4.6×250 mm, 4.7 mL/min, 10-75% acetonitrile/water over 15 min, 100% acetonitrile at 18 min, detector at 220). MS (ES): m/z 441.

The following Methods 1 and 2 were used as the HPLC analyses for the following compounds:

HPLC Method 1.

Column: 2×50 mm C18 Luna column (from Phenom-enex), flow rate: 0.3 mL/min, UV detection at 214 and 254 nm. Initial conditions: 2% solvent B in solvent A; t=3 min, 20% Solvent B; t=6 min, 80% Solvent B, where Solvent A=water with 0.05% formic acid and Solvent B=acetonitrile with 0.05% formic acid.

HPLC Method 2.

Column: 2×50 mm C18 Luna column (from Phenom-enex), flow rate: 0.3 mL/min, UV detection at 214 and 254 nm. Initial conditions: 0.10-100% solvent B in solvent A over 6 min, where Solvent A=water and Solvent B=acetonitrile.

Compounds D-070A and D-070B were prepared as follows:

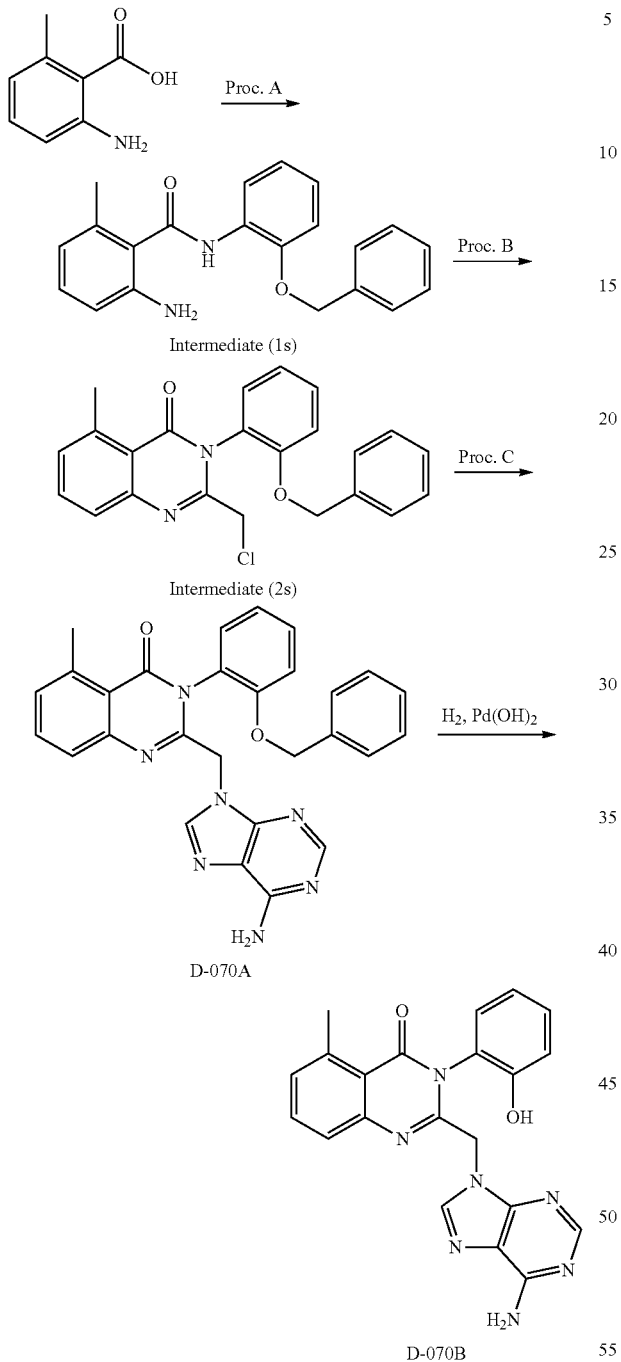

2-(6-Aminopurin-9-ylmethyl)-3-(2-benzyloxyphenyl)-5-methyl-3H-quinazolin-4-one (D-070A)

Using procedure A, 6-methylanthranilic acid and 2-benzyloxyaniline were converted to Intermediate (1s). Using procedure B, Intermediate (1s) was converted to Intermediate (2s). Using procedure C, Intermediate (2s) was converted to D-070A. Retention time using HPLC Method 2: 4.7 min. LRMS (ES pos.) m/z=490 (M+1).

2-(6-Aminopurin-9-ylmethyl)-3-(2-hydroxyphenyl)-5-methyl-3H-quinazolin-4-one (D-070B)

A mixture of D-070A (35 mg, 0.07 mmol) and Pd(OH)$_2$ (20% by wt. on C, 50 mg) in ethanol (5 mL) was shaken 24 hours under 40 psi of hydrogen gas. The catalyst was removed by filtration through a 0.22 um cellulose acetate membrane (Corning), and the filtrate was concentrated in vacuo to afford the solid product (10 mg). Retention time using HPLC Method 2: 3.6 min. LRMS (ES pos.) m/z=400 (M+1).

Compounds D-070C through D-070F were prepared according to the following scheme.

2-(6-Aminopurin-9-ylmethyl)-5-methyl-3-{2-(2-(1-methylpyrrolidin-2-yl)-ethoxy)-phenyl}-3H-quinazolin-4-one (D-070C)

A mixture of D-070B (30 mg, 0.075 mmol), 2-(2-chloroethyl)-1-methylpyrrolidine hydrochloride (28 mg, 0.15 mmol), and potassium carbonate (50 mg, 0.36 mmol) in DMF (0.3 mL) was stirred at 80° C. for 16 hours. The solvent was removed in vacuo, then the residue was dissolved in DMSO/water (1 mL) and purified by HPLC in two portions (C18 Luna column, 4.6×250 mm, 4.7 mL/min, 2-50% acetonitrile/water over 15 min, 100% acetonitrile at 18 min, 0.05% TFA in all solvents, detector at 2201). Appropriate fractions were concentrated in vacuo, then concentrated twice from 1 N HCl (1 mL) to yield the final product as the HCl salt (10 mg). Retention time using HPLC method 1: 4.7 min. LRMS (ES pos.) m/z=511 (M+1).

2-(6-Aminopurin-9-ylmethyl)-3-(2-(3-dimethyl-amino-propoxy)-phenyl)-5-methyl-3H-quinazolin-4-one (D-070D)

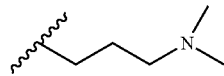 [SMILES: *CCCN(C)C]

A mixture of D-070B (30 mg, 0.075 mmol), 2-chloroethyl)-1-methylpyrrolidine hydrochloride (28 mg, 0.15 mmol), and potassium carbonate (50 mg, 0.36 mmol) in DMF (0.3 mL) was stirred at 80° C. for 16 h. The solvent was removed in vacuo, then the residue was dissolved in DMSO/water (1 mL) and purified by HPLC in two portions (C18 Luna column, 4.6×250 mm, 4.7 mL/min, 2-50% acetonitrile/water over 15 min, 100% acetonitrile at 18 min, 0.05% TFA in all solvents, detector at 2201). Appropriate fractions were concentrated in vacuo, then concentrated twice from 1 N HCl (1 mL) to yield the final product as the HCl salt (14 mg). Retention time using HPLC Method 1: 4.5 min. LRMS (ES pos.) m/z=485 (M+1).

2-(6-Aminopurin-9-ylmethyl)-5-methyl-3-(2-prop-2-ynyloxyphenyl)-3H-quinazolin-4-one (D-070E)

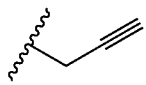 [SMILES: *CC#C]

A mixture of D-070B (20 mg, 0.05 mmol), propargyl chloride (0.025 mL, 0.33 mmol), and potassium carbonate (14 mg, 0.1 mmol) in DMF (0.3 mL) was stirred at 80° C. for 16 hours. The reaction mixture was cooled to room temperature, treated with water (5 mL), and the resulting dark brown precipitate was collected by filtration. The crude solid was dissolved in 0.6 mL DMSO and purified by HPLC (C18 Luna column, 4.6×250 mm, 4.7 mL/min, 10-75% acetonitrile/water over 15 min, 100% acetonitrile at 18 min, detector at 2201). Appropriate fractions were concentrated in vacuo to yield the final product as a white solid (4 mg.). Retention time using HPLC Method 2: 4.1 min. LRMS (ES pos.) m/z=438 (M+1).

2-{2-(2-(6-Aminopurin-9-ylmethyl)-5-methyl-4-oxo-4H-quinazolin-3-yl)-phenoxy}-acetamide (D-070F)

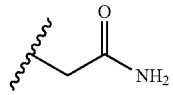

A mixture of D-070B (20 mg, 0.05 mmol), 2-chloroacetamide (14 mg, 0.15 mmol), and potassium carbonate (21 mg, 0.15 mmol) in DMF (0.3 mL) was stirred at 80° C. for 16 hours. The reaction mixture was cooled to room temperature, treated with water (5 mL), and the resulting precipitate was collected by filtration. Retention time using HPLC Method 2: 3.4 min. LRMS (ES pos.) m/z=457 (M+1).

Additional compounds of the present invention were prepared by the following synthetic procedures.

Additional compounds of the invention follow, together with the synthetic route to compounds D-071 to D-118.

Procedure D

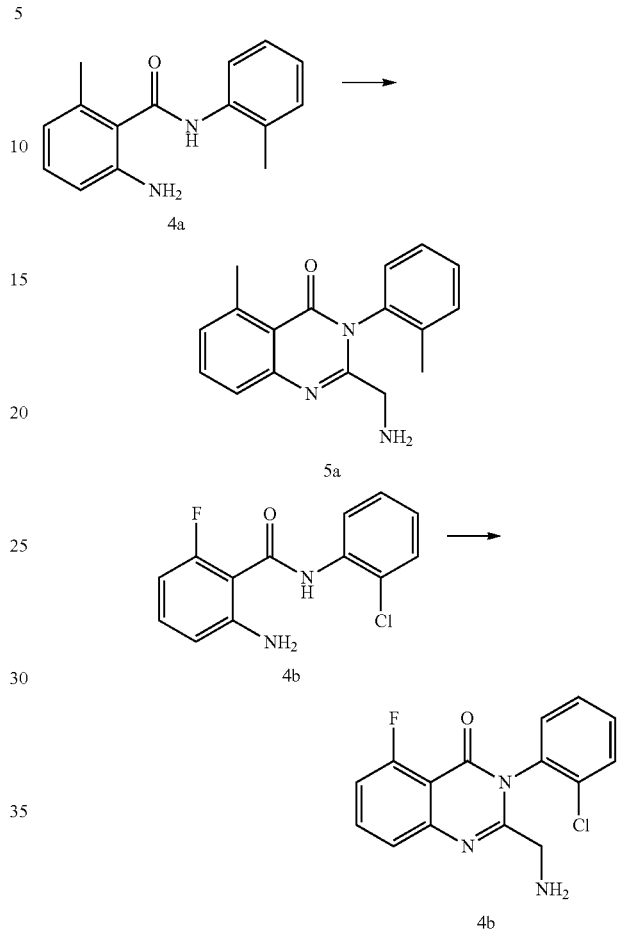

Procedure E

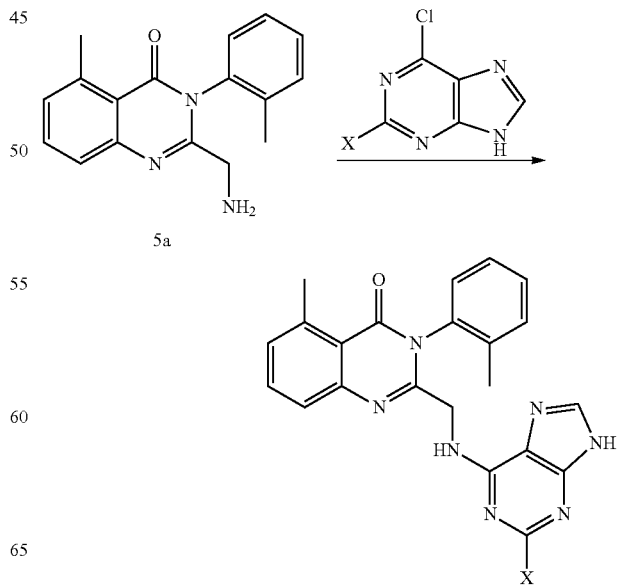

Procedure F

Procedure D:
A mixture of amide 4a or 4b, FMOC-glycyl-chloride, and glacial acetic acid was heated to 120° C. for 1 to 4 hours. The resulting mixture was concentrated in vacuo and purified by flash chromatography to provide the protected, cyclized amine. This material was combined with 10 equivalents octanethiol and a catalytic amount of DBU in THF and stirred at ambient temp until consumption of starting material was indicated by LCMS. The reaction was poured directly onto a flash column (equilibrated in $CH_2Cl_2$) and eluted with 0-5% MeOH/$CH_2Cl_2$ to provide the free amine, 5a or 5b. Compound 5c was prepared in an analogous manner using (±) FMOC-alanyl-chloride in place of FMOC-glycyl chloride.

Procedure D1:

Amide 4a was admixed with Cbz-α-aminobutyric acid OSu, DIEA, DMAP (cat.), and toluene, then stirred at reflux for 3 days. The resulting mixture was purified by flash chromatography (EtOAc/hexanes) to provide the protected, cyclized amine. The amine was dissolved in EtOH with a catalytic amount of Pd/C, and allowed to stir at ambient temperature under $H_2$ until a complete reaction was indicated by LCMS. The reaction mixture was filtered, and the filtrate concentrated in vacuo. Purification by flash chromatography (MeOH/$CH_2Cl_2$) provided the free amine 5d.

Procedure D2:

Amide 4a was combined with Boc-Serine(OBn)-OSu, DIEA, DMAP (cat.), and toluene, then stirred at reflux for 4 days. The resulting mixture was purified by flash chromatography (EtOAc/hexanes) to provide the protected, cyclized amine. The product was dissolved in a mixture of TFA and $CH_2Cl_2$, and allowed to stir at ambient temperature until a complete reaction was indicated by LCMS. The reaction was concentrated in vacuo and purified by flash chromatography (MeOH/$CH_2Cl_2$) to provide free amine 5e.

Procedure E:

Compounds 5(a-e), the appropriate 6-chloropurine or 6-bromopurine, and DIEA were combined with EtOH or DMF in a small vial and heated to 80° C. The reaction was monitored regularly by LCMS and purified as stated.

Procedure F:

A mixture of amide 4b, acetoxyacetyl chloride, and glacial acetic acid was heated to 120° C. and stirred for 2 hours. The cooled reaction was filtered and the solids washed with $CH_2Cl_2$ to provide the cyclized acetate as a white solid. This material was combined with $K_2CO_3$ in aqueous methanol and stirred for one hour, then concentrated in vacuo. The resulting solids were triturated from $H_2O$ to provide 6a as a white solid.

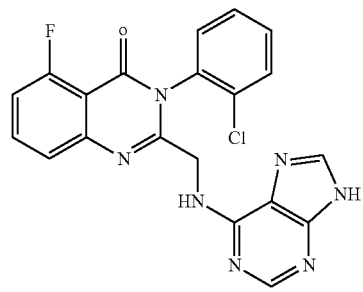

3-(2-Chlorophenyl)-5-fluoro-2-[(9H-purin-6-ylamino)-methyl]-3H-quinazolin-4-one (D-072)

Prepared according to procedure E using 5b (50 mg, 0.165 mmol) and 6-chloropurine (26 mg, 0.165 mmol) in 1 mL EtOH. After 5 days, reaction purified by HPLC (C18 Luna column, 4.6×250 mm, 4.7 mL/min, 10-75% acetonitrile/water over 15 min, 100% acetonitrile at 18 min, detector at 220λ). $^1$H NMR (DMSO-$d_6$) δ: 12.99 (br a, 1H); 8.14 (br s, 1H); 8.12 (s, 1H); 7.85 (dt, J=5.7, 8.1 Hz., 1H); 7.68-7.79 (m, 3H); 7.57 (t, J=6.2 Hz., 1H); 7.57 (d, J=7.7 Hz., 1H); 7.50 (d, J=8.1 Hz., 1H); 7.35 (dd, J=8.4, 10.7 Hz., 1H); 4.15-4.55 (m, 2H). MS (ES): m/z 422 (M+H), 211.

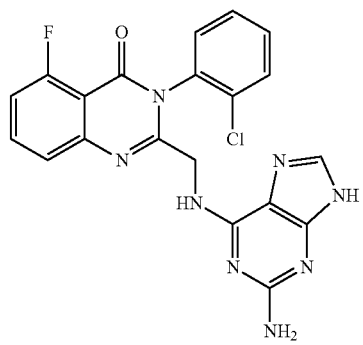 [SMILES: Nc1nc(NCc2nc3cccc(F)c3c(=O)n2-c2ccccc2Cl)c2nc[nH]c2n1]

2-[(2-Amino-9H-purin-6-ylamino)methyl]-3-(2-chlorophenyl)-5-fluoro-3H-quinazolin-4-one (D-074)

Prepared according to procedure E using 5b (50 mg, 0.165 mmol) and 2-amino-6-chloropurine (28 mg, 0.165 mmol) in 1 mL EtOH. After 5 days, reaction purified by HPLC (C18 Luna column, 4.6×250 mm, 4.7 mL/min, 10-75% acetonitrile/water over 15 min, 100% acetonitrile at 18 min, detector at 220λ). $^1$H NMR (DMSO-d) δ: 12.13 (br s, 1H); 7.86 (dt, J=5.6, 8.2 Hz., 1H); 7.76-7.83 (m, 2H); 7.68 (br a, 1H); 7.61 (t, J=5.7 Hz., 1H); 7.61 (d, J=7.2 Hz., 1H); 7.53 (d, J=8.2 Hz., 1H); 7.35 (dd, J=8.2, 10.9 Hz., 1H); 5.66 (br s, 2H); 4.16-4.50 (m, 1H); 4.09 (q, J=5.3 Hz., 2H). MS (ES): m/z 437 (M+H), 219.

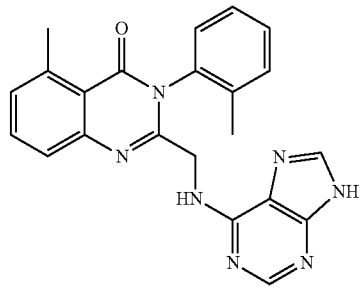 [SMILES: Cc1ccccc1-n1c(CNc2ncnc3[nH]cnc23)nc2cccc(C)c2c1=O]

5-Methyl-2-[(9H-purin-6-ylamino)methyl]-3-o-tolyl-3H-quinazolin-4-one (D-071)

Prepared according to procedure E using 6-chloropurine (11 mg, 0.072 mmol) and 5a (20 mg, 0.072 mmol). After 5 days, the reaction was quenched with water and the resulting suspension filtered. The solids were purified by HPLC (C18 Luna column, 4.6×250 mm, 4.7 mL/min, 10-75% acetonitrile/water over 15 min, 100% acetonitrile at 18 min, detector at 220k). $^1$H NMR (DMSO-d) δ: 12.98 (br s, 1H); 8.14 (br s, 1H); 8.10 (s, 1H); 7.58-7.79 (m, 2H); 7.37-7.48 (m, 4H); 7.26-7.36 (m, 2H); 3.93-4.39 (m, 2H); 2.75 (s, 3H); 2.18 (s, 3H). MS (ES): m/z 398 (M+H), 199.

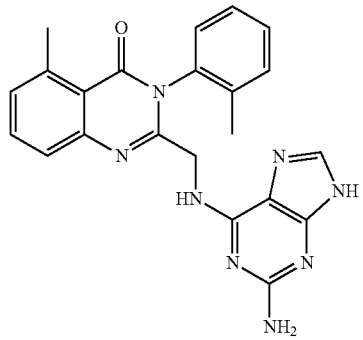 [SMILES: Cc1ccccc1-n1c(CNc2nc(N)nc3[nH]cnc23)nc2cccc(C)c2c1=O]

2-[(2-Amino-9H-purin-6-ylamino)methyl]-5-methyl-3-o-tolyl-3H-quinazolin-4-one (D-073)

Prepared according to procedure E using 5a (189 mg, 0.677 mmol) and 2-amino-6-chloropurine (115 mg, 0.677) in 3 mL EtOH. After 3 days, the reaction was filtered to remove excess purine and the filtrate purified by HPLC (C18 Luna column, 4.6×250 mm, 4.7 mL/min, 10-75% acetonitrile/water over 15 min, 100% acetonitrile at 18 min, detector at 220λ) to provide 7 mg of the product as the TFA salt. $^1$H NMR (DMSO-$d_6$) δ: 8.88 (br s, 1H); 8.21 (s, 1H); 7.71 (t, J=7.7 Hz., 1H); 7.45-7.56 (m, 2H); 7.38-7.44 (m, 3H); 7.35 (d, J=7.5 Hz., 1H); 7.30 (br s, 1H); 4.40 (dd, J=4.5, 17.5 Hz., 1H); 4.27 (dd, J=5.3, 17.4 Hz., 1H); 2.75 (s, 3H); 2.09 (s, 3H). MS (ES): m/z 413 (M+H), 207, 163.

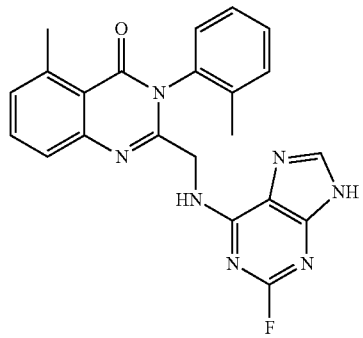 [SMILES: Cc1ccccc1-n1c(CNc2nc(F)nc3[nH]cnc23)nc2cccc(C)c2c1=O]

2-[(2-Fluoro-9H-purin-6-ylamino)methyl]-5-methyl-3-o-tolyl-3H-quinazolin-4-one (D-076)

Prepared according to procedure E using 5a (20 mg, 0.072 mmol) and 2-fluoro-6-chloropurine (16 mg, 0.094 mmol) in 1 mL EtOH. After 18 hours, the reaction was purified by HPLC (C18 Luna column, 4.6×250 mm, 4.7 mL/min, 10-75% acetonitrile/water over 15 min, 100% acetonitrile at 18 min, detector at 220λ) and subsequently recrystallized from EtOH to provide 14 mg of the product as a yellow solid. $^1$H NMR (DMSO-d) δ: 13.12 (br s, 1H); 8.40 (br s, 1H); 8.15 (s, 1H); 7.66 (t, J=7.7 Hz, 1H); 7.35-7.49 (m, 4H); 7.31 (d, J=7.2 Hz., 1H); 4.00-4.22 (m, 2H); 3.17 (s, 1H); 2.74 (s, 3H); 2.18 (s, 3H). MS (ES): m/z 416 (M+H), 208.

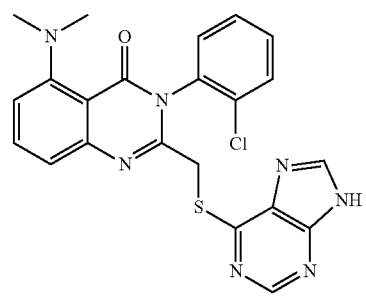 [SMILES: CN(C)c1cccc2nc(CSc3ncnc4[nH]cnc34)n(-c3ccccc3Cl)c(=O)c12]

(2-Chlorophenyl)-dimethylamino-(9H-purin-6-ylsulfanylmethyl)-3H-quinazolin-4-one (D-075)

D-015 (100 mg, 0.228 mmol) was combined with ammonium hydroxide (28-30%, 1 mL) in DMF (2 mL) and heated to 80° C. After 2 days, the reaction was purified by HPLC (C18 Luna column, 4.6×250 mm, 4.7 mL/min, 10-75% acetonitrile/water over 15 min, 100% acetonitrile at 18 min, detector at 220λ) to provide the product as a yellow solid, ~2 mg. $^1$H NMR (DMSO-$d_6$) δ: 13.52 (br s, 1H); 8.46 (s, 1H); 8.42 (s, 1H); 7.69 (dd, J=2.1, 7.3 Hz, 1H); 7.62 (dd, J=1.6, 7.6 Hz., 1H); 7.61 (t, J=8.0 Hz., 1H); 7.37-7.48 (m, 2H); 7.05 (d, J=7.9 Hz., 1H); 6.96 (d, J=7.8 Hz., 1H); 4.32-4.45 (m, 2H); 2.80 (s, 6H). MS (ES): m/z 464 (M+H), 232.

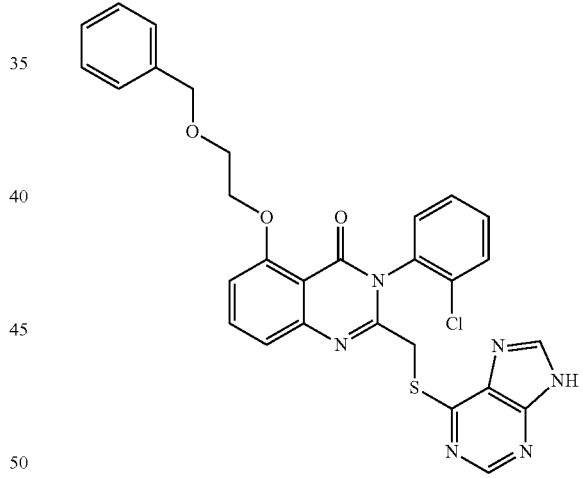

5-(2-Benzyloxyethoxy)-3-(2-chlorophenyl)-2-(9H-purin-6-ylsulfanylmethyl)-3H-quinazolin-4-one (D-078)

To a solution of 2-benzyloxyethanol (0.3 mL) in DMF (1.0 mL) was added NaH (50 mg, 2.08 mmol). After stirring for 5 minutes, 0.5 mL was added to a solution of D-015 (50 mg, 0.114 mmol) in anhydrous DMF (0.75 mL). The reaction was heated to 50° C. and stirred for 3 days. Purification by HPLC (C18 Luna column, 4.6×250 mm, 4.7 mL/min, 10-75% acetonitrile/water over 15 min, 100% acetonitrile at 18 min, detector at 220λ) provided the product as a heterogeneous solid, 150 μg. MS (ES): m/z 571 (M+H), 481.

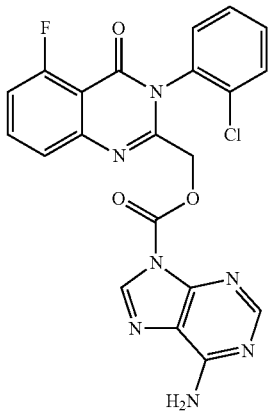 [SMILES: Nc1ncnc2c1ncn2C(=O)OCc1nc2cccc(F)c2c(=O)n1-c1ccccc1Cl]

6-Aminopurine-9-carboxylic acid 3-(2-chlorophenyl)-5-fluoro-4-oxo-3,4-dihydro-quinazolin-2-ylmethyl ester (D-079)

To a solution of 3b (20 mg, 0.066 mmol) in CH$_2$Cl, (500 µL) at 0° C. was added phosgene (2M/toluene, 36 µL, 0.072 mmol), followed by adenine (10 mg, 0.072 mmol), and DIEA (25 µL, 0.145 mmol). The reaction was allowed to attain ambient temperature and stir for 8 days. Purification by HPLC (C18 Luna column, 4.6×250 mm, 4.7 mL/min, 10-75% acetonitrile/water over 15 min, 100% acetonitrile at 18 min, detector at 220λ) provided the product as a mixture. $^1$H NMR (DMSO-d) δ: 11.04 (br s, 1H); 8.61 (s, 1H); 8.40 (s, 1H); 7.85-7.95 (m, 1H); 7.76 (dd, J=5.4, 9.6 Hz, 1H); 7.70-7.78 (m, 1H); 7.52-7.63 (m, 3H); 7.38 (dt, J=8.3, 10.6 Hz., 1H); 4.76-4.89 (m, 2H). MS (ES): m/z 466 (M+H), 331, 305.

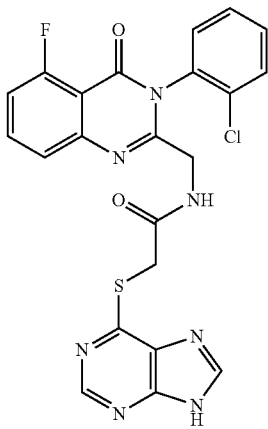 [SMILES: O=C(CSc1ncnc2[nH]cnc12)NCc1nc2cccc(F)c2c(=O)n1-c1ccccc1Cl]

N-[3-(2-Chlorophenyl)-5-fluoro-4-oxo-3,4-dihydro-quinazolin-2-ylmethyl]-2-(9H-purin-6-ylsulfanyl)-acetamide (D-077)

(9H-Purin-6-ylsulfanyl)-acetic acid (63 mg, 0.296 mmol), 5b (108 mg, 0.355 mmol), EDC (68 mg, 0.355 mmol), HOBT (48 mg, 0.355 mmol), DIEA (62 µL, 0.355 mmol), and DMF (1 mL) were combined in a flask and stirred at ambient temperature for one hour. The reaction was diluted with EtOAc (20 mL) and washed with dilute brine (2×13 mL). The organic phase was concentrated in vacuo and chromatographed in 5% MeOH/CH$_2$Cl$_2$ to provide the 91 mg of the product as a viscous, peach foam. $^1$H NMR (DMSO-d$_6$) δ: 12.88 (br s, 1H); 8.72 (s, 1H); 8.62 (t, J=5.0 Hz, 1H); 8.49 (s, 1H); 7.88 (dt, J=5.6, 8.2 Hz, 1H); 7.73-7.78 (m, 1H); 7.67-7.72 (m, 1H); 7.57-7.65 (m, 2H); 7.38 (d, J=8.1 Hz., 1H); 7.36 (dd, J=8.3, 11.1 Hz., 1H); 4.11-4.24 (m, 2H); 3.96 (dd, J=5.0, 17.4 Hz, 1H); 3.78 (dd, J=5.2, 17.4 Hz, 1H). MS (ES): m/z 496 (M+H), 248.

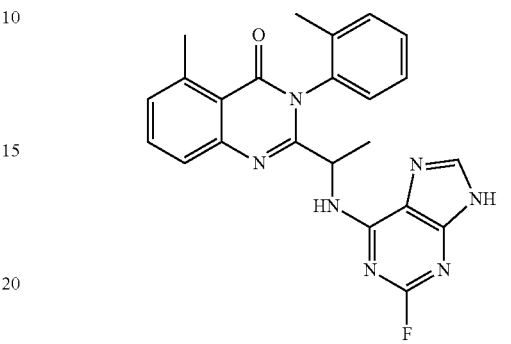

2-[1-(2-Fluoro-9H-purin-6-ylamino)ethyl]-5-methyl-3-o-tolyl-3H-quinazolin-4-one (D-080)

Prepared according to procedure E using 5c (50 mg, 0.17 mmol) and 2-fluoro-6-chloropurine (35 mg, 0.204 mmol) in 1.2 mL EtOH. Purification by HPLC (C18 Luna column, 4.6×250 mm, 4.7 mL/min, 10-75% acetonitrile/water over 15 min, 100% acetonitrile at 18 min, detector at 220λ) provided two atropisomers as white solids. Data for one of these follows: $^1$H NMR (DMSO-d$_6$) δ: 8.48 (br d, J=6.4 Hz, 1H); 8.17 (s, 1H); 7.69 (t, J=7.8 Hz, 1H); 7.53 (d, J=7.8 Hz, 1H); 7.44 (d, J=7.8 Hz, 2H); 7.33 (d, J=7.2 Hz, 2H); 7.07 (br t, J=7.2 Hz, 1H); 4.80 (br t, J=6.8 Hz, 1H); 2.74 (s, 3H); 2.09 (s, 3H); 1.38 (d, J=6.7 Hz, 3H). MS (ES): m/z 430 (M+H), 215.

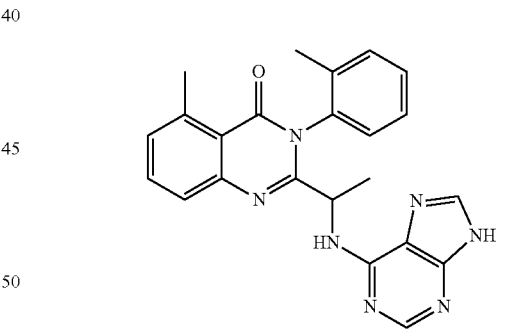

5-Methyl-2-[1-(9H-purin-6-ylamino)ethyl]-3-o-tolyl-3H-quinazolin-4-one (D-081)

Prepared according to procedure E using 5c (50 mg, 0.17 mmol) and 6-chloropurine (32 mg, 0.204 mmol) in 1.2 mL EtOH. Purification by HPLC (C18 Luna column, 4.6×250 mm, 4.7 mL/min, 10-75% acetonitrile/water over 15 min, 100% acetonitrile at 18 min, detector at 220λ) provided two atropisomers as yellow solids. Data for one of these follows: $^1$H NMR (DMSO-d) δ: 8.39 (s, 1H); 8.34 (s, 1H); 8.18 (s, 1H); 7.71 (t, J=7.7 Hz, 1H); 7.56 (d, J=7.9 Hz, 1H); 7.49 (d, J=6.9 Hz, 1H); 7.28-7.43 (m, 3H); 7.20 (br s, 1H); 5.06 (br s, 1H); 2.73 (s, 3H); 2.04 (s, 3H); 1.51 (d, J=6.6 Hz, 3H). MS (ES): m/z 412 (M+H), 206.

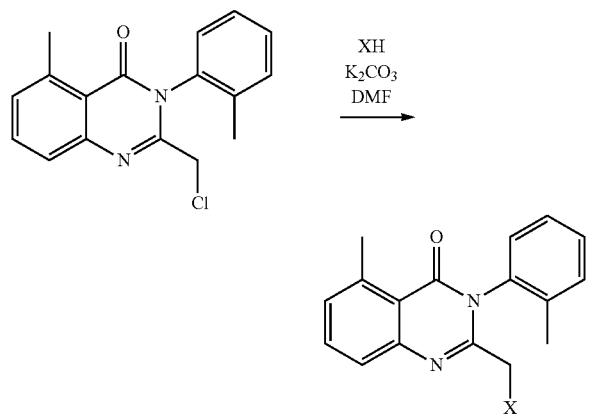

5-Methyl-2-(1-(9H-purin-6-ylamino)propyl)-3-o-tolyl-3H-quinazolin-4-one (D-081b)

Synthesized according to procedure E using compound 5d (100 mg, 0.325 mmol) and 6-bromopurine (78 mg, 0.390 mmol) in 2 mL EtOH. Purification by HPLC (C18 Luna column, 4.6×250 mm, 4.7 mL/min, 10-75% acetonitrile/water over 15 min, 100% acetonitrile at 18 min, detector at 2201) provided two atropisomers as yellow solids. Data for one isomer follows: $^1$H NMR (DMSO-$d_6$) δ: 8.64 (br s, 1H); 8.44 (s, 1H); 8.27 (s, 1H); 7.72 (t, J=7.7 Hz, 1H); 7.56 (d, J=8.0 Hz, 1H); 7.50 (d, J=6.6 Hz, 1H); 7.34-7.44 (m, 2H); 7.35 (d, J=7.4 Hz, 1H); 7.18-7.27 (m, 1H); 4.85-5.01 (m, 1H); 2.73 (s, 3H); 2.04-2.19 (m, 1H); 1.99 (s, 3H); 1.78-1.91 (m, 1H); 0.79 (t, J=7.0 Hz, 3H). MS (ES): m/z 426 (M+H), 213.

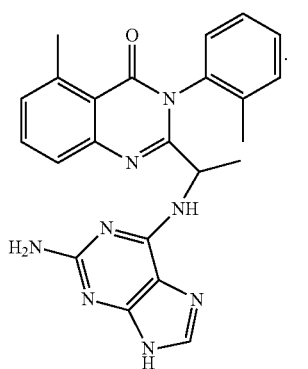 [SMILES: Cc1ccccc1-n1c(C(C)Nc2nc(N)nc3[nH]cnc23)nc2cccc(C)c2c1=O]

2-(1-(2-Amino-9H-purin-6-ylamino)ethyl)-5-methyl-3-o-tolyl-3H-quinazolin-4-one (D-081a)

Synthesized according to procedure E using compound 5c (61 mg, 0.209 mmol) and 2-amino-6-chloropurine (43 mg, 0.251 mmol) in 1 mL EtOH. Purification by HPLC (C18 Luna column, 4.6×250 mm, 4.7 mL/min, 10-75% acetonitrile/water over 15 min, 100% acetonitrile at 18 min, detector at 2201) provided a white solid consisting of a mixture of two atropisomers (in brackets in nmr). $^1$H NMR (DMSO-$d_6$) δ: 8.93-9.02 (m, 1H); [8.19 (s), 8.15 (s), 1H]; [7.76 (t, J=8.1 Hz), 7.73 (t, J=7.8 Hz), 1H]; [7.64 (d, J=7.9 Hz), 7.57 (d, J=8.0 Hz), 1H]; [7.50 (d, J=7.7 Hz), 7.45 (d, J=7.8 Hz), 1H]; 7.29-7.40 (m, 3H); [7.23 (t, J=7.5 Hz), 7.15-7.22 (m), 1H]; [7.09 (t, J=7.5 Hz), 6.98 (d, J=7.3 Hz), 1H]; [5.28 (dd, J=7.2, 8.0 Hz), 4.96 (pent, J=7.0 Hz), 1H]; 2.75 (s, 3H); [2.10 (s), 1.84 (s), 3H]; [1.51 (d, J=6.6 Hz), 1.39 (d, J=6.7 Hz), 3H]. MS (ES): m/z 427 (M+H), 214.

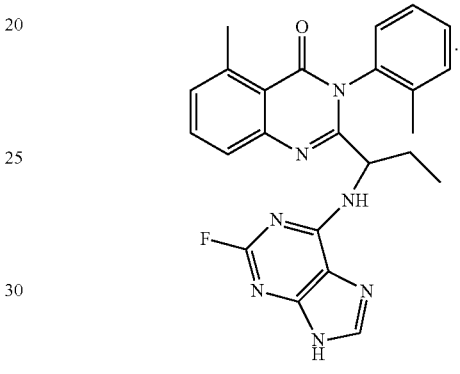

2-(1-(2-Fluoro-9H-purin-6-ylamino)propyl)-5-methyl-3-o-tolyl-3H-quinazolin-4-one (D-081c)

Synthesized according to procedure E using compound 5d (100 mg, 0.325 mmol) and 2-fluoro-6-chloropurine (78 mg, 0.455 mmol) in 2 mL EtOH. Purification by HPLC (C18 Luna column, 4.6×250 mm, 4.7 mL/min, 10-75% acetonitrile/water over 15 min, 100% acetonitrile at 18 min, detector at 2201) provided two atropisomers as off-white solids. Data for one isomer: $^1$H NMR (DMSO-$d_6$) δ: 8.46 (br d, J=7.1 Hz, 1H); 8.20 (s, 1H); 7.71 (t, J=7.7 Hz, 1H); 7.55 (d, J=7.9 Hz, 1H); 7.45 (d, J=7.3 Hz, 1H); 7.28-7.37 (m, 3H); 7.00 (t, J=7.3 Hz, 1H); 4.66 (q, J=6.7 Hz, 1H); 2.74 (s, 3H); 2.10 (s, 3H); 1.65-1.95 (m, 2H); 0.80 (t, J=7.1 Hz, 3H). MS (ES): m/z 444 (M+H), 222.

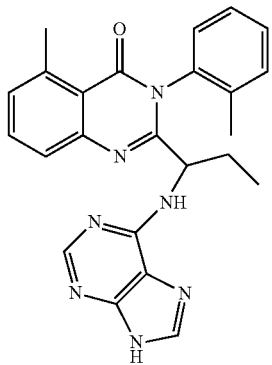 [SMILES: CCC(Nc1ncnc2[nH]cnc12)c1nc2cccc(C)c2c(=O)n1-c1ccccc1C]

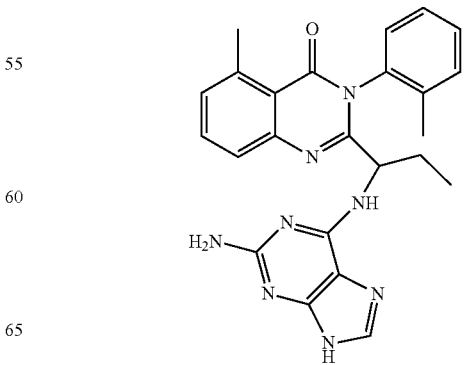

2-[1-(2-Amino-9H-purin-6-ylamino)propyl]-5-methyl-3-o-tolyl-3H-quinazolin-4-one (Compound 081d)

Synthesized according to procedure E using compound 5d (100 mg, 0.325 mmol) and 2-amino-6-bromopurine (104 mg, 0.488 mmol) in 2 mL EtOH. Purification by HPLC (C18 Luna column, 4.6×250 mm, 4.7 mL/min, 10-75% acetonitrile/water over 15 min, 100% acetonitrile at 18 min, detector at 220λ) provided an off-white solid consisting of a mixture of two atropisomers (in brackets in nmr). $^1$H NMR (DMSO-$d_6$) δ: 8.89 (br d, J=7.8 Hz, 1H); [8.20 (s), 8.17 (s), 1H]; 7.75 (q, J=7.6 Hz, 1H); [7.62 (d, J=7.9 Hz); 7.57 (d, J=7.8 Hz), 1H]; 7.48 (t, J=7.3 Hz, 1H); 7.25-7.43 (m, 4H); 7.15 (br s, 1H); 7.02-7.12 (m, 1H); [5.03-5.15 (m), 4.77-4.87 (m), 1H]; 2.74 (s, 3H); [2.11 (s), 1.83 (s), 3H]; 1.65-2.19 (m, 2H); [0.83 (t, J=7.3 Hz,), 0.80 (t, J=7.5 Hz), 3H]. MS (ES): m/z 441(M+H), 221.

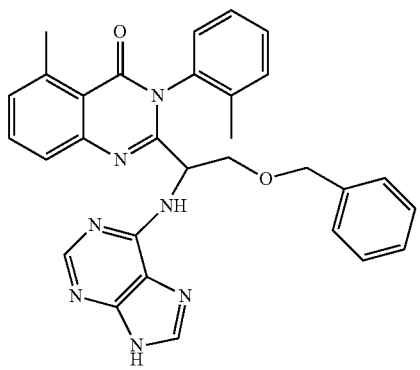 [SMILES: Cc1ccccc1-n1c(C(COCc2ccccc2)Nc2ncnc3[nH]cnc23)nc2cccc(C)c2c1=O]

2-[2-Benzyloxy-1-(9H-purin-6-ylamino)ethyl]-5-methyl-3-o-tolyl-3H-quinazolin-4-one (D-081e)

Synthesized according to procedure E using compound 5e (212 mg, 0.413 mmol) and 6-bromopurine (107 mg, 0.537 mmol) in 2 mL EtOH. Purification by HPLC (C18 Luna column, 4.6×250 mm, 4.7 mL/min, 10-75% acetonitrile/water over 15 min, 100% acetonitrile at 18 min, detector at 220λ) provided two atropisomers as brown solids. Data for one isomer: $^1$H NMR (DMSO-$d_6$) δ: 8.45-8.63 (m, 1H); 8.35-8.44 (m, 1H); 8.27 (s, 1H); 7.75 (t, J=7.7 Hz, 1H); 7.59 (d, J=7.8 Hz, 1H); 7.30-7.44 (m, 3H); 7.21-7.30 (m, 4H); 7.13-7.19 (m, 2H); 6.95-7.07 (m 1H); 5.35-5.45 (m, 1H); 5.14-5.26 (m, 1H); 4.43 (s, 2H); 3.94-4.04 (m, 1H); 3.67 (dd, J=6.0, 9.4 Hz, 1H); 2.74 (s, 3H); 2.01 (s, 3H). MS (ES): m/z 518 (M+H), 410.

The following compounds of the present invention (D-082 through D-109) were prepared as outlined in Procedure C, using 2-chloromethyl-5-methyl-3-o-tolyl-3H-quinazolin-4-one (10 mg), the appropriate nucleophile XH (20 mg, excess), and potassium carbonate (10 mg) in DMF (0.25 mL). The reaction mixture was stirred 16 h at room temperature, quenched with water, and the crude solid product was collected by filtration and air dried. The crude material was dissolved in 0.5 mL of DMSO and purified by reversed-phase HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final products.

2-(6-Dimethylaminopurin-9-ylmethyl)-5-methyl-3-o-tolyl-3N-quinazolin-4-one (D-082)

X=

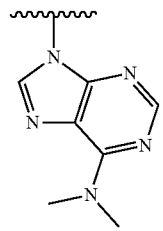 [SMILES: *n1cnc2c(N(C)C)ncnc21]

Yield: 8.1 mg. $^1$H NMR (300 MHz, $d_6$-DMSO) δ: 8.13 (s, 1H), 8.11 (s, 1H), 7.60 (t, J=7.8 Hz, 1H), 7.54-7.38 (m, 4H), 7.30 (d, J=7.4 Hz, 1H), 7.20 (d, J=8.1 Hz, 1H), 5.11 (d, J=17.4 Hz, 1H), 4.76 (d, J=17.4 Hz, 1H), 3.33 (s, 6H), 2.73 (s, 3H), 2.20 (s, 3H). LRMS (ES pos.) m/z=426 (M+1).

5-Methyl-2-(2-methyl-6-oxo-1,6-dihydro-purin-7-ylmethyl)-3-o-tolyl-3H-quinazolin-4-one (D-083)

X=

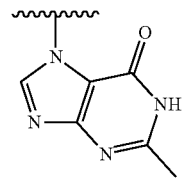 [SMILES: *n1cnc2nc(C)[nH]c(=O)c21]

Yield: 3.3 mg. $^1$H NMR (300 MHz, de-DMSO) δ: 12.06 (s, 1H), 8.12 (s, 1H), 7.60 (t, J=7.8 Hz, 1H), 7.55-7.38 (m, 4H), 7.30 (d, J=7.4 Hz, 1H), 7.15 (d, J=7.9 Hz, 1H), 5.26 (d, J=17.4 Hz, 1H), 4.94 (d, J=17.4 Hz, 1H), 2.73 (s, 3H), 2.32 (s, 3H), 2.24 (s, 3H). Alkylation at purine N, assigned arbitrarily based on downfield shift of methylene protons due to the carbonyl group. LRMS (ES pos.) m/z=413 (M+1).

5-Methyl-2-(2-methyl-6-oxo-1,6-dihydro-purin-9-ylmethyl)-3-o-tolyl-3H-quinazolin-4-one (D-084)

Purified from same reaction mixture as D-083. Yield: 3.6 mg. $^1$H NMR (300 MHz, $d_6$-DMSO) 12.17 (s, 1H), 7.96 (s, 1H), 7.63 (t, J=7.8 Hz, 1H), 7.57-7.39 (m, 4H), 7.32 (d, J=7.4 Hz, 1H), 7.26 (d, J=8.1 Hz, 1H), 5.08 (d, J=17.2 Hz, 1H), 4.70 (d, J=17.2 Hz, 1H), 2.73 (5, 3H), 2.27 (s, 3H), 2.17 (s, 3H). LRMS (ES pos.) m/z=413 (M+1).

2-(Amino-dimethylaminopurin-9-ylmethyl)-5-methyl-3-o-tolyl-3H-quinazolin-4-one (D-085)

X=

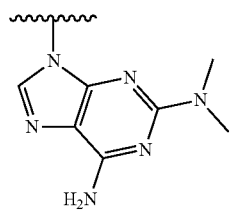 [SMILES: *n1cnc2c(N)nc(N(C)C)nc21]

Yield: 6.7 mg. $^1$H NMR (300 MHz, d$_6$-DMSO) δ: 7.66 (s, 1H0, 7.61 (d, J=7.8 Hz, 1H), 7.55-7.40 (m, 4H), 7.32-7.26 (m, 2H), 6.74 (s, 2H), 4.94 (d, J=17.2 Hz, 1H), 4.63 (d, J=17.2 Hz, 1H), 4.63 (d, J=17.2 Hz, 1H), 2.97 (s, 6H), 2.73 (s, 3H), 2.17 (s, 3H), 2.08 (s, 3H). LRMS (ES pos.) m/z=441 (M+1).

2-(2-Amino-9H-purin-6-ylsulfanylmethyl)-5-methyl-3-o-tolyl-3H-quinazolin-4-one (D-086)

X=

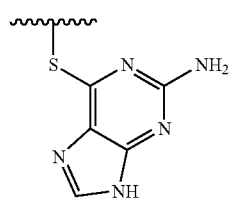 [SMILES: *Sc1nc(N)nc2[nH]cnc12]

Yield: 9.5 mg. $^1$H NMR (300 MHz, d$_6$-DMSO) δ: 12.54 (s, 1H), 7.89 (8, 1H), 7.69 (t, J=7.8 Hz, 1H), 7.51 (d, J=8.0 Hz, 1H), 7.51 (d, J=8.0 Hz, 1H), 7.43 (t, J=3.9 Hz, 1H), 7.34=7.26 (m, 4H), 6.16 (s, 2H), 4.32 (AB quartet, J=14.8 Hz, Δn=23.7), 2.74 (S, 3H), 2.09 (s, 3H). LRMS (ES pos.) m/z=430 (M+1).

2-(4-Amino-1,3,5-triazin-2-ylsulfanylmethyl)-5-methyl-3-o-tolyl-3H-quinazolin-4-one (D-087)

X=

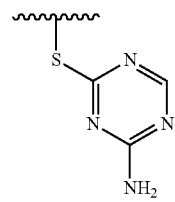 [SMILES: *Sc1ncnc(N)n1]

Yield: 5.8 mg. $^1$H NMR (300 MHz, d$_6$-DMSO) δ: 8.10 (s, 1H), 7.70 (t, J=7.8 Hz, 1H), 7.58 (s, 1H), 7.52 (d, J=8.0 Hz, 1H), 7.48-7.26 (m, 6H), 4.08 (s, 2H), 2.73 (s, 3H), 2.09 (s, 3H). LRMS (ES pos.) m/z=391 (M+1).

5-Methyl-2-(7-methyl-7H-purin-6-ylsulfanylmethyl)-3-o-tolyl-3H-quinazolin-4-one (D-088)

X=

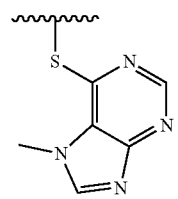 [SMILES: *Sc1ncnc2ncn(C)c12]

Yield: 3.1 mg. $^1$H NMR (300 MHz, d$_6$-DMSO) δ: 8.52 (s, 1H), 8.49 (s, 1H), 7.70 (t, J=7.8 Hz, 1H), 7.50 (d, J=7.8 Hz, 1H), 7.45 (d, J=7.1 Hz, 1H), 7.35-7.20 (m, 4H), 4.41 (AB quartet, J$_{AB}$=15.3 Hz, Δv=19.2 Hz), 4.08 (s, 3H), 2.73 (s, 3H), 2.12 (s, 3H). LRMS (ES pos.) m/z=406 (M+1).

5-Methyl-2-(2-oxo-1,2-dihydro-pyrimidin-4-ylsulfanylmethyl)-3-o-tolyl-3H-quinazolin-4-one (D-089)

X=

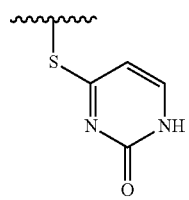 [SMILES: *Sc1cc[nH]c(=O)n1]

Yield: 2.4 mg. $^1$H NMR (300 MHz, d$_6$-DMSO) δ: 11.49 (s, 1H), 7.70 (t, J=7.8 Hz, 1H), 7.60 (brt, J=6.0 Hz, 1H), 7.53-7.48 (m, 2H), 7.46-7.28 (m, 4H), 6.31 (d, J=6.7 Hz, 1H), 4.05 (s, 2H), 2.73 (s, 3H), 2.12 (s, 3H). LRMS (ES pos.) m/z=391 (M+1).

5-Methyl-2-purin-7-ylmethyl-3-o-tolyl-3H-quinazolin-4-one (D-090)

X=

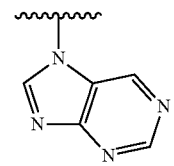 [SMILES: *n1cnc2ncncc21]

$^1$H NMR (300 MHz, d$_6$-DMSO) δ: 9.04 (s, 1H), 8.97 (s, 0.1H), 8.48 (s, 1H), 7.65-7.54 (m, 2H), 7.53-7.39 (m, 3H), 7.31 (d, J=7.4 Hz, 1H), 7.13 (d, J=8.0 Hz, 1H), 5.31 (d, J=17.6 Hz, 1H), 5.16 (d, J=17.6 Hz, 1H), 2.73 (s, 3H), 2.09 (s, 3H). Alkylation at purine N7 was determined by NOE enhancement between the purine 6-position proton and methylene protons on the linker between the purine and quinazolinone groups. LRMS (ES pos.) m/z=383 (M+1).

5-Methyl-2-purin-9-ylmethyl-3-o-tolyl-3H-quinazolin-4-one (D-091)

X=

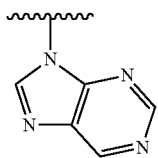

From same reaction that produced D-090. ¹H NMR (300 MHz, d₆-DMSO) b: 9.17 (s, 1H), 8.86 (s, 1H), 8.55 (s, 1H), 7.59 (t, J=7.8 Hz, 1H), 7.55-7.42 (m, 4H), 7.30 (d, J=7.4 Hz, 1H), 7.13 (d, J=8.0 Hz, 1H), 5.26 (d, J=17.5 Hz, 1H), 4.92 (d, J=17.5 Hz, 1H), 2.73 (s, 3H), 2.19 (s, 3H). Alkylation at purine N9 suggested by the lack of NOE enhancement between purine 6-position protons and the linker methylene protons. LRMS (ES pos.) m/z=383 (M+1).

5-Methyl-2-(9-methyl-9H-purin-6-ylsulfanylmethyl)-3-o-tolyl-3H-quinazolin-4-one (D-092)

X=

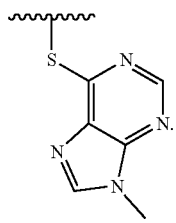 [SMILES: *Sc1ncnc2c1ncn2C]

¹H NMR (300 MHz, d₆-DMSO) δ: 8.52 (s, 1H), 8.42 (s, 1H), 7.69 (t, J=7.7 Hz, 1H), 7.50 (d, J=8.0 Hz, 1H), 7.44 (d, J=7.6 Hz, 1H), 7.36-7.27 (m, 4H), 4.38 (AB quartet, J$_{AB}$=15.5 Hz, Δv=21.0 Hz), 3.80 (s, 3H), 2.73 (s, 3H), 2.12 (s, 3H). LRMS (ES pos.) m/z=429 (M+1).

2-(2,6-Diamino-pyrimidin-4-ylsulfanylmethyl)-5-methyl-3-o-tolyl-3H-quinazolin-4-one (D-093)

X=

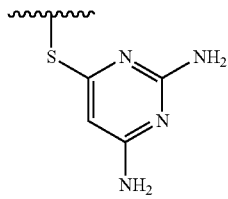 [SMILES: *Sc1cc(N)nc(N)n1]

¹H NMR (300 MHz, d₆-DMSO) δ: 7.70 (t, J=7.7 Hz, 1H), 7.54 (d, J=8.0 Hz, 1H), 7.45-7.27 (m, 5H), 6.22 (br s, 1H), 5.80 (br s, 1H), 3.99 (AB quartet, J$_{11B}$=14.6 Hz, Δv=26.9 Hz, 2H), 2.73 (s, 3H), 2.08 (s, 3H). LRMS (ES pos.) m/z=405 (M+1).

5-Methyl-2-(5-methyl-[1,2,4]triazolo[1,5-a]pyrimidin-7-ylsulfanylmethyl)-3-o-tolyl-3H-quinazolin-4-one (D-094)

X=

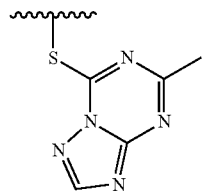 [SMILES: *Sc1nc(C)nc2ncnn12]

¹H NMR (300 MHz, d₆-DMSO) δ: 8.57 (s, 1H), 7.73 (t, J=7.8 Hz, 1H), 7.55-7.35 (m, 4H), 7.18 (s, 1H), 4.27 (s, 2H), 2.74 (s, 3H0, 2.55 (s, 3H1), 2.08 (s, 3H1). LRMS (ES pos.) m/z=429 (M+1).

5-Methyl-2-(2-methylsulfanyl-9H-purin-6-ylsulfanyl-methyl)-3-o-tolyl-3H-quinazolin-4-one (D-095)

X=

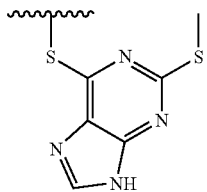 [SMILES: *Sc1nc(SC)nc2[nH]cnc12]

¹H NMR (300 MHz, d₆-DMSO) δ: 13.30 (s, 1H), 8.29 (s, 1H), 7.72 (t, J=7.8 Hz, 1H), 7.54 (d, J=7.8 Hz, 1H), 7.47 9d, J=6.3 Hz, 1H), 7.38-7.26 (m, 4H), 4.34 (AB quartet, J$_{AB}$=16.1 Hz, Δv=23.6 Hz, 2H), 2.74 (s, 3H), 2.32 (s, 3H), 2.10 (s, 3H). LRMS (ES pos.) m/z=461 (M+1).

2-(2-Hydroxy-9H-purin-6-ylsulfanylmethyl)-5-methyl-3-o-tolyl-3H-quinazolin-4-one. (D-096)

X=

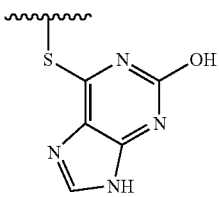 [SMILES: *Sc1nc(O)nc2[nH]cnc12]

¹H NMR (300 MHz, d₆-DMSO) δ: 8.08 (s, 1H$_1$), 7.69 (t, J=7.8 Hz, 1H), 7.50 (brd, J=t0.8 Hz, 2H), 7.33-7.50 (m, 4H), 4.28 (AB quartet, J$_{AB}$=15.5 Hz, Δv=21.3 Hz, 2H), 2.74 (s, 3H), 2.12 (s, 3H). LRMS (ES pos.) m/z=431 (M+1).

5-Methyl-2-(1-methyl-1H-imidazol-2-ylsulfanyl-
methyl)-3-o-tolyl-3H-quinazolin-4-one (D-097)

X=

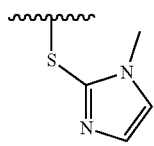 [SMILES: *Sc1nccn1C]

¹H NMR (300 MHz, d₆-DMSO) δ: 7.69 t, J=7.8 Hz, 1H), 7.46-7.37 (m, 5H), 7.32 (d, J=7.3 Hz, 1H), 7.20 (d, J=1.0 Hz, 1H), 6.48 (d, J=1.0 Hz, 1H), 3.83 (AB quartet, J$_{AB}$=15.0 Hz, Δν=18.8 Hz, 1H), 3.55 (s, 3H), 2.73 (s, 3H), 2.09 (s, 3H). LRMS (ES pos.) m/z=364 (M+1).

5-Methyl-3-o-tolyl-2-(1H-[1,2,4]triazol-3-ylsulfanyl-
methyl)-3H-quinazolin-4-one (D-098)

X=

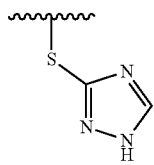 [SMILES: *Sc1nc[nH]n1]

¹H NMR (300 MHz, d₆-DMSO) δ: 13.98 (8, 1H), 8.47 (s, 1H), 7.70 (t, J=7.8 Hz, 1H), 7.49 (d, J=7.9 Hz, 1H), 7.44-7.31 (m, 5H), 4.04 (AB quartet, J$_{AB}$=15.5 Hz, Δν=19.1 Hz, 1H), 2.74 (s, 3H), 2.10 (s, 3H). LRMS (ES pos.) m/z=364 (M+1).

2-(2-Amino-6-chloro-purin-9-ylmethyl)-5-methyl-3-
o-tolyl-3H-quinazolin-4-one (D-099)

X=

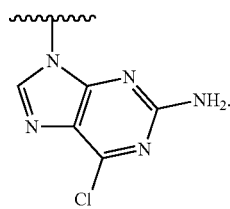 [SMILES: *n1cnc2c(Cl)nc(N)nc21]

LRMS (ES pos.) 432 (M+1).

2-(6-Aminopurin-7-ylmethyl)-5-methyl-3-o-tolyl-
3H-quinazolin-4-one (D-100)

X=

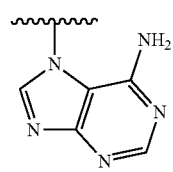 [SMILES: *n1cnc2ncnc(N)c21]

¹H NMR (300 MHz, d₆-DMSO) δ: 8.19 (s, 3H), 7.66 (t, J=7.8 Hz, 1H), 7.59-7.43 (m, 5H), 7.34 9d, J=7.4 Hz, 1H), 7.23 (d, J=8.0 Hz, 1H), 6.90 (s, 2H), 5.21 (AB quartet, J$_{AB}$=17.4 Hz, Δν=22.1 Hz, 2H), 2.72 (s, 3H), 1.93 (s, 3H). Alkylation at purine N7 was confirmed by NOE enhancements between the following protons: 1) Exocyclic amine and methylene protons; 2) Exocyclic amine and toluyl methyl protons. LRMS (ES pos.) m/z=398 (M+1).

2-(7-Amino-1,2,3-triazolo[4,5-d]pyrimidin-3-yl-
methyl)-5-methyl-3-o-tolyl-3H-quinazolin-4-one
(D-101)

X=

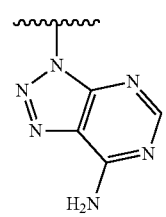

¹H NMR (300 MHz, d₆-DMSO) δ: 8.43 (br s, 1H), 8.19 (s, 1H), 8.10 (br s, 1H), 7.62 (t, J=7.8 Hz, 1H), 7.49-7.28 (m, 5H), 7.22 (d, J=8.1 Hz, 1H), 5.49 (d, J=17.0 Hz, 1H), 5.19 (d, J=17.0 Hz, 1H), 2.73 (s, 3H), 2.11 (s, 3H). Alkylation at purine N7 determined by similarity to nmr spectrum of D-030. LRMS (ES pos.) m/z=399 (M+1).

2-(7-Amino-1,2,3-triazolo[4,5-d]pyrimidin-1-yl-
methyl)-5-methyl-3-o-tolyl-3H-quinazolin-4-one
(D-102)

X=

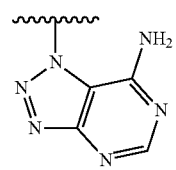

From same reaction mixture as D-101. ¹H NMR (300 MHz, d-DMSO) δ: 8.27 (s, 1H), 8.20 (br s, 1H), 8.05 (br a. 1H), 7.70 (t, J=7.8 Hz, 1H), 7.47-7.26 (m, 6H), 5.61 (AB quartet, J$_{M}$=16.0 Hz, Δν=20.7 Hz, 2H), 2.75 (s, 3H), 1.98 (s, 3H)). Alkylation at purine N7 determined by similarity to nmr spectrum of D-100. LRMS (ES pos.) m/z=399 (M+1).

2-(6-Amino-9H-purin-2-ylsulfanylmethyl)-5-methyl-
3-o-tolyl-3H-quinazolin-4-one (D-103)

X=

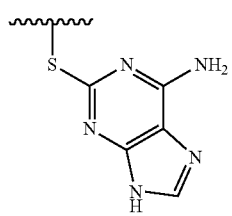 [SMILES: *Sc1nc(N)c2nc[nH]c2n1]

¹H NMR (300 MHz, d-DMSO) δ: 12.62 (s, 1H), 7.93 (s, 1H), 7.69 (t, J=7.7 Hz, 1H), 7.51 (d, J=8.1 Hz, 1H), 7.42 (dd, J=7.6, 1.7 Hz, 1H), 7.35-7.15 (m, 6H), 4.12 (AB quartet, $J_{AB}$=14.5 Hz, Δv=18.2 Hz, 2H), 2.73 (s, 3H), 2.10 (s, 3H). LRMS (ES pos.) m/z=430 (M+1).

2-(2-Amino-6-ethylamino-pyrimidin-4-ylsulfanyl-methyl)-5-methyl-3-o-tolyl-3H-quinazolin-4-one (D-104)

X=

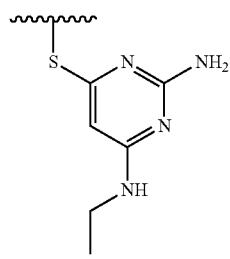 [SMILES: *Sc1cc(NCC)nc(N)n1]

¹H NMR (300 MHz, d₆-DMSO) δ: 7.70 (T, J=7.8 Hz, 1H), 7.53 (d, J=8.0 Hz, 1H), 7.44-7.31 (m, 5H), 6.69 (br s, 1H), 5.83, (br s, 2H), 5.61 (s, 1H), 4.03 (d, J=14.6 Hz, 1H), 3.95 (d, J=14.6 Hz, 1H), 3.22-3.11 (m, 2H), 2.73 (s, 3H), 2.08 (s, 3H), 1.06 (t, J=7.1 Hz, 3H). LRMS (ES pos.) m/z=433 (M+1).

2-(3-Amino-5-methylsulfanyl-1,2,4-triazol-1-yl-methyl)-5-methyl-3-o-tolyl-3H-quinazolin-4-one (D-105)

X=

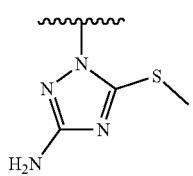

Yield: 5.0 mg. ¹H NMR (300 MHz, d₆-MeOH) δ: 7.67 (t, J=7.8 Hz, 1H), 7.55-7.37 (m, 4H), 7.35-7.27 (m, 2H), 4.77 (d, J=17.1 Hz, 1H), 4.60 (d, J=17.1 Hz, 1H), 2.80 (s, 3H), 2.43 (s, 3H), 2.14 (s, 3H). LRMS (ES pos.) m/z=393 (M+1).

2-(5-Amino-3-methylsulfanyl-1,2,4-triazol-1-ylm-ethyl)-5-methyl-3-o-tolyl-3-quinazolin-4-one (D-106)

X=

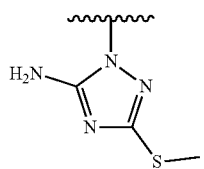 [SMILES: *n1nc(SC)nc1N]

Yield: 0.6 mg. Purified from same reaction mixture as D-105. ¹H NMR (300 MHz, d₆-MeOH) δ: 7.67 (t, J=7.8 Hz, 1H), 7.50-7.24 (m, 6H), 4.83 (d, J=16.5 Hz, 1H), 4.70 (d, J=16.5 Hz, 1H), 2.79 (s, 3H), 2.47 (s, 3H), 2.14 (s, 3H). LRMS (ES pos.) m/z=393 (M+1).

5-Methyl-2-(6-methylaminopurin-9-ylmethyl)-3-o-tolyl-3H-quinazolin-4-one (D-107)

X=

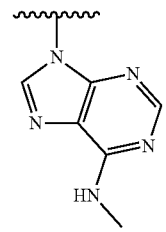 [SMILES: *n1cnc2c(NC)ncnc21]

Yield: 5.0 mg ¹H NMR (300 MHz, d₄-MeOH) δ: 8.17 (s, 1H), 8.03 (s, 1H), 7.54-7.43 (m 4H), 7.31-7.23 (m, 2H), 5.14 (d, J=17.5 Hz, 1H), 4.90 (d, J=17.5 Hz, 1H), 3.14 (br a, 3H), 2.79 (s, 3H), 2.22 (s, 3H). LRMS (ES pos.) m/z=412 (M+1).

2-(6-Benzylaminopurin-9-ylmethyl)-5-methyl-3-o-tolyl-3H-quinazolin-4-one (D-108)

X=

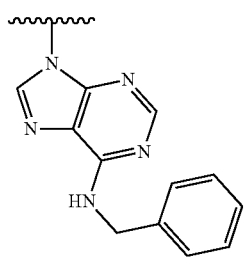 [SMILES: *n1cnc2c(NCc3ccccc3)ncnc21]

Yield: 6.7 mg. ¹H NMR (300 MHz, d₄-MeOH) δ: 8.13 (s, 1H), 8.04 (s, 1H), 7.58 (t, J=7.8 Hz, 1H), 7.51-7.21 (m, 11H), 5.15 (d, J=17.5 Hz, 1H), 4.91 (d, J=17.5 Hz, 1H), 4.83 (s, 2H, under H₂O Peak), 2.79 (s, 3H), 2.22 (s, 3H). LRMS (ES pos.) m/z=488 (M+1).

2-(2,6-Diaminopurin-9-ylmethyl)-5-methyl-3-o-tolyl-3H-quinazolin-4-one (D-109)

X=

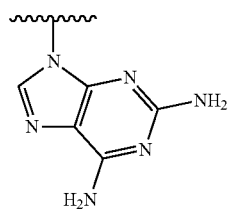 [SMILES: *n1cnc2c(N)nc(N)nc21]

Doubled the amounts of all reactants. Yield: 14 mg. ¹H NMR (300 MHz, d-DMSO) δ: 8.53 (br s, 2H), 8.01 (s, 1H), 7.64 (t, J=7.8 Hz, 1H), 7.53-7.40 (m, 4H), 7.33 (d, J=7.4 Hz, 1H), 7.27 9d, J=7.9 Hz, 1H), 4.96 (d, J=17.5 Hz, 1H), 4.64 (d, J=17.5 Hz, 1H), 2.74 (s, 3H), 2.17 (s, 3H). LRMS (ES pos.) m/z=413 (M+1).

Compounds D-110 through D-115 of the following general structure were prepared from the following Intermediates E-1 through E-3.

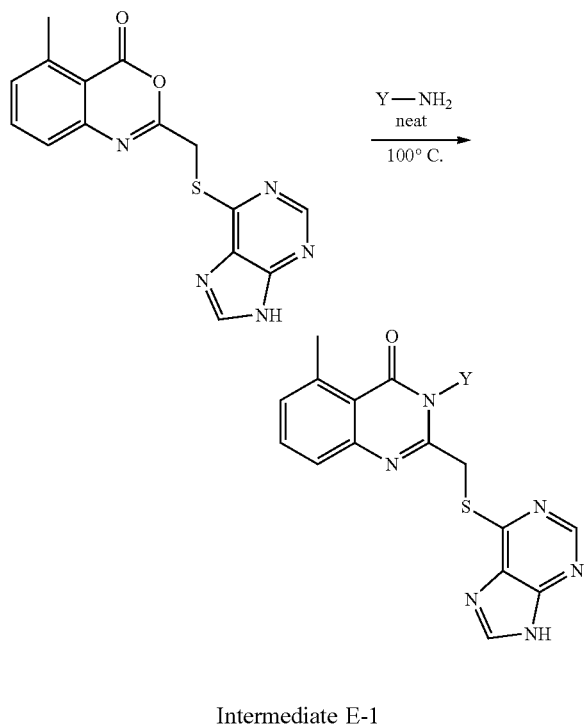

Intermediate E-1

5-Methyl-2-(9H-purin-6-ylsulfanylmethyl)-3,1-benzoxazin-4-one

Step 1.

A suspension of 6-methylanthranilic acid (2 g, 13.2 mmol) in chloroacetyl chloride (12 mL, large excess) was stirred at 115° C. in a sealed vial for 30 min. The resulting solution was cooled to room temperature and treated with ether (~5 mL). After cooling at 4° C. overnight, the resulting tan precipitate was collected by filtration, washed with ether, and dried in vacuo to yield the chloro intermediate (1.39 g, 50%). $^1$H NMR (300 MHz, CDCl$_3$) δ: 7.67 (t, J=7.8 Hz, 1H), 7.46 (d, J=7.9 Hz, 1H), 7.35 (d, J=7.6 Hz, 1H), 4.39 (s, 2H), 2.81 (s, 3H). LRMS (ES pos.) m/z=210, (M+1).

Step 2.

A mixture of the chloro intermediate (50 mg, 0.25 mmol), 6-mercaptopurine monohydrate (43 mg, 0.25 mmol), and potassium carbonate (25 mg, 0.25 mmol) in dry DMF (0.5 mL) was stirred at room temperature for 30 min. The mixture was poured into ethyl acetate (20 mL) and all insoluble material was filtered off and discarded. The filtrate was concentrated in vacuo to remove all ethyl acetate, and the residue was treated with ether, resulting in a light orange precipitate. The precipitate was collected by filtration, washed with ether, and dried in vacuo to afford Intermediate E-1 (41 mg, 51%). $^1$H NMR (300 MHz, d$_6$-DMSO) δ: 8.64 (s, 1H), 8.39 (s, 1H), 7.73 (t, J=7.8 Hz, 1H), 7.44-7.37 (m, 2H), 4.69 (s, 2H), 2.69 (s, 3H). LRMS (ES pos.) m/z=326 (M+1).

Intermediate E-2

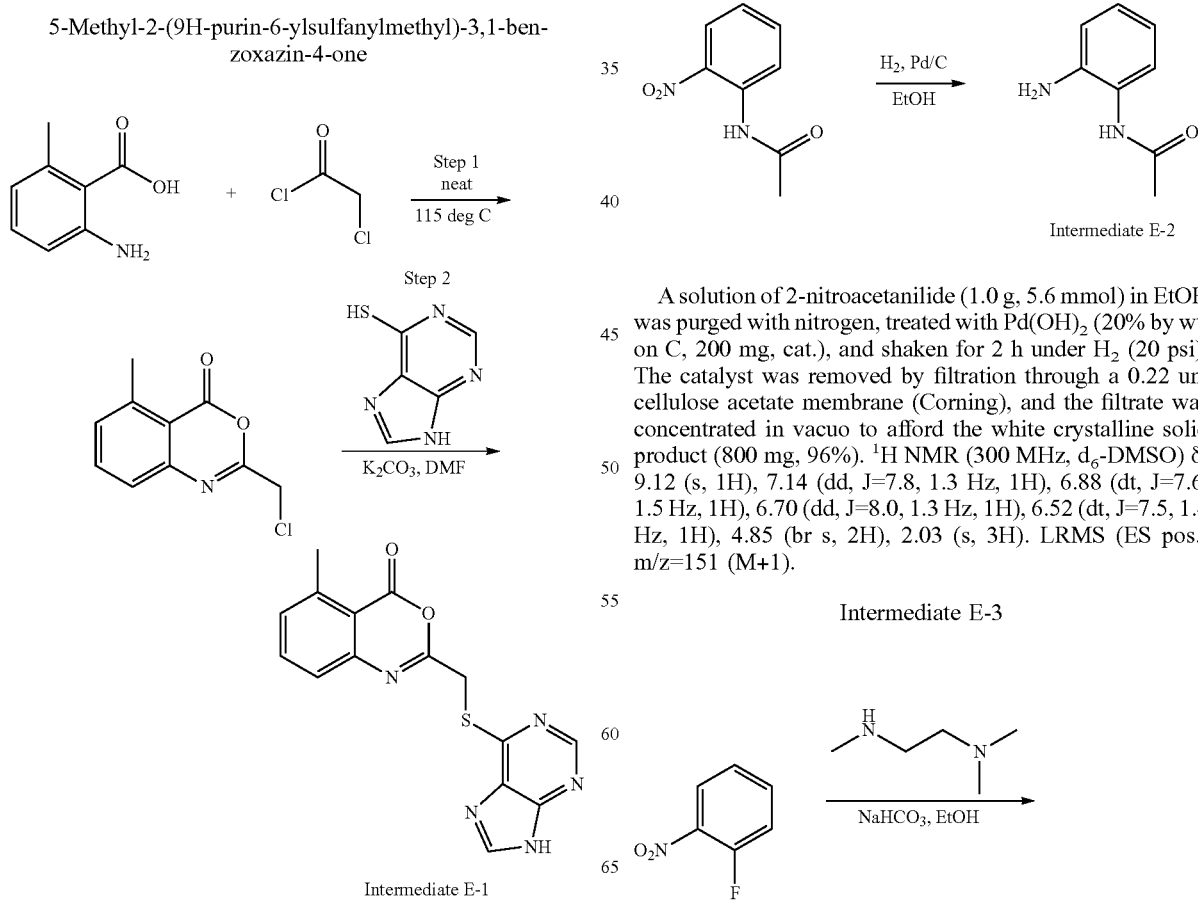

Intermediate E-2

A solution of 2-nitroacetanilide (1.0 g, 5.6 mmol) in EtOH was purged with nitrogen, treated with Pd(OH)$_2$ (20% by wt. on C, 200 mg, cat.), and shaken for 2 h under H$_2$ (20 psi). The catalyst was removed by filtration through a 0.22 um cellulose acetate membrane (Corning), and the filtrate was concentrated in vacuo to afford the white crystalline solid product (800 mg, 96%). $^1$H NMR (300 MHz, d$_6$-DMSO) δ: 9.12 (s, 1H), 7.14 (dd, J=7.8, 1.3 Hz, 1H), 6.88 (dt, J=7.6, 1.5 Hz, 1H), 6.70 (dd, J=8.0, 1.3 Hz, 1H), 6.52 (dt, J=7.5, 1.4 Hz, 1H), 4.85 (br s, 2H), 2.03 (s, 3H). LRMS (ES pos.) m/z=151 (M+1).

Intermediate E-3

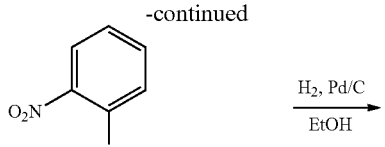

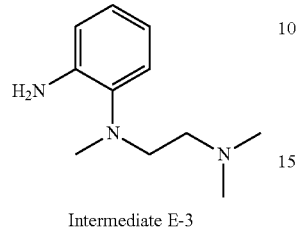

Intermediate E-3

A mixture of 2-fluoro-nitrobenzene (1.41 g, 10 mmol) and NaHCO₃ in EtOH (20 mL) was treated with (N,N,N'-trimethyl)-1,2-diaminoethane (1.1 g, 11 mmol) and was stirred 16 h at 80° C. Solvent was removed in vacuo, residue was treated with 0.1 M NaOH (120 mL), and the mixture was extracted with ethyl acetate (2×50 mL). The organic layers were combined and washed with 20 mL of water (1×) and brine (2×), dried with sodium sulfate, and concentrated in vacuo to an orange liquid (2.2 g, 100%; ESMS: m/z=224, M+1).

This intermediate was dissolved in EtOH, the solution was purged with nitrogen, treated with Pd(OH)₂ (20% by wt. on C, 180 mg, cat.), and shaken for 2 h under H₂ (50 psi). The catalyst was removed by filtration through a 0.22 um cellulose acetate membrane (Corning), and the filtrate was concentrated in vacuo to afford the red liquid product E-3 (1.8 g, 95%). ¹H NMR (300 MHz, CDCl₃) δ: 8.64 (s, 1H), 7.03 (dd, J=8.3, 1.4 Hz, 1H), 6.91 (ddd, J=7.6, 7.2, 1.4 Hz, 1H), 6.73-6.67 (m, 2H), 4.20 (br s, 2H), 2.95 (t, J=6.7 Hz, 2H), 2.68 (s, 3H), 2.41 (t, J=6.7 Hz, 1H), 2.26 (s, 6H). LRMS (ES pos.) m/z=194 (M+1).

Compounds D-110 through D-115 were prepared as follows:

5-Methyl-2-(9H-purin-6-ylsulfanylmethyl)-3-o-tolyl-3H-quinazolin-4-one (D-110)

Y=

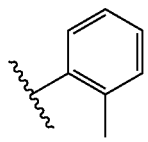 [SMILES: *c1ccccc1C]

A mixture of Intermediate E-1 (40 mg) and o-toluidine (0.3 mL, large excess) was warmed at 100° C. in a sealed vial for 16 h. The reaction mixture was cooled, treated with 1N HCl (2 mL) and ether (2 mL), and the resulting gray precipitate was collected by filtration, washed with ether, and air dried (19 mg crude). The crude solid was dissolved in 0.5 mL DMSO and purified by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (4 mg). ¹H NMR (300 MHz, d-DMSO) δ: 13.52 (s, 1H), 8.47 (s, 1H), 8.43 (s, 1H), 7.69 (t, J=7.8 Hz, 1H), 7.50 (d, J=7.9 Hz, 1H), 7.46-7/43 (m, 1H), 7.37-7.25 (m, 4H), 4.37 (AB quartet, $J_B$=15.4 Hz, Δv=22.4 Hz, 2H), 2.74 (5, 3H), 2.12 (5, 3H). LRMS (ES pos.) m/z=415 (M+1).

3-Isobutyl-5-methyl-2-(9H-purin-6-ylsulfanylmethyl)-3H-quinazolin-4-one (D-111)

Y=

A mixture of Intermediate E-1 (40 mg) and isobutylamine (0.4 mL, large excess) was warmed at 120° C. in a sealed vial for 16 h. Excess isobutylamine was allowed to evaporate, residue was dissolved in 1 mL DMSO and purified in two portions by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (4 mg). ¹H NMR (300 MHz, d₆-DMSO) δ: 13.75 (br s, 1H), 8.73 (s, 1H), 8.50 (s, 1H), 7.63 (t, J=7.7 Hz, 1H), 7.42 (d, J=8.0 Hz, 1H), 7.28 (d, J=7.3 Hz, 1H), 4.96 (s, 2H), 4.00 (d, J=7.5 Hz, 2H), 2.77 (s, 3H), 2.30-2.15 (m, 1H), 0.98 (d, J=6.7 Hz, 1H). LRMS (ES pos.) m/z=381 (M+1).

N-{2-[5-Methyl-4-oxo-2-(9H-purin-6-ylsulfanylmethyl)-4H-quinazolin-3-yl]-phenyl}-acetamide (D-112)

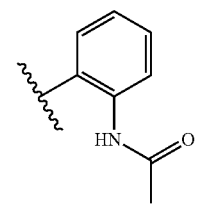

A mixture of Intermediate E-1 (80 mg, 0.25 mmol) and Intermediate E-2 (75 mg, 0.5 mmol, 2 eq) was warmed until melted in a sealed vial using a heat gun. The reaction mixture was triturated with ether and the solids were collected by filtration. The crude material was dissolved in 1 mL DMSO and purified in two portions by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid. ¹H NMR (300 MHz, d₆-DMSO) δ: 13.52 (s, 1H), 9.52 (s, 1H), 8.48 (s, 3H), 8.42 (s, 3H), 8.02 (d, J=8.0 Hz, 1H), 7.69 (t, J=7.8 Hz, 1H), 7.51 (d, J=7.9 Hz, 1H), 7.45-7.37 (m, 2H), 7.31 (d, J=7.3 Hz, 1H), 7.19 (t, J=7.5 Hz, 1H), 4.38 (s, 2H), 2.74 (s, 3H), 1.93 (s, 3H). LRMS (ES pos.) m/z=458 (M+1).

5-Methyl-3-(E-2-methyl-cyclohexyl)-2-(9H-purin-6-ylsulfanylmethyl)-3H-quinazolin-4-one (D-113)

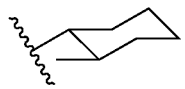

A mixture of Intermediate E-1 (80 mg, 0.25 mmol) and trans-2-methyl-1-aminocyclohexane (0.25 mL, large excess) was warmed in a sealed vial at 100° C. for 16 h. The reaction mixture was triturated with ether and the solids were collected by filtration. The crude material was dissolved in 0.5 mL DMSO and purified by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (1.5 mg). $^1$H NMR (300 MHz, $d_6$-DMSO) δ: 13.5 (br s, 1H), 8.82 (s, 1H), 8.51 (s, 1H), 7.63 (t, J=7.7 Hz, 1H), 7.43 (d, J=7.9 Hz, 1H), 7.27 (d, J=7.4 Hz, 1H), 5.11 (d, J=14.5 Hz, 1H), 3.78-3:69 (m, 1H), 2.73 (s, 3H), 2.55-2.40 (m, 3H), 1.88-1.46 (m, 4H), 1.31-1.11 (m, 1H), 0.90-0.65 (m, 1H), 0.74 (d, J=6.7 Hz, 3H). LRMS (ES pos.) m/z=421 (M+1).

2-[5-Methyl-4-oxo-2-(9H-purin-6-ylsulfanylmethyl)-4H-quinazolin-3-yl]-benzoic acid (D-114)

Y=

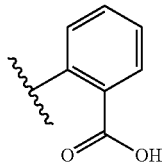 [SMILES: *c1ccccc1C(=O)O]

A mixture of Intermediate E-1 (80 mg, 0.25 mmol) methyl anthranilate (0.25 mL, large excess) was warmed in a sealed vial at 100° C. for 16 h. The reaction mixture was triturated with ether and the solids were collected by filtration. The crude material was dissolved in 0.5 mL DMSO and purified by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (8 mg). $^1$H NMR (300 MHz, $d_6$-DMSO) δ: 13.51 (s, 1H), 8.51 (s, 1H), 8.42 (s, 1H), 8.11 (dd, J=7.4, 1.1 Hz, 1H), 7.88 (dt, J=7.7, 1.4 Hz, 1H), 7.70 (d, J=8.0 Hz, 1H), 7.57 (t, J=7.2 Hz, 1H), 7.49-7.35 (m, 3H), 4.58 (d, J=15.5 Hz, 1H), 4.35 (d, J=15.5 Hz, 1H), 2.44 (s, 3H). LRMS (ES pos.) m/z=445 (M+1).

3-{2-[(2-Dimethylamino-ethyl)-methyl-amino]-phenyl}-5-methyl-2-(9H-purin-6-ylsulfanylmethyl)-3H-quinazolin-4-one (D-115)

Y=

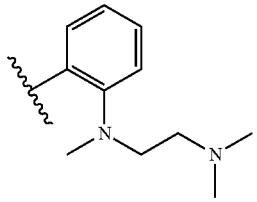 [SMILES: *c1ccccc1N(C)CCN(C)C]

A mixture of Intermediate E-1 (40 mg, 0.25 mmol) Intermediate E-3 (0.2 mL, large excess) was warmed in a sealed vial at 100° C. for 16 h. The reaction mixture was triturated with ether and the solids were collected by filtration. The crude material was dissolved in 1 mL DMSO and purified by HPLC in two portions (C18 Luna column, 4.6×250 mm, 4.7 mL/min, 10-75% acetonitrile/water over 15 min, 100% acetonitrile at 18 min, 0.05% TFA in all solvents, detector at 220λ). Appropriate fractions were concentrated in vacuo to yield the final product as the TFA salt (11 mg). $^1$H NMR (300 MHz, $d_6$-DMSO) δ: 13.4 (br s, 1H), 9.27 (s, 1H), 8.52 (s, 1H), 8.44 (s, 1H), 7.72 (t, J=7.8 Hz, 1H), 7.53 (d, J=7.9 Hz, 1H), 7.40-7.33 (m, 4H), 7.10-7.04 (m, 1H), 4.42 (s, 3H), 3.5 (m, 2H), 3.23-3.03 (m, 3H), 2.75 (s, 3H), 2.68-2.56 (m, 8H). LRMS (ES pos.) m/z=501 (M+1).

Compounds D-116 through D-118 were prepared as follows:

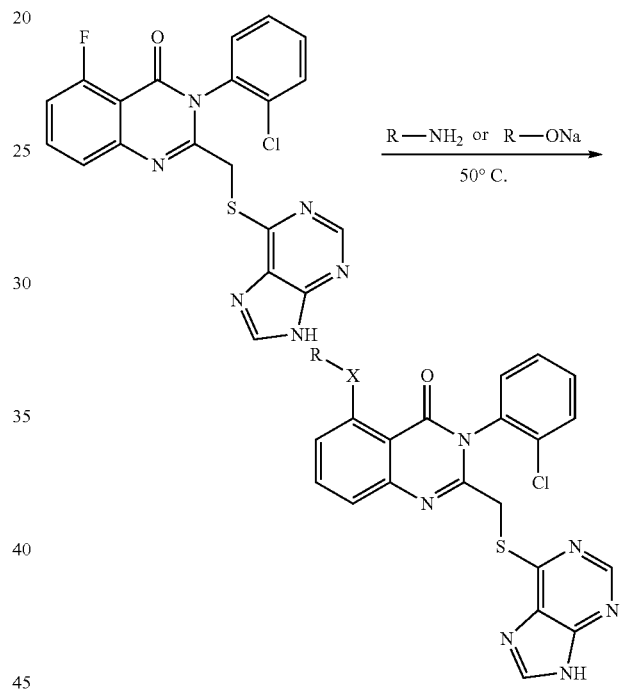

3-(2-Chlorophenyl)-5-methoxy-2-(9H-purin-6-ylsulfanylmethyl)-3H-quinazolin-4-one (D-116)

(R=Me, X=O)

A mixture of D-015 (25 mg) in 0.5 M NaOMe (2 mL in MeOH; large excess) was stirred at 50° C. for 16 h in a sealed vial. The reaction mixture was cooled to room temperature, treated with water (5 mL), and the resulting precipitate was collected by filtration, washed with water, and air dried. The crude material was dissolved in 0.5 mL DMSO and purified by HPLC (C18 Luna column, 4.6×250 mm, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (5.3 mg). $^1$H NMR (300 MHz, $d_6$-DMSO) δ: 13.52 (s, 1H), 8.48 (s, 1H), 8.44 (br s, 1H), 7.77 (t, J=8.2 Hz, 1H), 7.71-7.60 (m, 2H), 7.51-7.34 (m, 2H), 7.23 (d, J=8.2 Hz, 1H), 7.10 (d, J=8.4 Hz, 1H), 4.39 (AB quartet, $J_{AB}$=5.2 Hz, Δν=23.2 Hz, 2H), 3.85 (s, 3H). LRMS (ES positive) m/z=451 (M+1).

3-(2-Chlorophenyl)-5-(2-morpholin-4-yl-ethyl-amino)-2-(9H-purin-6-ylsulfanylmethyl)-3H-quinazolin-4-one (D-117)

R=

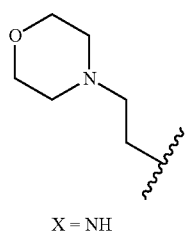 [SMILES: *CCN1CCOCC1]

X = NH

A mixture of D-015 (25 mg) and 4-(aminoeth-2-yl)-morpholine (650 mg, large excess) was stirred at 50° C. for 16 h. The crude reaction mixture was purified by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product. $^1$H NMR (300 MHz, $d_6$-acetone) δ: 8.57 (br s, 1H), 8.47 (s, 1H), 8.37 (s, 1H), 7.72 (dd, J=7.7, 1.6 Hz, 1H), 7.65 (dd, J=8.0, 1.2 Hz, 1H), 7.57 (t, J=8.1 Hz, 1H), 7.49 (dt, J=7.7, 1.6 Hz, 1H), 7.40 (dt, J=7.7, 1.5 Hz, 1H), 6.86 (d, J=7.4 Hz, 1H), 6.82 (d, J=8.3 Hz, 1H), 4.55 (d, J=15.0 Hz, 1H), 4.42 (d, J=15.1 Hz, 1H), 4.05-3.90 (m, 4H), 3.90 (t, J=6.9 Hz, 2H), 3.75-3.4 (m, 4H), 3.54 (t, J=6.9 Hz, 2H). LRMS (ES positive) m/z=549 (M+1).

3-Benzyl-5-methoxy-2-(9H-purin-6-ylsulfanylmethyl)-3H-quinazolin-4-one (D-118)

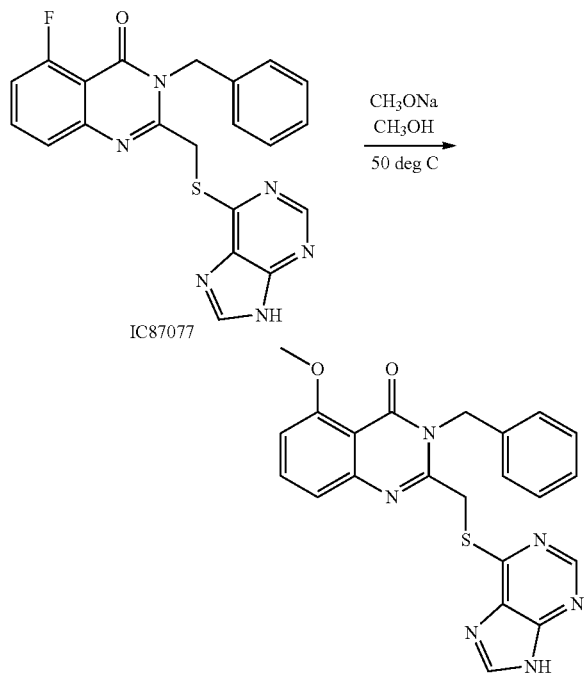

Scheme H

A mixture of D-043 (25 mg) in 0.5 M NaOMe (2 mL in MeOH; large excess) was stirred at 50° C. for 16 h in a sealed vial. The reaction mixture was treated with 1 N HCl (1 mL) and aliquots of this solution (0.5 mL each) were purified by HPLC (C18 Luna column, 4.6×250 mm, 4.7 mL/min, 10-75% acetonitrile/water over 15 min, 100% acetonitrile at 18 min, detector at 220λ). Appropriate fractions were concentrated in vacuo to yield the final product as a white solid (6.6 mg). $^1$H NMR (300 MHz, $d_6$-DMSO) δ: 13.57 (s, 1H), 8.60 (S, 1H), 8.45 (s, 1H), 7.72 (t, J=8.1 Hz, 1H), 7.42-7.30 (m, 2H), 7.30-7.19 (m, 3H), 7.15 (d, J=8.0 Hz, 1H), 7.06 (d, J=8.3 Hz, 1H), 5.43 (s, 2H), 4.80 (s, 2H), 3.87 (s, 3H). LRMS (ES positive) m/z=431 (M+1).

Compound D-999 (Comparative)

3-(2-Chlorophenyl)-2-(1H-pyrazolo[3,4-d]pyrimidin-4-ylsulfanylmethyl)-3H-quinazolin-4-one An analog compound, 3-(2-chlorophenyl)-2-(1H-pyrazolo[3,4-d]pyrimidin-4-ylsulfanylmethyl)-3H-quinazolin-4-one, also was synthesized generally in accordance with the described methods, except that a 4-mercapto-1H-pyrazolo[3,4-d]pyrimidine was substituted for the mercaptopurine in the final step.

Example 11

Biochemical Assays of PI3K Potency and Selectivity

A. Biochemical Assay Using 20 µM ATP

Using the method described in Example 2, above, compounds of the invention were tested for inhibitory activity and potency against PI3Kδ, and for selectivity for PI3Kδ versus other Class I PI3K isozymes. In Table 2, $IC_{50}$ values (µM) are given for PI3K ("Alpha"), PI3Kδ ("Beta"), PI3γ ("Gamma"), and PI3Kδ ("Delta"). To illustrate selectivity of the compounds, the ratios of the $IC_{50}$ values of the compounds for PI3Kα, PI3Kβ, and PI3Kγ relative to PI3Kδ are given, respectively, as "Alpha/Delta Ratio," "Beta/Delta Ratio," and "Gamma/Delta Ratio."

The initial selectivity assays were done identically to the selectivity assay protocol in Example 2, except using 100 µL Ecoscint for radiolabel detection. Subsequent selectivity assays were done similarly using the same 3× substrate stocks except they contained 0.05 mCi/mL γ[$^{32}$P]ATP and 3 mM $PIP_2$. Subsequent selectivity assays also used the same 3× enzyme stocks, except they now contained 3 nM of any given PI3K isoform.

For all selectivity assays, the test compounds were weighed out and dissolved into 10-50 mM stocks in 100% DMSO (depending on their respective solubilities) and stored at −20° C. Compounds were thawed (to room temperature or 37° C.), diluted to 300 µM in water from which a 3-fold dilution series into water was done. From these dilutions, 20 µL was added into the assay wells alongside water blanks used for the enzyme (positive) control and the no enzyme (background) control. The rest of the assay was essentially done according to the selectivity assay protocol in Example 2.

For those cases in which the greatest concentration used in the assay, i.e., 100 µM, did not inhibit activity of the enzyme by at least 50%, the table recites the percent activity remaining at that concentration (i.e., at 100 µM). In these cases, the true activity ratio(s) for the compounds cannot be calculated, since one of the required $IC_{50}$ values is missing. However, to provide some insight into the characteristics of these compounds, a hypothetical activity ratio is calculated using 100 µM substituted for the missing value. In such cases, the selectivity ratio must in fact be greater than the hypothetical value, and this is indicated by use of a greater than (>) symbol.

TABLE 2

| Compound | Alpha IC$_{50}$ | Beta IC$_{50}$ | Delta IC$_{50}$ | Gamma IC$_{50}$ | Alpha/Delta Ratio | Beta/Delta Ratio | Gamma/Delta Ratio |
|---|---|---|---|---|---|---|---|
| D-000 | 86% | 74% | 0.33 | 7.7 | >302 | >302 | 23 |
| D-001 | 83% | 45 | 68 | | >1.5 | 0.66 | |
| D-002 | 88% | 78% | 44 | | >2.3 | >2.3 | |
| D-003 | 92 | 53% | 4 | | 22 | >24 | |
| D-004 | 93% | 89% | 64 | | >2 | >1.6 | |
| D-005 | 89% | 46 | 0.8 | | >121 | 56 | |
| D-006 | 78% | 6 | 0.15 | | >652 | 38 | |
| D-007 | 82% | 30 | 0.16 | | >619 | 188 | |
| D-008 | 82% | 68 | 1.2 | | >85 | 57 | |
| D-009 | 82 | 6 | 0.12 | | 683 | 50 | |
| D-010 | 48 | 11 | 0.06 | 0.70 | 800 | 183 | 12 |
| D-011 | 72% | 55 | 0.10 | 1.0 | >1,000 | 550 | 10 |
| D-012 | 69% | 11 | 0.17 | | >588 | 65 | |
| D-013 | 71% | 13 | 0.05 | 2.1 | >2,000 | 260 | 42 |
| D-014 | 63% | 3.6 | 0.06 | 0.56 | >1,667 | 60 | 9.3 |
| D-015 | 65% | 69% | 0.21 | 3.6 | >480 | >480 | 17 |
| D-016 | 91% | 81% | 40 | | >2.5 | >3 | |
| D-017 | 89% | 108% | 12 | | >8 | >8 | |
| D-018 | 88% | 93% | 4.2 | | >24 | >24 | |
| D-019 | 67 | 105 | 7 | | 10 | 15 | |
| D-020 | 69% | 69% | 1.9 | | >53 | >53 | |
| D-021 | 100 | 110 | 1.6 | | 62 | 68 | |
| D-022 | 81% | 110 | 0.8 | 40 | >125 | 137.50 | 50 |
| D-023 | 83% | 91% | 26 | | >4 | >3.9 | |
| D-024 | 100 | 76% | 2.6 | | 38 | >38 | |
| D-025 | 73% | 61% | 0.11 | 1.5 | >909 | >909 | 14 |
| D-026 | 68% | 54% | 0.08 | 1.7 | >1,250 | >1,250 | 21 |
| D-027 | 59% | 58 | 0.6 | | >169 | 97 | |
| D-028 | 67% | 13 | 0.18 | | >556 | 69 | |
| D-029 | 49 | 3.0 | 0.06 | | 882 | 54 | |
| D-030 | 50 | 5 | 0.07 | | 758 | 70 | |
| D-031 | 74 | 10 | 0.12 | | >833 | 83 | |
| D-034 | 19 | 11 | 0.15 | | 131 | 74 | |
| D-035 | 9 | 3 | 0.05 | | 199 | 65 | |
| D-036 | 63% | 31 | 0.4 | | >226 | 69 | |
| D-037 | 64% | 80 | 0.8 | | >125 | 100 | |
| D-039 | 77% | 66% | 0.9 | 38 | >111 | >111 | 42 |
| D-038 | 77% | 63% | 0.6 | 60 | >167 | >170 | 100 |
| D-040 | 77% | 64% | 1.7 | | >61 | >61 | |
| D-041 | 67% | 65% | 4 | | >25 | >25 | |
| D-042 | 70% | 25 | 3 | | >32 | 8 | |
| D-043 | 83% | 77% | 2.1 | | >47 | >47 | |
| D-044 | 105 | 61 | 4.2 | | 25 | 15 | |
| D-045 | 98% | 74% | 7.6 | | >13 | >13 | |
| D-046 | 64% | 95 | 9 | | >11 | 11 | |
| D-047 | 30 | 9 | 0.09 | 0.5 | 333 | 100 | 5.6 |
| D-048 | 70 | 14 | 0.16 | | 449 | 90 | |
| D-049 | 110% | 30 | 1.0 | | >100 | 30 | |
| D-050 | 99% | 41 | 1.6 | | >63 | 26 | |
| D-051 | 89% | 57% | 3.3 | | >31 | >31 | |
| D-052 | 0.7 | 69% | 8 | | 0.09 | >13 | |
| D-121 | 69% | 70% | 0.48 | | >211 | >211 | |
| D-999 | 105 | 71% | 47 | 60 | 2.2 | 2.1 | 1.3 |
| LY294002 | 1.2 | 0.4 | 0.23 | | 5.3 | 1.7 | |

1)Compound D-121 is a 3-phenyl-2-(9H-purin-6-ylsulfanylmethyl)-3H-quinazolin-4-one B. Biochemical Assay Using 200 μN ATP In Part A, above, compounds of the invention were tested to establish their IC$_{50}$ for inhibition of the alpha, beta, delta, and gamma isoforms of PI3K using 20 μM ATP. A further screen was performed to establish the IC$_{50}$ for inhibition of the four PI3K isoforms at a final concentration of 200 μM ATP, 10-fold greater, and substantially closer to the normal physiological concentration of ATP in cells. This selectivity protocol is identical to that described above, except the 3× stock ATP concentration was 600 μM. Data from this assay are summarized in Table 3, below. The observed sensitivity to ATP concentration suggests that these PI3Kδ inhibitor compounds act as ATP competitors.

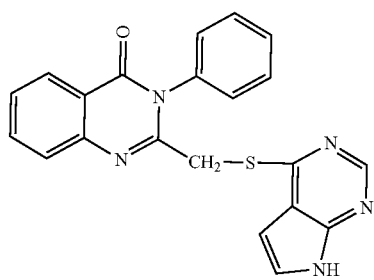 [SMILES: O=c1c2ccccc2nc(CSc2ncnc3[nH]ccc23)n1-c1ccccc1]

TABLE 3

| Compound | Alpha IC$_{50}$ | Beta IC$_{50}$ | Delta IC$_{50}$ | Gamma IC$_{50}$ | Alpha/Delta Ratio | Beta/Delta Ratio | Gamma/Delta Ratio |
|---|---|---|---|---|---|---|---|
| D-000 | 91 ± 1% | 84 ± 2% | 2 ± 1 | 35 ± 35 | 91 | 84 | 18 |
| D-005 | 104% | 82% | 11 | 91% | 20 | 16 | 17 |
| D-006 | 104 ± 1% | 44 ± 5 | 0.92 ± 0.1 | 87 ± 33 | 226 | 48 | 95 |
| D-007 | 92 ± 11% | 72 ± 12 | 0.73 ± 0.2 | 88 ± 4 | 252 | 99 | 121 |
| D-009 | 70% | 18 | 0.7 | 53 | 200 | 26 | 76 |
| D-010 | 74 ± 18% | 33 ± 4 | 0.23 ± 0.2 | 6 ± 3 | 658 | 144 | 27 |
| D-011 | 88 ± 4% | 105 ± 35 | 0.25 ± 0.2 | 61 ± 70 | 700 | 420 | 244 |
| D-012 | 70 ± 4% | 108 ± 4 | 1.3 ± 0.4 | 50 ± 0 | 107 | 83 | 38 |
| D-015 | 117 ± 8% | 73 ± 24% | 0.51 ± 0.6 | 12 ± 1 | 461 | 289 | 24 |
| D-014 | 100 ± 6% | 13 ± 0 | 0.5 ± 0.4 | 5 ± 3 | 398 | 26 | 10 |
| D-015 | 95 ± 221 | 81 ± 3% | 1.1 ± 0.5 | 83 ± 37% | 180 | 154 | 160 |
| D-019 | 100% | 100 | 30 | 33 | 7 | 3 | 1 |
| D-022 | 86% | 101% | 4.2 | 60% | 42 | 48 | 29 |
| D-025 | 89 ± 11% | 77 ± 6% | 0.32 ± 0.3 | 7.8 ± 3 | 556 | 478 | 24 |
| D-026 | 83 ± 1% | 77 ± 8% | 0.38 ± 0.2 | 13 ± 10 | 443 | 411 | 34 |
| D-027 | 74% | 110 | 4 | 60 | 37 | 28 | 15 |
| D-026 | 100% | 81% | 1.6 | 29 | 125 | 101 | 18 |
| D-029 | 110 ± 12% | 34 ± 4 | 0.34 ± 0.08 | 13 ± 0.7 | 553 | 101 | 37 |
| D-030 | 95 ± 11% | 80 ± 14 | 0.53 ± 0.05 | 31 ± 10 | 362 | 152 | 59 |
| D-031 | 87 ± 10% | 137 ± 23 | 0.2 ± 0.01 | 155 ± 60 | 903 | 707 | 802 |
| D-034 | 92 ± 11% | 103 ± 4 | 1.2 ± 0.3 | 34 ± 1 | 153 | 85 | 28 |
| D-035 | 95 ± 6 | 34 ± 6 | 0.49 ± 0.1 | 6.8 ± 1 | 193 | 69 | 14 |
| D-036 | 99% | 73% | 4.1 | 72 | 48 | 36 | 18 |
| D-037 | 112% | 58% | 3.5 | 45 | 64 | 33 | 13 |
| D-038 | 69% | 74% | 1.8 | 55 | 77 | 82 | 31 |
| D-039 | 85% | 65% | 2.6 | 57% | 65 | 50 | 44 |
| D-047 | 81% | 30 | 0.2 | 4.5 | 810 | 150 | 23 |
| D-048 | 90 ± 57 | 95 ± 7 | 1.4 ± 0.9 | 123 ± 40 | 67 | 70 | 91 |
| D-121 | 71% | 62% | 0.9 | 61% | 158 | 138 | 136 |
| D-999 | 62% | 71% | 75 | 90 | 2 | 2 | 1 |
| LY294002 | 23 ± 5 | 3.7 ± 2 | 2.1 ± 1.5 | 29 ± 13 | 11 | 2 | 13 |

Example 12

Cell-Based Assay Data for Inhibitors of PI3Kδ Activity

Using the methods described in Examples 3-5, above, compounds of the invention were tested for inhibitory activity and potency in assays of stimulated B and T cell proliferation, neutrophil (PMN) migration, and neutrophil (PMN) elastase release. Data from these assays are set forth in Table 4, below. In Table 4, the values shown are effective concentrations of the compound (EC$_{50}$; μM). Where no value is given, no assay was performed.

TABLE 4

| Compound | Mouse BCR Stim (EC$_{50}$) | Mouse TCE Stim (EC$_{50}$) | Human PMN Elastase (EC$_{50}$) | Human PMN Migration (EC$_{50}$) |
|---|---|---|---|---|
| D-000 | 0.9 ± 0.4 | 5.5 ± 4 | 2.2 ± 2 | 1-5 |
| D-003 | 3.9 | 5.7 | | |
| D-005 | 0.7 ± 0.1 | 3.9 | 4.3 ± 1 | |
| D-006 | 0.2 ± 0.1 | 5.3 | 0.3 ± 0.1 | |
| D-007 | 0.3 ± 0.1 | 4.2 | 0.4 | |
| D-008 | 1.0 | | | |
| D-009 | 0.3 ± 0.2 | | 10.5 | |
| D-010 | 0.2 ± 0.1 | | 0.3 ± 0.3 | |
| D-011 | 0.3 ± 0.1 | | 0.9 ± 0.7 | |
| D-012 | 0.3 ± 0.2 | | 0.3 | |
| D-013 | 1.4 | | | |
| D-014 | 0.2 ± 0.1 | 4.3 | | |
| D-015 | 1.2 ± 0.2 | 1.8 | 1.3 ± 0.4 | 2.0 |
| D-019 | 0.9 ± 0.01 | 0.9 | | |
| D-021 | 1.8 | 3.5 | | |

TABLE 4-continued

| Compound | Mouse BCR Stim (EC$_{50}$) | Mouse TCE Stim (EC$_{50}$) | Human PMN Elastase (EC$_{50}$) | Human PMN Migration (EC$_{50}$) |
|---|---|---|---|---|
| D-022 | 1.8 | 2.3 | | |
| D-024 | | | 2.9 | |
| D-025 | 0.3 ± 0.1 | 4.4 ± 0.6 | 0.3 ± 0.2 | 0.3 ± 0.3 |
| D-026 | 0.3 ± 0.1 | 3.5 | 0.2 ± 0.2 | 0.3 ± 0.3 |
| D-027 | >2 | | 2 | |
| D-028 | 0.4 ± 0.2 | | 1 | |
| D-029 | 0.1 ± 0.03 | 3.4 ± 2 | 0.5 ± 0.6 | 0.3 |
| D-030 | 0.1 ± 0.1 | 6 | 0.4 ± 0.5 | 0.2 |
| D-031 | 0.2 ± 0.1 | | 0.7 ± 0.1 | |
| D-034 | 0.6 ± 0.4 | | | |
| D-035 | 0.2 ± 0.1 | 2.9 ± 0.7 | 0.3 ± 0.1 | |
| D-036 | 0.9 ± 0.04 | 4.1 | 5.5 ± 5 | 0.2 |
| D-037 | 1.2 ± 0.4 | | 1.3 ± 0.4 | 2.0 |
| D-038 | 1.4 ± 0.1 | 2.9 | 5 | |
| D-039 | 0.9 ± 0.1 | | 5 | |
| D-043 | 1.4 | 2.6 | | |
| D-045 | | | 9.0 | |
| D-047 | 0.3 ± 01. | | 0.5 ± 0.2 | |
| D-048 | 0.4 ± 0.2 | 5 | 0.9 ± 0.2 | |
| D-049 | 2.0 | 6.3 | 5.0 | |
| D-121 | 1.4 | | | |
| D-999 | 3.1 ± 0.7 | 5.9 | >20 | 1 |
| LY294002 | 0.9 ± 0.5 | | | |

Example 13

Assay of Inhibitors of PI3Kδ Activity in Cancer Cells

The effect of compounds of the invention on cancer cell proliferation was evaluated by testing one of the compounds against a panel of Chronic Myeloid Leukemia (CML) cell lines, including KU812, RWLeu4, K562, and MEG-01.

The inhibitory activity of the compound (D-000, dissolved in DMSO) was determined as follows. The tested compound was added in a series of concentrations (0.001 µM to 20 µM) to 96-well microtiter plates with cells (1000 to 5000 cells/-well). Plates were incubated for five days at 37° C. during which the control cultures without test compound were able to undergo at least two cell-division cycles. Cell growth was measured by incorporation of [$^3$H]-thymidine for eighteen hours added at days three, four, and five. Cells were transferred to a filter, washed and the radioactivity counted using a Matrix 96 beta counter (Packard). The percentage of cell growth was measured as follows:

$$\% \text{ Cell growth} = \frac{(\text{average counts of cells incubated with a given inhibitor concentration}) \times 100}{(\text{average counts of the cells without inhibitor})}$$

The EC$_{50}$ value in these experiments was determined by the concentration of the test compound that resulted in a radioactivity count 50% lower than that obtained using the control without inhibitor. The D-000 compound exhibited inhibitory activity with an EC$_{50}$ of approximately 2 µM for the KU812 and RWLeu4 lines. The compound was not found to exhibit an effect in the K562 and MEG-01 lines.

PI3Kδ inhibitors of the invention appear to inhibit CML cell growth and therefore could be useful in the treatment of benign or malignant tumors. PI3Kδ expression has been demonstrated so far mostly in cells of hematopoietic origin. However, it could be present in a broader variety of proliferating cells. Therefore, the compounds of the invention could be used to induce tumor regression and to prevent the formation of tumor metastasis in both leukemia and solid tumor or in proliferation of nontumoral origin. In addition, the compounds could be used both alone and in combination with other pharmacologically active compounds or in combination with radiation as a sensitizing agent.

Example 14

Measurement of Elastase Exocytosis in Mouse Air Pouch Lavage

The effect of D-030 on leukocyte influx and neutrophil elastase exocytosis in animal models was tested. The six-day air pouch model is an in vivo inflammation model that histologically resembles a joint synovium. A lining of organized mononuclear cells and fibroblasts develops that closely resembles a synovial cavity. The model represents an "acute" model of a chronic disease (e.g., rheumatoid arthritis). This model allows for the in vivo evaluation of agents to block cellular influx into the air pouch under the influence of an inflammatory stimulus.

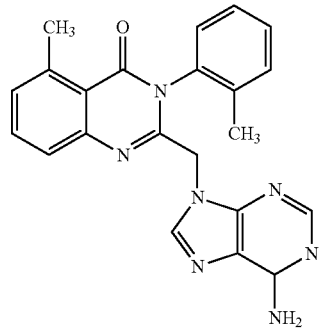

D-030

The test was performed as follows: on day zero, groups of rats were shaved and 10 ml of air was injected subcutaneously on the back of each, forming a pouch. On day three, 10 ml of air was reinjected. Six hours prior to TNF challenge on day six, one group of rats (n=6) received D-030 (100 mg/kg in PEG 400 vehicle) orally, and another group (n=12) received vehicle alone orally. Six hours following dosing, the air pouches of both groups received 2.5 ng of TNF. Twelve hours following dosing, the pouches were washed with saline, and the resulting lavage fluid was analyzed for leukocyte counts and neutrophil elastase activity. In addition, blood was drawn to determine the levels of D-030 in circulation. The results were as follows: rats that received D-030 for twelve hours had an average of 8.7 µM of compound in circulation and had an 82% reduction in total leukocytes in the lavage fluid compared to vehicle controls. Reductions in specific leukocyte counts were as follows: neutrophils (90%), eosinophils (66%), and lymphocytes (70%). Quantitation of neutrophil elastase showed that D-030-treated rats had elastase levels that were somewhat reduced (15%) versus vehicle controls.

In another test, an area of the mouse back was shaved using clippers, and an air pouch was created by injecting 3 ml air subcutaneously. On day three, the air injection was repeated. On day six, the animals were dosed with either D-030 (32 mg/kg in LABRAFIL®) or LABRAFIL® only one hour before and two hours after challenge with TNF-α (0.5 ng in 1 ml PBS), or PBS only. PBS is phosphate buffered saline. Four hours after TNF challenge, the animals were anesthetized and the pouches were lavaged with 2 mL of 0.9% saline with 2 mM EDTA. The lavages were centrifuged at 14,000 rpm in a microcentrifuge. Fifty microliters of the supernatant was used to measure elastase exocytosis according to the procedure described above.

Figure 9:
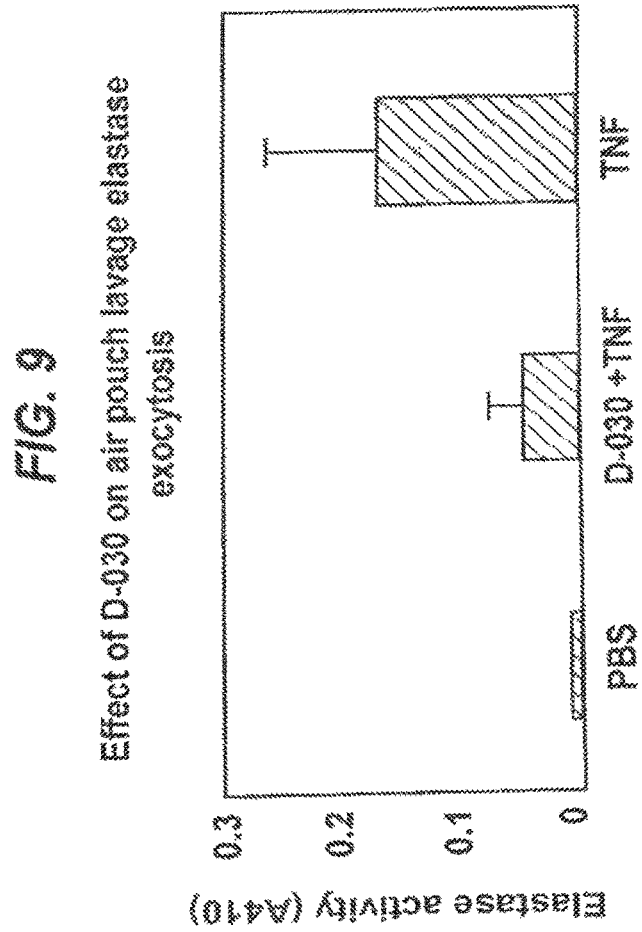
FIG. 9 shows the effect of a selective PI3Kδ inhibitor on elastase exocytosis in an animal model.

As shown in FIG. 9, TNF challenge induced a high level of elastase exocytosis compared to PBS challenged animals. However, when the TNF challenged animals were treated with D-030, a significant decrease in the elastase activity in the air pouch lavages was observed.

All publications and patent documents cited in this specification are incorporated herein by reference for all that they disclose.

While the present invention has been described with specific reference to certain preferred embodiments for purposes of clarity and understanding, it will be apparent to the skilled artisan that further changes and modifications can be practiced within the scope of the invention as it is defined in the claims set forth below. Accordingly, no limitations should be placed on the invention other than those specifically recited in the claims.

What is claimed is:
1. A method of preparing a compound having a structure:
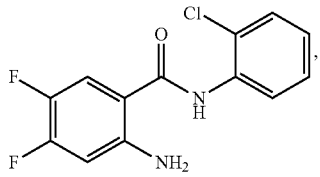 [SMILES: Nc1cc(F)c(F)cc1C(=O)Nc1ccccc1Cl]
comprising reacting
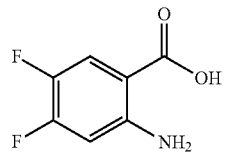
with
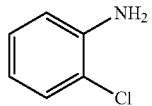
in the presence of thionyl chloride.
2. A compound having a structure
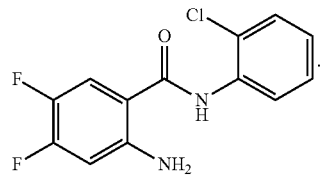
* * * * *